United States Patent
Knox et al.

(10) Patent No.: US 12,310,954 B2
(45) Date of Patent: May 27, 2025

(54) SALIVARY GLAND REGENERATION

(71) Applicants: The Regents of the University of California, Oakland, CA (US); Case Western Reserve University, Cleveland, OH (US)

(72) Inventors: Sarah Knox, San Francisco, CA (US); Chelsea S. Bahney, Edwards, CO (US); Eben Alsberg, Chicago, IL (US); Oju Jeon, Broadview Heights, OH (US)

(73) Assignees: Case Western Reserve University, Cleveland, OH (US); The Regents of the University of California, Oakland, CA (US)

( * ) Notice: Subject to any disclaimer, the term of this patent is extended or adjusted under 35 U.S.C. 154(b) by 912 days.

(21) Appl. No.: 17/312,196

(22) PCT Filed: Dec. 10, 2019

(86) PCT No.: PCT/US2019/065415
§ 371 (c)(1),
(2) Date: Jun. 9, 2021

(87) PCT Pub. No.: WO2020/123470
PCT Pub. Date: Jun. 18, 2020

(65) Prior Publication Data
US 2022/0054462 A1   Feb. 24, 2022

Related U.S. Application Data

(60) Provisional application No. 62/777,459, filed on Dec. 10, 2018.

(51) Int. Cl.
*A61K 31/439*   (2006.01)
*A61K 9/00*   (2006.01)
(Continued)

(52) U.S. Cl.
CPC .......... *A61K 31/439* (2013.01); *A61K 9/0019* (2013.01); *A61K 9/006* (2013.01); (Continued)

(58) Field of Classification Search
CPC ........ A61K 31/439; A61K 9/006; A61K 9/06; A61K 31/27; A61K 31/4178; A61K 47/36; A61K 9/0019; A61P 1/02; A61P 39/00
See application file for complete search history.

(56) References Cited

U.S. PATENT DOCUMENTS

2011/0104052 A1   5/2011   Barnett et al.

FOREIGN PATENT DOCUMENTS

BR   PI0805520-3 A2   8/2010
JP   2007176906 A   7/2007
(Continued)

OTHER PUBLICATIONS

Emmerson, Elaine, et al. "Salivary Glands Regenerate after Radiation Injury through SOX2-mediated Secretory Cell Replacement." EMBO Molecular Medicine, vol. 10, No. 3, Mar. 2018, p. e8051. DOI.org (Crossref), https://doi.org/10.15252/emmm.201708051. (Year: 2018).*

(Continued)

*Primary Examiner* — Clinton A Brooks
*Assistant Examiner* — Kyle Nottingham
(74) *Attorney, Agent, or Firm* — Jenny L. Buchbinder; Bozicevic, Field & Francis LLP

(57) ABSTRACT

A method is provided for promoting salivary gland regeneration in a subject in need thereof comprising administering to acinar progenitor cells of the salivary gland at least one of a cholinergic agonist or muscarinic agonist to promote acinar cell generation. In particular, formulations comprising a muscarinic agonist such as cevimeline encapsulated in
(Continued)

an alginate hydrogel can be formulated for local administration to a salivary gland and used in treatment of xerostomia.

10 Claims, 68 Drawing Sheets

(51) Int. Cl.
    *A61K 9/06*     (2006.01)
    *A61K 31/27*     (2006.01)
    *A61K 31/4178*     (2006.01)
    *A61K 47/36*     (2006.01)
    *A61P 1/02*     (2006.01)

(52) U.S. Cl.
    CPC ............... *A61K 9/06* (2013.01); *A61K 31/27* (2013.01); *A61K 31/4178* (2013.01); *A61K 47/36* (2013.01); *A61P 1/02* (2018.01)

(56) References Cited

FOREIGN PATENT DOCUMENTS

| | | |
|---|---|---|
| JP | 2009120855 A | 6/2009 |
| JP | 2016210701 A | 12/2016 |
| JP | 2017-066126 A | 4/2017 |
| WO | 2013090924 A1 | 6/2013 |

OTHER PUBLICATIONS

Cohen, Smadar, et al. "A Novel in Situ-Forming Ophthalmic Drug Delivery System from Alginates Undergoing Gelation in the Eye." Journal of Controlled Release, vol. 44, No. 2-3, Feb. 1997, pp. 201-208. DOI.org (Crossref), https://doi.org/10.1016/S0168-3659(96)01523-4. (Year: 1997).*
Emmerson et al. (2017) SOX2 regulates acinar cell development in the salivary gland. eLIFE:1-22.
Arnold et al. (2011) Sox2(+) adult stem and progenitor cells are important for tissue regeneration and survival of mice. Cell Stem Cell. 9: 317-329.
Aure (2015) Salivary gland homeostasis is maintained through acinar cell self-duplication. Dev. Cell 33: 231-237.
Lombaert et al. (2008) Rescue of salivary gland function after stem cell transplantation in irradiated glands. PLoS One 3: e2063.
Van Iuijk et al. (2015) Sparing the region of the salivary gland containing stem cells preserves saliva production after radiotherapy for head and neck cancer. Sci Transl Med 7: 305ra147.
Xiao et al (2014) Neurotrophic factor GDNF promotes survival of salivary stem cells. J. Clin. Invest. 124: 3364-3377.
Coppes et al. (1997) Muscarinic receptor stimulation increases tolerance of rat salivary gland function to radiation damage. Int. J. Radiat. Biol. 72(5):615-25.
Proctor et al. (2007) Regulation of salivary gland function by autonomic nerves. Auton. Neurosci. 133(1):3-18.
Salum et al. (2018) Salivary hypofunction: An update on therapeutic strategies. Gerodontology 35(4):305-316.
Cifuentes et al. (2018) Pilocarpine and artificial saliva for the treatment of xerostomia and xerophthalmia in Sjögren syndrome: a double-blind randomized controlled trial. Br. J. Dermatol. 179(5):1056-1061.
Mercadante et al. (2017) Interventions for the management of radiotherapy-induced xerostomia and hyposalivation: A systematic review and meta-analysis. Oral Oncol. 66:64-74.
Fox (2004) Salivary enhancement therapies. Caries Res 38(3):241-246.
Lee et al. (2012) Alginate: properties and biomedical applications. Prog. Polym. Sci. 37(1):106-126.
Wang et al. (2015) Calcium alginate enhances wound healing by up-regulating the ratio of collagen types I/III in diabetic rats. Int. J. Clin. Exp. Pathol. 8(6):6636-6645.
Qisheng et al., (2015) "Alginate Based Biomedical Materials and Clinical Medicine", Shanghai Scientific & Technical Publishers, pp. 438-440.
Li et al., (2016) "Designing hydrogels for controlled drug delivery", Nature Review Materials, 1(12):1-38.
Gu et al., (2015) "Alginate Based Biomedical Materials and Clinical Medicine", pp. 438-440.
Lin et al., (2015) "In Situ Gelling of Alginate/Pluronic Solutions for Ophthalmic Delivery of Pilocarpine", Biomacromolecules, 5:2358-2365.
Tønnesen & Karlsen, (2002) "Alginate in Drug Delivery Systems", Drug Development and Industrial Pharmacy, 28(6):621-630.

* cited by examiner

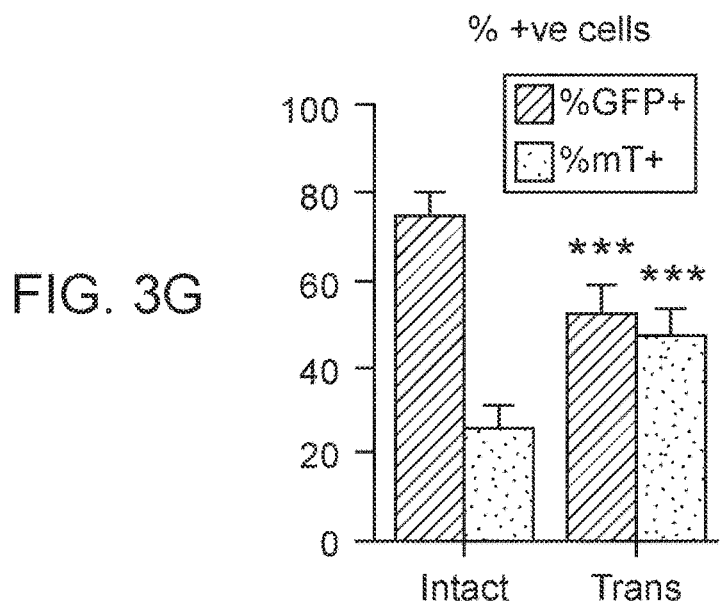
FIG. 3G
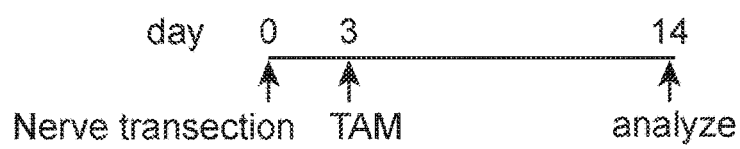
FIG. 3H
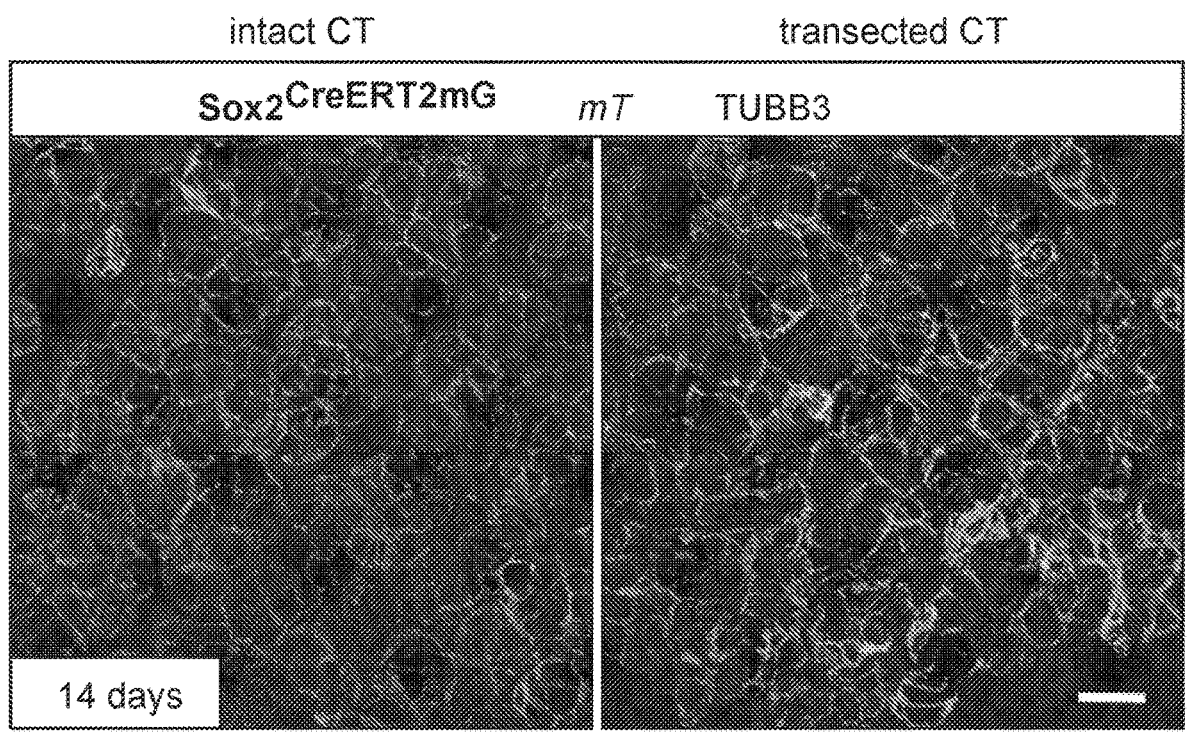

FIG. 5A
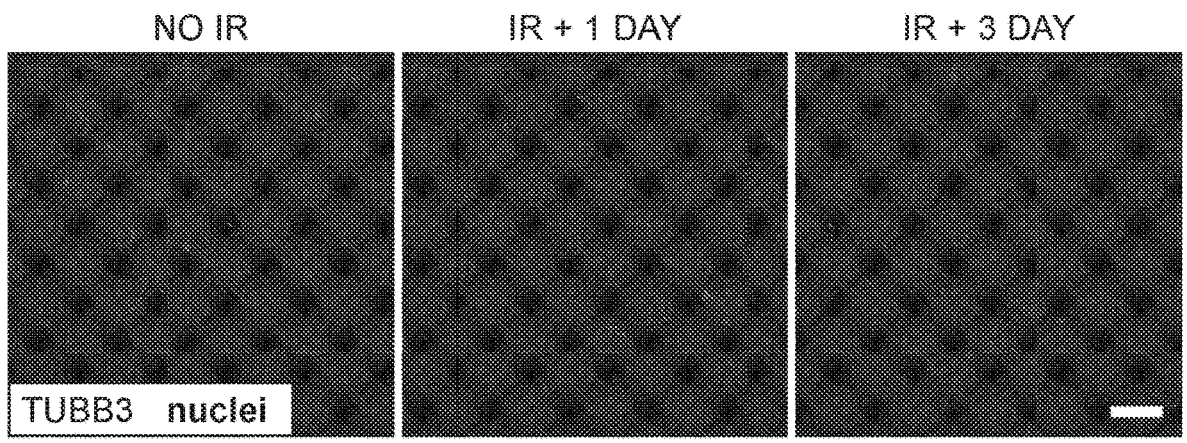
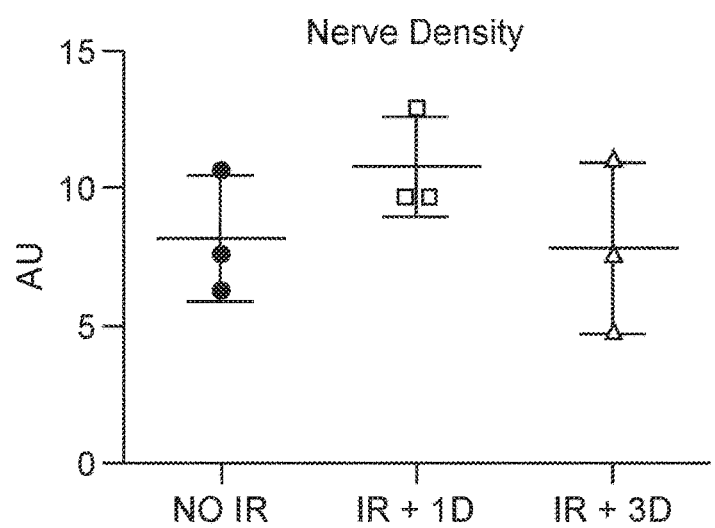
FIG. 5B
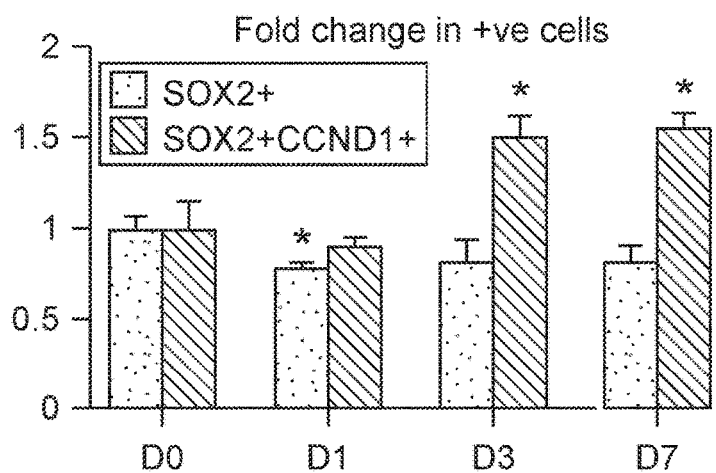
FIG. 5C

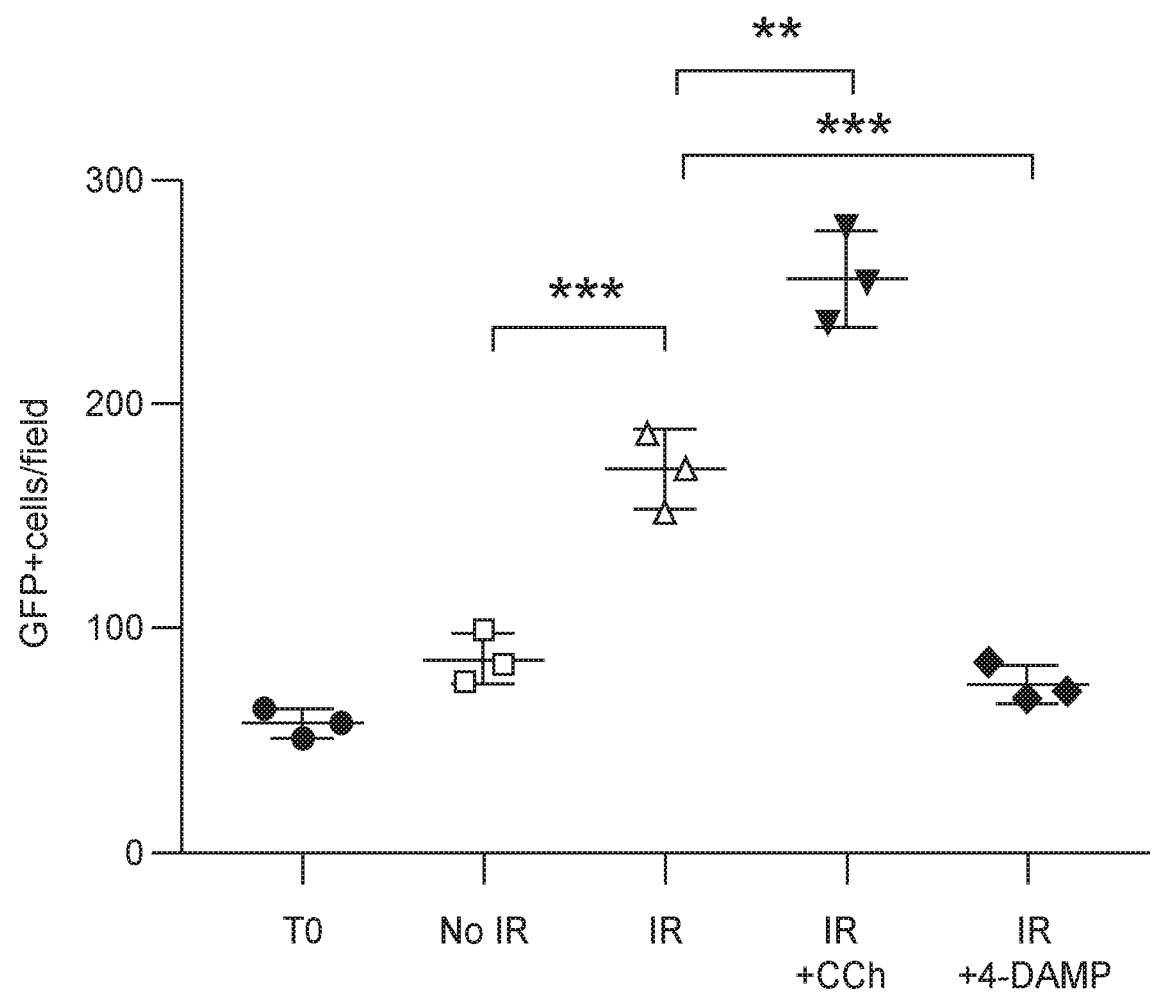

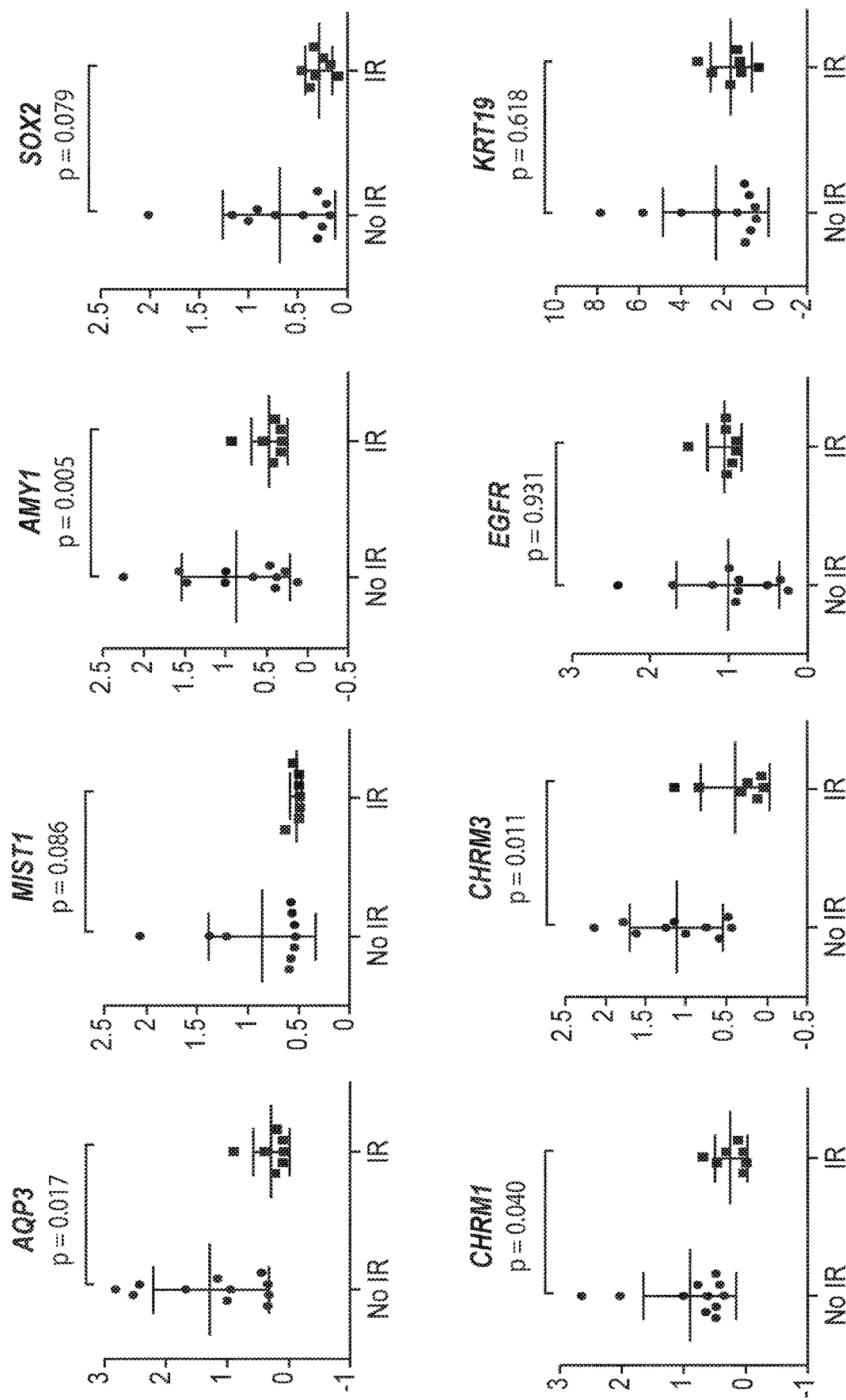

FIG. 12E
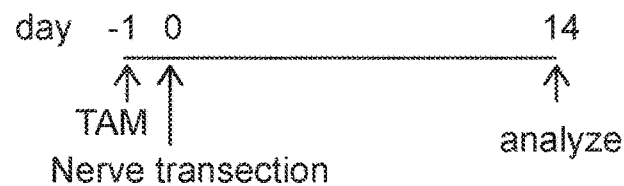
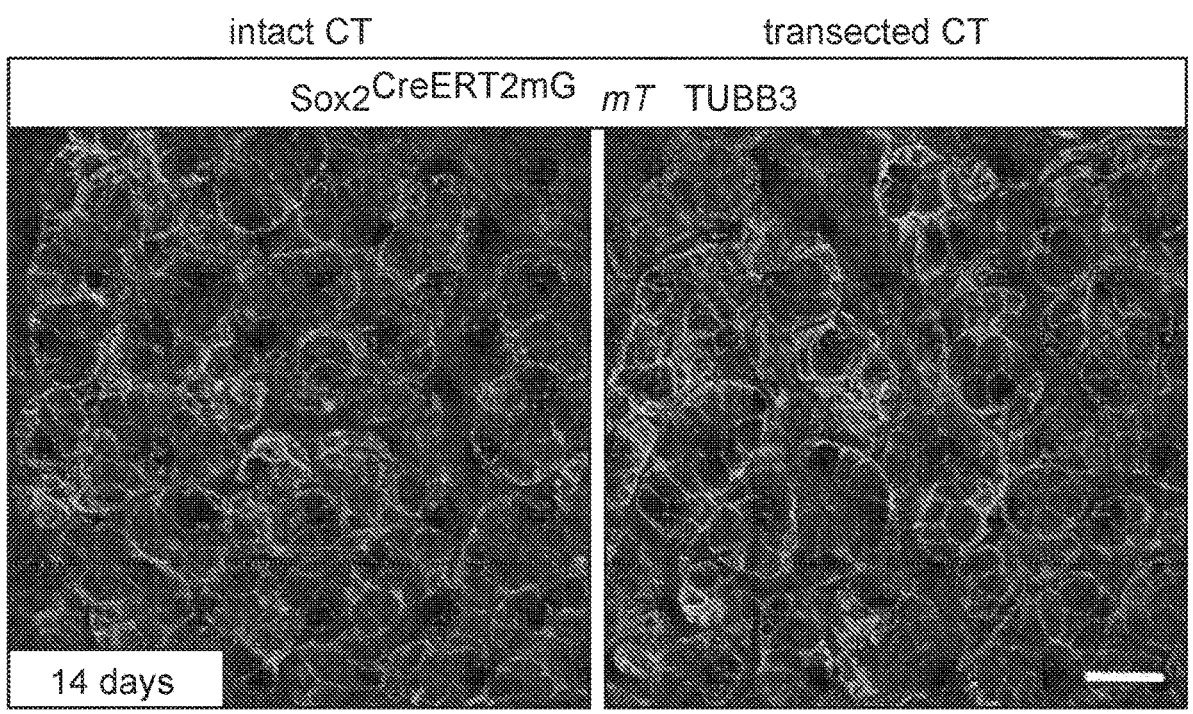
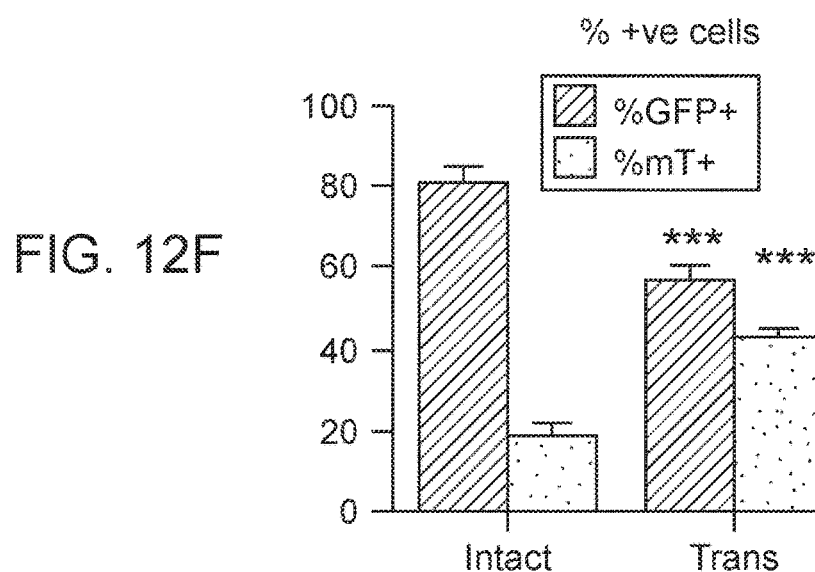
FIG. 12F

* indicates significance (p<0.05)

| 4 hours | 1 day | 3 days | 5 days | 7 days |
|---|---|---|---|---|
| 0.196993 | 0.000203 * | 0.000307* | 0.230164 | 0.000529* |

* indicates significance (p<0.05)

|  | 4 hours | 1 day | 3 days | 5 days | 7 days |
|---|---|---|---|---|---|
| 2% wt vs 5% wt | 0.8346 | 0.4683 | 0.534 | 0.4293 | 0.4116 |
| 2% wt vs 10% wt | 0.02* | 0.0037* | 0.0019* | 0.0001* | 0.0163 * |
| 5% wt vs 10% wt | 0.0006* | 0.0221* | <0.0001* | 0.0004* | 0.0531 * |

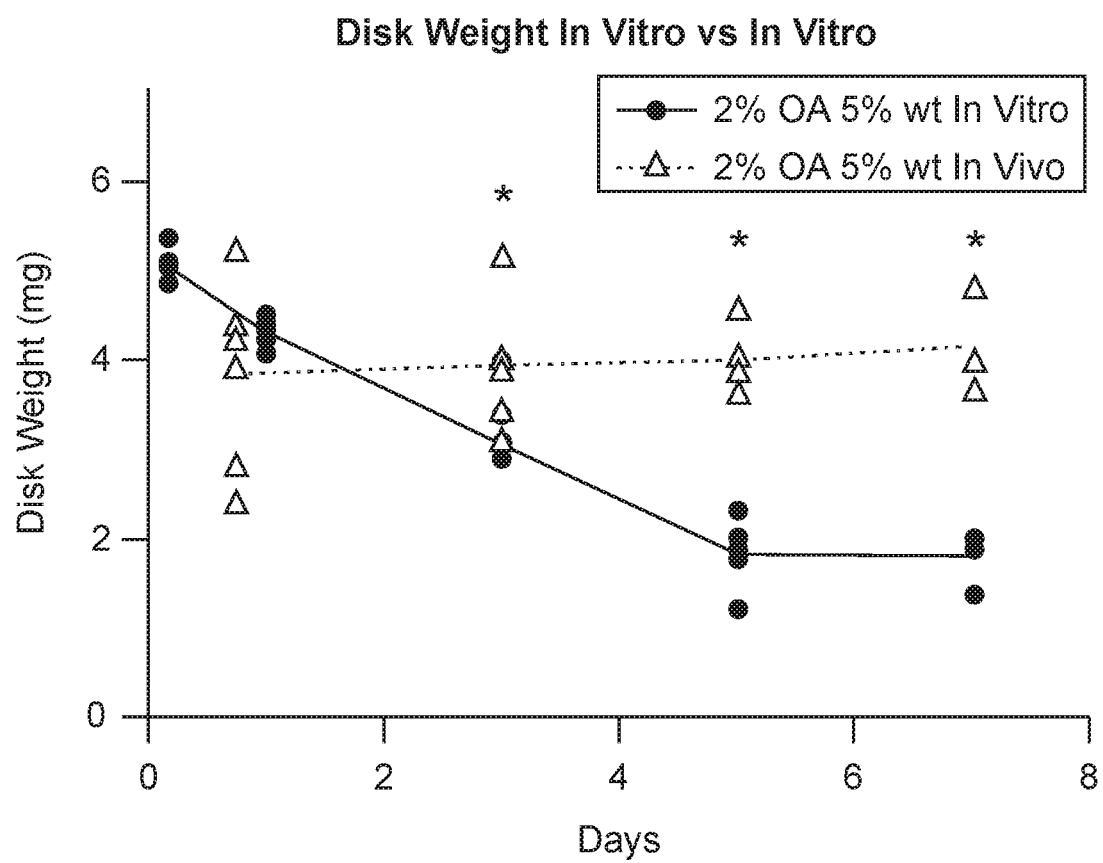

* Indicates significance

| 0 days | 1 day | 4 days | 10 days | 20 days | 30 days |
|---|---|---|---|---|---|
| >0.999999 | 0.970738 | 0.876479 | 0.061278 | 0.004914 * | 0.000792 * |

* Indicates significance (p<0.05)

|  | 4 hours | 1 day | 2 days | 3 days | 4 days |
|---|---|---|---|---|---|
| 2% OA vs | 0.856077 | 0.738832 | 0.871381 | 0.137966 | 0.17817 |

* Indicates significance (p<0.05)

|  | 4 hours | 1 day | 2 days | 3 days | 4 days |
|---|---|---|---|---|---|
| 2% wt vs 5% wt | 0.8725 | 0.6151 | 0.9078 | 0.0833 | 0.0111* |
| 2% wt vs 10% wt | 0.1021 | 0.1333 | 0.051 | 0.2319 | 0.9052 |
| 5% wt vs 10% wt | 0.0163* | 0.0407* | 0.9129 | 0.1511 | 0.0167* |

* indicates significance (p<0.05)

|  | 4 hours | 1 day | 2 days | 3 days | 4 days |
|---|---|---|---|---|---|
| 3000ng vs 6000 ng | 0.0011* | 0.0086* | 0.3069 | 0.8551 | N/A |
| 3000 ng vs 12000 ng | 0.0056* | 0.0165* | 0.0004* | 0.05 | N/A |
| 6000 ng vs 12000 ng | 0.0167* | 0.0784 | 0.9973 | 0.1019 | 0.000988* |

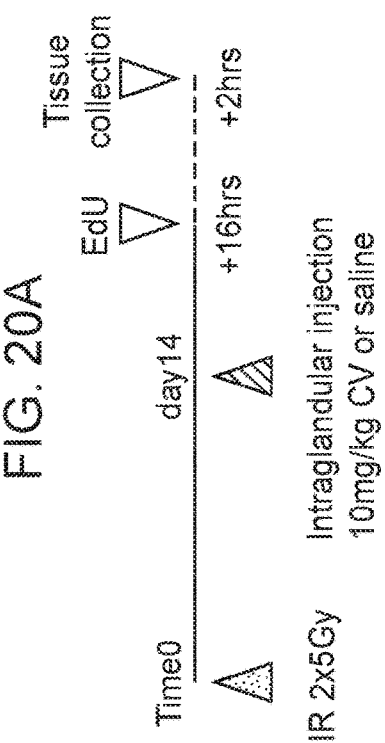
FIG. 20A
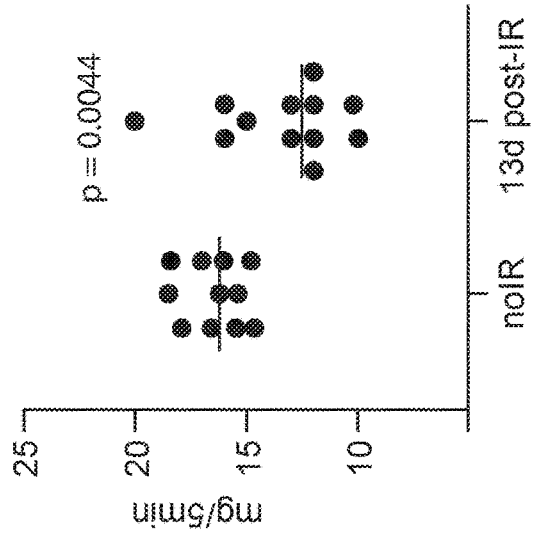
FIG. 20B
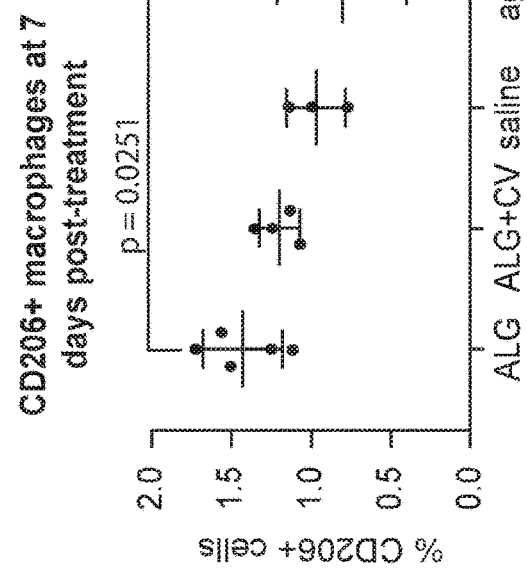
FIG. 19E
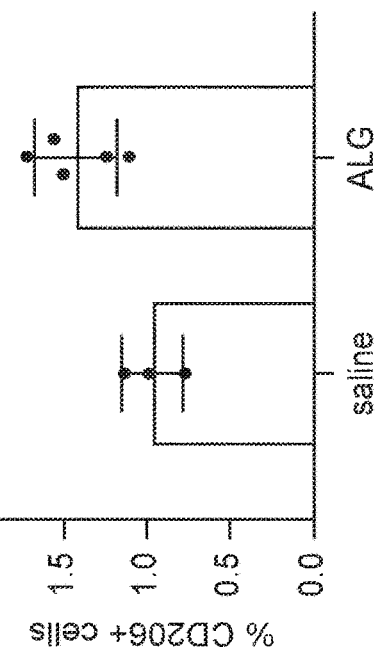

- Dog: Injection of 1.5 mL alginate into mandibular glad
- Human: 1.5-2 mL injected directly into submandibular glad

SALIVARY GLAND REGENERATION

CROSS-REFERENCE TO RELATED APPLICATION

This application claims benefit under 35 U.S.C. § 119(e) of provisional application 62/777,459, filed Dec. 10, 2018, which is hereby incorporated herein by reference in its entirety.

STATEMENT REGARDING FEDERALLY SPONSORED RESEARCH OR DEVELOPMENT

This invention was made with government support under grant no. U24 DE026914 awarded by The National Institutes of Health. The government has certain rights in the invention.

BACKGROUND OF THE INVENTION

Salivary gland (SG) dysfunction severely compromises the oral health and quality of life of patients: saliva protects the oral mucosa, facilitates food digestion and articulation, and aids in the remineralization of dental hard tissues. Dry mouth, or xerostomia, can occur from irreversible pathological injury due to the autoimmune disease Sjogren's Syndrome (1-2 million in US) or from therapeutic radiation for head and neck cancer (60,000/yr in USA) where SGs are inadvertently irradiated along with the tumor. Loss of regenerative capacity in this tissue eliminates saliva production and significantly compromises quality of life for these patients. There are no available regenerative treatments for salivary dysfunction, driving a need for new, translatable solutions.

Currently, the standard of care is to recommend palliative treatments, such as salivary substitutes or artificial saliva, and/or systemic sialogogues. Cevimeline and pilocarpine are two FDA approved muscarinic agonists that promote temporary secretion of saliva. Pilocarpine is a nonselective muscarinic agonist, while cevimeline has higher affinity for M1 and M3 muscarinic receptor subtypes, both of which are expressed in the submandibular and sublingual salivary gland. While these drugs are effective in promoting short term saliva production when taken 3-4 times daily, they are associated with undesirable parasympathetomimetic side-effects including, excessive sweating and diarrhea, headaches, and blurred vision that reduce patient compliance. It was recently reported that long term oral use of cevimeline or pilocarpine in patients improves salivary gland function (Barbe (2017) J. Evid. Based Dent. Pract. 17(3):268-270). Furthermore, continuous oral administration of pilocarpine to mice treated with gamma radiation to the head and neck promoted salivary flow compared to untreated controls (Taniguchi et al. (2019) Acta Histochem Cytochem. 52(3): 45-58), suggesting that muscarinic agonism may promote salivary gland repair, although how this was achieved was not determined.

There remains a need for better methods of treating salivary dysfunction, particularly regenerative treatments that can restore saliva-secreting acinar cells and saliva production.

SUMMARY OF THE INVENTION

Compositions and methods for salivary gland regeneration by promoting acinar cell replacement are provided. It was found that acinar progenitor cells including $SOX2^+$ progenitor cells in the adult salivary gland are essential to the replenishment of acinar cells with the unexpected capacity to repopulate the tissue after radiation-induced damage. It was also found that that cholinergic nerves play a vital role in controlling acinar cell replacement during homeostasis and that this neuronal influence can be replicated through addition of cholinergic mimetics to the acinar progenitor cells. Accordingly, by directly targeting acinar progenitor cells within tissue with cholinergic agonists and/or muscarinic agonists, secretory units of salivary glands can be regenerated to provide recovery of functional salivary acini and treat oral disorders, such as xerostomia following radiation therapy or associated with Sjogren syndrome.

In one aspect, a composition is provided comprising a muscarinic agonist encapsulated in a hydrogel formulated for local administration to a salivary gland for use in the treatment of xerostomia. Such a composition may be used for treatment of xerostomia such as caused by damage to the salivary gland from radiation or an autoimmune disease (e.g., Sjogren syndrome).

In certain embodiments, the muscarinic agonist is selective for an M1 and/or an M3 muscarinic receptor subtype. In one embodiment, the muscarinic agonist is cevimeline.

In certain embodiments, the muscarinic agonist is pilocarpine.

In certain embodiments, the hydrogel comprises alginate. The alginate may be ionically cross-linked with divalent cations. In some embodiments, the alginate is ionically cross-linked with divalent calcium cations ($Ca^{2+}$).

In certain embodiments, the alginate concentration in the hydrogel ranges from about 2 to about 10 percentage by weight (wt %), including any wt % within this range, such as 2, 2.5, 3, 3.5, 4, 4.5, 5, 5.5, 6, 6.5, 7, 7.5, 8, 8.5, 9, 9.5, or 10 wt %.

In certain embodiments, the alginate is at least partially oxidized. In some embodiments, about 2% to about 10% of the alginate is oxidized, including any percent in this range, such as 2%, 2.5%, 3%, 3.5%, 4%, 4.5%, 5%, 5.5%, 6%, 6.5%, 7%, 7.5%, 8%, 8.5%, 9%, 9.5%, or 10%. In one embodiment, the alginate in the hydrogel is about 2% oxidized and at a concentration of 5 wt %.

In certain embodiments, the hydrogel sustains delivery of the muscarinic agonist for at least 1 week, at least 2 weeks, at least 3 weeks, or at least 4 weeks, or more after administration to a subject. In some embodiments, the hydrogel sustains delivery of the muscarinic agonist for up to 30 days.

In certain embodiments, the composition further comprises a contrast agent, for example, to allow confirmation of localization of the composition to the salivary gland by medical imaging after administration. In some embodiments, the contrast agent is a microbubble (e.g., for use in ultrasound) or a radiopaque contrast agent (e.g., for use in radiography).

In certain embodiments, the composition further comprises a pharmaceutically acceptable excipient.

In another aspect, a kit is provided comprising a composition comprising a muscarinic agonist encapsulated in a hydrogel, as described herein, and instructions for treating xerostomia. In some embodiments, the kit further comprises means for delivering said composition to a subject. For example, the kit may comprise a first syringe containing a composition comprising a muscarinic agonist encapsulated in an alginate hydrogel, and a second syringe containing a solution comprising calcium chloride, and a luer lock, wherein the second syringe can be connected to the first syringe through the luer lock. The first syringe containing the composition comprising the muscarinic agonist encapsulated in an alginate hydrogel may be stored frozen. In some embodiments, the muscarinic agonist in the kit is cevimeline or pilocarpine.

In another aspect, a method of treating a subject for xerostomia is provided, the method comprising administering a therapeutically effective amount of a composition comprising a muscarinic agonist encapsulated in a hydrogel locally into a salivary gland of the subject.

In certain embodiments, the composition is injected into the salivary gland or adjacent to the salivary gland.

In certain embodiments, multiple therapeutically effective doses of the composition are administered to the subject.

In certain embodiments, the xerostomia is caused by damage to the salivary gland from radiation or Sjogren syndrome.

In certain embodiments, the method further comprises performing medical imaging (e.g., ultrasound) or palpation to locate the salivary gland prior to injection.

In certain embodiments, a method of promoting salivary gland regeneration in a subject in need thereof, the method comprising: administering locally to acinar progenitor cells and acinar cells of the salivary gland at least one of a cholinergic agonist or muscarinic agonist to promote proliferation of the acinar progenitor cells and the acinar cells and thereby increase saliva production.

In certain embodiments, the cholinergic agonist comprises at least one of acetylcholine or an acetylcholine analogue. In some embodiments, the acetylcholine analogue is carbachol.

In certain embodiments, the acinar progenitor cells are $SOX2^+$ acinar progenitor cells. In some embodiments, the $SOX2^+$ acinar progenitor cells are $AQP5^+/Ki67^+$ cells. In other embodiments, the $SOX2^+$ acinar progenitor cells including the $SOX2^+/AQP5^+/Ki67^+$ acinar progenitor cells are mucin $(MUC)19^-$ cells.

In some embodiments, the method further comprises isolating $SOX2^+$ acinar progenitor cells from the salivary gland of the subject being treated, expanding the isolated $SOX2^+$ acinar progenitor cells, and then implanting the expanded cells in the salivary gland of the subject.

In some embodiments, prior to implantation, the expanded cells are provided in an engineered tissue construct or biocompatible substrate that provides controlled release of the at least one cholinergic agonist or muscarinic agonist to the expanded cells. The controlled release can include at least one of a delayed, sustained, gradient, temporal, patterned, or spatial release. The engineered tissue construct or biocompatible substrate can include a biodegradable natural polymer or macromer, such as biocompatible hydrogel.

In some embodiments, the subject being treated by a method described herein has an oral disorder, such as a disorder that effects the production of saliva. Examples of oral disorders include, but are not limited to, salivary gland tumors, cystic fibrosis, Sjogren's syndrome, sialoadenitis, parotitis, sialoangitis, sialodochitis, sialolithiasis, sialodocholithiasis, mucocele, ranula, hyposecretion, ptyalism, sialorrhea, xerostomia, benign lymphoepithelial lesion of salivary gland; sialectasia; sialosis; stenosis of salivary duct; and stricture of salivary duct. In other embodiments, the subject can have been previously treated with radiation effective to cause xerostomia. The methods described herein can be used for treating a human subject for such an oral disorder that effects production of saliva (i.e., xerostomia). The methods described herein will also find use in veterinary applications for treatment of xerostomia in domestic animals, including, without limitation, pets, such as dogs and cats, and farm animals, such as sheep, goats, pigs, horses and cattle.

Other embodiments described herein relate to a method of promoting salivary gland regeneration in a subject in need thereof by isolating and expanding $SOX2^+$ acinar progenitor cells of the salivary gland of the subject and then implanting the expanded cells in the salivary gland of the subject. The expanded $SOX2^+$ acinar progenitor cells can be $AQP5^+/Ki67^+/MUC19^-$ cells.

In some embodiments, prior to and/or after implantation of the expanded cells, the expanded cells can be administered at least one of a cholinergic agonist or muscarinic agonist to promote acinar cell generation.

In other embodiments, the expanded cells can be provided in an engineered tissue construct or biocompatible substrate. The engineered tissue construct or biocompatible substrate can provide controlled release of the at least one cholinergic agonist or muscarinic agonist to the expanded cells, the controlled release comprising at least one of a delayed, sustained, gradient, temporal, patterned, or spatial release.

BRIEF DESCRIPTION OF THE DRAWINGS

FIG. 1A Representative image of adult human submandibular (SMG), sublingual (SLG), and parotid (PG) salivary gland (non-IR, 28-33 years) immunostained for SOX2, epithelia (E-cadherin; ECAD) or CD44, and nuclei. Single arrows indicate SOX2 expressing acinar cells. Scale bar is 20 µm. FIG. 1B Wild-type murine SMG and SLG stained for SOX2, ECAD, and nuclei. Arrowheads indicate SOX2 expressing cells. Scale bar is 50 µm. Yellow dashed line denotes border between SMG and SLG. FIG. 1C $Sox2^{eGFP}$ sublingual salivary glands (SLG) were immunostained for GFP and differentiated acinar marker mucin 19 (MUC19). White dashed lines outline $Sox2^{eGFP+}$ MUC19 (−) cells. Scale bar=20 µm. FIG. 1D $AQP5^+SOX2^+$ cells as a percentage of total $AQP5^+$ acinar cells. FIG. 1E SLG immunostained for SOX2, Ki67, and epithelial marker E-cadherin (ECAD). White arrow indicates proliferating $Ki67^+SOX2^+$ cell. White lines outline individual cells and nuclei. Scale bar=10 µm. FIG. 1F Representative images of Sox2 lineage-traced SLG. Recombination was induced in $Sox2^{CreERT2}$; $Rosa26^{mTmG}$ mice and salivary gland traced for 24 h and 30 days before immunostaining for SOX2, acinar markers AQP5 and MUC19, and ductal marker KRT8. * indicates MUC19(−) $Sox2^{CreERT2}$GFP(+) cells. Scale bars=30 µm. mT=membrane-bound Tomato. Data information: Cells quantified in (FIG. 1D) were counted from three non-consecutive sections of n=5 female adult SLGs. Data are presented as mean±SD.

FIGS. 2A, 2B Sox2 or $SOX2^+$ cells were ablated in SLG of $Sox2^{CreERT2}$; $Sox2^{fl/fl}$; $Rosa26^{mTmG/+}$ mice (FIG. 2A; see schematic) or $Sox2^{CreERT2}Rosa26^{DTA}$; $Rosa26^{mTmG/+}$ mice (FIG. 2B; see schematic). Sections were immunostained for AQP5, KRT8, or ECAD and nuclei. Scale bars=50 µm. Dashed white lines outline ducts. n=3 per genotype. FIGS. 2C, 2D Quantification of ductal area in $Sox2^{CreERT2}$; $Sox2^{fl/fl}$ (FIG. 2C) or $Sox2^{CreERT2}Rosa26^{DTA}$; $Rosa26^{mTmG/+}$ SLG (FIG. 2D) expressed as a percentage of total epithelial area. In (FIG. 2C), right graph, the number of $SOX2^+$ cells in $Sox2^{CreERT2}$; $Sox2^{fl/fl}$ SLG expressed as a percentage of total cells. In (FIG. 2D), right graph, the total number of $KRT8^+$ ductal, AQP5⁺ and SOX2⁺ acinar cells in wild-type and Sox2$^{CreERT2}$Rosa26$^{DTA}$; Rosa26$^{mTmG/+}$ mice was counted. Data information: Calculations of cell numbers/duct areas were performed on three non-consecutive fluorescent sections of each SLG from n=3 mice/genotype. Data in (FIGS. 2C and 2D) (n=3) are means±SD and were analyzed by Student's t-test. In (FIG. 2C), *P=0.011 and P=0.0041, and in (FIG. 2D), left graph P=0.0015 and right graph *P=0.0007 and P=0.0018.

FIGS. 3A-3H show that parasympathetic nerves are necessary for maintaining SOX2⁺ cells and promoting SOX2-mediated acinar cell replacement. FIG. 3A Schematic shows time course of denervation and location of chorda tympani (CT) in adult mice. FIG. 3B Gene expression (qPCR) analysis of intact (uninjured contralateral gland) and nerve transected SLG 7 and 30 days (D7 or D30) after surgery. Gene expression was normalized to Rsp18 and intact controls for each time point. FIGS. 3C-3F Control and nerve transected SLG were immunostained 7 days after denervation for nerves (GFRa2), acinar cells (AQP5 and MIST1), ductal cells (KRT8), and epithelial cells (ECAD). The number of SOX2⁺, AQP5⁺, MIST1⁺, KRT8⁺, and KRT5⁺ cells in control and transected SLG was counted and represented as a percentage of the number of cells in control SLG (FIG. 3F). Scale bars in (FIGS. 3C, 3D and 3E)=25 μm. FIG. 3G, 3H Recombination was induced in Sox2$^{CreERT2}$; Rosa$^{26mTmG}$ mice 3 days after nerve transection and SLG traced for 11 days before being immunostained for TUBB3. The percentage of GFP⁺ and mT⁺ acinar cells in control and transected glands are shown in (FIG. 3G). Scale bar in (FIG. 3H)=25 μm. Data information: Data in (FIG. 3B) (n=5) are means±SEM and were analyzed using a one-way analysis of variance with a post hoc Dunnett's test. Sox2 (D7) *P=0.0455, Tubb3 (D7) P=0.0082, Tubb3 (D30) P=0.0091, Vip (D7) P=0.0098, Vip (D30) P=0.0063, Vacht (D7) **P=0.0071, Muc19 (D7) *P=0.0419, Aqp5 (D7) *P=0.0468. Data in (FIGS. 3F and 3G) were calculated from three non-consecutive fluorescent sections of each SLG from n=5 mice/group or genotype, are means±SD, and were analyzed by Student's t-test. SOX2⁺*P=0.0197, AQP5⁺*P=0.0106, % GFP⁺ *P=0.0000096, % mT⁺ *P=0.0000096.

FIG. 4A Adult SLG was immunostained for SOX2, CHRM3, and nuclei. Images are a 6 μm (left) and 1 μm (right) projection of 1-μm and 0.175-μm confocal sections. Scale bar=10 μm. FIG. 4B The percentage of epithelial SOX2⁺ cells that are CHRM1⁺ or CHRM3⁺ were counted using flow cytometry and expressed as a percentage of the total EpCAM⁺SOX2⁺ cells. FIGS. 4C, 4D Adult SLG from mice treated with pilocarpine or saline (control) was immunostained for SOX2, Ki67, and nuclei. White arrows indicate proliferating SOX2⁺ (SOX2⁺Ki67⁺) cells (FIG. 4C). Scale bar=20 μm. (FIG. 4D) The fold changes in % of SOX2⁺ and SOX2⁺Ki67⁺ cells with pilocarpine treatment. Data information: (FIG. 4B) SLG were pooled from n=3 mice (10,000 events). Data in (FIG. 4D) were calculated from three non-consecutive fluorescent sections of each SLG from n=4 (saline) or n=5 (pilocarpine) mice, are means±SD, and were analyzed by Student's t-test. *P=0.0487.

FIGS. 5A-5E show that Sox2 is essential for SLG regeneration following radiation injury. FIGS. 5A-5D Representative images of control (0 Gy; no IR) and irradiated (10 Gy; IR) SLG from wild-type (FIG. 5A) and Sox2$^{CreERT2}$; Rosa2$^{6mTmG}$ (FIG. 5D) mice and analyzed 1, 3, and 14 days later. (FIGS. 5A-5C) SLG was stained for nerves (TUBB3), SOX2, CyclinD1 (CCND1), and nuclei (FIGS. 5A, 5C), and nerve density calculated (FIG. 5B). (FIG. 5C) The number of SOX2⁺ and COND1⁺ cells was quantified. (FIG. 5D) SOX2$^{CreERT2}$; Rosa26$^{mTmG}$ mice were traced for 14 days post-irradiation (IR) and immunostained for SOX2 (FIG. 5D, red). White arrowheads indicate SOX2-negative progeny. Scale bars in (FIGS. 5A and 5D) are 50 μm. FIG. 5E Sox2$^{CreERT2}$; Sox2$^{fl/fl}$ mice and wild-type littermates were irradiated with 10 Gy IR and SLG analyzed 13 days later. SLG was immunostained for SOX2, AQP5, and nuclei. Scale bar=50 μm. Data information: Data in (FIG. 5B) are means±SD, n=3 with individual values plotted. Data in (FIG. 5C) were calculated from three non-consecutive fluorescent sections of each SLG from n=3 mice/treatment, are means±SD, and data were analyzed using a one-way analysis of variance with post hoc Dunnett's test. SOX2⁺ (D1) *P=0.0487, SOX2⁺CCND1⁺ (D3) *P=0.318, SOX2⁺ CCND1⁺ (D7) *P=0.0291.

FIGS. 6A-6C show that SOX2⁺ progenitors can replenish acinar cells after radiation-induced damage in response to muscarinic stimulation. FIG. 6A SLG from Sox2$^{CreERT2}$; Rosa26$^{mTmG}$ mice was collected following a single 15 Gy dose of IR and explants cultured for 0-48 h. Schematic shows the timing of recombination, culture, and analysis. FIG. 6B Representative images of lineage-traced explants immunostained for nuclei. Scale bar is 50 μm. FIG. 6C Quantification of the number of GFP⁺ cells. Data information: Data in (FIG. 6C) were calculated from three random areas of n=3 immunostained explants for each treatment with individual values plotted, and data were analyzed using a one-way analysis of variance with post hoc Dunnett's test. Error bars show mean±SD. No IR vs. IR *P=0.0022, IR vs. IR+CCh P=0.0058, IR vs. IR+4-DAMP ***P=0.0010.

FIGS. 7A-7E show that acetylcholine/muscarinic signaling maintains SOX2 and the acinar lineage in human SG. FIG. 7A Human salivary gland obtained from healthy individuals (no IR; submandibular) or patients who received radiation therapy for head and neck cancer (IR) were subjected to qPCR. FIGS. 7B-7D Human SMG explants cultured for 7 days with either murine embryonic day (E) 13 parasympathetic ganglia (nerves) or E13 mesenchyme (MES). Explants were analyzed by immunostaining for markers of nerves (FIG. 7B, TUBB3) or cell proliferation (FIG. 7C, Ki67) or by qPCR (FIG. 7D). Scale bars=50 μm (FIGS. 7B, 7C). FIG. 7E qPCR analysis of adult human salivary gland (SMG or PG) explants of four different individuals cultured for 4 h±CCh (200 nM, n=4). Individual datasets are shown in FIG. 14D. Data information: Data in (FIG. 7A) n=11 for no IR and n=7 for IR; 30-85 years. Data were normalized to GAPDH with individual values plotted and analyzed using a Student's t-test with a false discovery rate set to 0.05. Error bars show mean±SD. AQP3 P=0.017, MIST1 P=0.086, AMY1 P=0.005, SOX2 P=0.079, CHRM1 P=0.040, CHRM3 P=0.011, EGFR P=0.931, KRT19 P=0.618. Data in (FIG. 7D) are means±SD of n=2 individuals where solid line columns represent individual #1 and broken line columns represent individual #2. Data were normalized to salivary glands from the same individuals cultured with murine mesenchyme (Control, black dashed line). Data in (FIG. 7E) are box and whisker plots of n=4 different individuals, showing means (horizontal line), upper and lower quartiles (box) and upper and lower values (whiskers). Data were normalized to the untreated control (black dashed line). n=5-8 explants per individual. Data were analyzed using a one-way analysis of variance with post hoc Dunnett's test. SOX2 **P=0.00834, CHRM3

*P=0.0449, CHRM1 P=0.0093, AQP5 P=0.0069, AQP3 *P=0.0375, MIST1 *P=0.0379, CD44 *P=0.0485, KRT19 *P=0.0461

Figure 8A:
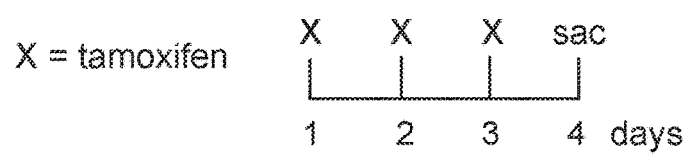
Figure 8A:
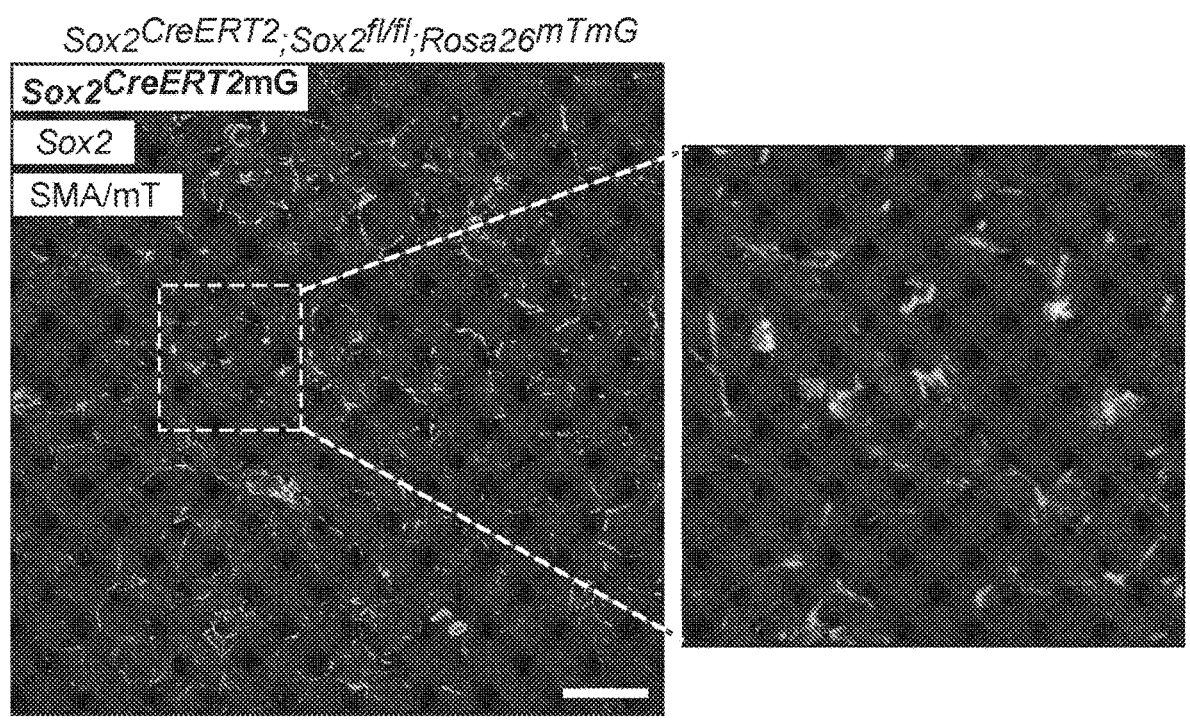
Figure 8B:
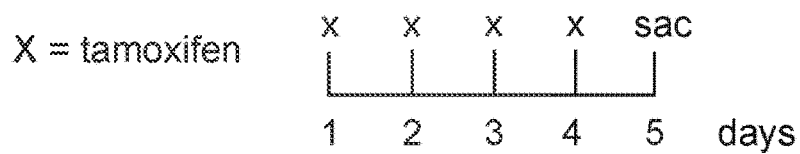
Figure 8B:
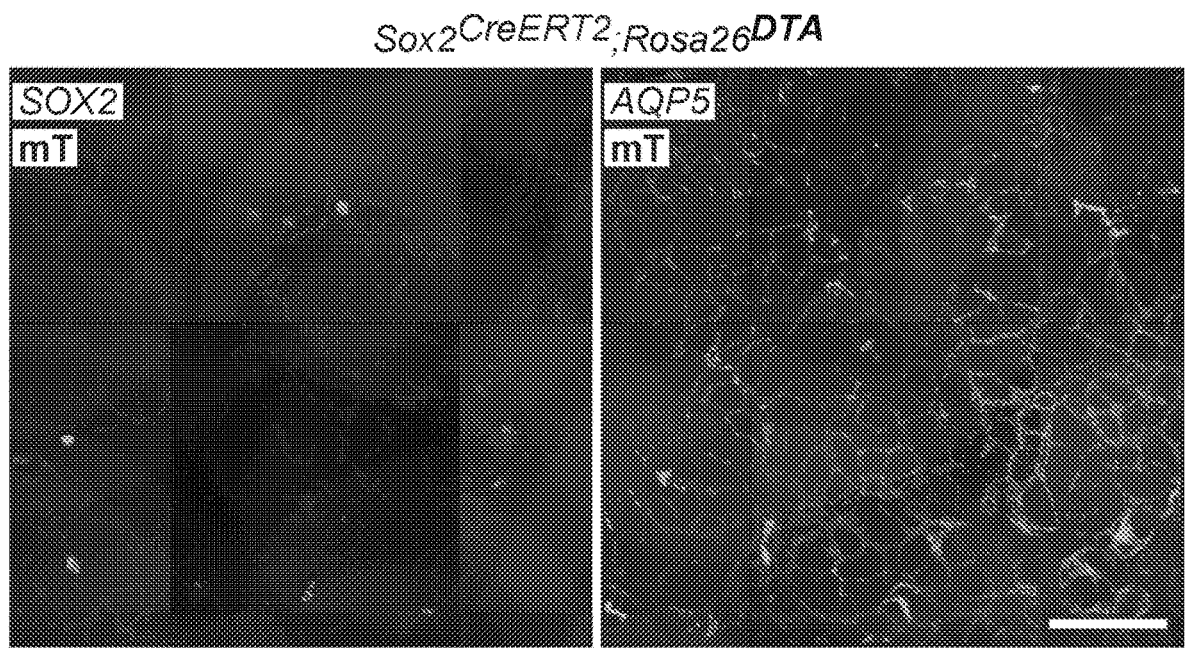
Figure 8B:
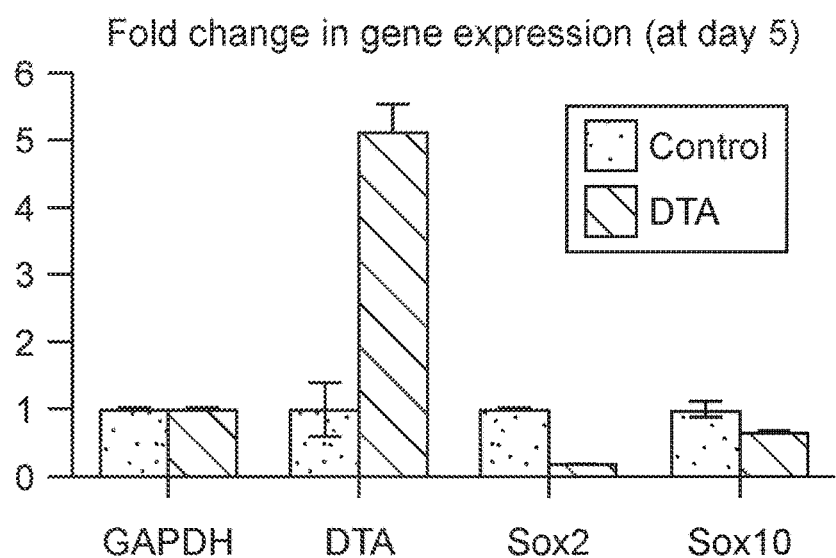

FIGS. 8A-8B show that short-term ablation of SOX2$^+$ cells reduces acinar cell replacement. (FIG. 8A) SOX2$^+$ cells were ablated in SLG of Sox2$^{CreERT2}$; Sox2$^{fl/fl}$; Rosa26$^{mTmG/+}$ mice over 3 days and SLG analyzed on day 4 (see schematic). Sections of Sox2$^{CreERT2}$; Sox2$^{fl/fl}$; Rosa26$^{mTmG/+}$ SLG were immunostained for SOX2 and myoepithelial cells (a-smooth muscle actin; SMA). Scale bar=50 μm (FIG. 8B) SOX2$^+$ cells were ablated in SLG of Sox2$^{CreERT2}$Rosa26$^{DTA}$; Rosa26$^{mTmG/+}$ mice over 4 days and SLG analyzed on day 5 (see schematic). Sections of Sox2$^{CreERT2}$Rosa26$^{DTA}$ SLG were immunostained for SOX2 and acinar cells (aquaporin 5; AQP5) or subjected to qPCR. Scale bar=50 μm. Data information: Data in FIG. 8B were normalized to Gapdh and the wild-type control. Data is mean±S.D. (n=1, 3 technical replicates).

Figure 9A:
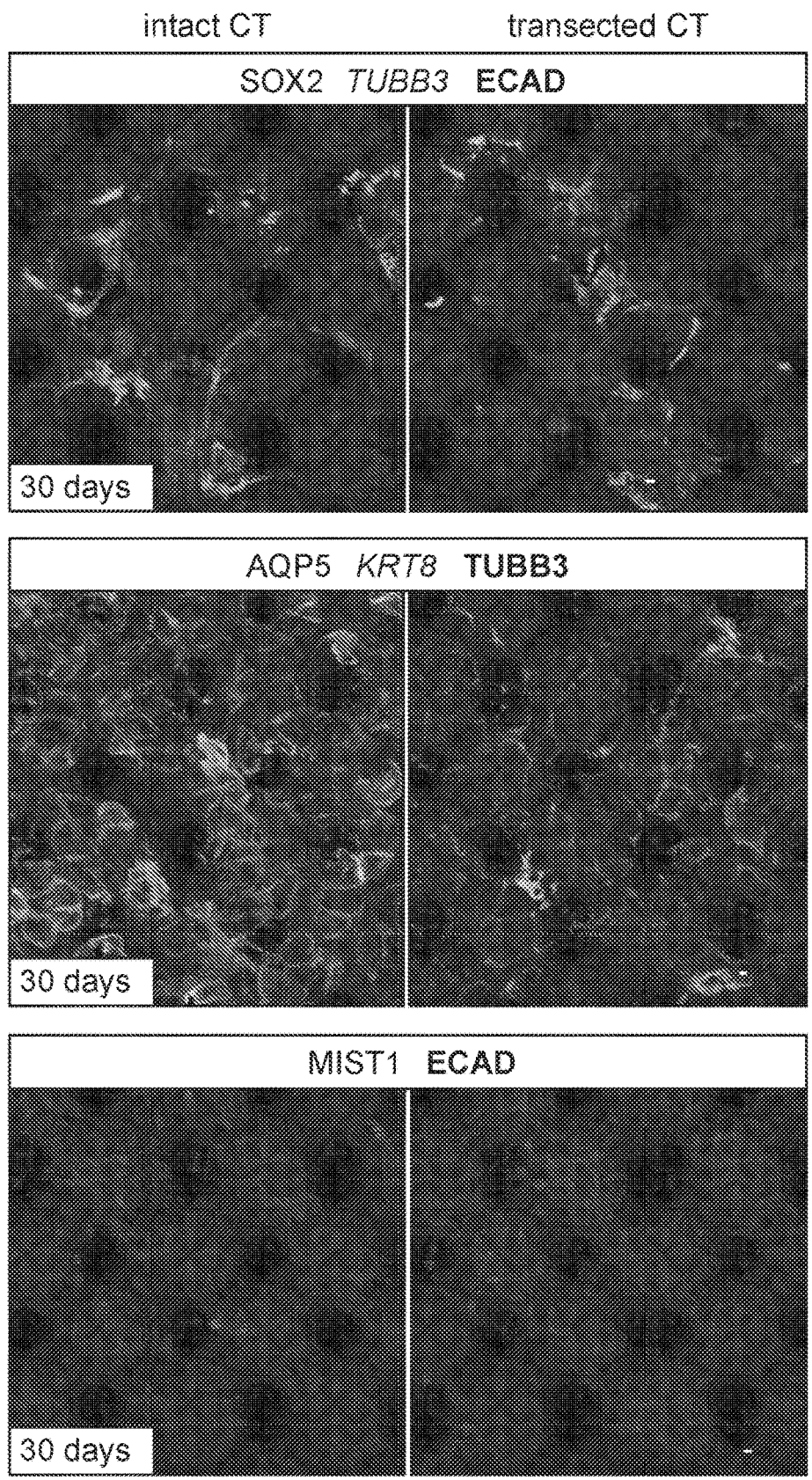
Figure 9B:
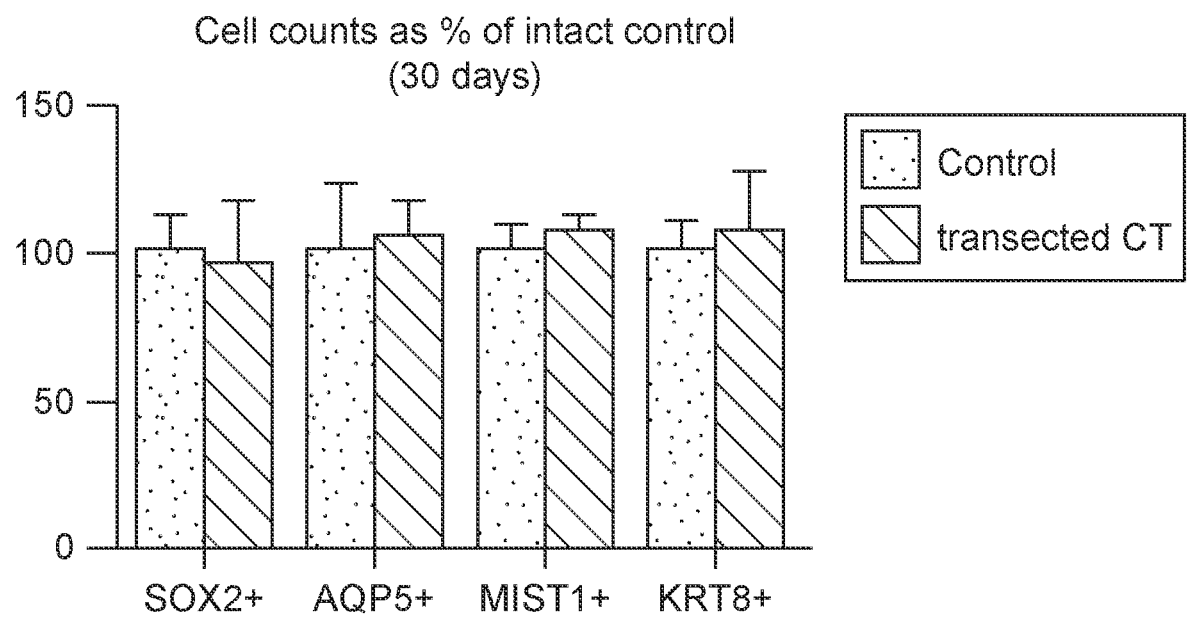
Figure 9C:
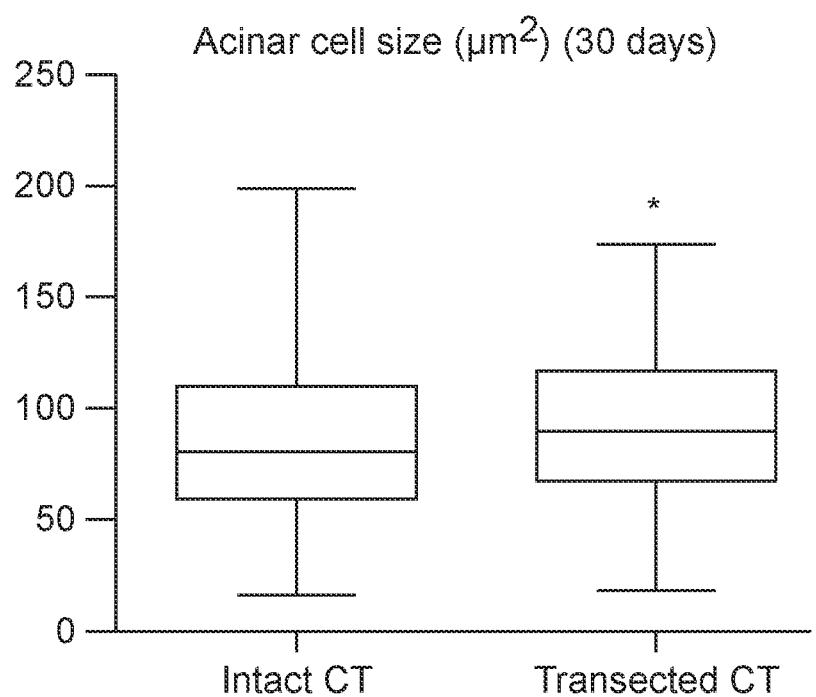

FIGS. 9A-9C show that reinnervation 30 days following transection of the chorda tympani restores the acinar lineage (FIG. 9A-9C) SLG were immunostained for SOX2, TUBB3, AQP5, MIST1 and ECAD (FIG. 9A) and numbers of SOX2$^+$, AQP5$^+$, MIST1$^+$ and KRT8$^+$ cells (FIG. 9B) as well as acinar cells size (FIG. 9C) was measured 30 days after denervation. n=5 mice per time point per condition. Cells were counted in 3-4 fields of view per animal. Data information: Data in FIG. 9B and FIG. 9C n=5. Data in FIG. 9B are mean±S.E.M and were analyzed using a one-way analysis of variance test, data in FIG. 9C are a box and whisker plot of n=5 mice, showing mean±S.E.M. and were analyzed using students t-test. *p=0.0498.

Figure 10C:
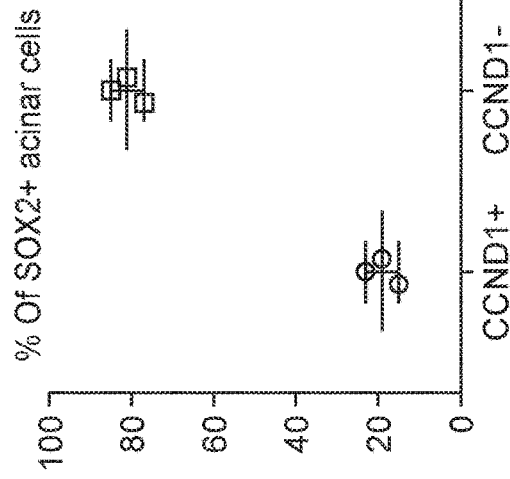
Figure 10A:
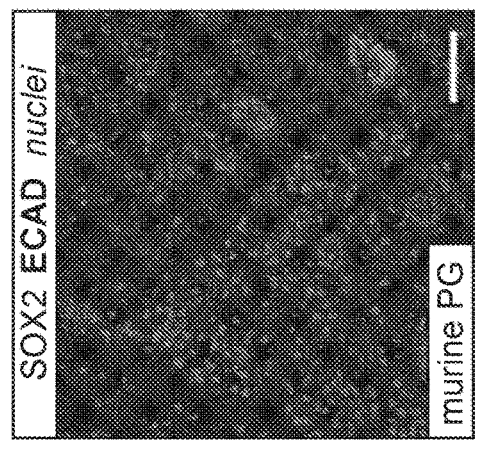
Figure 10B:
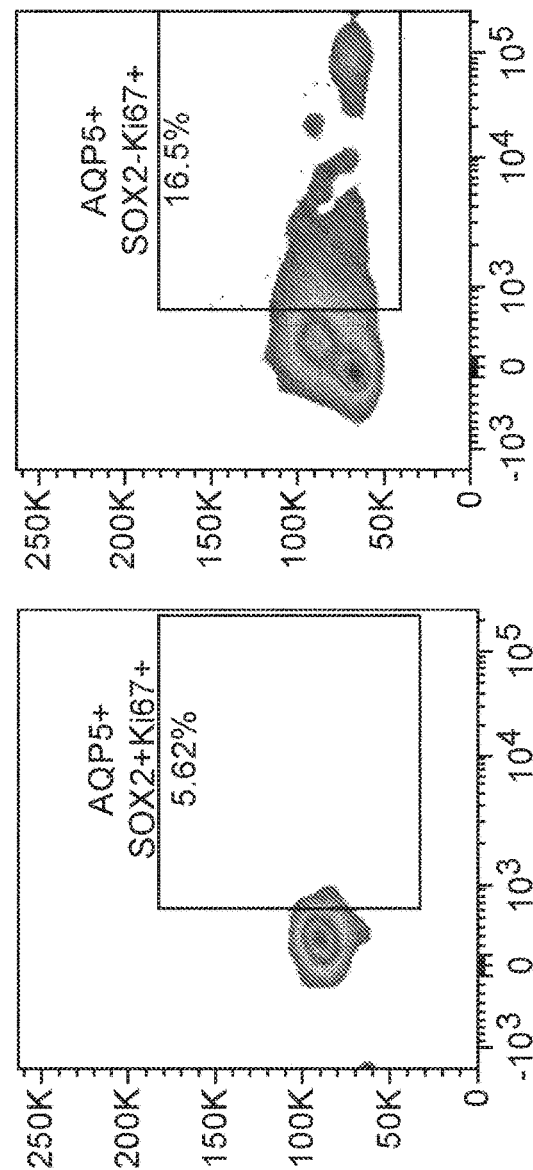
Figure 10D:
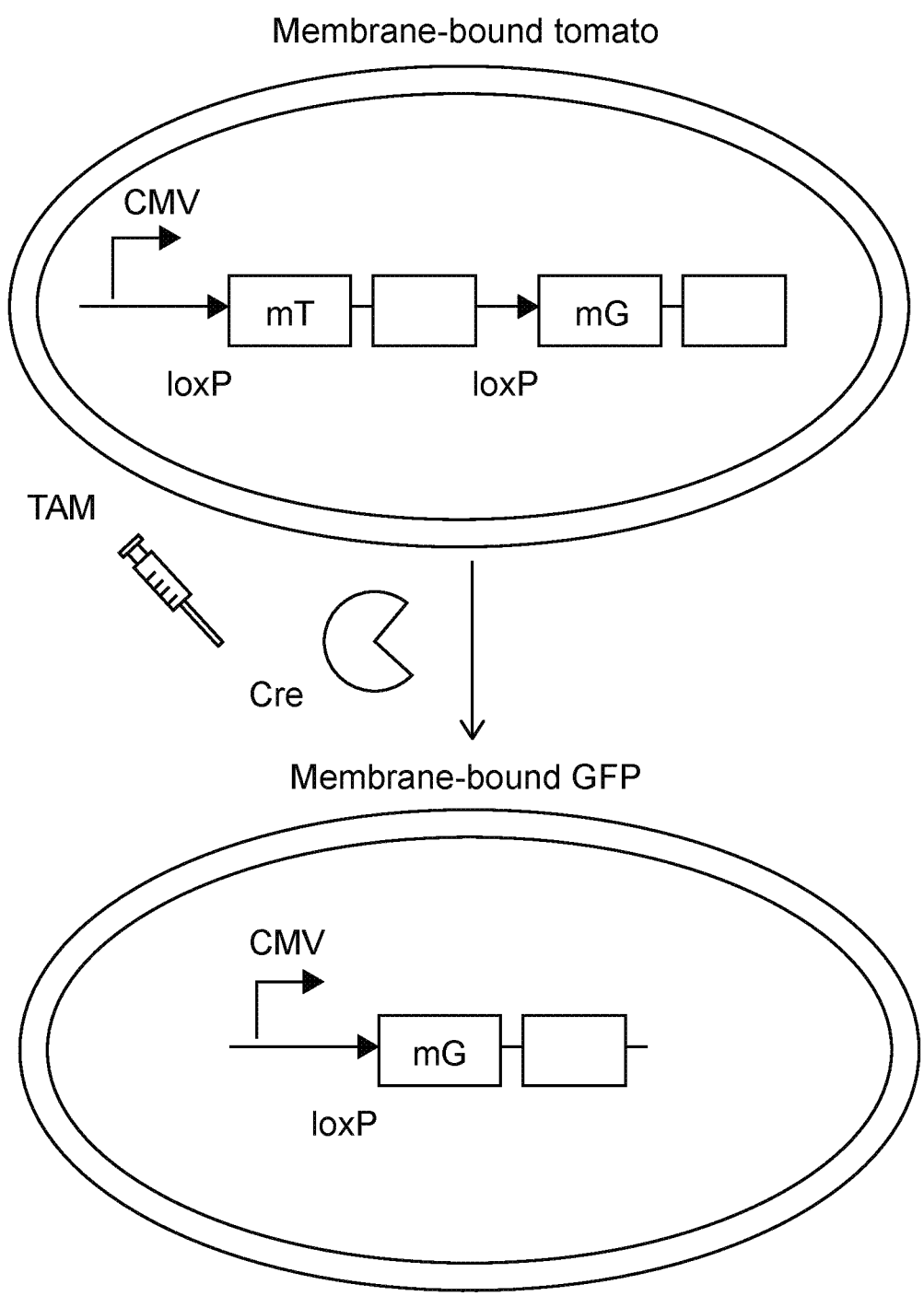
Figure 10E:
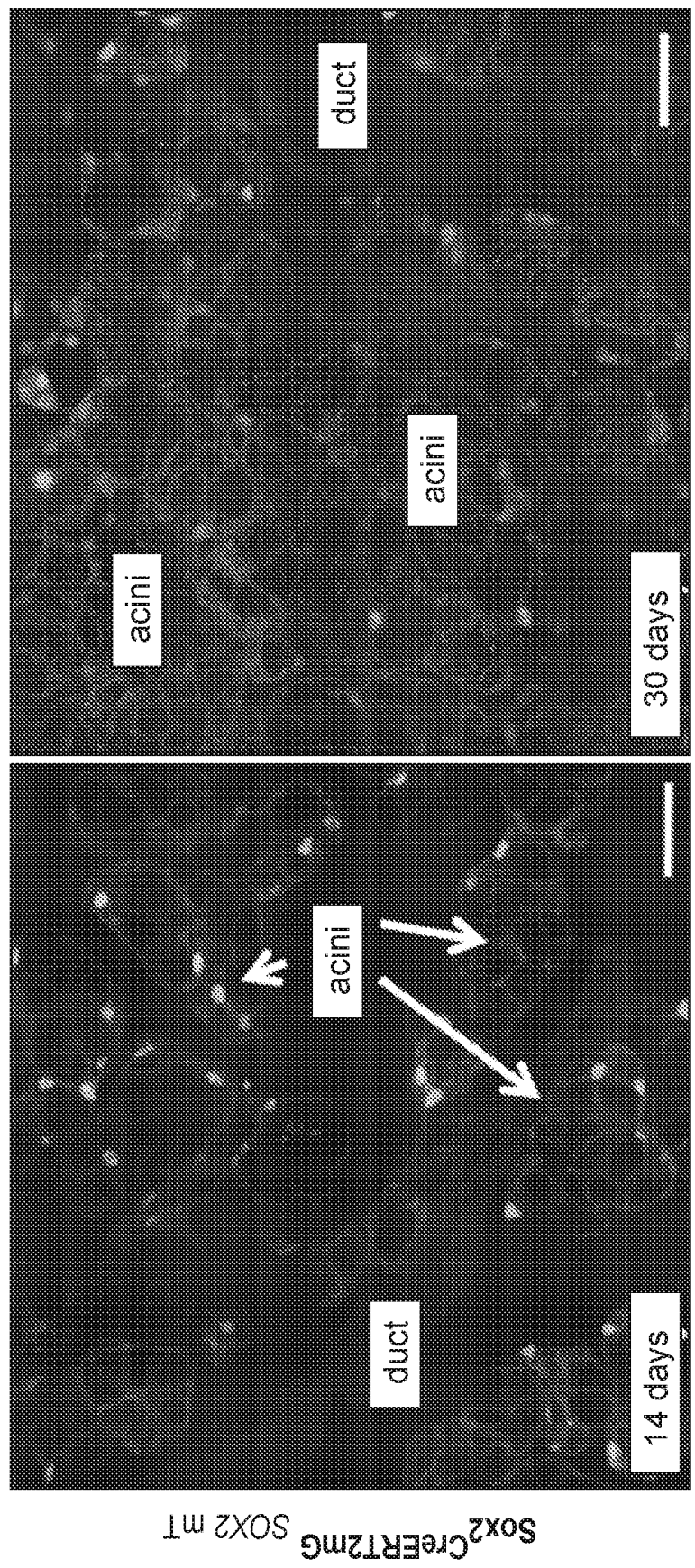
Figure 10F:
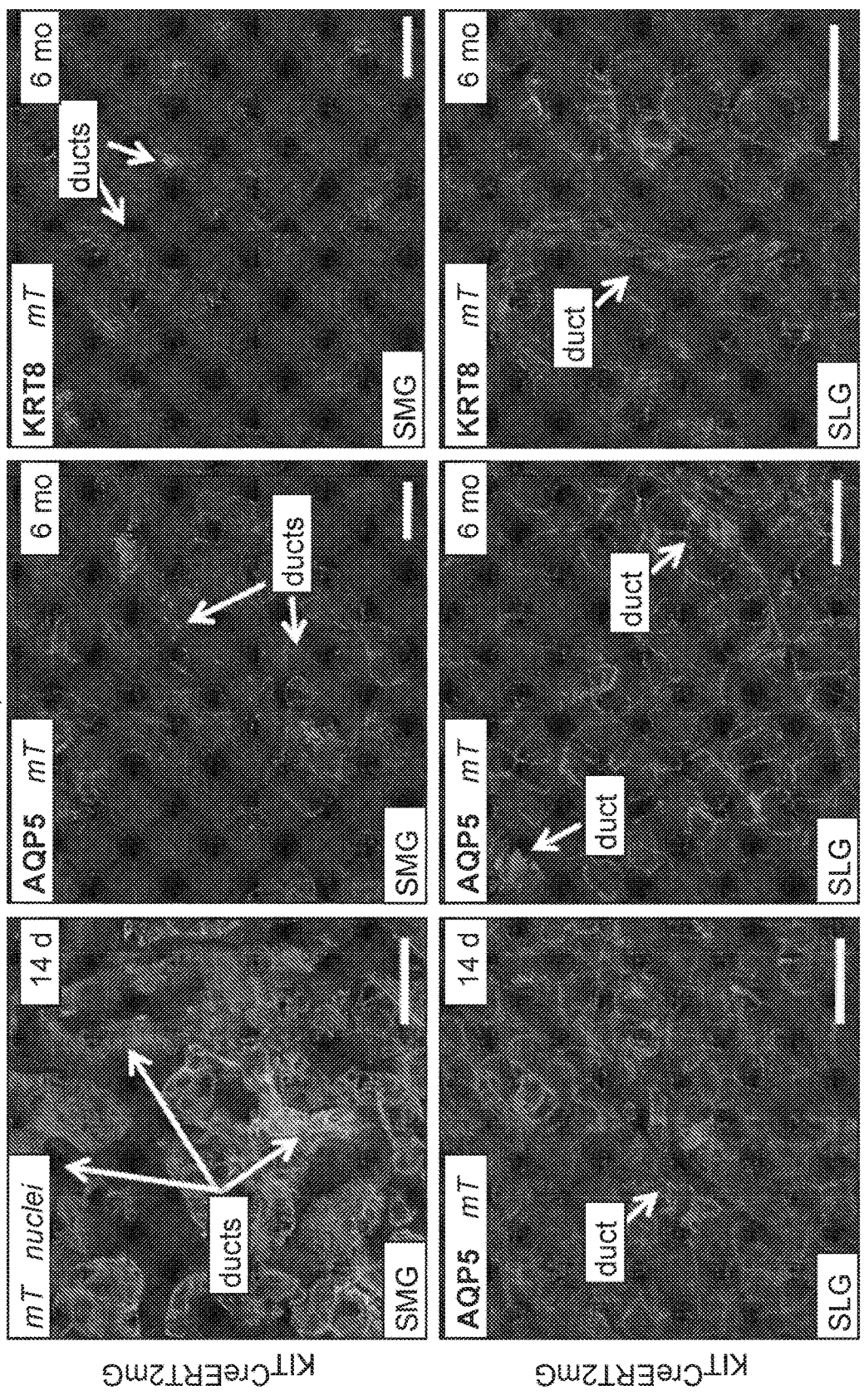

FIGS. 10A-10F show that SOX2 marks a subset of acinar cells that replenish acini. FIG. 10A Wild-type murine PG stained for SOX2, ECAD, and nuclei. Scale bar is 50 μm. FIG. 10B The percentage of acinar SOX2$^+$ and SOX2$^-$ cells that are Ki67$^+$ were counted using FACS and shown as a percentage of total AQP5$^+$SOX2$^+$ or AQP5$^+$SOX2$^-$ cells. FIG. 10C The % of SOX2$^+$ acinar cells that are either CyclinD1$^+$ or CyclinD1$^-$. FIG. 10D Schematic of Rosa26$^{mTmG}$ Cre-mediated gene excision (adapted from Muzumdar et al., 2007). FIG. 10E Representative image of Sox2 lineage-traced SLG. Cre-mediated recombination was induced in Sox2$^{CreERT2}$; Rosa26$^{mTmG}$ mice and SLG analyzed 14 or 30 days later by immunostaining for SOX2. Scale bar=25 μm. FIG. 10F Representative images of Kit lineage-traced SLG and SMG. Cre-mediated recombination was induced in Kit$^{CreERT2}$; Rosa26$^{mTmG}$ mice and SMG/SLG analyzed 14 days and 6 months later. Tissue was stained with AQP5 to mark acinar cells and KRT8 to mark intercalated duct cells. Scale bar=25 μm. mT=membrane-bound Tomato. Data information: Data in (FIG. 10B), SLG were pooled from n=2 mice (85,000 events). Data in (FIG. 10C) were calculated from three non-consecutive fluorescent sections of each SLG from n=3 mice with individual values plotted. Error bars show mean±SD.

Figure 2A:
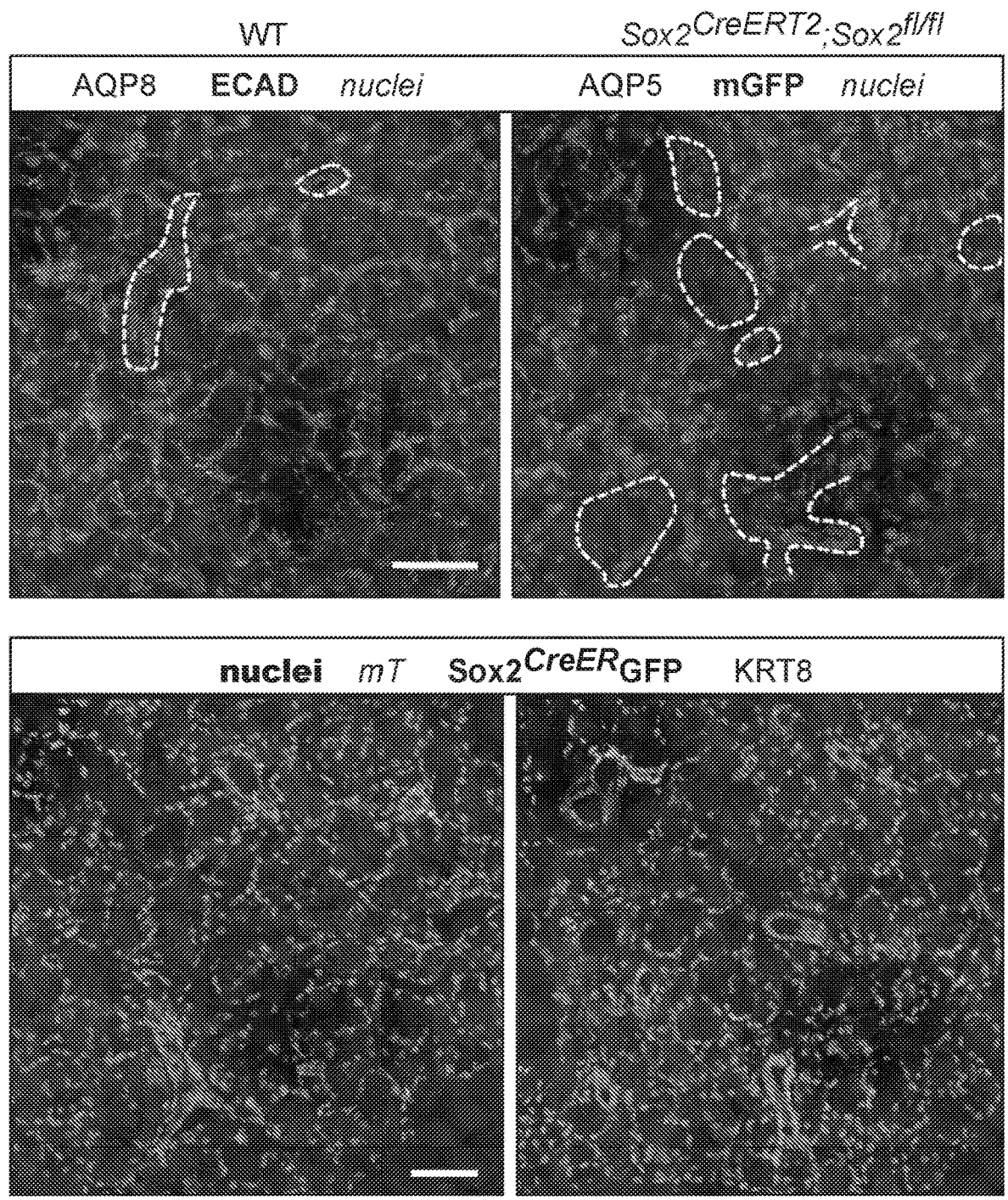
FIGS. 2A-2D show SOX2 and $SOX2^+$ cells are essential for the replenishment of salivary acinar cells.
Figure 2B:
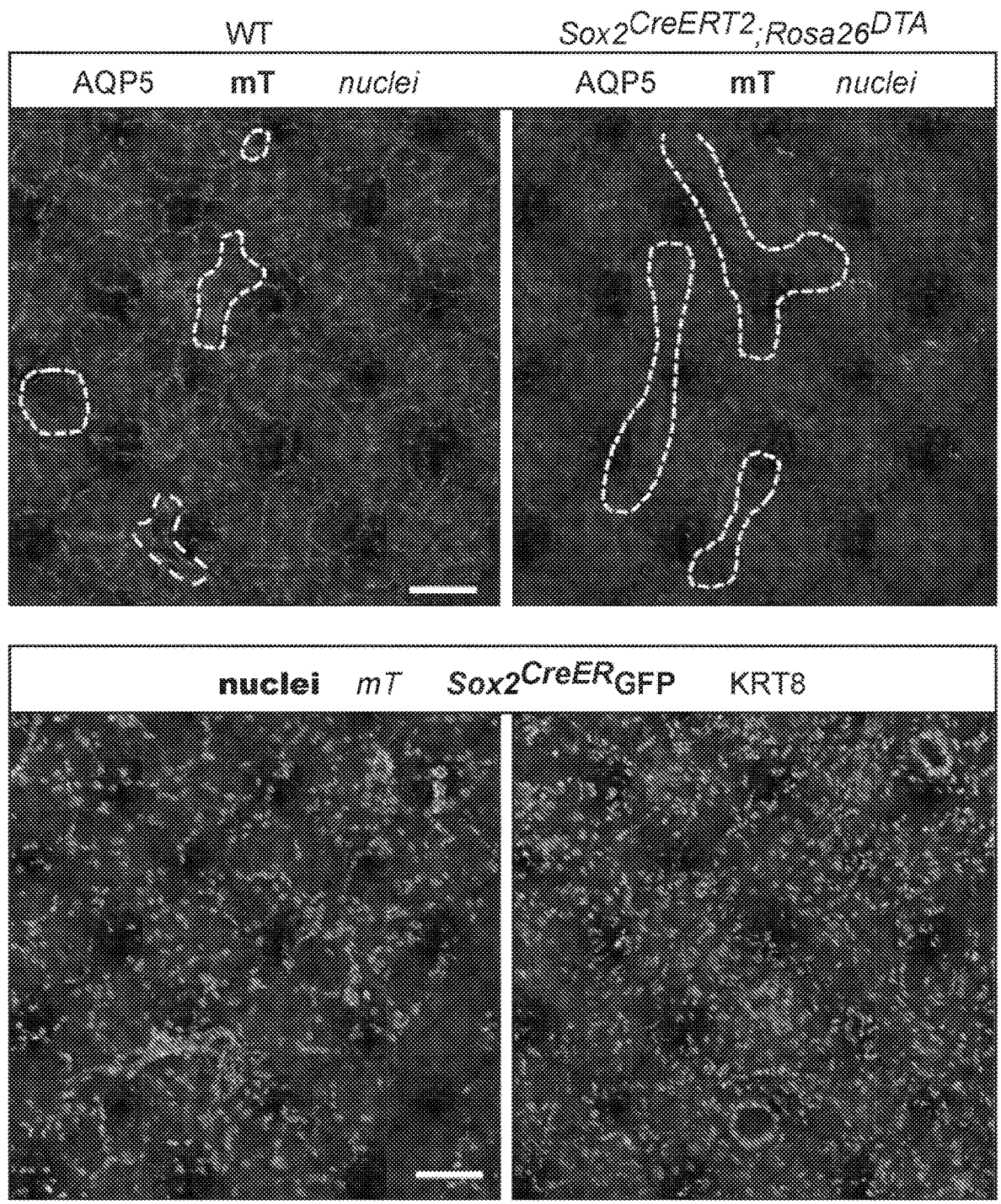
Figure 11A:
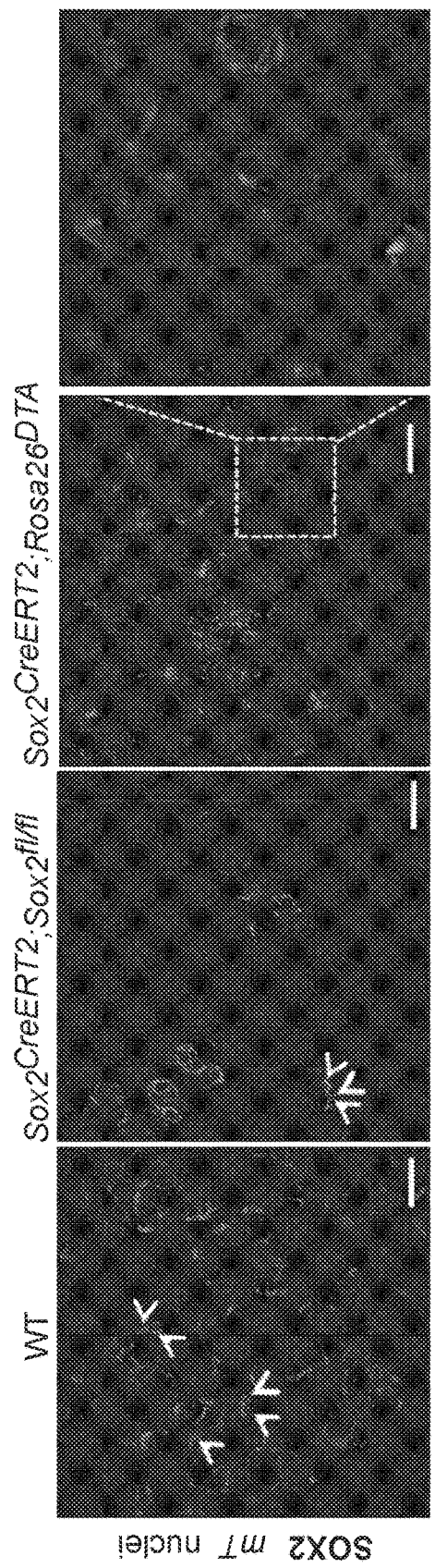
Figure 11B:
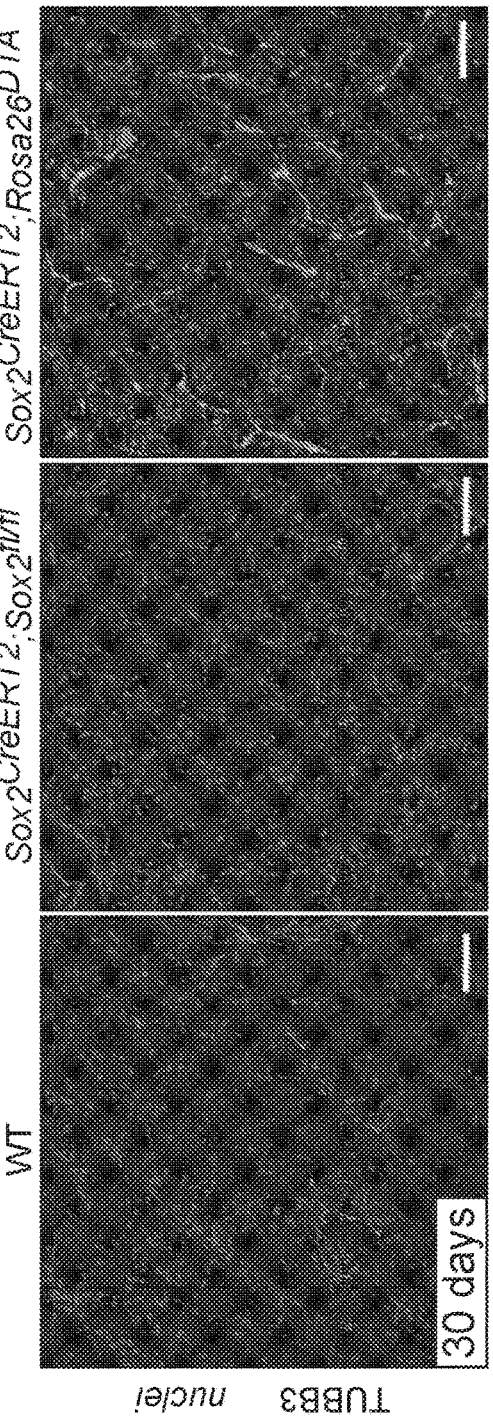
Figure 11C:
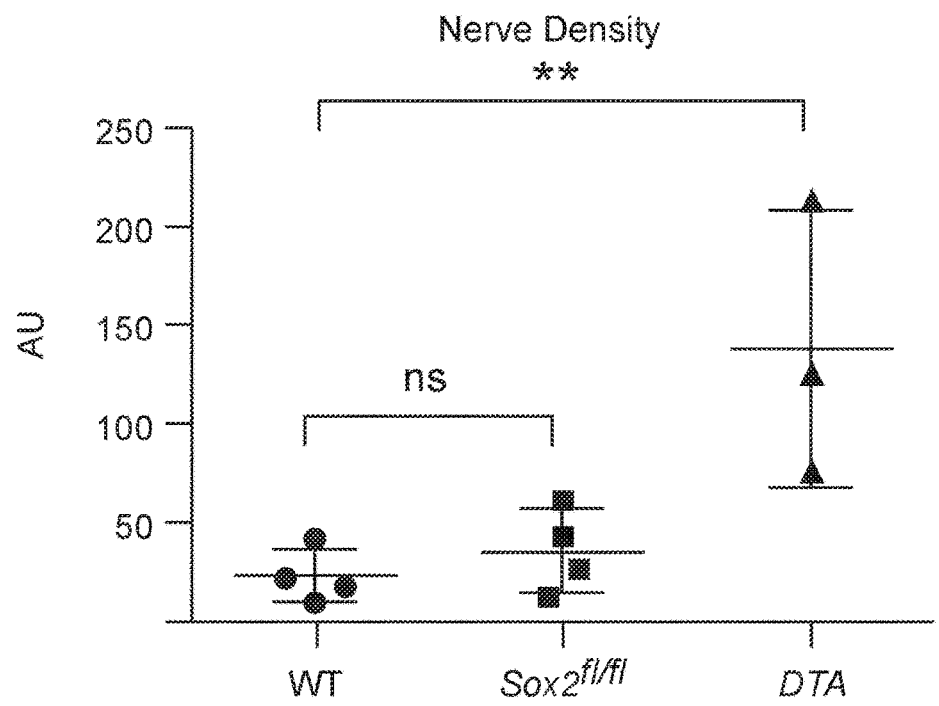
Figure 11D:
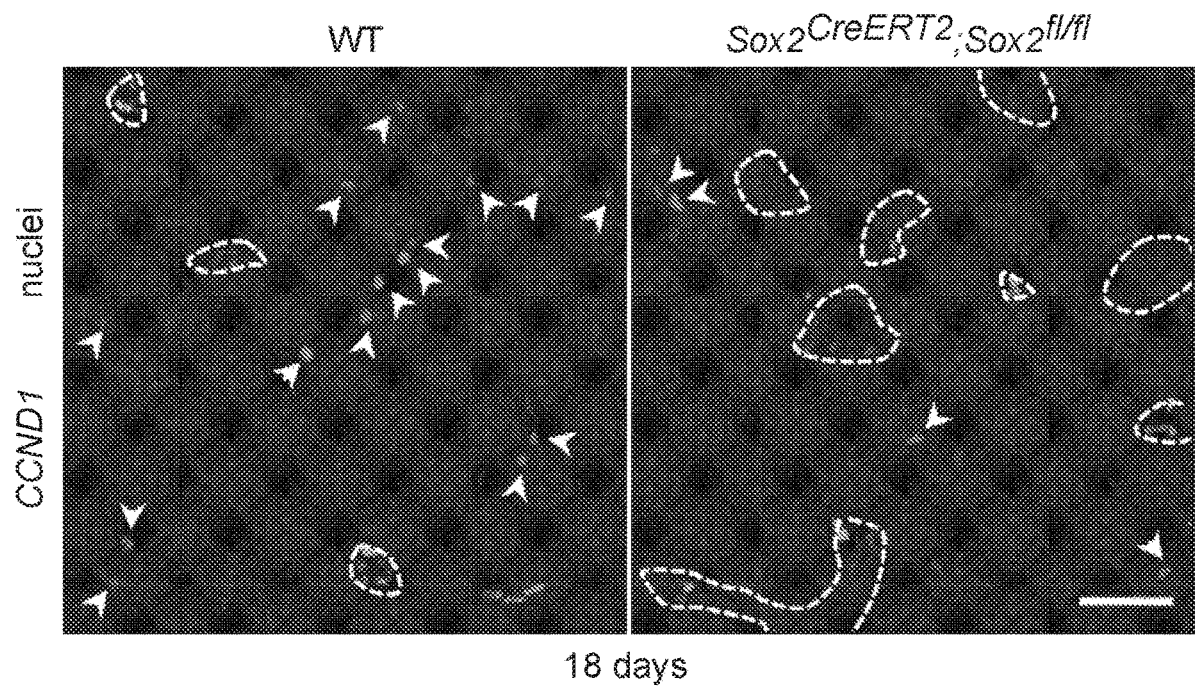

FIGS. 11A-11D show that ablation of Sox2 or SOX2$^+$ cells reduces acinar cell replacement despite the presence of nerves. FIGS. 11A-11C Sox2 or SOX2$^+$ cells were ablated in SLG of Sox2$^{CreERT2}$; Sox2$^{fl/fl}$, Rosa26$^{mTmG/+}$ mice (FIG. 2A; see schematic) or Sox2$^{CreERT2}$; Rosa26$^{DTA}$; Rosa26$^{mTmG/+}$ mice (FIG. 2B; see schematic). (FIG. 11A, 11B) Sections of WT, Sox2$^{CreERT2}$; Sox2$^{fl/fl}$, and Sox2$^{CreERT2}$; Rosa26$^{DTA}$ SLG were immunostained for SOX2 or TUBB3 and nuclei. White arrowheads indicate SOX2$^+$ cells. White dotted square is magnified in the image to the right to highlight that there are few SOX2$^+$ cells remaining in tissue and that non-nuclear (green) staining is suggestive of debris. Scale bar=50 μm. (FIG. 11C) Raw integrated density of nerves was calculated using ImageJ. FIG. 11D WTorSox2$^{CreERT2}$; Sox2$^{fl/fl}$ SLG immunostained for cyclin D1 (CCND1) and nuclei. Dashed lines=ducts; arrowheads=CCND1$^+$ acinar cells. Scale bar=50 μm. Data information: Data in (FIG. 11C), WT n=4, Sox2$^{fl/fl}$ n=4, DTA n=3. Individual values were plotted, as means±SD, and data were analyzed using a one-way analysis of variance with post hoc Dunnett's test. **P=0.0091. Data in (FIG. 11D) are a representative image from n=4 mice.

Figure 12A:
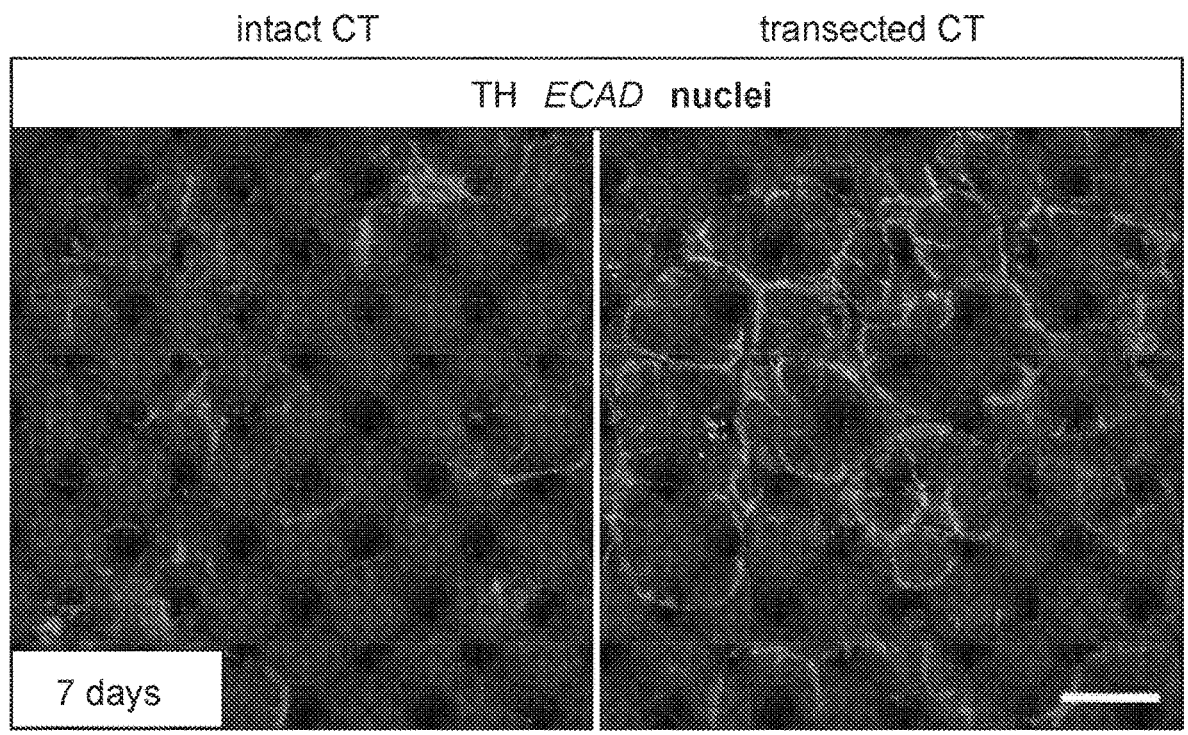
Figure 12B:
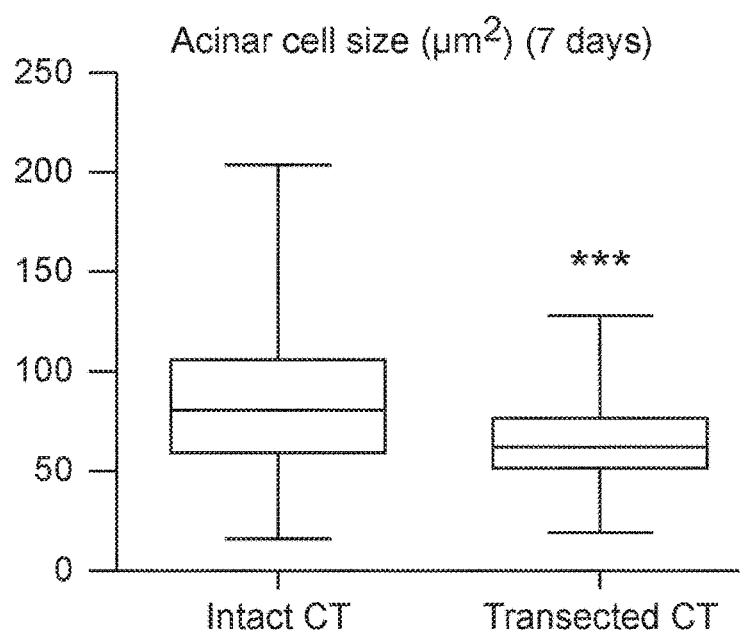
Figure 12C:
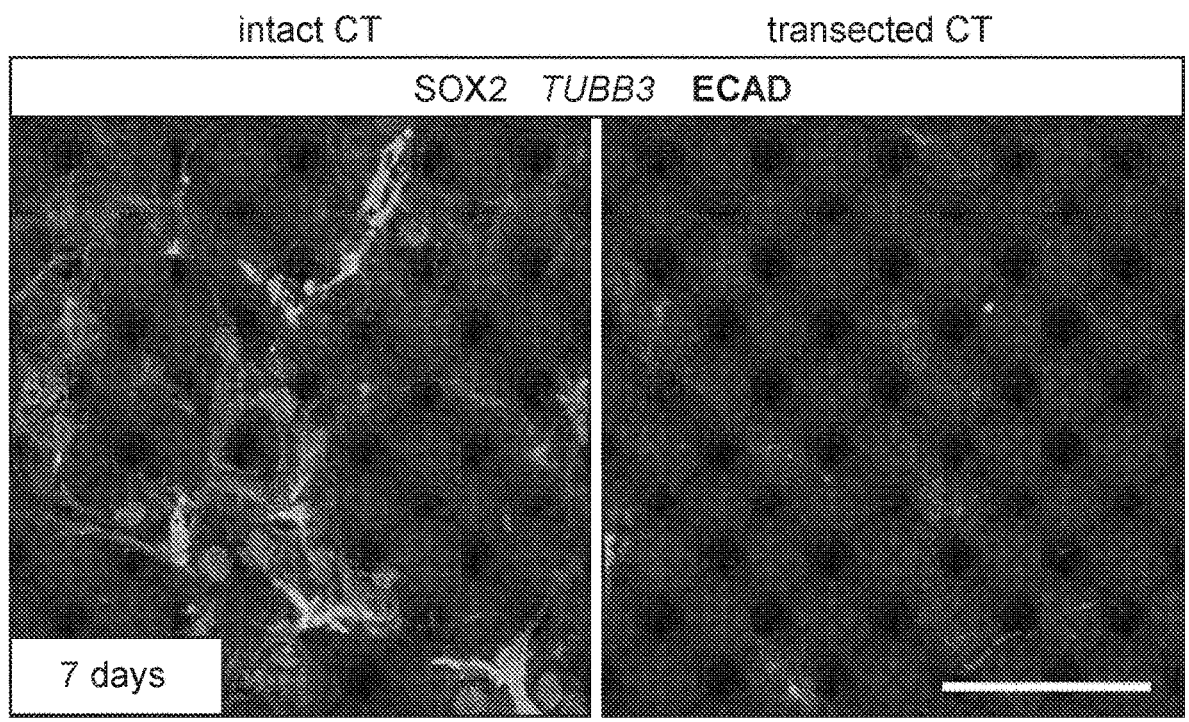
Figure 12D:
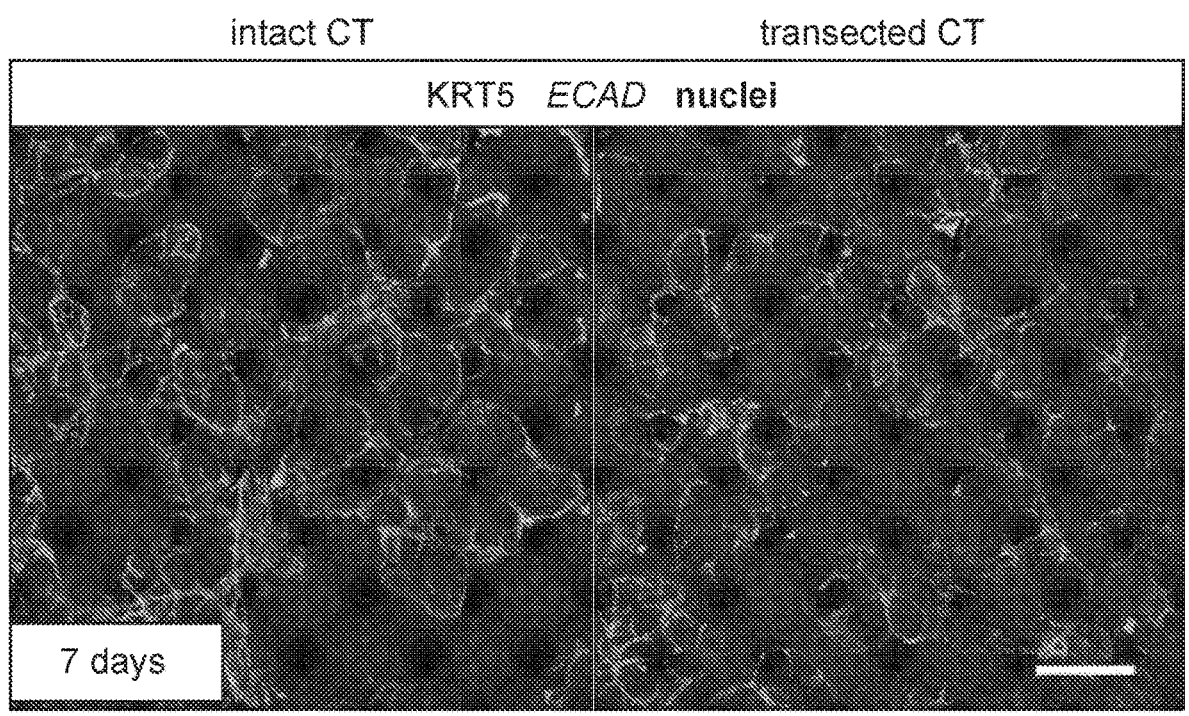
Figure 12G:
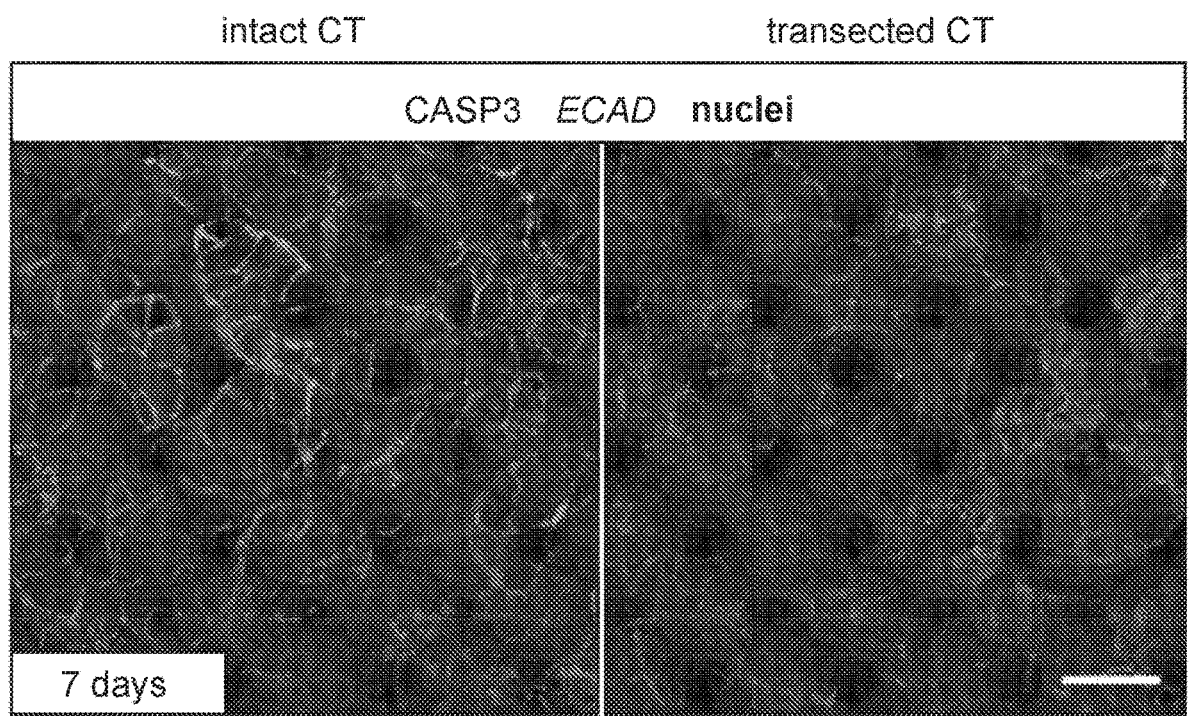
Figure 12H:
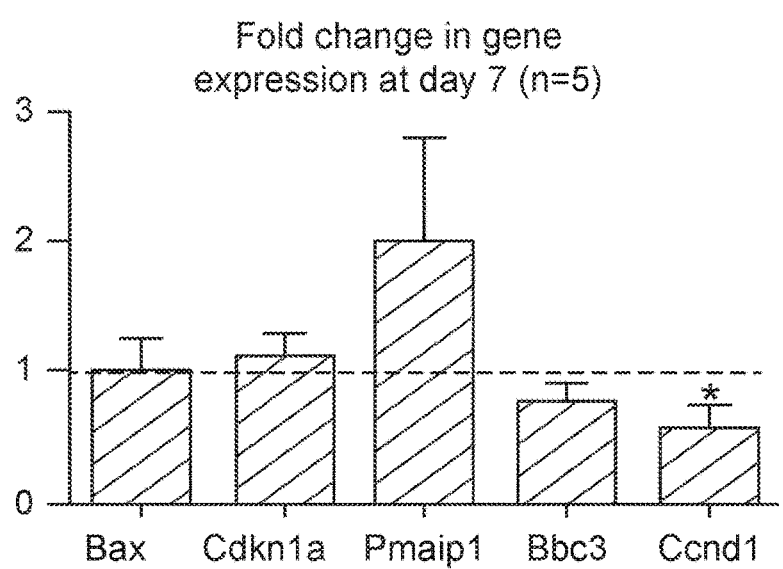

FIGS. 12A-12H show that transection of the chorda tympani depletes acinar cells at 7 days. (FIGS. 12A, 12C, 12D, 12G) Control and nerve transected SLG were immunostained 7 days after denervation for tyrosine hydroxylase (TH; FIG. 12A), SOX2 and TUBB3 (FIG. 12C), KRT5 (FIG. 12D), caspase-3 (CASP3; FIG. 12G), epithelial cells (ECAD), and nuclei. Quantification of the size of acinar cells (FIG. 12B) in adult wild-type (WT) SLG with intact or transected chorda tympani (CT) 7 days after denervation. Scale bars in (FIG. 12A, 12C, 12D, 12G)=25 μm. (FIGS. 12E, 12F) Recombination was induced in Sox2$^{CreERT2}$; Rosa26$^{mTmG}$ mice 24 h before nerve transection and SLG traced for 15 days before being immunostained for TUBB3. The percentage of GFP$^+$ and mT$^+$ acinar cells in control and transected glands are shown in (FIG. 12F). Scale bar in (FIG. 12E)=25 μm. (H) Fold change in expression of genes involved in cell cycle and apoptosis 7 days after denervation, compared to intact control. Dashed line denotes the intact control. Data information: Data in (FIGS. 12B, 12F, and 12H) n=5. Data in (FIG. 12B) are a box and whisker plot of n=5 mice, showing means (horizontal line), upper and lower quartiles (box) and upper and lower values (whiskers) and were analyzed using Student's t-test. *P=0.00000347. Data in (FIG. 12F) are means±SD and were analyzed by Student's t-test. % GFP$^+$ *P=0.0000208, % mT$^+$ ***P=0.0000208. Data in (FIG. 12H) were normalized to Rsp18 and the intact control (dashed line). Ccnd1 *P=0.0477.

Figure 13A:
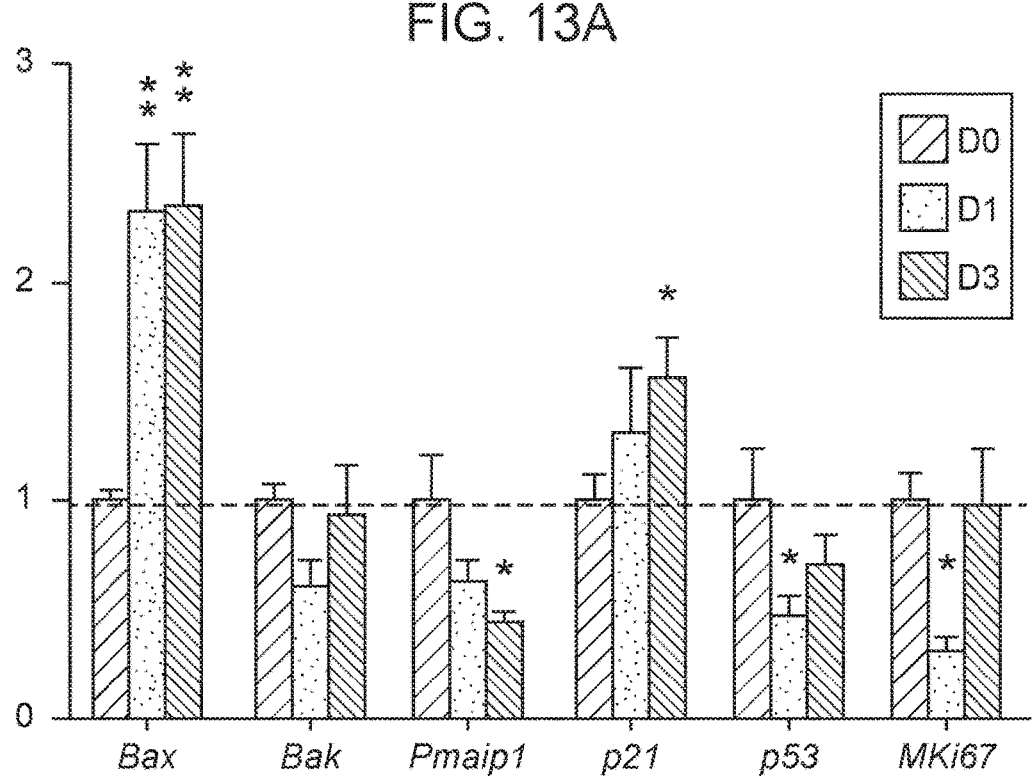
Figure 13B:
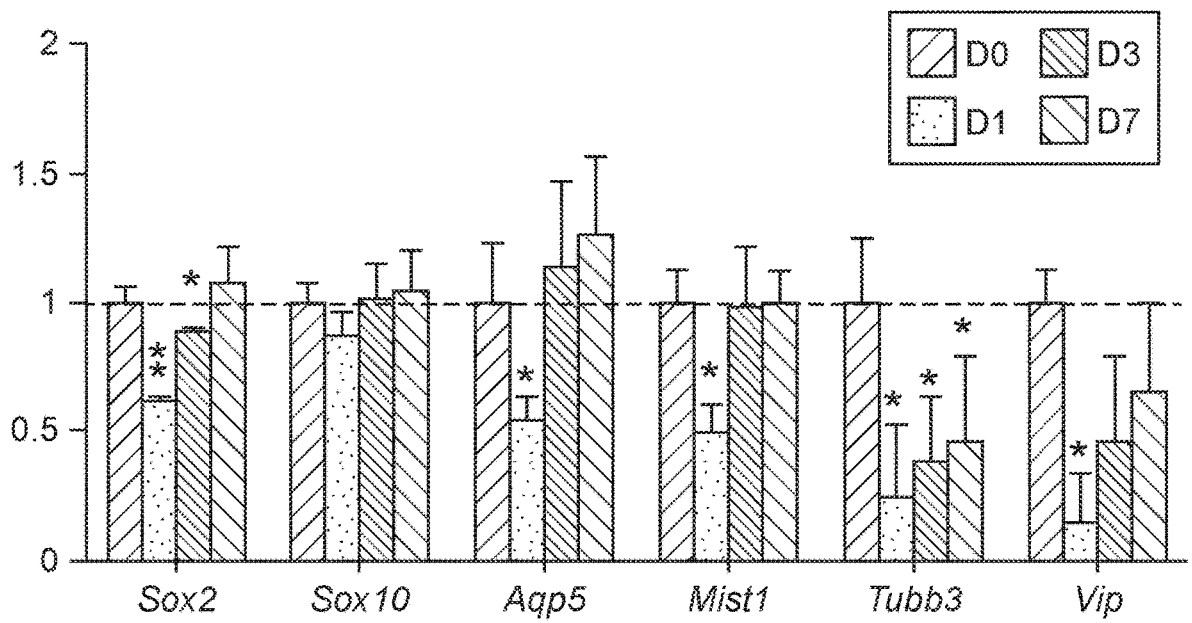
Figure 13C:
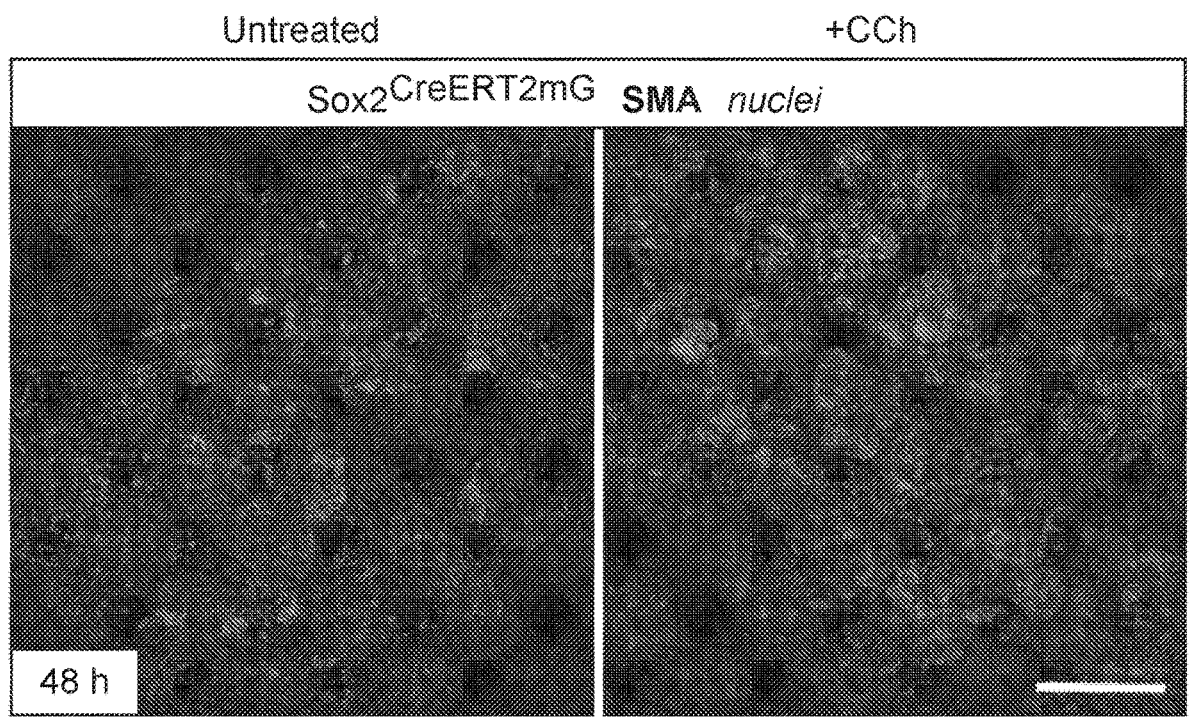
Figure 13D:
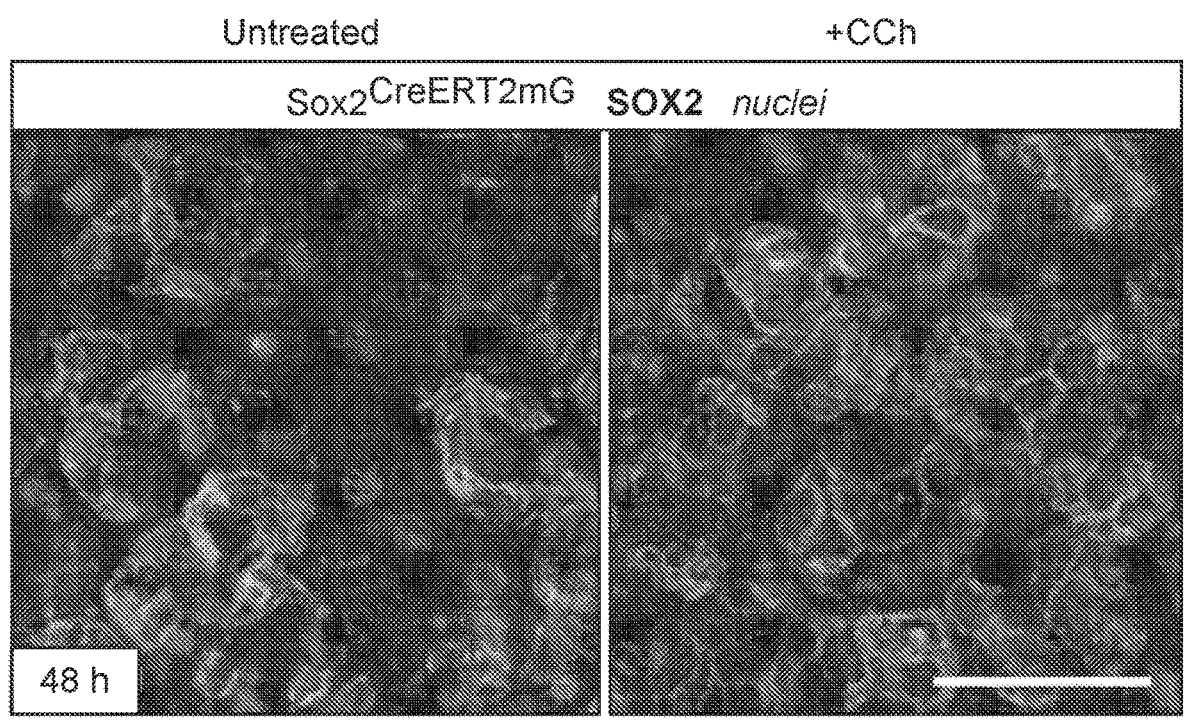
Figure 13E:
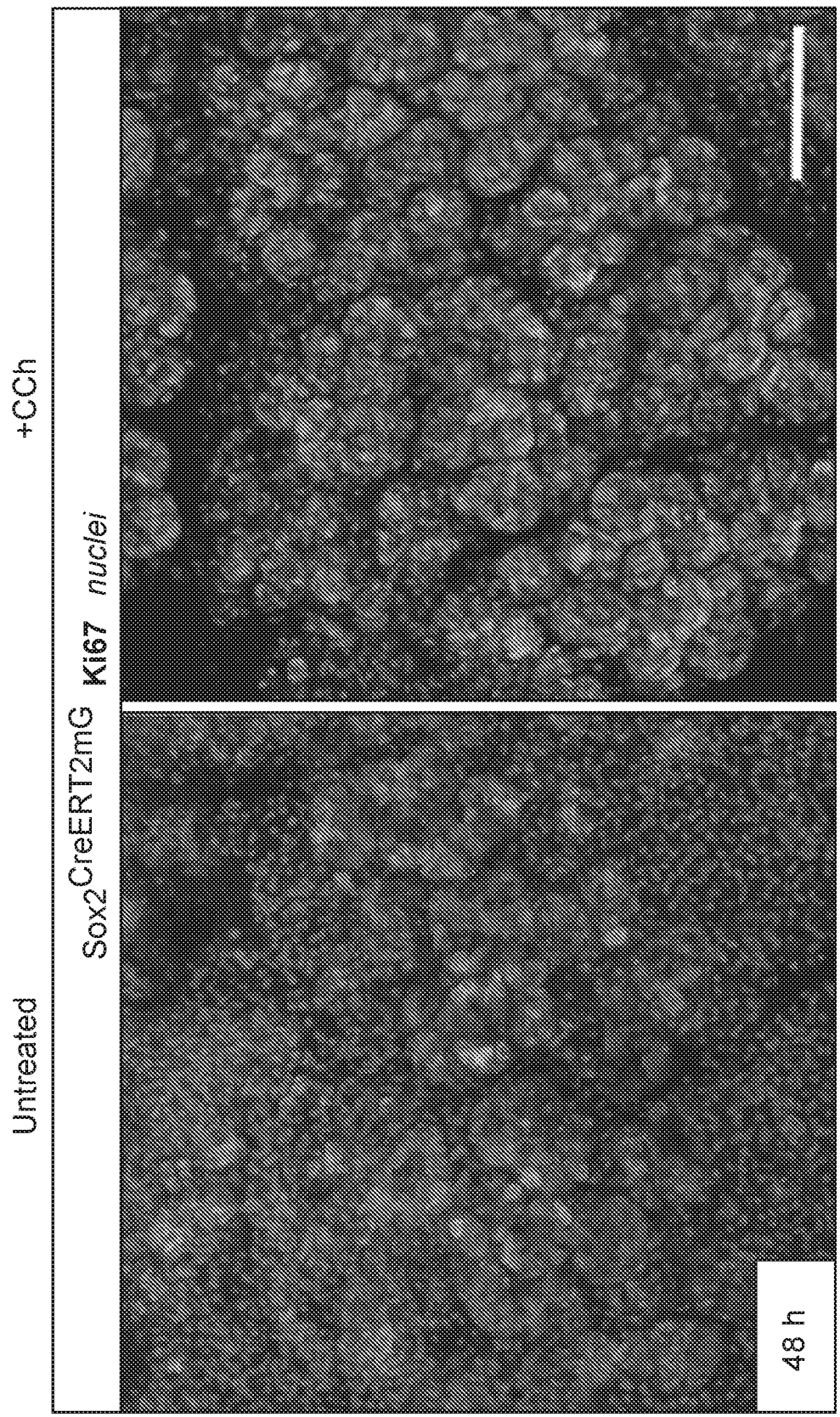

FIGS. 13A-13E show that IR induces cellular damage and a loss of nerves and SOX2 and SOX2$^+$ progenitors can replenish mouse acinar cells in response to cholinergic mimetics. FIGS. 13A, 13B Murine SLG was analyzed for transcriptional changes by qPCR at days 0, 1, 3, and 7 days following 10 Gy of IR. FIGS. 13C-13E Sox2$^{CreERT2}$; Rosa26$^{mTmG}$ murine SLG explants cultured ex vivo for 48 h and immunostained for smooth muscle actin (SMA, FIG. 13C), SOX2 (FIG. 13D) or Ki67 (FIG. 13E) and nuclei. Recombination was induced 24 h before SLG was harvested for culture. Scale bar=50 μm. Data information: Data in (FIGS. 13A and 13B) were normalized to Rsp29 and the day 0 control. Data in (FIGS. 13A and 13B) (n=3 per time point) are means±SEM and were analyzed using a one-way analysis of variance with a post hoc Dunnett's test. Bax (D1) P=0.00826, Bax (D3) P=0.0871, Pmaip1 (D3) *P=0.0369, p21 (D3) *P=0.0481, p53 (D1) *P=0.0337, MKi67 (D1) *P=0.0319, Sox2 (D1) **P=0.0072, Sox2 (D3) *P=0.0418, Aqp5 (D1) *P=0.0421, Mist1 (D1) *P=0.0432, Tubb3 (D1) *P=0.0467, Tubb3 (D3) *P=0.0470, Tubb3 (D7) *P=0.0489, Vip (D1) *P=0.0402. Images in (FIGS. 13C, 13D, and 13E) are representative of three experiments, n=3 SLG fragments per experiment.

Figure 14A:
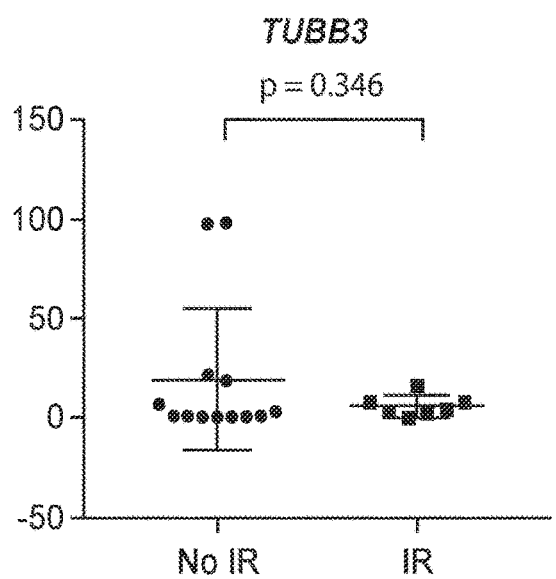
Figure 14A:
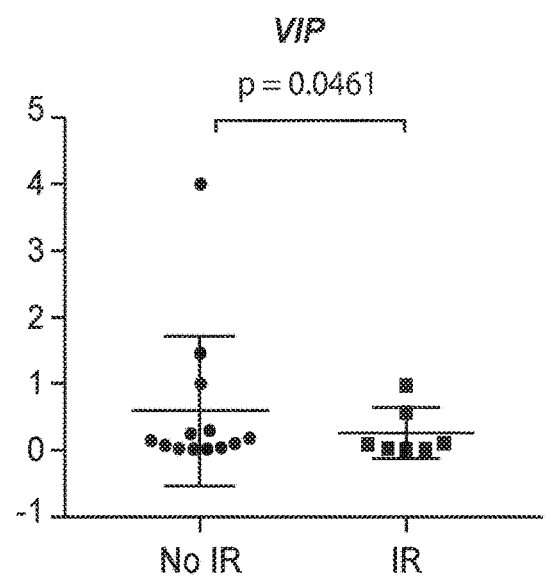
Figure 14A:
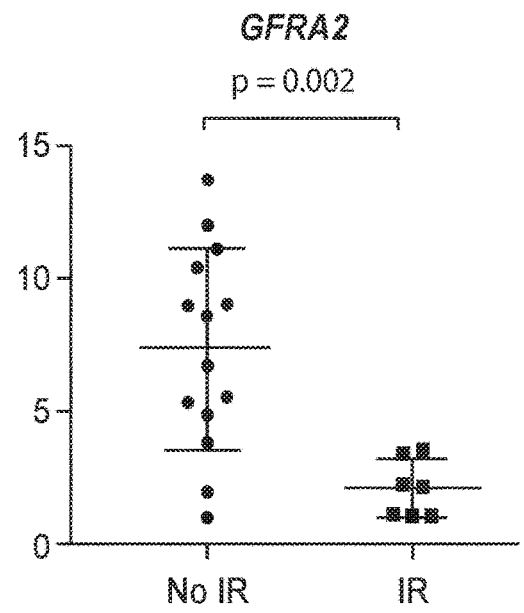
Figure 14A:
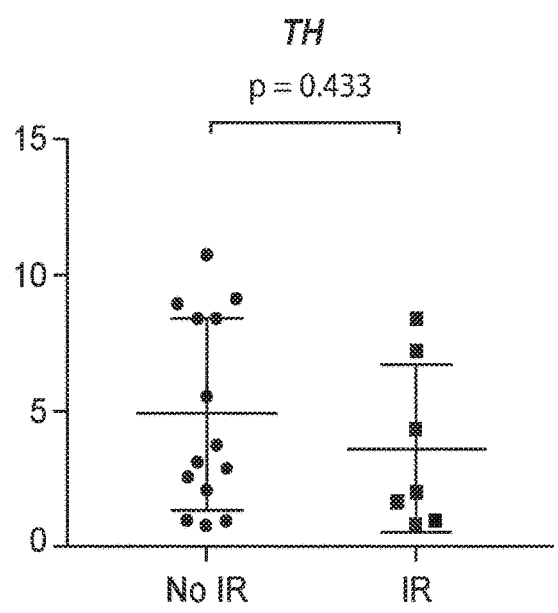
Figure 14B:
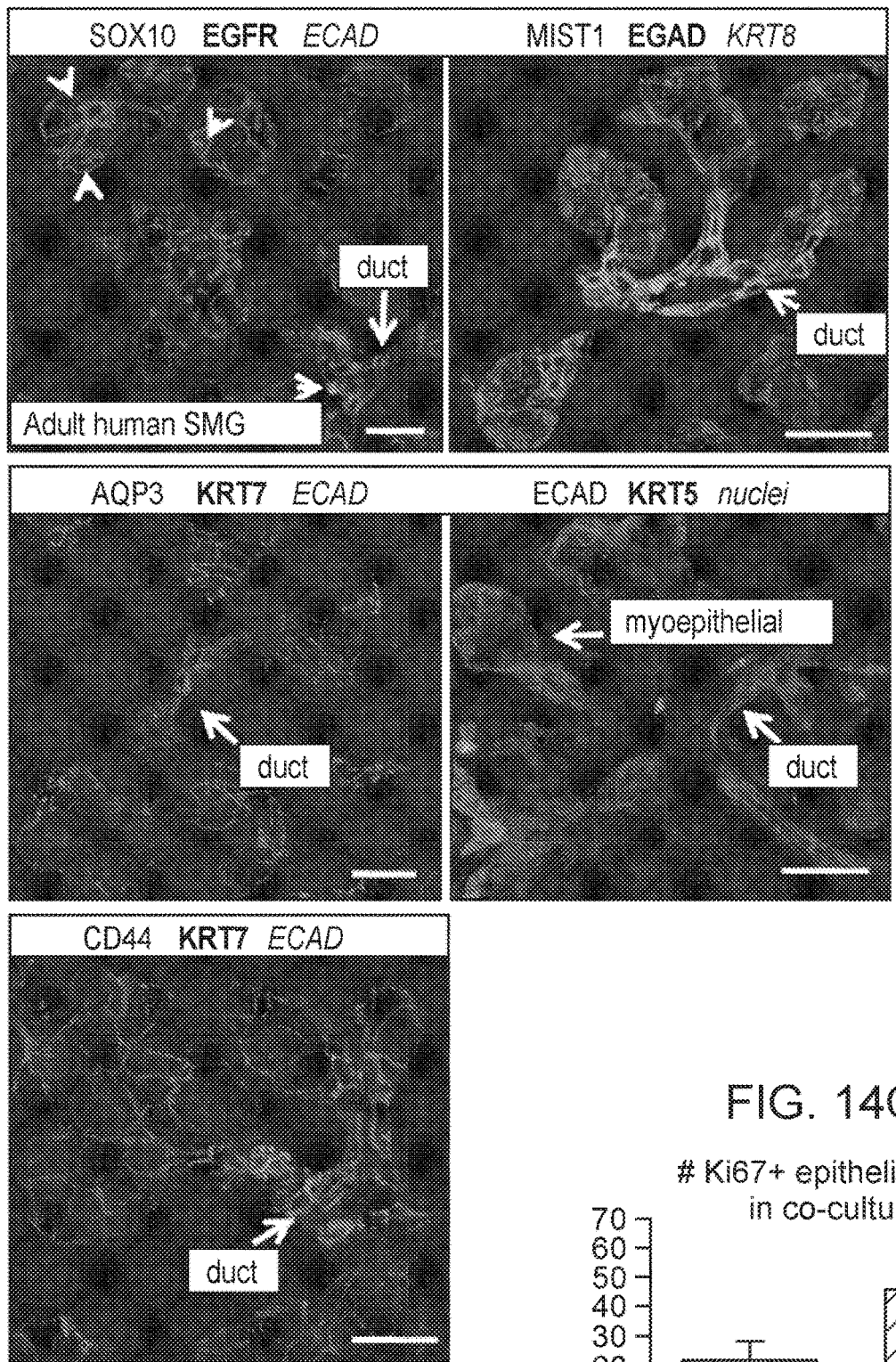
Figure 14C:
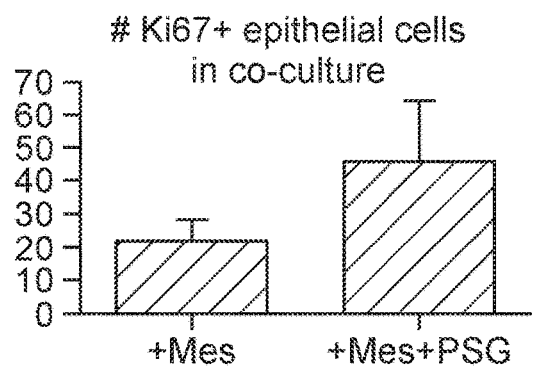
Figure 14D:
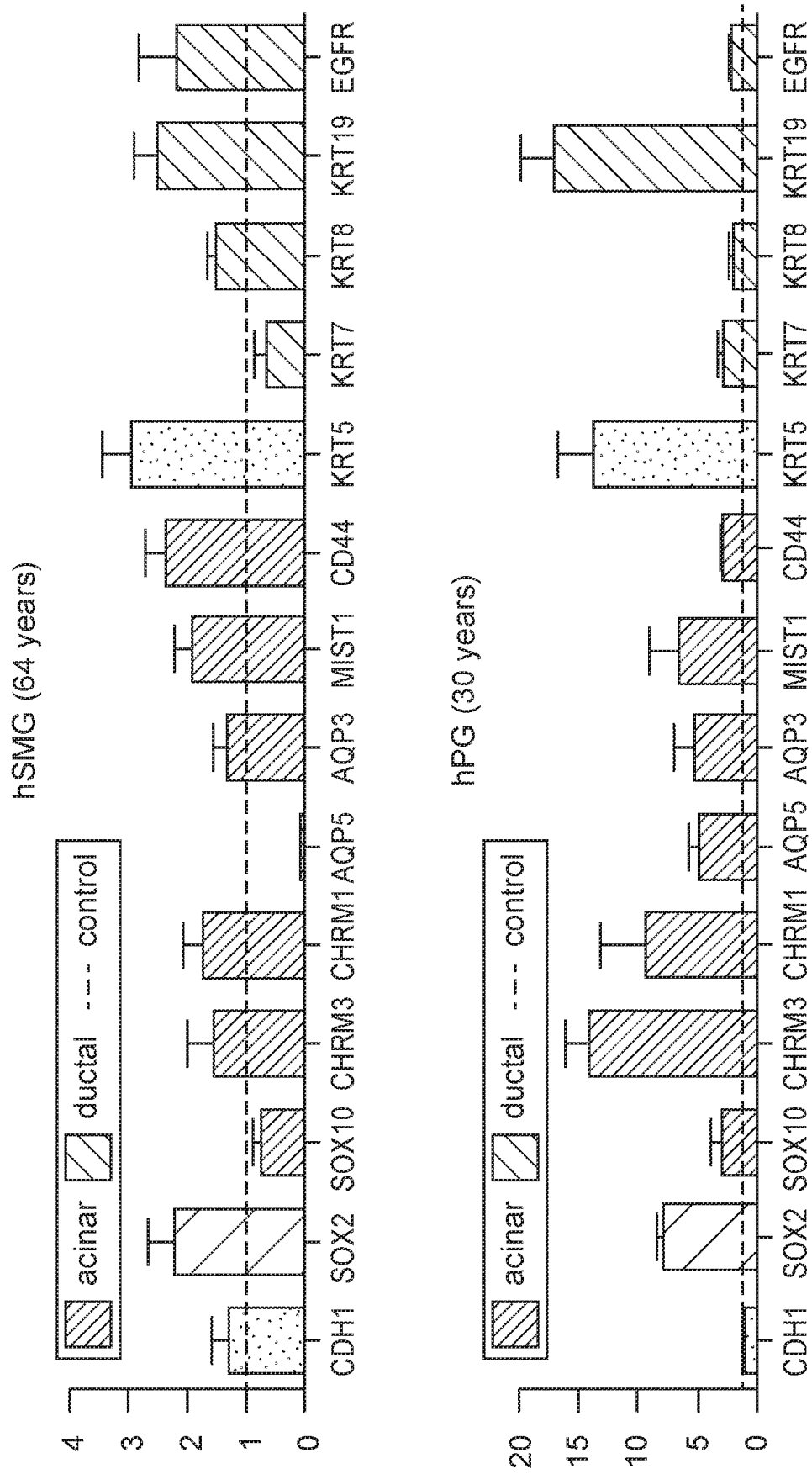
Figure 14D:
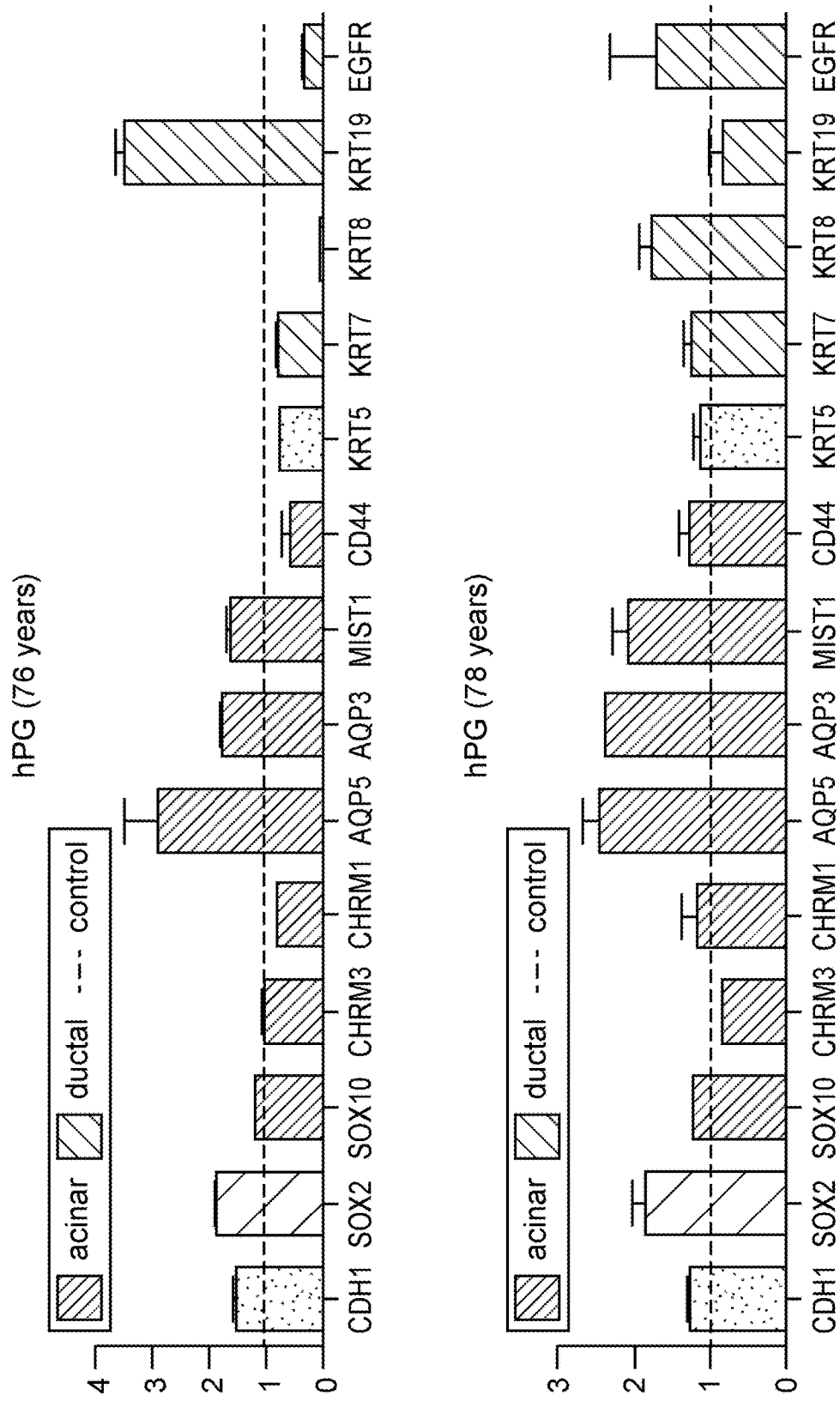

FIGS. 14A-14O show that muscarinic activation is sufficient to increase SOX2 expression and the acinar lineage in human adult salivary gland. FIG. 14A Human salivary gland obtained from healthy individuals (no IR; submandibular) or patients who received radiation therapy for head and neck cancer (IR) were subjected to qPCR. FIG. 14B Representative images of adult human (h) salivary gland (non-IR, 22-31 years; SMG) immunostained for endogenous SOX10, MIST1, EGFR, CD44, KRT7, AQP3, KRT5, ECAD, and nuclei. Single arrowheads indicate SOX10-expressing acinar and ductal cells. Scale bars=50 μm. FIG. 14C Quantification of number of Ki67$^+$ cells in nerve co-culture (representative images shown in FIG. 7C). FIG. 14D Adult human salivary gland explants (SMG or PG) from four individual patients (healthy, non-IR) were cultured for 4 h±200 nM CCh. Pooled data presented in FIG. 7E. Data information: Data in (FIG. 14A) n=11 for no IR and n=7 for IR; 30-85 years. Data were normalized to GAPDH with individual values plotted and analyzed using a Student's t-test with a false discovery rate set to 0.05. Error bars show mean±SD. TUBB3 P=0.346, VIP P=0.461, GFRA P=0.002, TH P=0.433. Data in (FIG. 14C) are n=3 and mean±SEM and were analyzed using a Student's t-test. *P=0.0151. Data in (FIG. 14D) (n=4 separate individuals) were normalized to GAPDH expression and salivary gland from the same individuals cultured with no CCh (control; black dashed line) and run in triplicate and are presented as mean±SD.

Figure 15A:
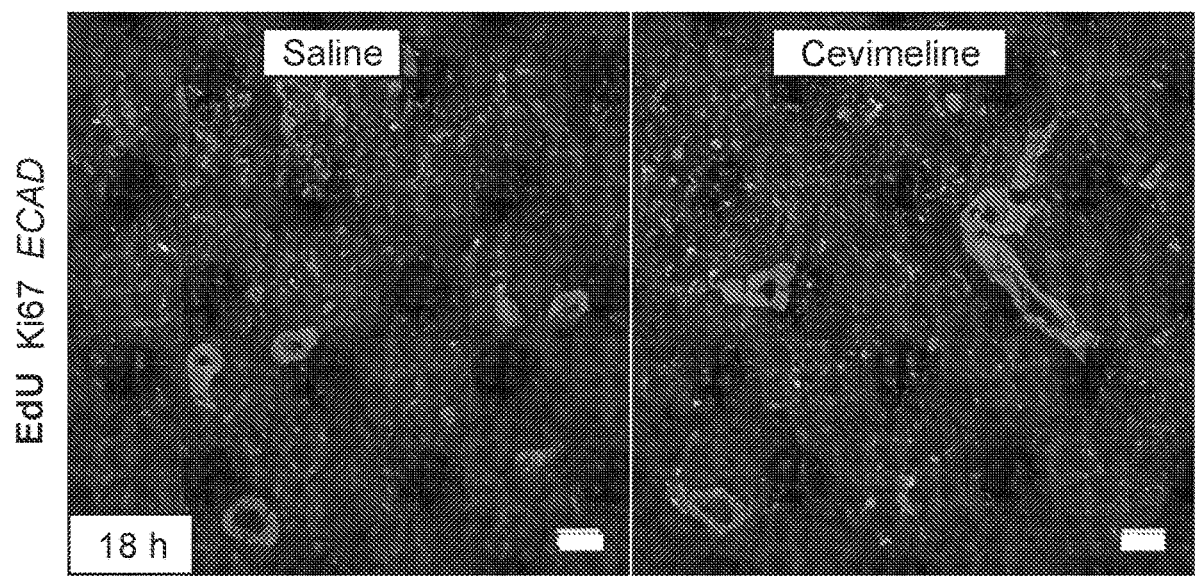
Figure 15B:
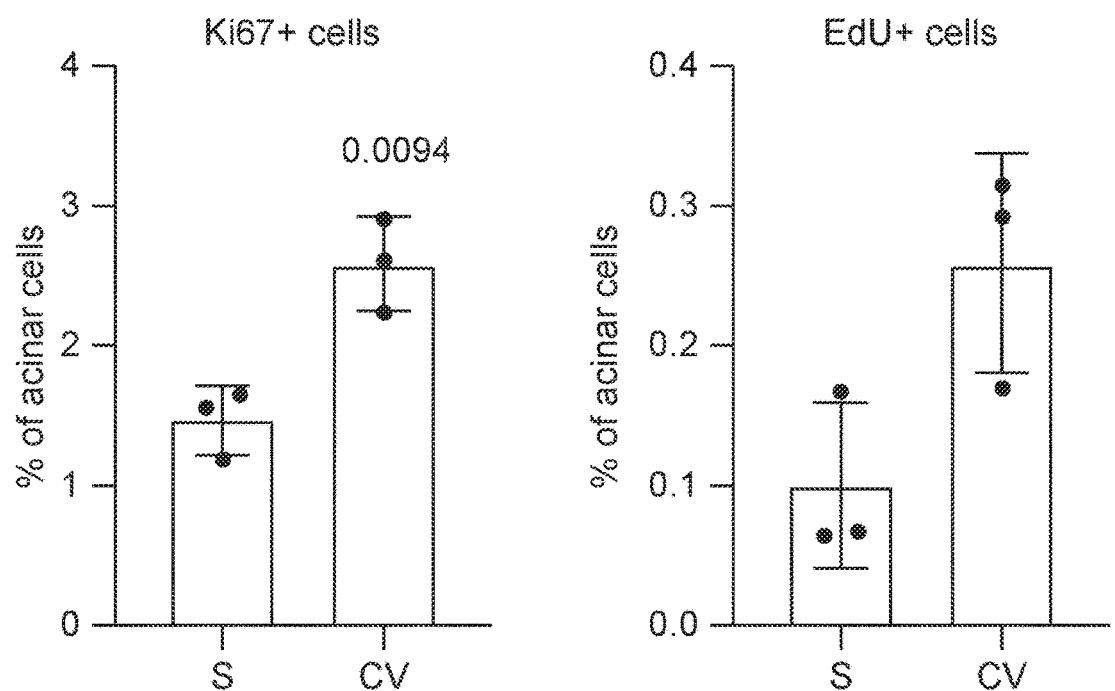

FIGS. 15A-15B show intraglandular injection of cevimeline promotes acinar cell proliferation in mouse salivary gland. Mice were injected intra-glandularly with cevimeline (CV) or saline (S, control). Mice were sacrificed after 18 h and proliferating cells quantified from tissue sections (3 sections/gland, 3 mice/treatment). Scale bars=60 μm (representative image shown in FIG. 15A; plots comparing % acinar cells for cevimeline treatment versus saline shown in FIG. 15B).

FIGS. 16A-16D show physical degradation of oxidized alginate (OA) hydrogels. (FIG. 16A) Effect of oxidation on physical degradation, wt % held constant at 5 wt %. (FIG. 16B) Effect of wt % on physical degradation, OA % held constant at 2% OA. (FIG. 16C) In vitro versus in vivo degradation of 2% OA at 5 wt %. (FIG. 16D) Stability of 2% OA at 5 wt % under refrigeration (4° C.) versus frozen (−20° C.).

FIGS. 17A-17D show Cevimeline release from oxidized alginate (OA) hydrogels. (FIG. 17A) Effect of oxidation on cevimeline release, wt % held constant at 5 wt %. (FIG. 17B) Effect of wt % on cevimeline, OA % held constant at 2% OA. (FIG. 17C) Effect of increased initial drug loading of cevimeline on release kinetics from 2% OA hydrogels at 5 wt %. (FIG. 17D) Cevimeline release per time from 2% OA hydrogels at 5 wt % with different initial cevimeline concentrations.

Figure 18A:
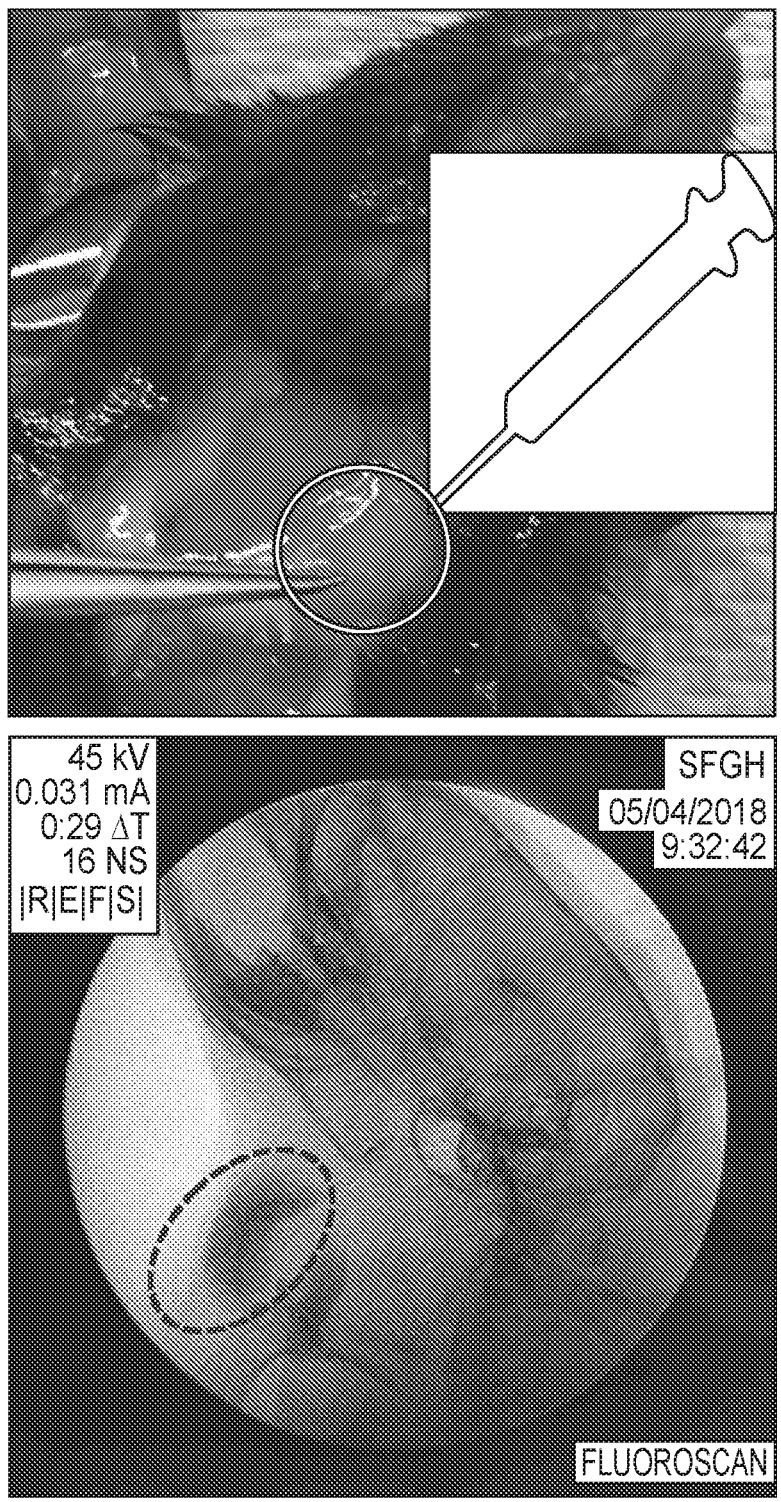
Figure 18B:
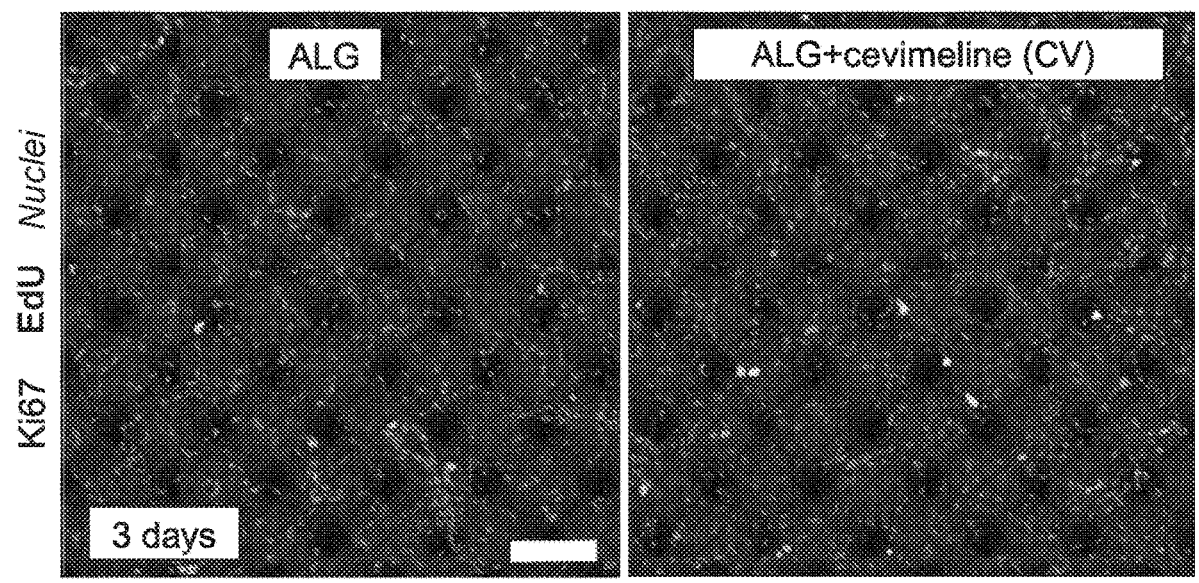
Figure 18C:
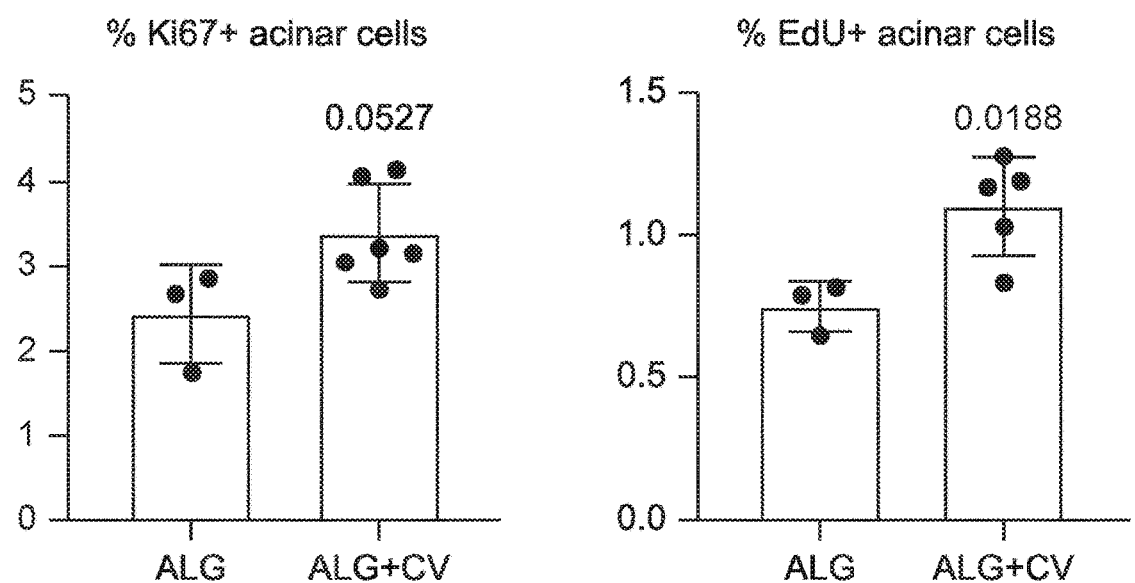

FIGS. 18A-18C show cevimeline release from bulk alginate promotes glandular cell proliferation by 3 days. Alginate (ALG, 5% WT:2% OA) or alginate+cevimeline (ALG+CV) were injected immediately adjacent to the salivary glands (FIG. 18A). Red circle highlights alginate post-injection. Mice were sacrificed at 3 days and proliferating Ki67$^+$ and EdU$^+$ cells quantified (FIG. 18B and FIG. 18C, 3 sections/gland, 3-4 mice/treatment). Students t-test comparing +CV to ALG control, *p<0.05. Scale bar=40 μm.

FIGS. 19A-19E show alginate, with or without cevimeline, promotes a pro-repair inflammatory response 7 days after injection. Alginate (ALG, 5% WT:2% OA) or alginate+cevimeline (ALG+CV) were injected immediately adjacent to the salivary glands. Mice were sacrificed at 7 days. Salivary gland tissue sections were immunostained for CD3+ T cells (FIGS. 19A and 19B) CD68+ macrophages (FIGS. 19C and 19D) or CD206+ reparative macrophages (FIG. 19E) and nuclei. Macrophage density was quantified and compared to aged matched saline injected animals (i.p.) or 22 month-old mice (3 sections/gland, 3-4 mice/treatment). One-way ANOVA test comparing +CV to ALG control to controls, *p<0.05, p<0.01, **p<0.00001. Scale bar=40 μm.

FIGS. 20A-20F show that cevimeline promotes proliferation of acinar cells after radiation induced damage. (FIG. 20A) Schematic of radiation treatment. (FIG. 20B) Citrate stimulated saliva secretion is reduced in 6-8 wks C57/BL6 female mice 13 days after receiving a 10Gy dose of radiation. (FIGS. 20C-20F) After 14 days, the animals were injected i.p. (FIGS. 20B and 20D) or injected intraglandularly (FIGS. 20C and 20D) with saline or 10 mg/kg cevimeline. Animals were euthanized 18 hrs after injection for tissue processing and immunofluorescence. Quantification of proliferation and SOX2+ cells was done from tissue sections (3 sections per animal).

Figure 21A:
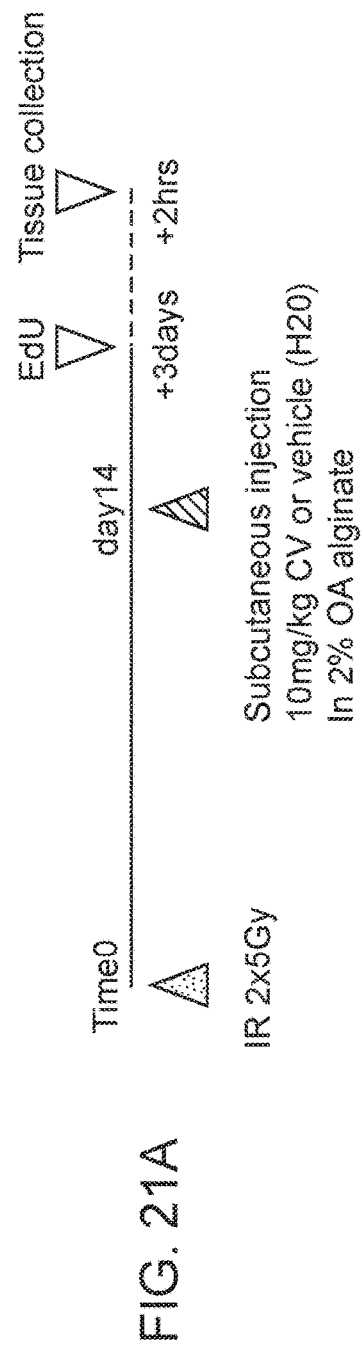
Figure 21B:
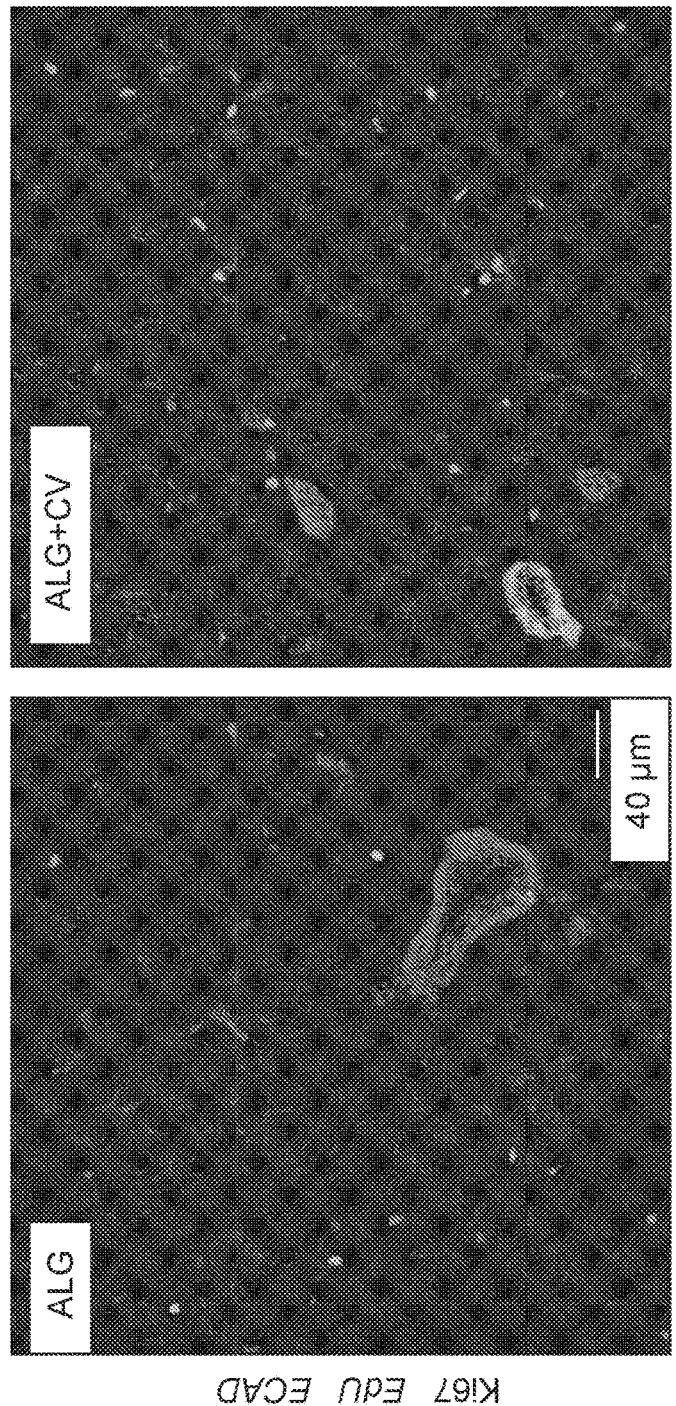
Figure 21C:
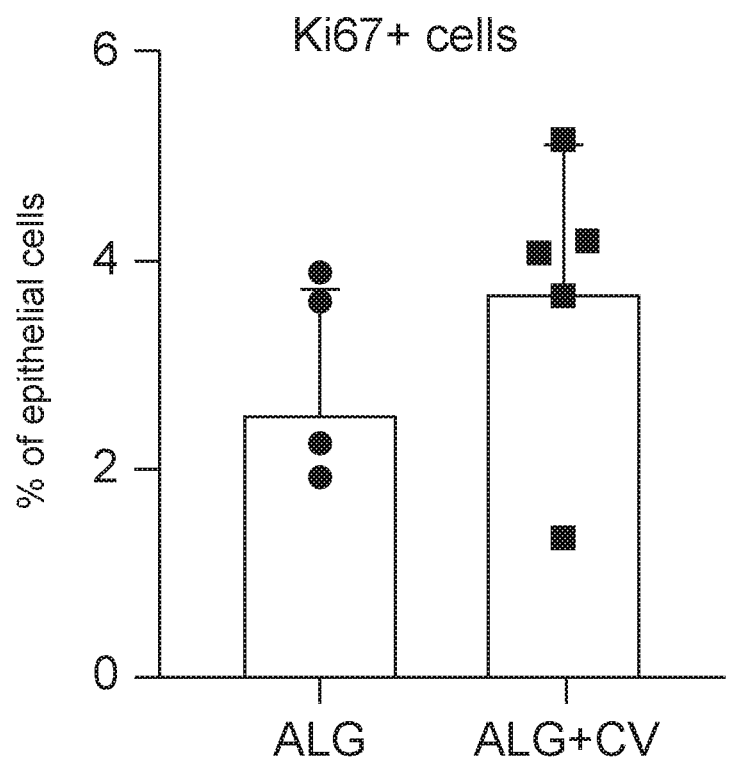
Figure 21D:
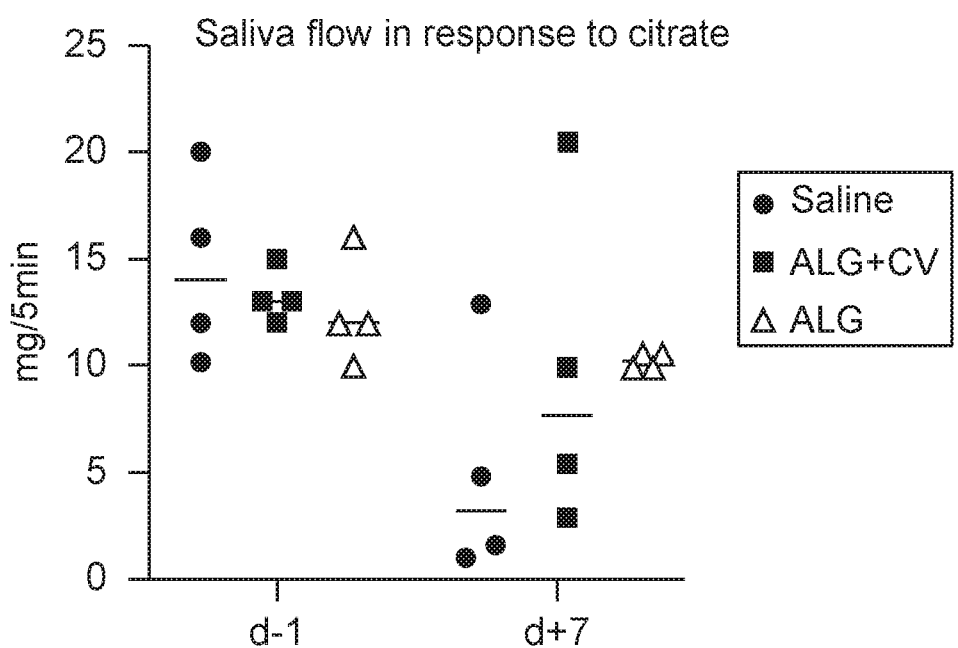

FIGS. 21A-21D show treatment of irradiated salivary glands with alginate+cevimeline promotes acinar cell proliferation and improves salivary flow. FIG. 21A shows schematic of timeline of treatment of mice. Mice were injected with alginate or alginate+cevimeline 14 days post-radiation and sacrificed at 3 days for analysis of proliferation. FIG. 21B shows that alginate+cevimeline increased proliferation rates above alginate only levels. FIG. 21C compares the percentage of epithelial cells after treatment with alginate+cevimeline of only alginate. FIG. 21D shows that thirteen days post-radiation, saliva was measured 1 day before and 7 days after subcutaneous injection of saline, alginate or alginate+cevimeline. Two way-ANOVA, no RM, p=0.0244 for time parameter.

Figure 22:
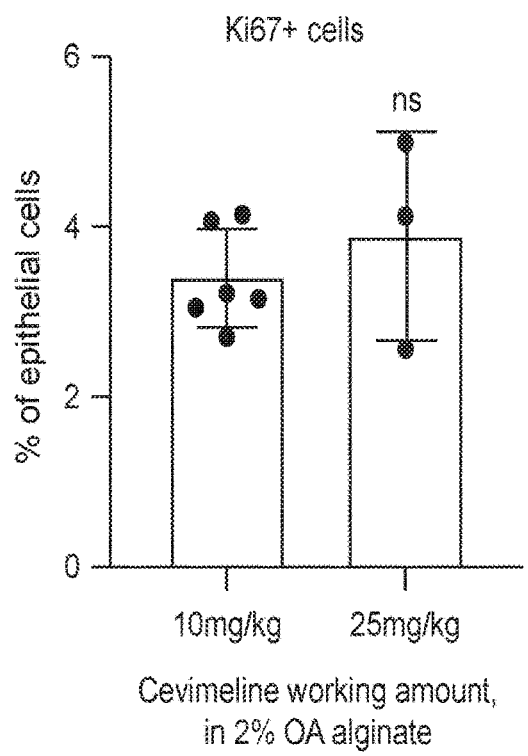

FIG. 22 shows no increase in proliferation with an increase in cevimeline. Alginate containing 10 mg or 25 mg/kg was delivered to mice and proliferation (Ki67+) acinar cells was quantified at 3 days.

Figure 23:
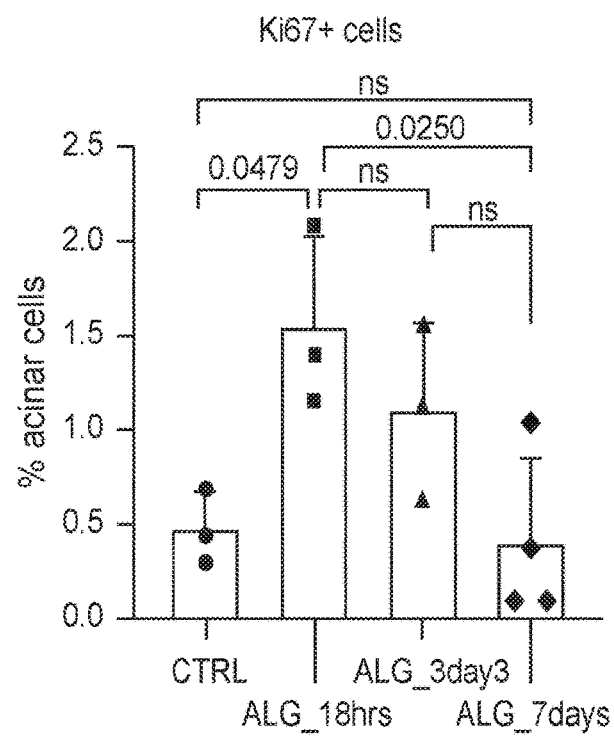

FIG. 23 shows that alginate promotes acinar cell proliferation.

Figure 24:
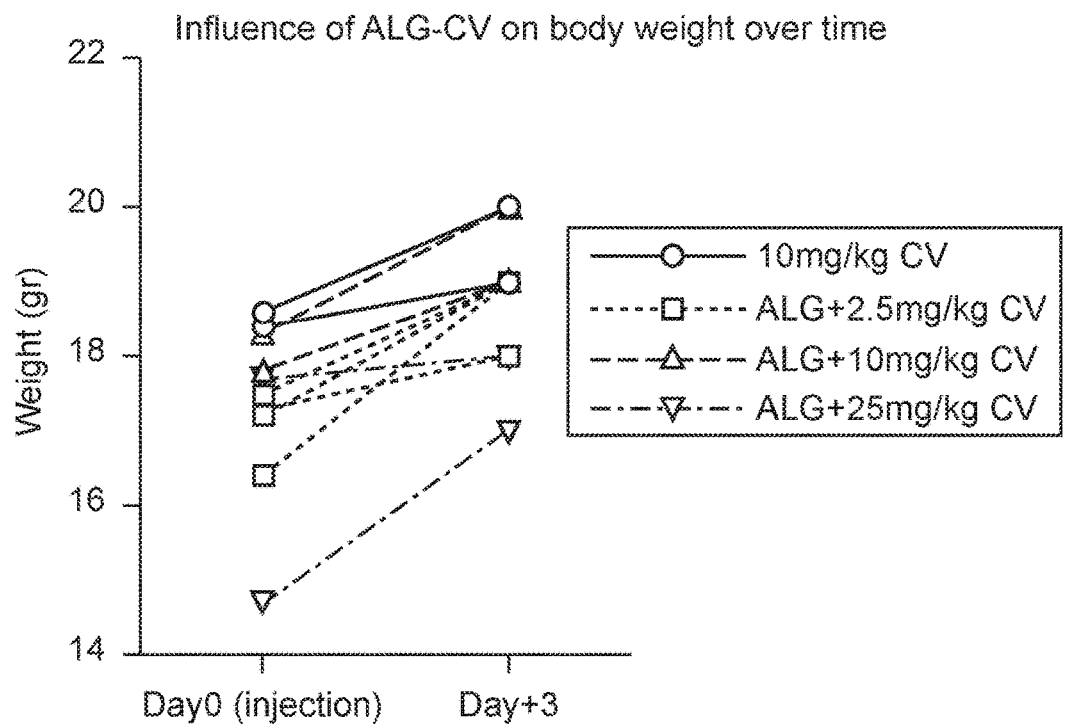

FIG. 24 shows that alginate, with or without cevimeline, does not negatively impact mouse health.

Figure 25:
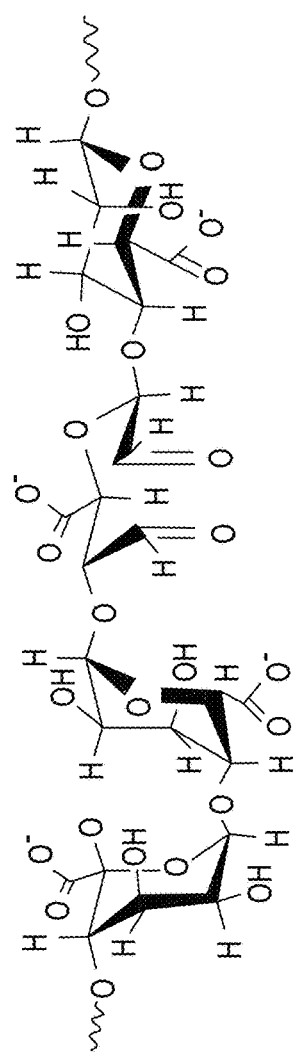
Figure 25:
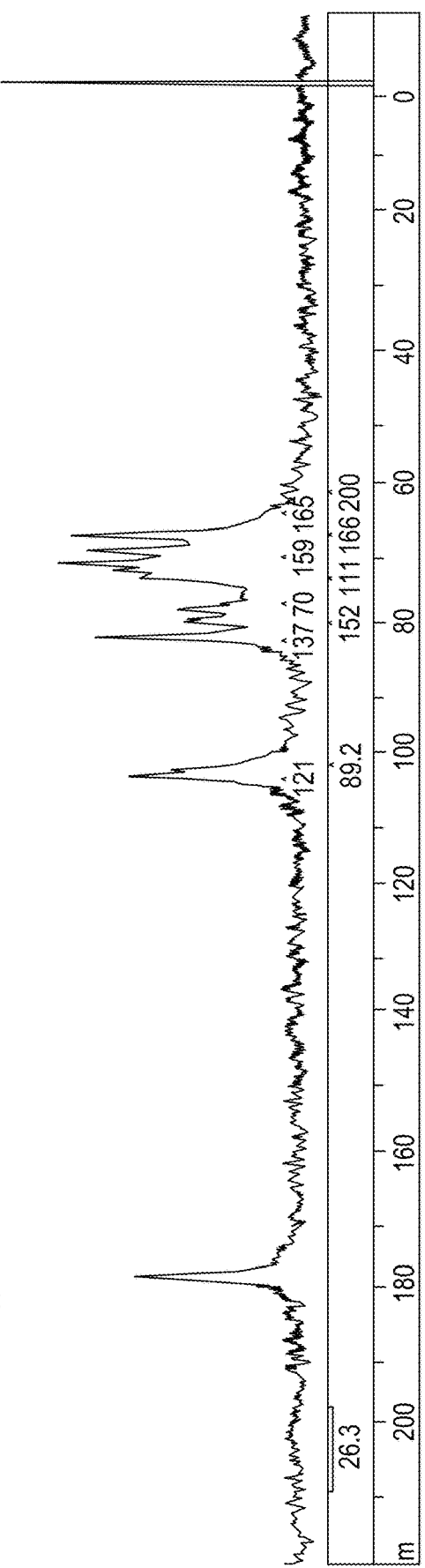

FIG. 25 shows a $^{13}C$ nuclear magnetic resonance (NMR) spectrum to analyze oxidation efficiency of alginate. 3-(trimethylsilyl)propionic acid-d4 sodium salt (0.05 w/v %) was used as an internal standard.

Figure 26:
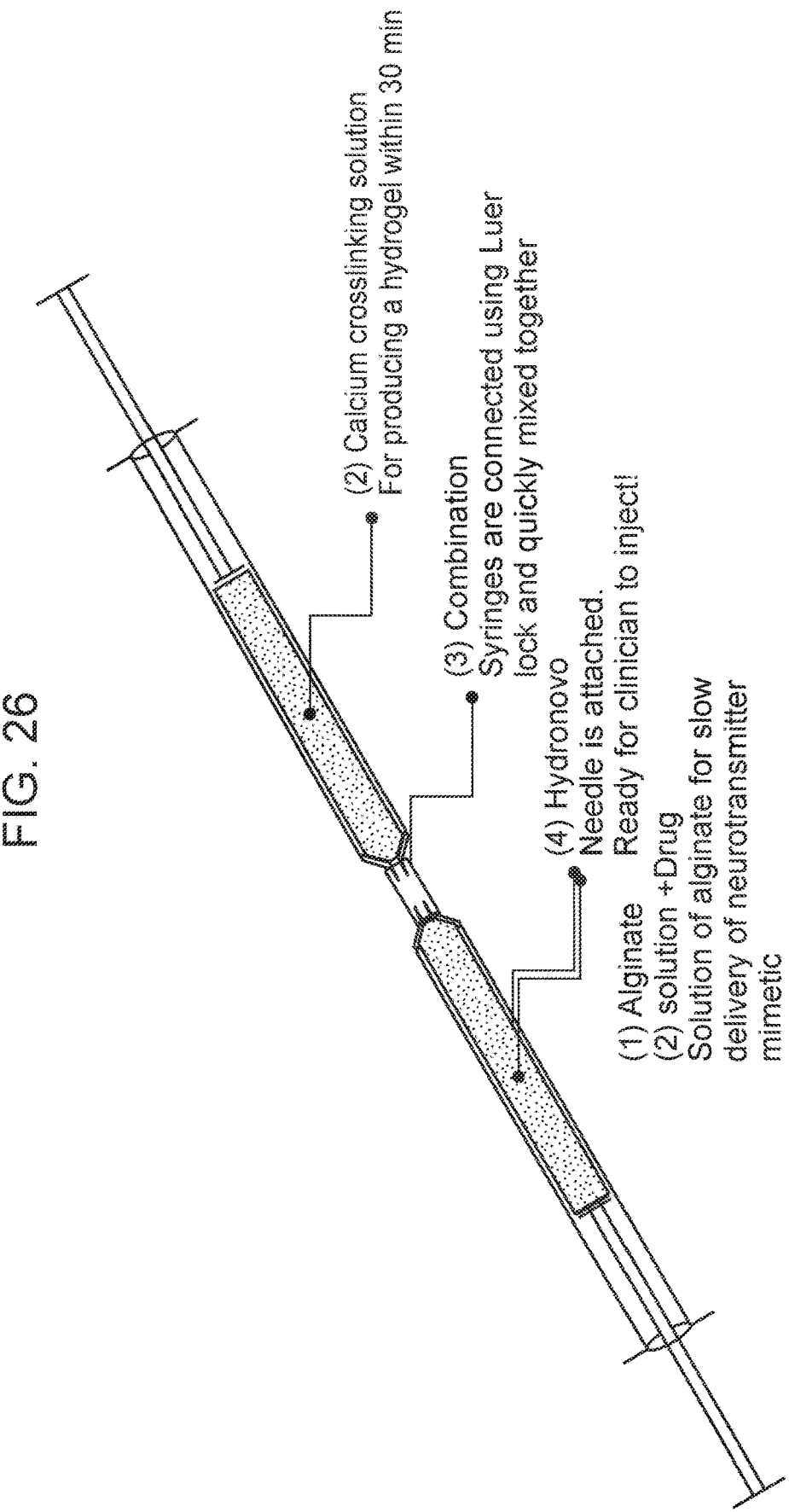

FIG. 26 shows pair of syringes for producing an injectable hydrogel. A syringe containing a calcium crosslinking solution for producing a hydrogel is connected through a luer lock to a second syringe containing a solution of the alginate and a neurotransmitter mimetic (e.g., cholinergic agonist and/or muscarinic agonist).

Figure 27A:
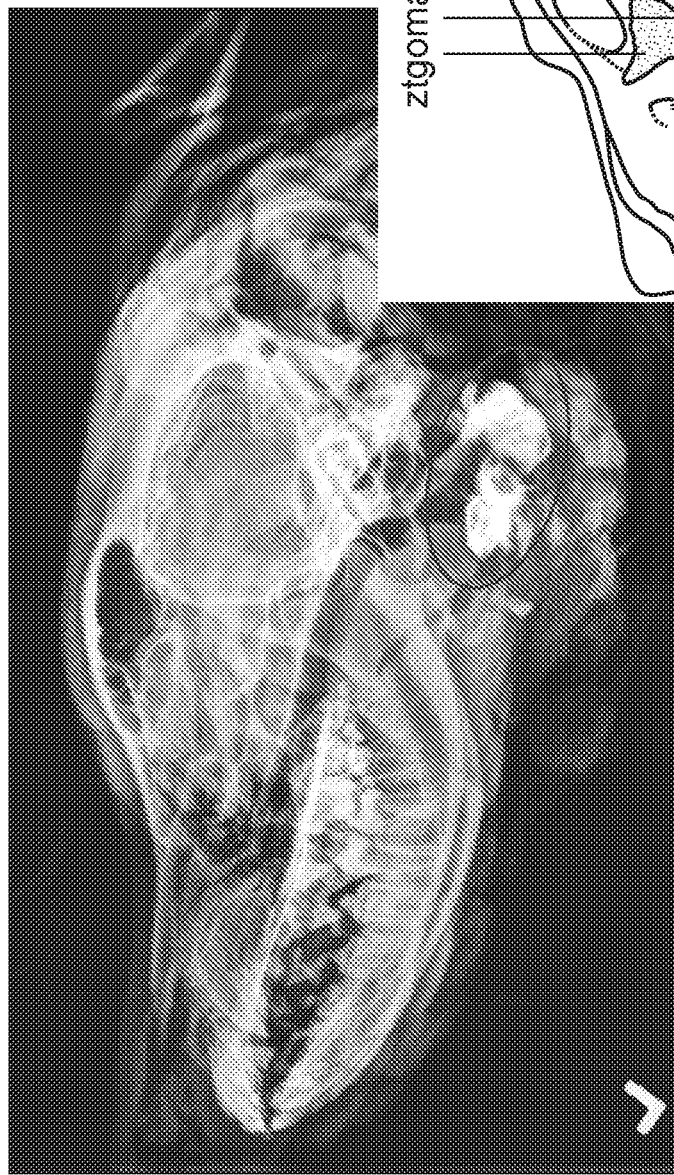
Figure 27A:
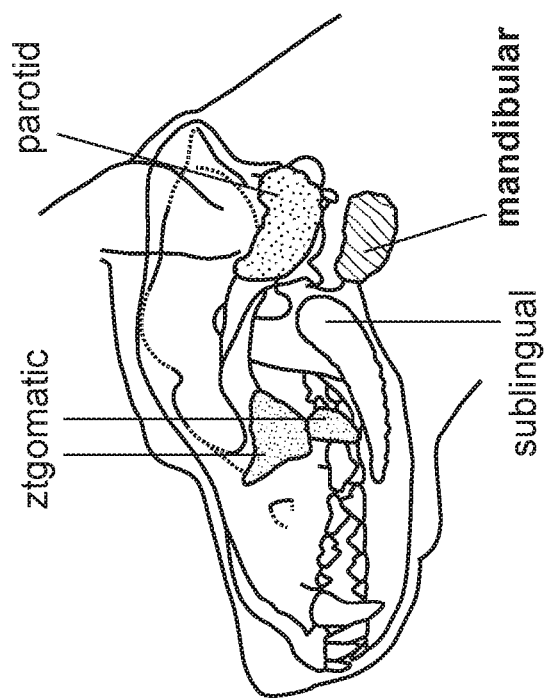
Figure 27B:
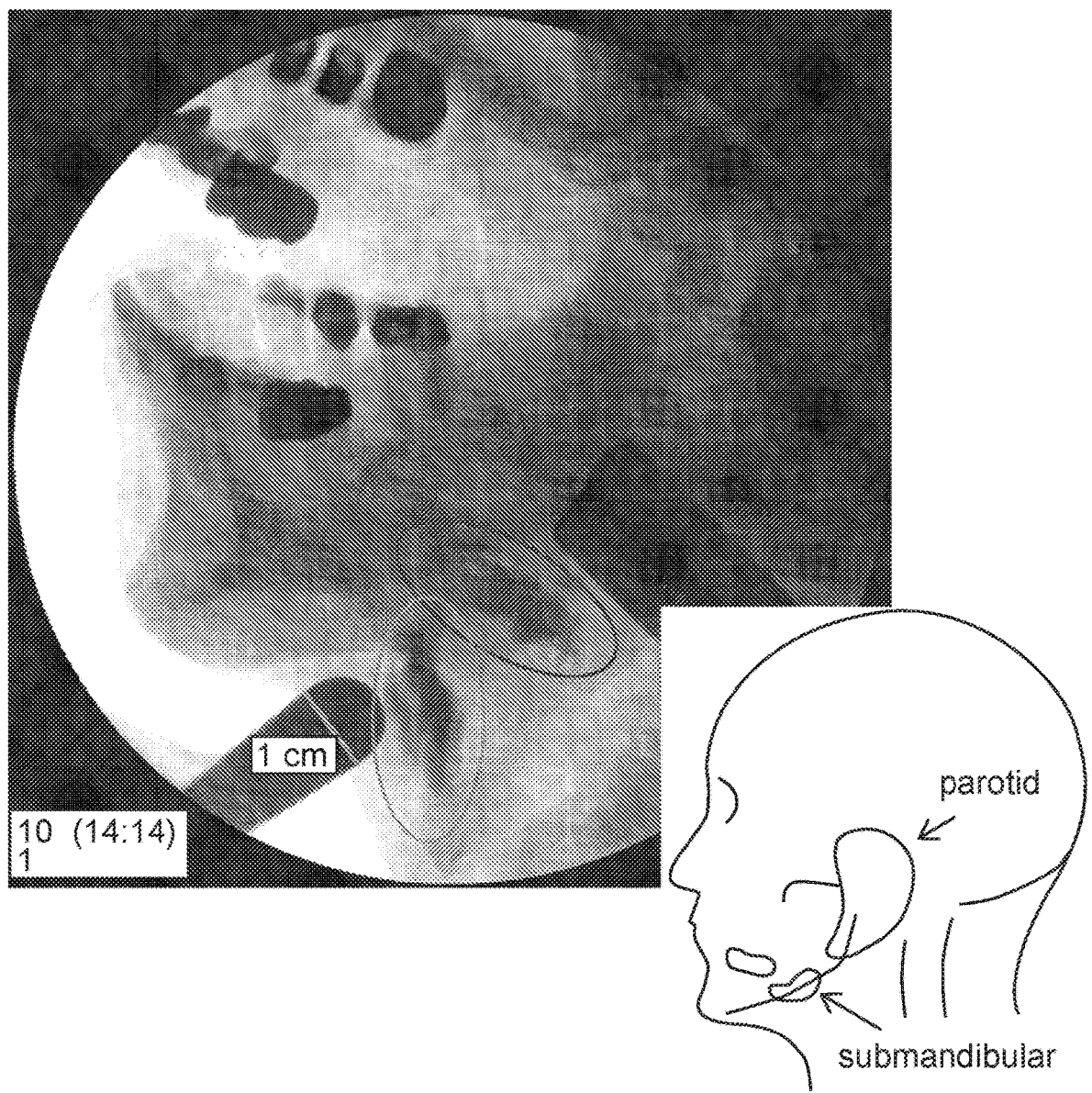

FIG. 27 shows the locations of canine and human salivary glands. 1.5 ml to 2 ml of alginate hydrogel can be injected directly into the submandibular gland in either human or canine subjects.

Figure 28:
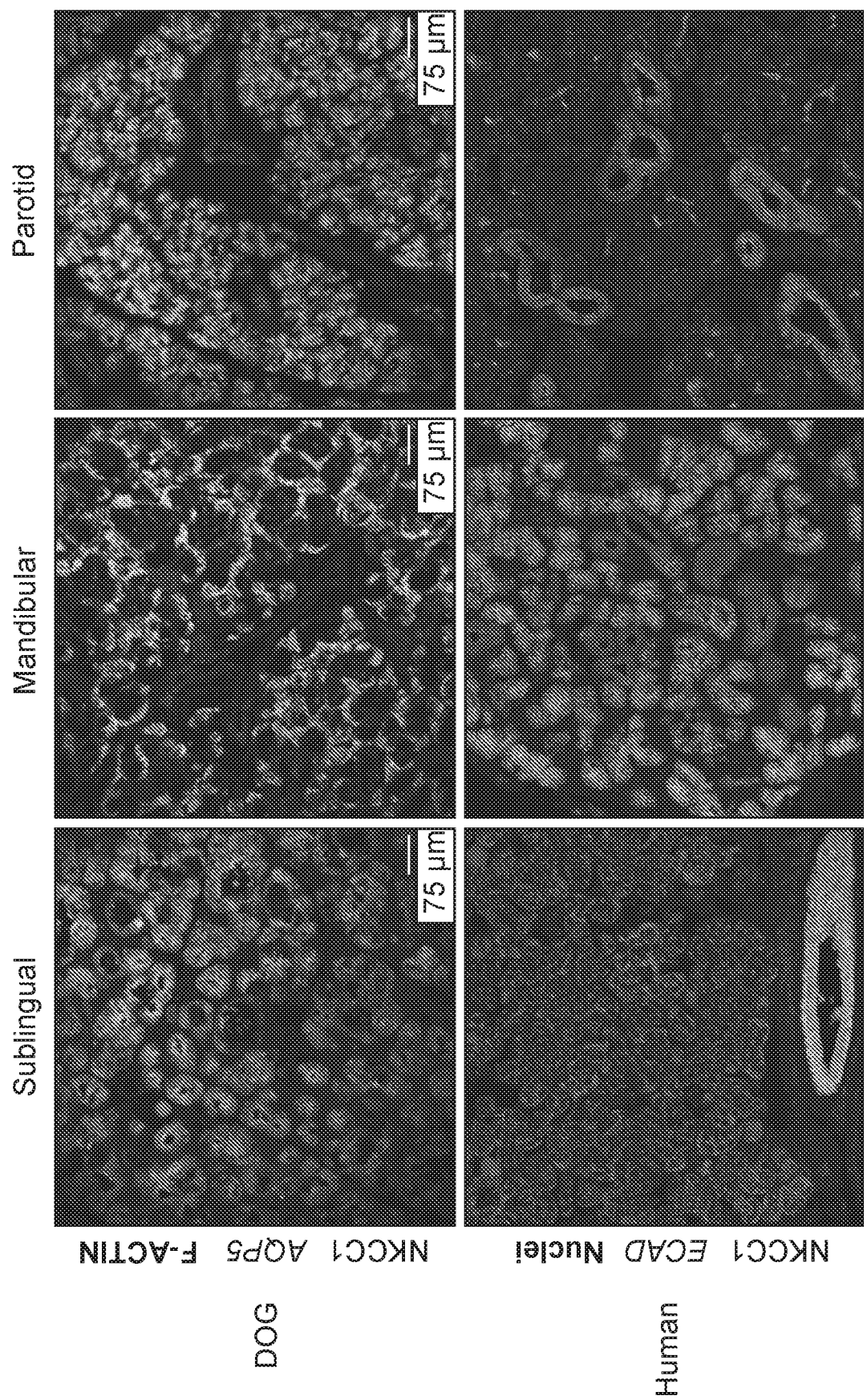

FIG. 28 shows that canine and human salivary glands are similar. The parotid and sublingual glands of a dog and human appear to be the most similar. The canine submandibular gland is similar to that of a human in that it is a mixed cell gland.

Figure 29:
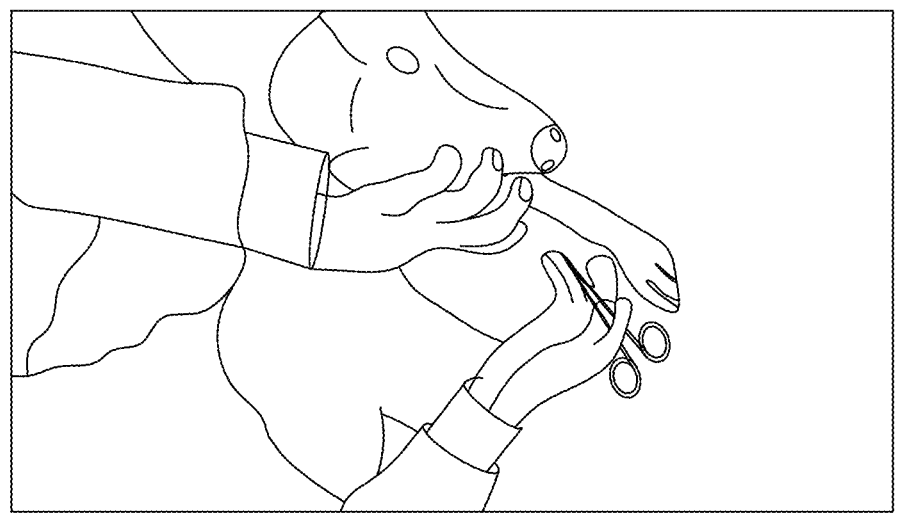
Figure 29:
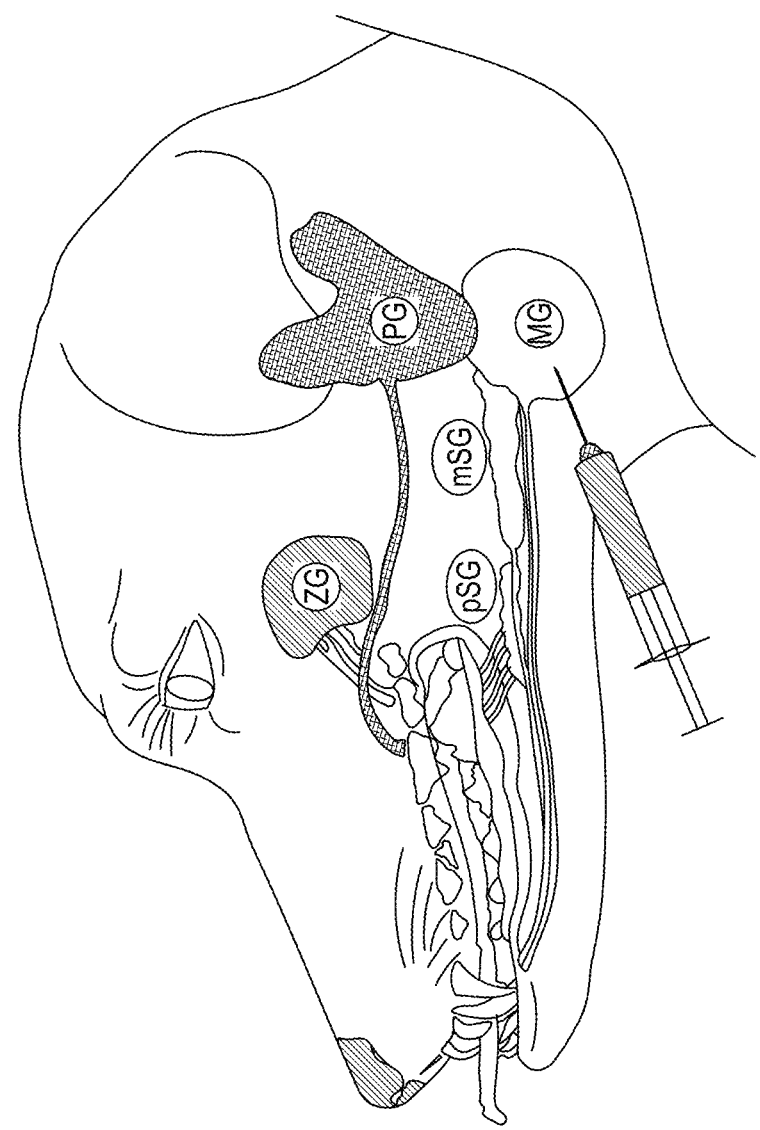

FIG. 29 shows injection of alginate hydrogel into the submandibular gland of a dog.

DETAILED DESCRIPTION OF THE INVENTION

Compositions, methods, and kits are provided for salivary gland regeneration by promoting acinar cell replacement. The inventors have shown that that progenitor cells, including SOX2$^+$ acinar progenitor cells in the adult salivary gland are essential to the replenishment of acinar cells with the unexpected capacity to repopulate the tissue after radiation-induced damage (Example 1). The inventors have further shown that cholinergic nerves play a vital role in controlling acinar cell replacement during homeostasis and that this neuronal influence can be replicated through addition of cholinergic mimetics to the acinar progenitor cells. Accordingly, by directly targeting progenitor cells, including SOX2+ acinar progenitor cells within tissue with cholinergic agonists and/or muscarinic agonists, secretory units of salivary glands can be regenerated to provide recovery of functional salivary acini and treat oral disorders, such as xerostomia following radiation therapy or associated with Sjogren syndrome. In particular, formulations comprising a muscarinic agonist such as cevimeline encapsulated in an alginate hydrogel can be formulated for local administration to a salivary gland and used in treatment of xerostomia (Example 2).

Before the present compositions, methods, and kits are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the agonist" includes reference to one or more agonists and equivalents thereof, e.g. ligands or activators known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "about," particularly in reference to a given quantity, is meant to encompass deviations of plus or minus five percent.

The term "agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

The term "agonist" refers to a substance that binds to a specific receptor and triggers a response in a cell. It mimics the action of an endogenous ligand (such as hormone or neurotransmitter) that binds to the same receptor. A "full agonist" binds (has affinity for) and activates a receptor, displaying full efficacy at that receptor. One example of a drug that acts as a full agonist is isoproterenol, which mimics the action of acetylcholine at β adrenoreceptors. A "partial agonist" (such as buspirone, aripiprazole, buprenorphine, or norclozapine) also binds and activates a given receptor, but has only partial efficacy at the receptor relative to a full agonist.

A "partial agonist" may also be considered a ligand that displays both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone. A "co-agonist" works with other co-agonists to produce the desired effect together. An antagonist blocks a receptor from activation by agonists. Receptors can be activated or inactivated either by endogenous (such as hormones and neurotransmitters) or exogenous (such as drugs) agonists and antagonists, resulting in stimulating or inhibiting a biological response. A ligand can concurrently behave as agonist and antagonist at the same receptor, depending on effector pathways.

The potency of an agonist is usually defined by its $EC_{50}$ value. This can be calculated for a given agonist by determining the concentration of agonist needed to elicit half of the maximum biological response of the agonist. Elucidating an $EC_{50}$ value is useful for comparing the potency of drugs with similar efficacies producing physiologically similar effects. The lower the $EC_{50}$, the greater the potency of the agonist, and the lower the concentration of drug that is required to elicit a maximum biological response.

A "biocompatible substrate" as used herein refers to a material that is suitable for implantation into a subject that may be used to encapsulate one or more cholinergic agonists and/or muscarinic agonists or onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. In another embodiment, the biocompatible substrate linearly deforms to fill a salivary gland with distribution to the entire gland. The biocompatible substrate provides for sustained release of the one or more cholinergic agonists and/or muscarinic agonists and may also provide a supportive framework that allows cells to attach to it, and grow on it. In some embodiments, cultured populations of cells are grown on the biocompatible substrate, which provides the appropriate interstitial distances required for cell-cell interaction The terms "differentiate", "differentiation", "transdifferentiate", or "transdifferentiation" as used herein, generally refers to the process by which precursor or progenitor cells differentiate into specific cell types. The term may refer to the process by which acinar progenitor cells, such as SOX2 expressing acinar progenitor cells, become differentiated acinar cells. Differentiated cells can be identified by their patterns of gene expression and cell surface protein expression. As used herein, the term "differentiate" refers to having a different character or function from the original type of tissues or cells. Thus, "differentiation" is the process or act of differentiating.

The terms "modulation" or "modulates" or "modulating" refers to up regulation (i.e., activation or stimulation), down regulation (i.e., inhibition or suppression) of a response, or the two in combination or apart, such as the ability to alter by either up-regulating or down-regulating the activity of a protein, nucleic acid encoding a protein, a pathway, a protein within a pathway and the like.

The phrase "oral tissue cells" refers to any cell population derived from the mouth. These include one or more different cells types that can be isolated from the salivary glands, submandular gland, sublingual gland, lingual glands, labial glands, buccal glands, palatine glands, striated ducts, excretory ducts, dental pulp tissue, dentin, periodontium, bone, cementum, gingival submucosa, oral submucosa, tongue and taste bud tissues. In a preferred embodiment, the oral tissue cells are derived from the salivary gland. Examples of oral tissue cells include, but are not limited to, myoepithelial cells, epithelial cells, and the like.

The phrase "oral tissue" refers to any aggregate of cells that forms a structure in the mouth. By way of example only, oral tissue includes salivary glands, submandular gland, sublingual gland, lingual glands, labial glands, buccal glands, palatine glands, striated ducts, excretory ducts, dental pulp tissue, dentin, periodontium, bone, cementum, gingival submucosa, oral submucosa, tongue and taste bud tissues. In a preferred embodiment, the oral tissue is a salivary gland. The phrase also refers to a part of the oral tissue, e.g., a part of the salivary gland.

The phrase "oral tissue construct" refers to a substrate, preferably a biocompatible substrate that has been seeded with oral tissue cells in which the cells have attached, grown, proliferated, differentiated and populated the biocompatible substrate. This phrase also refers to a neomorphic structure representing the early stages of development of the oral tissue.

The phrase "salivary gland construct" refers to a substrate, preferably biocompatible substrate that has been seeded with salivary gland cells in which the cells have attached, grown, proliferated, differentiated, and populated the biocompatible substrate. This phrase also refers to the neomorphic structure representing the early stages of development of the salivary gland.

The phrase "oral disorder" refers to diseases or disorders that affect the mouth. In particular, diseases or disorders that effect the production of saliva. Examples of oral disorders include, but are not limited to, salivary gland tumors, cystic fibrosis, Sjogren's syndrome, sialoadenitis, parotitis, sialoangitis, sialodochitis, sialolithiasis, sialodocholithiasis, mucocele, ranula, hyposecretion, ptyalism, sialorrhea, xerostomia, benign lymphoepithelial lesion of salivary gland; sialectasia; sialosis; stenosis of salivary duct; and stricture of salivary duct.

The terms "treatment" or "treating" refers to therapy, prevention and prophylaxis and particularly refers to administering medicine or performing medical procedures on a patient, for either prophylaxis (prevention) or to cure or reduce the extent of or likelihood of occurrence of the infirmity or malady or condition or event. The treatments using the agents described herein may be provided to stimulate or promote salivary gland regeneration and/or acinar cell replacement in salivary glands.

The terms "individual", "subject", and "patient" are used interchangeably herein and refer to any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In some cases, the methods of the invention find use in experimental animals, in veterinary application, and in the development of animal models for disease, including, but not limited to, rodents including mice, rats, and hamsters; primates, and transgenic animals.

A "therapeutically effective dose" or "therapeutic dose" is an amount sufficient to effect desired clinical results (i.e., achieve therapeutic efficacy). A therapeutically effective dose can be administered in one or more administrations.

By "therapeutically effective dose or amount" of a composition comprising a cholinergic agonist (e.g., acetylcholine or carbachol) and/or a muscarinic agonist (e.g., cevimeline encapsulated in a hydrogel) is intended an amount that, when administered as described herein, brings about a positive therapeutic response, such as improved recovery from xerostomia. Improved recovery may include improved salivary gland function and increased saliva production and salivary flow. Additionally, a therapeutically effective dose or amount may stimulate proliferation of acinar cells and acinar cell progenitors resulting in repopulation of salivary glands with acinar cells. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein. A therapeutically effective dose can be administered in one or more administrations.

The phrase "pharmaceutically acceptable" refers to molecular entities and compositions that are physiologically tolerable and do not typically produce an allergic or similar untoward reaction, such as gastric upset, dizziness and the like, when administered to a human (or non-human animal in the case of veterinary use). Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

As used herein, the term "contrast agent" refers to a substance that improves contrast for medical imaging of a target tissue, fluid, or structure (e.g., salivary gland) within the body of a subject. Exemplary contrast agents include, without limitation, ultrasound contrast agents (e.g. SonoVue microbubbles comprising sulfur hexafluoride, Optison microbubbles comprising an albumin shell and octafluoropropane gas core, Levovist microbubbles comprising a lipid/galactose shell and an air core, Perflexane lipid microspheres comprising perfluorocarbon microbubbles, and Perflutren lipid microspheres comprising octafluoropropane encapsulated in an outer lipid shell), magnetic resonance imaging (MRI) contrast agents (e.g., gadodiamide, gadobenic acid, gadopentetic acid, gadoteridol, gadofosveset, gadoversetamide, gadoxetic acid), and radiocontrast agents, such as for computed tomography (CT), radiography, or fluoroscopy (e.g., diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, and calcium iopodate).

Salivary Gland Regeneration by Promoting Acinar Cell Replacement

Compositions and methods are provided for salivary gland regeneration by promoting acinar cell replacement. Salivary gland regeneration potentially offers permanent relief of xerostomia. The autonomic nervous system innervates salivary acinar, myoepithelial, vascular and intercalated duct cells. Salivary acinar cells secrete most of the fluid, electrolyte and proteins in saliva. Neurotransmitter receptors are present on the basolateral membranes of acinar cells that possess α-adrenergic, β-adrenergic, M3 muscarinic, and cholinergic substance P receptors. The major pathway for protein exocytosis occurs via activation of β-adrenergic receptors (sympathetic pathway), while the primary stimulation for fluid secretion occurs through activation of the M3 muscarinic receptors (parasympathetic pathway).

It was found that progenitor cells, including $SOX2^+$ acinar progenitor cells in the adult salivary gland are essential to the replenishment of acini with the unexpected capacity to repopulate the tissue after radiation-induced damage. It was also found that that cholinergic nerves play a vital role in controlling acinar cell replacement during homeostasis and that this neuronal influence can be replicated through addition of cholinergic mimetics to the acinar progenitor cells. Accordingly, by directly targeting acinar progenitor cells within tissue with cholinergic agonists and/or muscarinic agonists or by isolating and expanding acinar progenitor cells for transplantation and activation with cholinergic agonists and/or muscarinic agonists, secretory units of salivary glands can be regenerated to provide recovery of functional salivary acini and treat oral disorders, such as xerostomia following radiation therapy or associated with Sjogren syndrome. Given organs, such as the intestine, glandular stomach, trachea, and taste buds express SOX2, are heavily innervated by the autonomic nervous system and are damaged by therapeutic radiation for the elimination of cancers, such a strategy may be applicable to the repair of multiple organ systems.

In some embodiments, a method of promoting salivary gland regeneration in a subject in need thereof comprises administering to acinar progenitor cells of the salivary gland at least one of a cholinergic agonist or muscarinic agonist to promote acinar cell generation. The cholinergic agonist and/or muscarinic agonist can mimic parasympathetic nerve acetylcholine/muscarinic signaling that was found to maintain acini in human salivary glands. In some embodiments, one or more cholinergic agonists and/or muscarinic agonists are administered locally to the salivary gland to promote acinar cell proliferation and increase saliva production.

In some embodiments, the acinar progenitor cells to which one or more cholinergic agonists and/or muscarinic agonists are administered include $SOX2^+$ acinar progenitor cells. The $SOX2^+$ acinar progenitor cells may include $AQP5^+/Ki67^+$ cells and/or mucin (MUC)19− cells. Exposure of endogenous acinar progenitor cells to the cholinergic agonist and/or muscarinic agonist causes the acinar progenitor cells to proliferate and develop secretory acinar cells. Such treatment can be used to repopulate a salivary gland with functional secretory acinar cells, for example, to treat a subject with an oral disorder e.g., a salivary gland disorder, by restoring salivary flow. The subject can be monitored after treatment for amelioration of the salivary gland disorder and the production and secretion of saliva.

In some embodiments, the cholinergic agonist can be selected from the group consisting of acetylcholine, bethanechol, carbachol, methacholine, arecoline, nicotine, galantamine, cevimeline, levamisole, muscarine, pilocarpine, donepezil, edrophonium, neostigmine, physostigmine, pyridostigmine, rivastigmine, tacrine, caffeine, huperzine, echothiophate, isoflurophate, cisapride, droperidol, domperidone, metoclopramide, risperidone and paliperidone. In other embodiments, the cholinergic agonist can include at least one of acetylcholine or an acetylcholine analogue. For example, the acetylcholine analogue can include carbachol.

In some embodiments, the muscarinic agonist can include agonists that activate muscarinic acetylcholine receptors ("muscarinic receptors"). Muscarinic receptors are divided into five subtypes named M1-M5. Muscarinic agonists can include but are not limited to pilocarpine, aceclidine, xanomeline, talsaclidine, sabcomeline, cevimeline, alvameline, arecoline, milameline, SDZ-210-086, YM-796, RS-86, CDD-0102A (5-[3-ethyl-1,2,4-oxasdiazol-5-yl]-1,4,5,6-tetrahydropyrimidine hydrocholoride), N-arylurea-substituted 3-morpholine arecolines, VUO255-035 (N-[3-oxo-3-[4-(4-pyridinyl)-1-piperazinyl]propyl]-2,1,3-benzothiadiazole-4-sulfonamide), benzylquinolone carboxylic acid (BQCA), WAY-132983, AFB267B (NGX267), AC-42, AC-260584, chloropyrazines including but not limited to L-687, 306, L-689-660, 77-LH-28-1, LY593039, and any quiniclidine ring with one or more carbon substitutions particularly that include an ester, sulfur, or 5 or 6 carbon ring structure including with substituted nitrogen(s) and or oxygen(s), or any pharmaceutically acceptable salts, esters, analogues, prodrugs or derivatives thereof. In some embodiments, a muscarinic agonist selective for an M1 and/or an M3 muscarinic receptor subtype such as cevimeline is used.

The cholinergic agonist and/or muscarinic agonist can be provided in a pharmaceutical composition that can be administered to acinar progenitor cells including $SOX2^+$ acinar progenitor cells in vivo or ex vivo. The pharmaceutical composition may be formulated into various dosage forms. The dosage can be a pharmaceutically or therapeutically effective amount to promoting acinar cell replacement and/or acinar progenitor cell maintenance and survival.

Therapeutically effective dosage amounts of the cholinergic agonist and/or muscarinic agonist described herein may be present in varying amounts in various embodiments. For example, in some embodiments, a therapeutically effective amount of the cholinergic agonist and/or muscarinic agonist may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the 15-PGDH inhibitor is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the 15-PGDH inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount of the cholinergic agonist and/or muscarinic agonist may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. weight.

In still other embodiments, a therapeutically effective dosage amount of the cholinergic agonist and/or muscarinic agonist may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight.

In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage of the cholinergic agonist and/or muscarinic agonist may be a dosage of 10 µg/kg/day, 50 µg/kg/day, 100 µg/kg/day, 250 µg/kg/day, 500 µg/kg/day, 1000 µg/kg/day or more. In various embodiments, the amount of the cholinergic agonist and/or muscarinic agonist is sufficient to provide a dosage to a patient of between 0.01 µg/kg and 10 µg/kg; 0.1 µg/kg and 5 µg/kg; 0.1 µg/kg and 1000 µg/kg; 0.1 µg/kg and 900 µg/kg; 0.1 µg/kg and 900 µg/kg; 0.1 µg/kg and 800 µg/kg; 0.1 µg/kg and 700 µg/kg; 0.1 µg/kg and 600 µg/kg; 0.1 µg/kg and 500 µg/kg; or 0.1 µg/kg and 400 µg/kg.

Various embodiments may include differing dosing regimens. In some embodiments, the cholinergic agonist and/or muscarinic agonist can be administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

Depending on the subject to be treated, the mode of administration, and the type of treatment desired, e.g., prevention, prophylaxis, therapy; the compositions are formulated in ways consonant with these parameters. A summary of such techniques is found in Remington's Pharmaceutical Sciences, latest edition, Mack Publishing Co., Easton, Pa.

The preparation of therapeutic compositions containing small organic molecules polypeptides, analogs or active fragments as active ingredients is well understood in the art. The compositions of the present invention may be administered parenterally, topically, or via an implanted reservoir. Such compositions may be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients, which are pharmaceutically acceptable and compatible with the active ingredient. Suitable excipients are, for example, water, saline, dextrose, glycerol, ethanol, or the like and combinations thereof. The formulation will generally include a diluent as well as, in some cases, adjuvants, buffers, preservatives and the like. In addition, if desired, the composition can contain minor amounts of auxiliary substances such as wetting or emulsifying agents, pH buffering agents, which enhance the effectiveness of the active ingredient.

The compositions may also be administered locally to sites in subjects using a variety of techniques known to those skilled in the art. For example, these may include sprays, lotions, gels or other vehicles, such as alcohols, polyglycols, esters, oils and silicones. The administration of the compositions described herein may be pharmacokinetically and pharmacodynamically controlled by calibrating various parameters of administration, including the frequency, dosage, duration mode and route of administration. Variations in the dosage, duration and mode of administration may also be manipulated to produce the activity required. The therapeutic compositions are conventionally administered in the form of a unit dose, for instance intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions can be administered in a manner compatible with the agent selected for treating the subject, the dosage formulation, and in a therapeutically effective amount. If one desires to achieve the desired effect in vitro, the effective amounts of the cholinergic agonist and/or muscarinic agonist may range from about 0.1 nM to about 10 M, more preferably about 0.1 nM to about 5 M, and most preferably from about 0.1 nM to about 1 M. The desired effect refers to the effect of the agent on promoting acinar cell replacement and/or acinar progenitor cell maintenance and survival. Precise amounts of the active ingredients required to be administered depend on the judgment of the practitioner and are peculiar to each individual.

The agents described herein may be modified or formulated for administration at the site of pathology. Such modification may include, for instance, formulations, which facilitate or prolong the half-life of the compound or composition, particularly in the environment. Additionally, such modification may include the formulation of a compound or composition to include a targeting protein or sequence, which facilitates or enhances the uptake of the compound/composition to acinar progenitor cells. In a particular embodiment, such modification results in the preferential targeting of the compound to $SOX2^+$ acinar progenitor cells in the saliva gland versus other locations or cells.

Sterile injectable forms of the compositions may be aqueous or oleaginous suspensions. The suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents, which are commonly, used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis. The pharmaceutical compositions may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Alternatively, the pharmaceutical compositions may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols. The pharmaceutical compositions of this invention may also be administered topically. Topical application can be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In some embodiments, the cholinergic agonist and/or muscarinic agonist can be formulated to provide controlled release of the cholinergic agonist and/or muscarinic agonist to endogenous salivary acinar progenitor cells. The controlled release can include at least one of a delayed, sustained, gradient, temporal, patterned, or spatial release. Delayed, sustained, gradient, temporal, patterned, or spatial release is a mechanism used in medicine to allow release to the active ingredient over time. The advantages of controlled release formulations are that they delivered less frequently and in defined release patterns than immediate-release formulations of the same active compound.

A controlled release formulation can be designed to release the active agents at a predetermined rate so as to maintain a constant agent level for a specified, extended period of time, such as up to about 1 hour, about 12 hours, about 24 hours, about 2 days, about 3 days, about 1 week, about 2 weeks, about 3 weeks, about 4 weeks or more following administration or following a lag period associated with delayed-release of the agent. In certain embodiments, the active agents are released over a time interval of between about 1 week to about 2 weeks or more. Alternatively, the active agents may be released for at least 1 week, at least 2 weeks, at least 3 weeks, or up to 14 days, up to 20 days, up to 30 days, or longer. In yet other embodiments, the active agents are released over a time period between about 1 week to about 3 weeks or more following administration.

In other embodiments, the cholinergic agonist or muscarinic agonist is provided in a biocompatible carrier, matrix, or scaffold that can be administered to a subject. By way of example, the biocompatible substrate can include a polymeric macro- or micro-scaffold and at least one carrier material incorporated on or within the polymeric macro- or micro-scaffold. The at least one carrier material, matrix, or scaffold can include a material capable of carrying and differentially and/or controllably releasing at least one cholinergic agonist or muscarinic agonist to endogenous salivary acinar progenitor cells.

The carrier, matrix or scaffold may be of any material that will allow the cholinergic agonist and/or muscarinic agonist to be incorporated and may be compatible with the addition of expanded acinar progenitor cells (e.g., SOX2$^+$ cells) or in the presence of cells. The carrier, matrix, or scaffold can be predominantly non-immunogenic and biodegradable. Examples of biodegradable materials include, but are not limited to, alginate, polyglycolic acid (PGA), polylactic acid (PLA), hyaluronic acid, catgut suture material, gelatin, cellulose, nitrocellulose, collagen, albumin, fibrin, cotton, or other naturally occurring biodegradable materials. It may be preferable to sterilize the matrix or scaffold material prior to administration or implantation, e.g., by treating it with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids, such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof.

Suitable matrices include a polymeric mesh or sponge and a polymeric hydrogel. A hydrogel is defined as a substance formed when an organic polymer (natural or synthetic) is cross-linked via covalent, ionic, or hydrogen bonds to create a three-dimensional open-lattice structure, which entraps water molecules to form a gel. In general, these polymers are at least partially soluble in aqueous solutions, such as water, buffered salt solutions, or aqueous alcohol solutions that have charged side groups, or a monovalent ionic salt thereof.

In some embodiments, the matrix is biodegradable over a time period of less than a year, more preferably less than six months, most preferably over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.).

For example, a muscarinic agonist can be encapsulated in an alginate hydrogel. In some embodiments, the encapsulated muscarinic agonist is selective for an M1 and/or an M3 muscarinic receptor subtype (e.g., cevimeline). In other embodiments, the muscarinic agonist is a nonselective muscarinic agonist (e.g., pilocarpine). The alginate in the hydrogel may be ionically cross-linked with divalent cations (see, e.g., Example 2 for a description of a biodegradable calcium crosslinked alginate hydrogel encapsulating cevimeline). In some embodiments, the alginate concentration in the hydrogel ranges from about 2 to about 10 percentage by weight (wt %), including any wt % within this range, such as 2, 2.5, 3, 3.5, 4, 4.5, 5, 5.5, 6, 6.5, 7, 7.5, 8, 8.5, 9, 9.5, or 10 wt %. In some embodiments, the alginate is partially oxidized. For example, about 2% to about 10% of the alginate may be oxidized, including any percent in this range, such as 2%, 2.5%, 3%, 3.5%, 4%, 4.5%, 5%, 5.5%, 6%, 6.5%, 7%, 7.5%, 8%, 8.5%, 9%, 9.5%, or 10%. In one embodiment, the alginate in the hydrogel is about 2% oxidized and at a concentration of 5 wt %. Such alginate hydrogels are capable of sustaining delivery of a muscarinic agonist for at least 7 days after administration to a subject (see, e.g., Example 2)

Compositions comprising an encapsulated cholinergic agonist and/or muscarinic agonist are suitable for local delivery to the salivary gland. A medical practitioner may locate the salivary gland to be injected, for example, by palpation or medical imaging (e.g. ultrasound, radiography, or MRI). In some embodiments, a contrast agent is included in the composition comprising the encapsulated cholinergic agonist and/or muscarinic agonist to allow confirmation of localization of the composition to the salivary gland by medical imaging after administration. In some embodiments, the contrast agent is a microbubble (e.g., for use in ultrasound) or a radiopaque contrast agent (e.g., for use in radiography). The contrast agent may be contained in the same composition as the cholinergic agonist and/or muscarinic agonist or in a different composition and used prior to or after administration of the cholinergic agonist and/or muscarinic agonist.

In certain embodiments, the composition is injected into the salivary gland or adjacent to the salivary gland. Salivary glands that may be treated by the subject methods include, without limitation, parotid, submandibular, and sublingual glands as well as minor salivary glands, including serous, mucous, or seromucous salivary glands.

In some embodiments, the subject being treated has an oral disorder, such as a disorder that effects the production of saliva. Examples of oral disorders include, but are not limited to, salivary gland tumors, cystic fibrosis, Sjogren's syndrome, sialoadenitis, parotitis, sialoangitis, sialodochitis, sialolithiasis, sialodocholithiasis, mucocele, ranula, hyposecretion, ptyalism, sialorrhea, xerostomia, benign lymphoepithelial lesion of salivary gland; sialectasia; sialosis; stenosis of salivary duct; and stricture of salivary duct. In other embodiments, the subject can have been previously treated with radiation effective to cause xerostomia. The methods described herein can be used for treating a human subject for such an oral disorder that effects production of saliva (e.g., xerostomia). The methods described herein will also find use in veterinary applications for treatment of xerostomia, for example, in domestic animals including, without limitation, pets, such as dogs and cats, and farm animals, such as sheep, goats, pigs, horses and cattle.

Kits

Also provided are kits for treating a subject for xerostomia with at least one of a cholinergic agonist or muscarinic agonist to promote acinar cell generation. Cholinergic agonists and/or muscarinic agonists may be contained in separate compositions or in the same composition. Kits may include unit doses of the formulations comprising the cholinergic agonists and/or muscarinic agonists suitable for use in the treatment methods described herein, e.g., injectable dose(s). In such kits, in addition to the containers containing the unit doses will be an informational package insert describing the use and attendant benefits of the treatment for xerostomia. The kit can include, for example, a dosing regimen for the cholinergic agonists and/or muscarinic agonists included in the kit.

Formulations suitable for local administration to a saliva gland are of particular interest, and in such embodiments the kit may further include one or more syringes or other devices to accomplish such administration. In some embodiments, the kit includes a first syringe or device pre-filled with a composition (e.g., a muscarinic agonist such as cevimeline encapsulated in an alginate hydrogel, which may be stored frozen). The kit may further include a second syringe filled with calcium chloride, which can be connected to the first syringe through a luer lock. The kit may be used, for example, by thawing the contents of the first syringe (e.g., cevimeline encapsulated in an alginate hydrogel) and mixing with the contents of the second syringe (e.g., $CaCl_2$, which generates a calcium cross-linked alginate hydrogel encapsulating the cevimeline) before injection into a salivary gland. A medical practitioner may locate the salivary gland to be injected, for example, by palpation or ultrasound.

In some embodiments, the kit further comprises a contrast agent to allow confirmation of localization of the composition comprising the muscarinic agonist (e.g., cevimeline encapsulated in an alginate hydrogel) to the salivary gland by medical imaging after administration. In some embodiments, the contrast agent is a microbubble (e.g., for use in ultrasound) or a radiopaque contrast agent (e.g., for use in radiography). The contrast agent may be contained in the same composition as the muscarinic agonist or in a different composition and added prior to or after administration of the muscarinic agonist.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Other embodiments described herein will be apparent to those skilled in the art from consideration of the specification and practice of the invention disclosed herein. All U.S. patents and other references noted herein for whatever reason are specifically incorporated by reference. The specification and examples should be considered exemplary only with the true scope and spirit of the invention indicated by the following claims.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Regeneration of Salivary Acini after Radiation in Response to Cholinergic Activation Through a Progenitor Cell-Dependent Mechanism Introduction Therapeutic radiation continues to be a life-saving treatment for cancer patients and is utilized for a spectrum of malignancies including those of the head and neck. Indeed, the vast majority of patients suffering head and neck cancer will receive radiotherapy in addition to chemotherapy and surgery (~60,000 new patients per year in US; Siegel et al., 2015). Although this combination treatment is highly efficacious in eliminating tumors, a severe side effect is damage and/or destruction of healthy tissue lying in the field of radiation. Such organs include the salivary glands, which exhibit tissue dysfunction even after low doses of radiation (Grundmann et al., 2009). At the higher doses routinely given to patients (60 Gy), off-target radiation destroys saliva-synthesizing acinar cells (Sullivan et al., 2005; Redman, 2008) and results in a lifetime of dry mouth and co-morbidities (e.g., tooth decay, oral infections, poor wound healing (Brown et al., 1975; Dreizen et al., 1977; Dusek et al., 1996). Although there has been success with intensity modulated radiation to spare one of the three major salivary glands (parotid), the proximity of the glands to the tumor sites often prevents application of this technique, leaving 80% of head and neck cancer patients with dry mouth syndrome (Lee & Le, 2008).

As with all other organs damaged by radiation, including the lungs, heart, and bladder (Emami et al., 1991) there are few, if any, treatments available to improve or restore tissue function. Current treatment options for cancer survivors suffering radiation-induced salivary dysfunction and degeneration focus on short-term relief from the symptoms, but no long-term restorative therapies are available. Regenerative strategies such as reactivating endogenous stem cells or transplanting non-irradiated stem cells have been proposed (Lombaert et al., 2008; Ogawa et al., 2013; Pringle et al., 2016). However, these applications are curtailed by the dearth of knowledge regarding the identity of adult salivary progenitor cells that contribute to acini under homeostatic or injury conditions. Although it was recently proposed that acinar cells are derived through self-duplication rather than from defined progenitors (Aure et al., 2015), an analysis of subpopulations of these cells for progenitor-like activity was not performed. It also remains to be determined whether acinar cells, either through self-duplication or through progenitor cell expansion, are capable of repopulating cells after genotoxic damage. Although a plethora of studies have utilized irradiated salivary glands as a model of degeneration (Zeilstra et al., 2000; Coppes et al., 2001, 2002), the regenerative capacity of adult salivary cells damaged by radiation has not been investigated in vivo.

How acinar cells are replaced during salivary gland homeostasis is also poorly understood. Studies in adult organs over the last 150 years have clearly shown that peripheral nerves are essential for the maintenance of organ and tissue integrity (Erb, 1868). Skeletal muscle atrophies in the absence of stimulation by motor neurons (Fu & Gordon, 1995; Batt & Bain, 2013) and epithelial organs such as fungiform taste buds (Von Vintschgau & Honigschmied, 1877), prostate (Wang et al., 1991; Lujan et al., 1998) and the salivary gland degenerate after ablation of sensory and/or autonomic nerves (Schneyer & Hall, 1967; Mandour et al., 1977; Kang et al., 2010). Although it is unclear how nerves control tissue homeostasis for these organs, studies in skin indicate sensory nerves, through sonic hedgehog secretion, promote the self-renewal of adult epithelial stem cells and consequently the maintenance of the downstream cell lineage, that is, dome cells in the skin (Peterson et al., 2015; Xiao et al., 2015). In addition, studies in the salamander (Wallace, 1972) and embryonic salivary gland (Knox et al., 2013) suggest that peripheral nerves have the capacity to regenerate tissue via activation of multipotent stem cells, but evidence for this in the adult mammalian system is lacking.

Using a combination of mouse genetics, ex vivo cultures, and human tissue explants, we unexpectedly discover that salivary acini are capable of regenerating after radiation and do so in response to cholinergic activation through a progenitor cell-dependent mechanism. We show that SOX2 marks the sole progenitor for the acinar lineage that can replace acinar cells during homeostasis and after radiation-induced injury, indicating that salivary progenitors can withstand, at least in the short term, genotoxic shock. Importantly, treatment of healthy and irradiated tissue with cholinergic mimetics stimulated acinar cell replenishment. Thus, our data reveal the extensive regenerative capacity of the tissue even under genotoxic shock and suggest that targeting of SOX2$^+$ cells might be a therapeutic approach to regenerate tissue damaged by radiation therapy.

Results

Figure 1A:
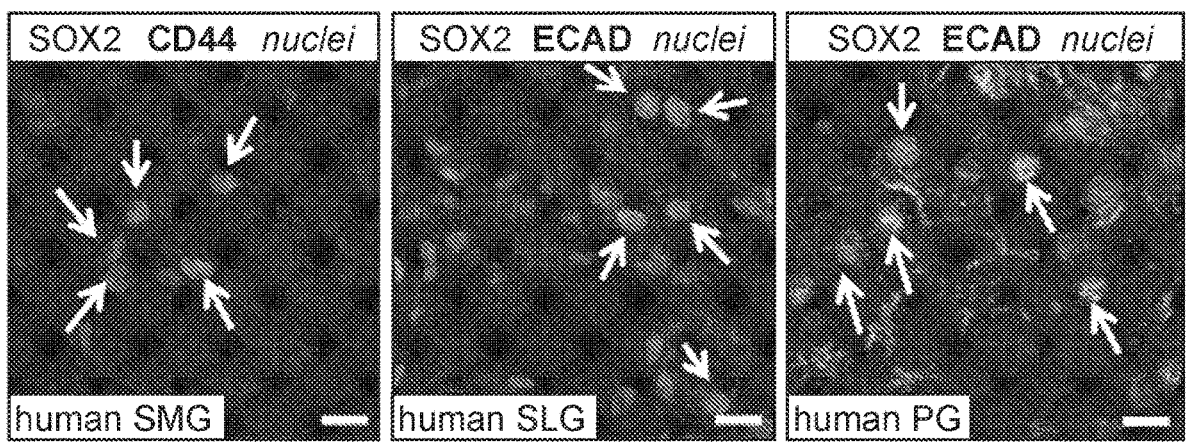
FIGS. 1A-1F show SOX2 marks a progenitor cell that gives rise to acinar but not duct cells in the adult salivary gland.
Figure 1B:
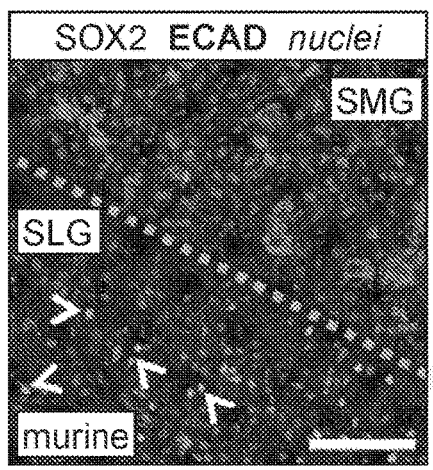
Figure 1C:
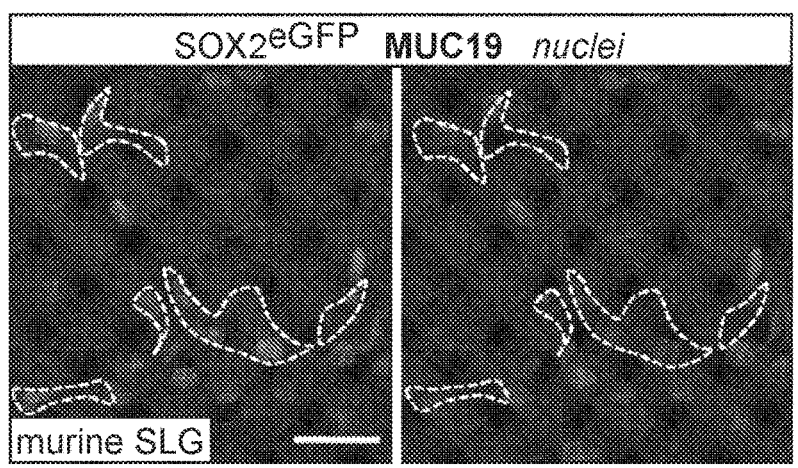
Figure 1D:
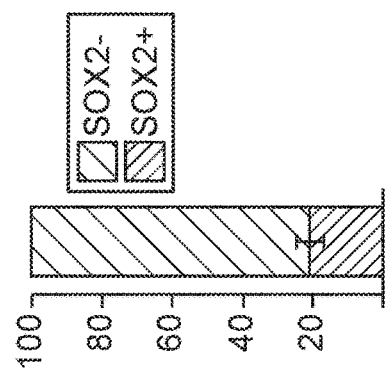
Figure 1E:
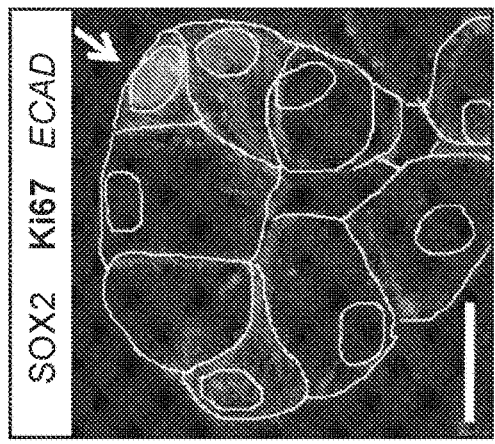
Figure 1F:
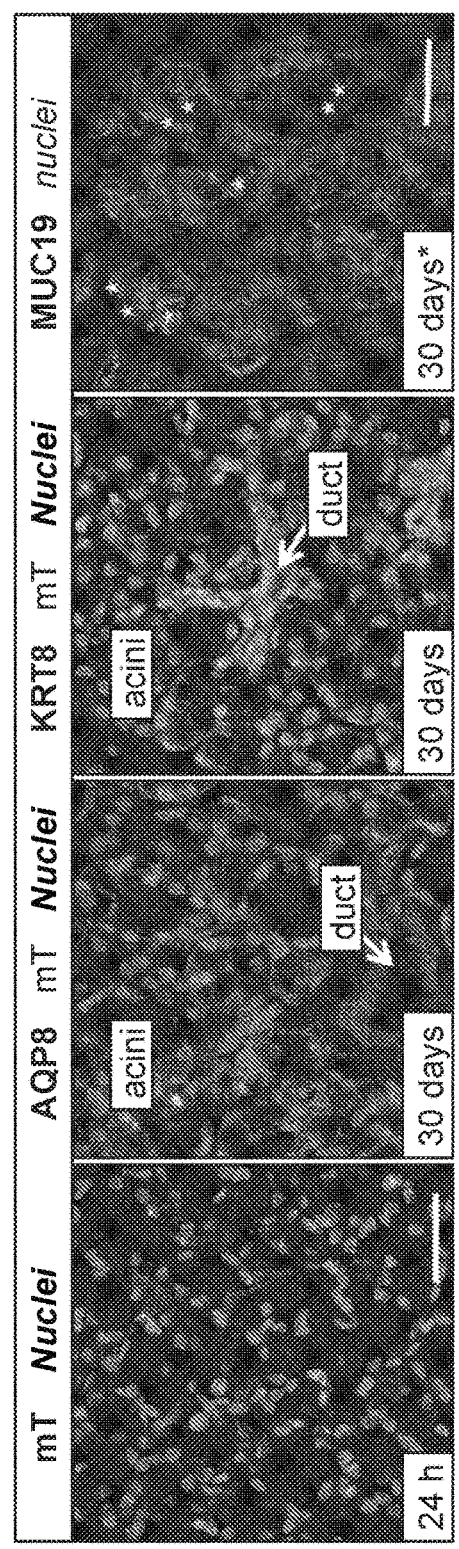

SOX2 Marks a Progenitor Cell that Gives Rise to Acinar but not Duct Cells During Salivary Gland Homeostasis SOX2 has been established as a progenitor cell marker in the fetal mouse submandibular and sublingual salivary glands, but whether SOX2$^+$ cells in the adult tissue also produce acinar and duct cells is unclear (Arnold et al., 2011; Emmerson et al., 2017). Furthermore, whether these cells are also present in adult human salivary glands is not known. We found SOX2 to be expressed by a subset of acinar cells in all three of the major adult human salivary glands [FIG. 1A, submandibular gland (SMG), sublingual gland (SLG), parotid gland (PG)]. In the mouse, SOX2 protein was restricted to the adult murine SLG (absent from the SMG and PG, FIGS. 1B and 10A) where it was expressed by undifferentiated aquaporin (AQP)5-positive, mucin (MUC) 19-negative acinar cells (21±4% of all AQP5$^+$ acinar cells; FIGS. 1C and 1D). Consistent with their potential role as a progenitor cell, ~6% of SOX2$^+$AQP5$^+$ cells co-expressed Ki67 (FIGS. 1E and 10B) while 19±4% were in the cell cycle (CyclinD1$^+$; FIG. 10C). To determine whether SOX2$^+$ cells contributed to acinar and duct lineages, we performed genetic lineage tracing using Sox2$^{CreERT2}$ mice (Arnold et al., 2011) crossed to a Rosa26$^{mTmG}$ reporter strain. The Rosa26$^{mTmG}$ mouse is a double-fluorescent reporter which when crossed with a Cre line expresses membrane-targeted tandem dimer Tomato (mT) prior to Cre-mediated excision and membrane-targeted green fluorescent protein (mG) after excision (Muzumdar et al., 2007; FIG. 10D). As such, lineage-traced cells will express mG. As shown in FIG. 1F, SOX2$^+$ cells self-renew and produce differentiated acinar cells marked by AQP5 and MUC19 but not KRT8$^+$ duct cells after 14 or 30 days (FIG. 1F and EV1E). Thus, our lineage tracing results indicate that SOX2$^+$ cells are lineage-restricted progenitor cells that give rise to differentiated progeny, similar to what has been observed in the epidermis, intestine, and incisor (Owens & Watt, 2003; Barker, 2014; Seidel et al., 2017).

Given KIT$^+$ cells, which reside primarily in the intercalated ducts of the SLG and SMG (Andreadis et al., 2006; Nelson et al., 2013), have previously been proposed to give rise to acinar cells in adult tissue (Lombaert et al., 2008; Nanduri et al., 2013, 2014; Pringle et al., 2016), we genetically traced these cells using the Kit$^{CreERT2}$ promoter crossed to the Rosa26$^{mTmG}$ reporter at 6 weeks of age. However, no KIT$^+$ cell-derived acinar cells (i.e., double positive for AQP5 and mG) were evident in either the SLG or SMG at 14 days or 6 months after induction (FIG. 10F). Instead, KIT$^+$ cells contributed exclusively to the intercalated ducts in the SLG (as can be observed by co-staining for the intercalated duct marker KRT8) and intercalated and larger ducts in the SMG. Thus, these data indicate that KIT$^+$ cells are progenitors for the ductal and SOX2$^+$ cells for the acinar lineage.

SOX2 and SOX2+ Cells are Essential for Production of Secretory Acini

Figure 2C:
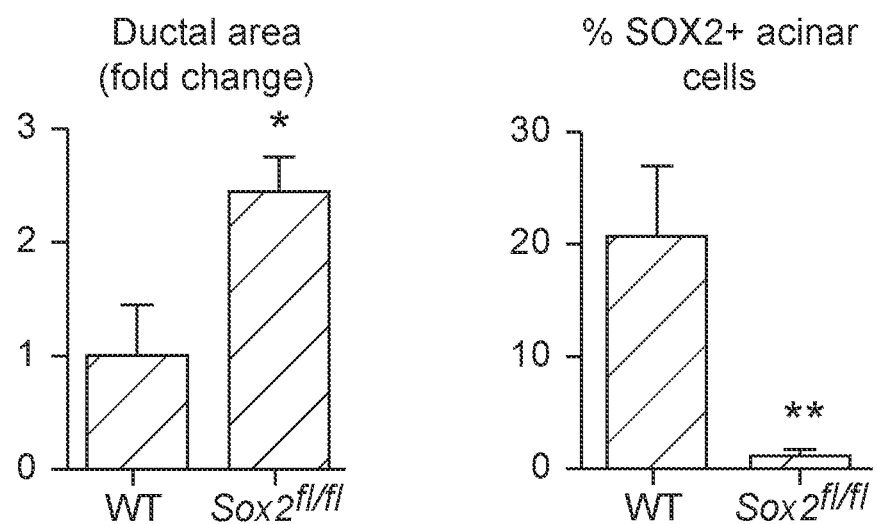
Figure 2D:
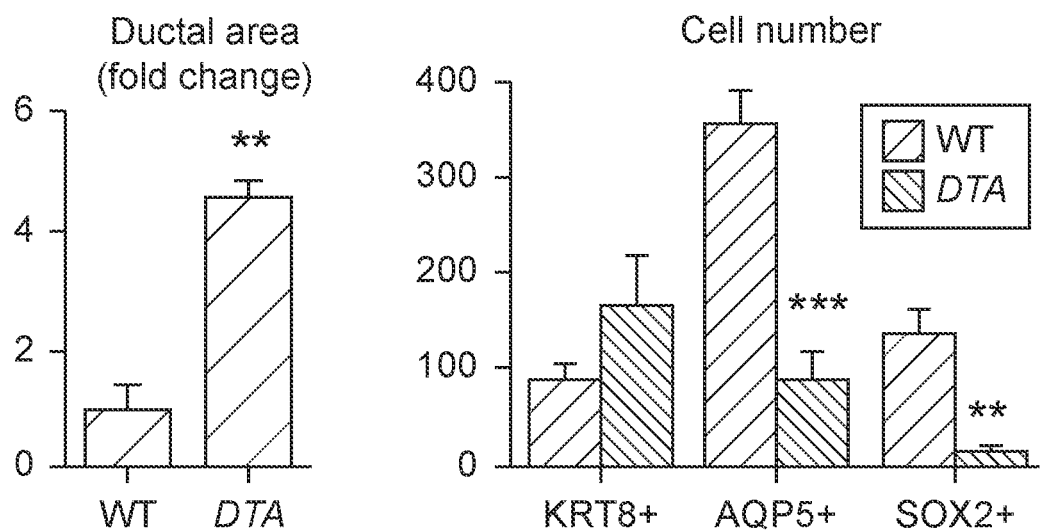

Our lineage tracing analysis confirmed that SOX2+ cells give rise to acinar but not duct cells. However, as we also observed the presence of Ki67+SOX2− acinar cells (~6% SOX2+Ki67+ and 16.5% SOX2−Ki67+ cells, FIG. 10B), suggestive of an alternative progenitor cell or a transit-amplifying cell for the acinar lineage, we investigated the requirement of SOX2 and SOX2+ cells in SLG maintenance and repair by genetically removing Sox2 in SOX2+ cells using $Sox2^{CreERT2}$; $Sox2^{fl/fl}$ mice (FIGS. 2A and 2C) or ablating SOX2+ cells using diphtheria toxin (DTA) expressed under the control of the inducible Sox2 promoter ($Sox2^{CreERT2}$; $Rosa26^{DTA}$; FIGS. 2B and 2D). In the latter assay, SOX2+ cells undergo cell death in response to intracellular production of DTA. Ablation of Sox2 from SOX2+ cells or elimination of SOX2+ cells via DTA severely depleted SOX2+ and AQP5+ cells but not KRT8+ ductal cells indicating Sox2 and SOX2+ cells were necessary for maintaining functional acini (FIGS. 2A-2D; efficiency of Sox2 or SOX2+ cell ablation is shown in FIG. 11A). In the absence of Sox2, acinar but not ductal cells exited the cell cycle, as shown by the decrease in cyclin D1 (COND1)+ acinar cells (FIG. 11D; arrowheads indicate COND1+ cells and dotted white lines highlight ductal cells). Furthermore, ablation of SOX2+ cells resulted in few remaining acini by 8 days (FIGS. 2B and 2D, and 11A), as shown by large regions of the ductal network completely devoid of AQP5+ cells (ducts are marked by dashed lines or KRT8 in FIG. 2B). To exclude the possibility that tissue degeneration was solely due to destabilization of the tissue rather than loss of acinar cell replacement, we examined SLG after a short-term ablation. As shown in FIG. 8, at day 4 or 5 (3 or 4 days of tamoxifen treatment), few SOX2+ cells remained in the gland of both the $Sox2^{CreERT2}$; $Sox2^{fl/fl}$ and $Sox2^{CreERT2}$; $Rosa26^{DTA}$ SLG (FIGS. 8A and 8B) and Sox2 transcripts were substantially reduced (FIG. 8B). However, acini were present albeit disorganized and atrophic in appearance. Furthermore, we did not observe an increase in SOX2+ cells (or Sox2 transcripts), indicating that SOX2 is not ectopically expressed in acinar cells in response to tissue damage. We also determined whether alterations in tissue composition were due to reduced innervation, an essential regulator of tissue function. However, we measured similar innervation in $Sox2^{CreERT2}$; $Sox2^{fl/fl}$ SLG to wild-type controls and a significant increase in axon bundles in $Sox2^{CreERT2}$; $Rosa26^{DTA}$ SLG (FIGS. 11B and 11C). The latter finding suggests ablation of cells triggers the release of factors that promote innervation but that, even with increased innervation, regeneration is not possible without SOX2+ cells. In sum, these results indicate that SOX2+ cells, at least under the conditions tested, are the sole acinar progenitors in the SLG and that acini do not arise from the self-duplication of fully differentiated acinar cells, as suggested previously (Aure et al., 2015). Similar to studies in the epidermis, intestine, and incisor (Owens & Watt, 2003; Barker, 2014; Seidel et al., 2017), our data also suggest the presence of a transit-amplifying population derived from SOX2+ cells that may be involved in rapidly repopulating the acinar compartment.

Parasympathetic Nerves Preserve SOX2+ Progenitors and Promote SOX2-Mediated Acinar Cell Replacement Adult murine and human salivary glands atrophy after removal of parasympathetic activity. However, the effect of denervation on acinar cell replacement and progenitor cells has not been investigated (Garrett et al., 1999; Raz et al., 2013). To this end, we denervated one of the two pairs of murine SLGs by transecting the chorda tympani (FIG. 3A; contralateral glands were used as internal controls). After 7 days, transcript levels of neuronal genes Tubb3, Vip, and Vacht (FIG. 3B, red bars) and GFRa2+ or TUBB3+ nerves (FIGS. 3C and 12C) were severely reduced, indicating successful denervation. We did not observe a concurrent loss of the cholinergic muscarinic receptors Chrm1 and Chrm3 transcripts (FIG. 3B, red bars); however, it is possible that in the absence of parasympathetic innervation a compensatory mechanism may maintain Chrm1 and Chrm3 transcription. Although the SLG is predominately served by the parasympathetic branch with very little sympathetic innervation in comparison (Emmelin et al., 1965), we did observe a reduction in sympathetic innervation following chorda tympani transection (FIG. 12A). As such, although the levels of sympathetic nerves are minor, we cannot rule out that some of the effects of denervation may be due to a loss of sympathetic input.

Figure 3A:
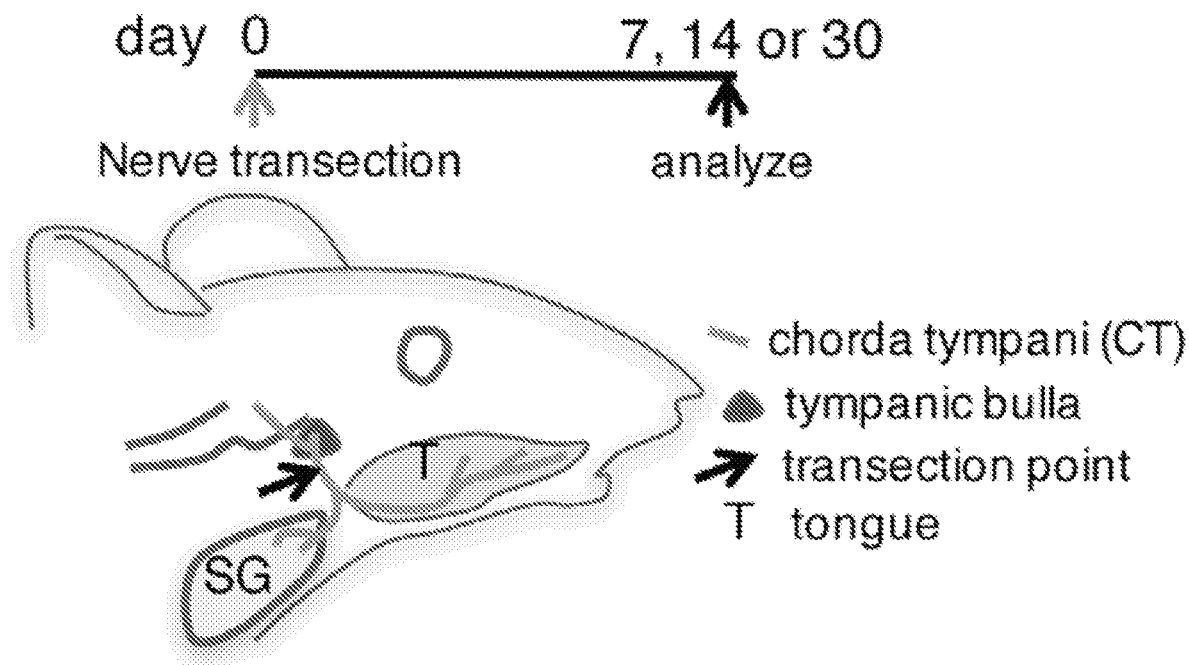
Figure 3B:
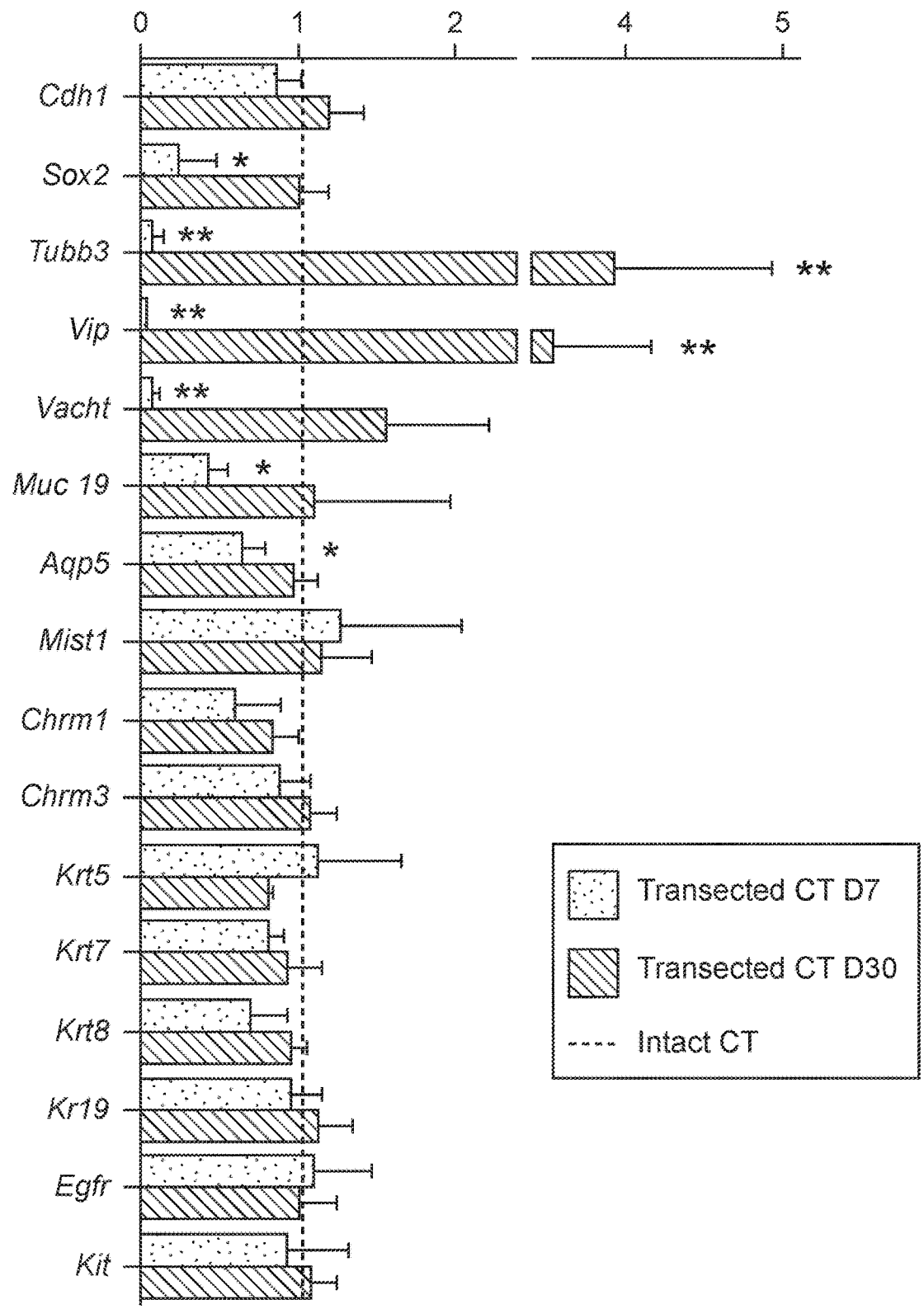
Figure 3C:
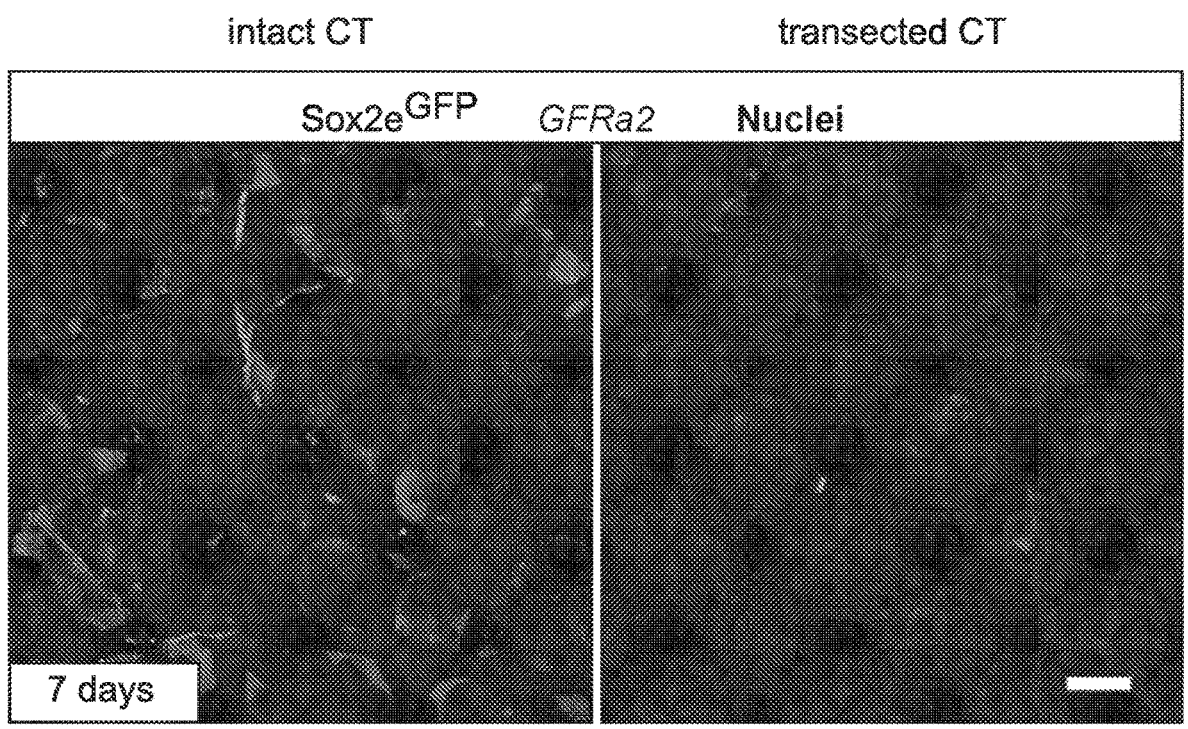
Figure 3D:
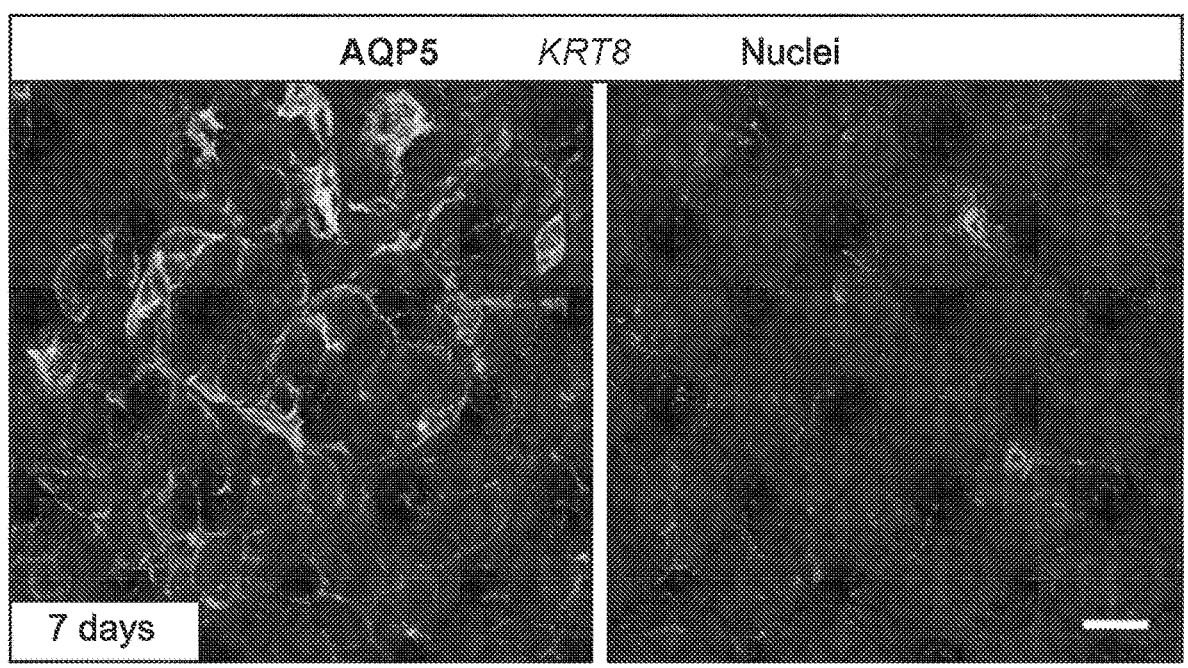
Figure 3E:
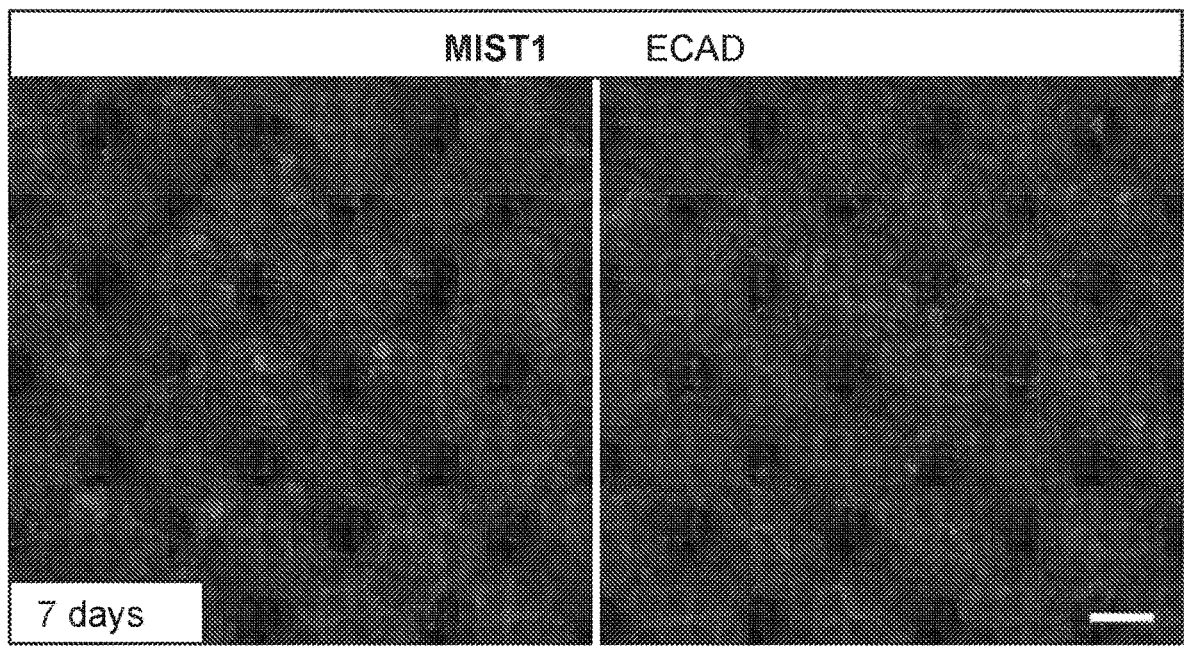

Similar to the effect of radiation therapy on tissue structure (Sullivan et al., 2005; Redman, 2008) adult acinar cells, as well as SOX2+ progenitors, were more sensitive to the loss of innervation than ducts. Denervation resulted in reduced acinar cell size (as observed previously; Patterson et al., 1975; FIG. 12B) decreased AQP5 protein and transcript levels of the differentiated acinar cell marker Muc19 (FIGS. 3B and 3D). Interestingly, transcript and protein levels of MIST1 were unchanged following denervation (FIGS. 3B, 3E and 3F), suggesting that while functional markers of acinar cells are disrupted in the absence of innervation, acinar cell identity is not adversely affected. Strikingly, SOX2+ cells lose expression of Sox2 (demonstrated using the $Sox2^{eGFP}$ mouse) and the levels of SOX2 protein and transcript were greatly reduced (FIGS. 3B, 3C and 3F, and 12C), indicating SOX2 maintenance requires innervation. To determine whether SOX2+ cells remained capable of repopulating the tissue after denervation, we performed genetic lineage tracing where Cre driven by the endogenous Sox2 promoter ($Sox2^{CreERT2}$ $Rosa26^{mTmG}$) was activated 3 days after denervation and traced until day 14. As shown in FIGS. 3G and 3H, acinar cell replacement by SOX2+ progenitors was significantly reduced (~50%) 14 days after transection. Similarly, in SLG in which recombination was induced before nerve transection (tamoxifen 1 day prior to transection), acinar cell replacement by SOX2+ progenitors was significantly depleted (~50%) after 14 days (FIGS. 12E and 12F). Reduced acinar cell replacement is likely due to decreased cell proliferation rather than cell death as we measured a reduction in Ccnd1, while markers of cell death [activated caspase-3 (CASP3+) cells in FIG. 12G or Bax, Pmaip1 (NOXA) and Bbc3 (PUMA) in FIG. 12H)] were either not observed or remained unchanged. The absence of cell death also suggests that cells that were previously positive for SOX2 continue to be present but that cholinergic innervation is essential for maintaining SOX2 expression.

Figure 3F:
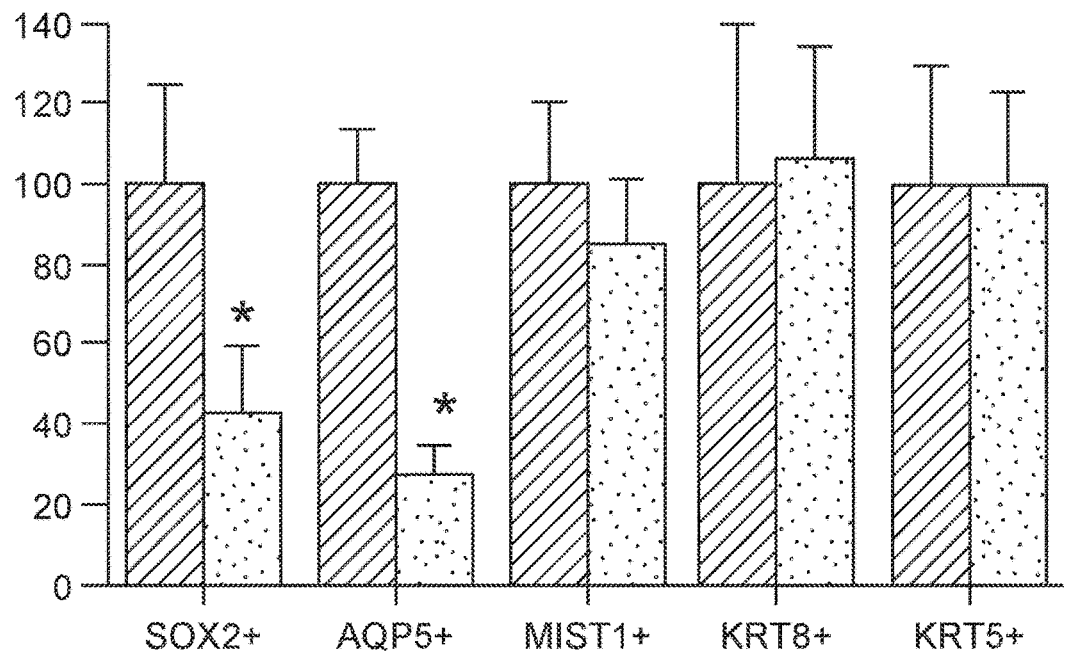

To confirm that denervation preferentially affects the acinar lineage in the SLG, we also analyzed other epithelial cell lineages. KRT8+ ducts in denervated glands resembled innervated controls, as did transcript levels of the ductal genes Krt7, Krt8, and Krt19 (FIGS. 3B, 3D and 3F). Furthermore, KRT5+ cells, progenitors in developing SMG/SLG (Knox et al., 2010; Lombaert et al., 2013) that are maintained by parasympathetic nerves (Knox et al., 2010), were unaffected by denervation (FIGS. 3F and 12; for transcript Krt5 expression see FIG. 3B). Based on these findings, we conclude that parasympathetic innervation is required for adult SLG tissue homeostasis by preferentially maintaining and replacing functional acini through regulation of SOX2 and SOX2+ cells.

To determine whether resupplying salivary gland with nerves could rescue acini and SOX2, we examined murine salivary gland 30 days after denervation. Due to the plasticity of the peripheral nervous system, murine salivary glands become reinnervated over time, as shown by the reappearance of TUBB3+ nerves 30 days after transection (FIG. 9A) and reexpression of the neuronal genes Tubb3, Vip, and Vacht (FIG. 3B, blue bars; Yawo, 1987). Surprisingly, we found elevated expression of these neuronal genes at day 30 (FIG. 3B), suggestive of hyperinnervation, in response to the original injury. Remarkably, upon reinnervation the levels of Sox2 and Aqp5 transcripts and SOX2 protein as well as numbers of SOX2+ and AQP5+ cells and acinar cell size returned to at or above control levels (FIGS. 3B and 9A-9C).

Figure 4A:
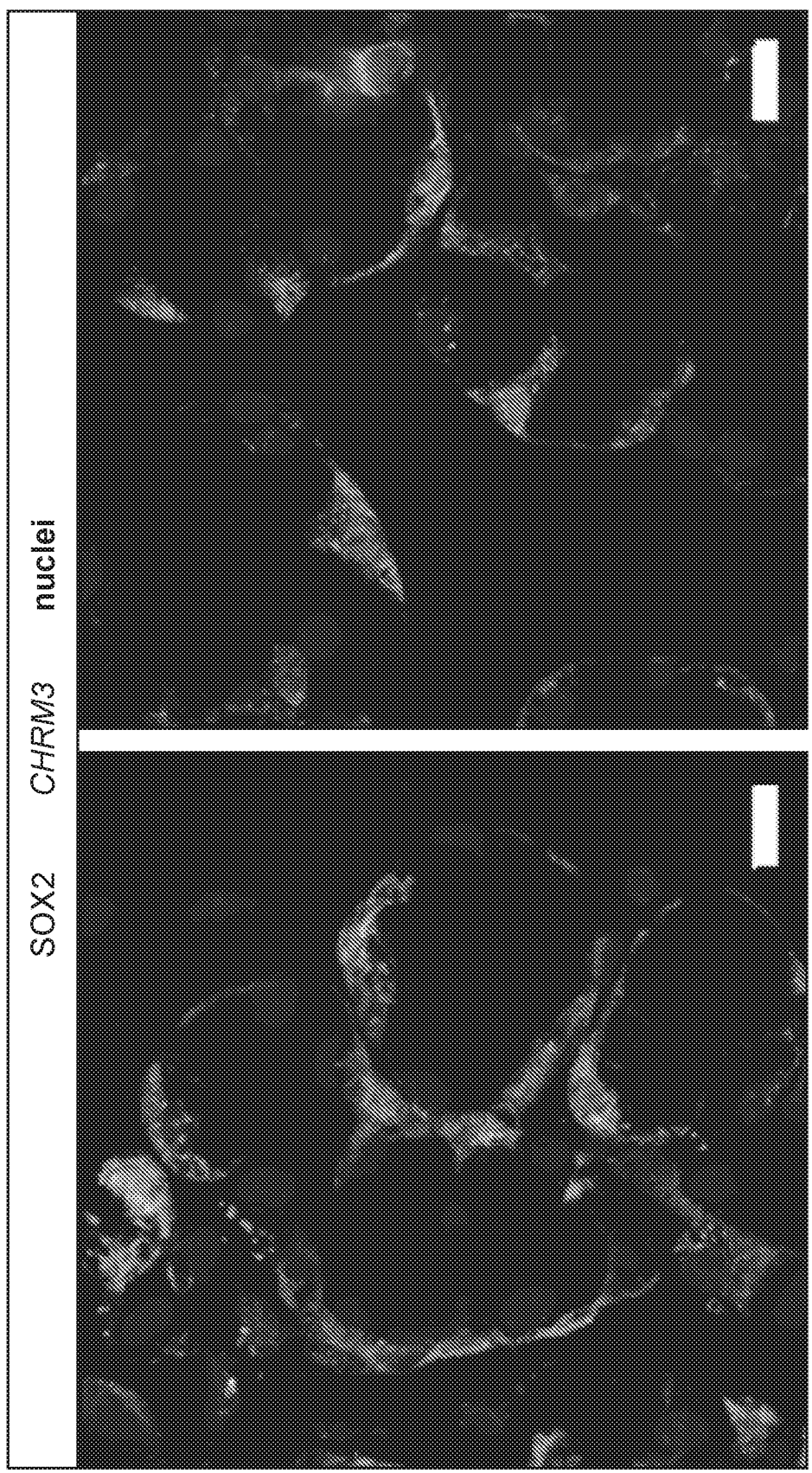
FIGS. 4A-4D show that muscarinic signaling promotes SOX2⁺ cell proliferation.
Figure 4B:
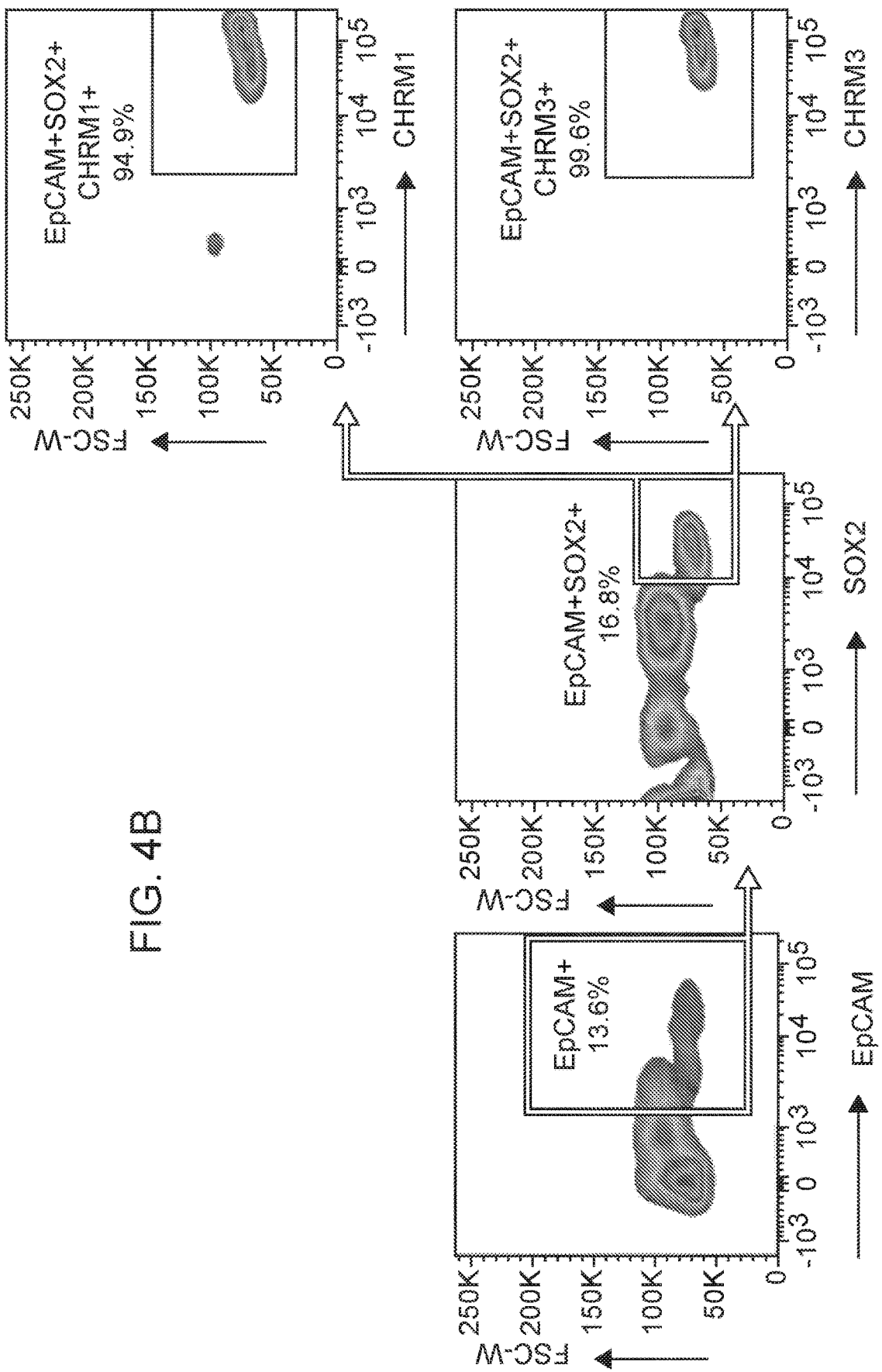
Figure 4C:
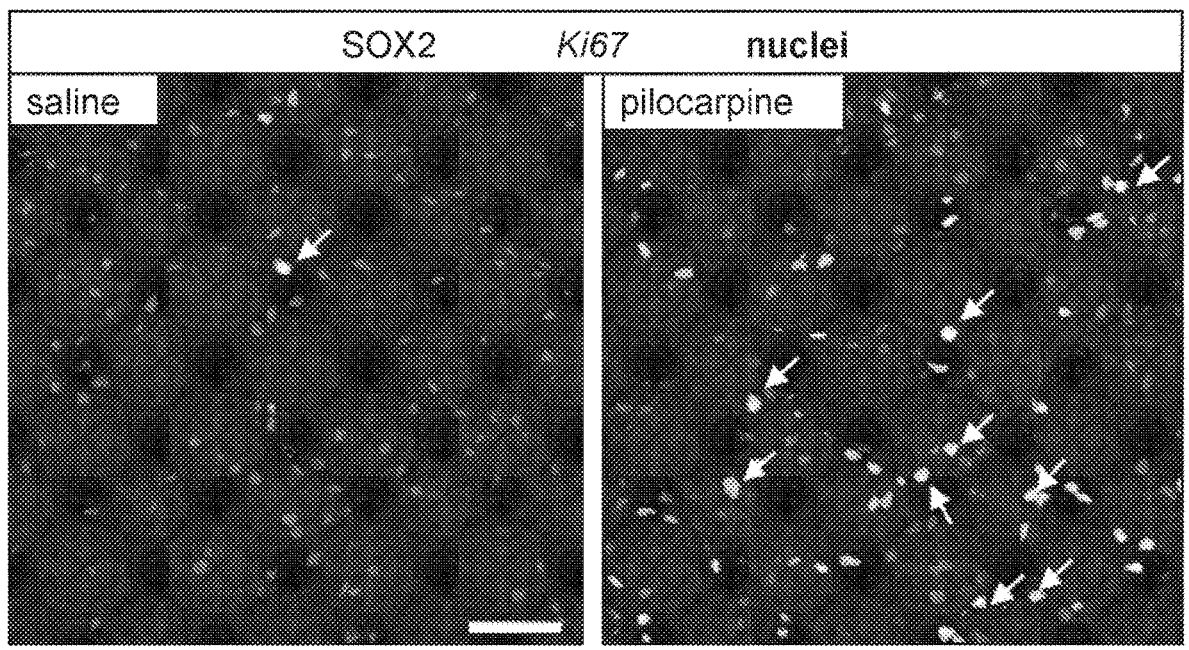
Figure 4D:
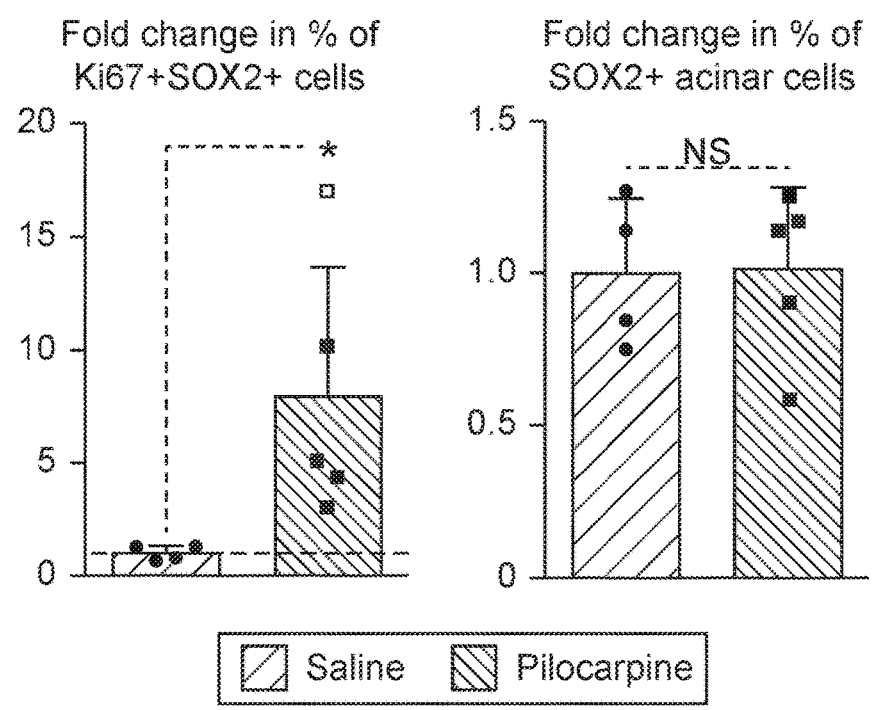

To ensure that SOX2+ cells of the SLG were capable of responding directly to acetylcholine produced by the parasympathetic nerves, we analyzed expression of acetylcholine/muscarinic receptors by SOX2+ cells as well as their ability to respond to muscarinic agonists in vivo. SOX2+ cells expressed both CHRM1 and CHRM3 (95 and 99%, respectively; FIGS. 4A and 4B) and short-term treatment of wild-type mice with the muscarinic agonist pilocarpine (delivered I.P. and sacrificed at 18 h) increased the percentage of proliferating SOX2+ cells (SOX2+Ki67+ cells; FIGS. 4C and 4D). The percentage of SOX2+ cells, however, was not significantly changed by 18 h post-injection (FIG. 4D), indicating that muscarinic activation does not induce ectopic expression of SOX2. Thus, these data support our hypothesis that parasympathetic nerves via acetylcholine muscarinic signaling maintain SOX2+ progenitors and acini and promote acinar cell replenishment.

Murine Salivary Glands Regenerate after Radiation-Induced Damage Via SOX2

Figure 5D:
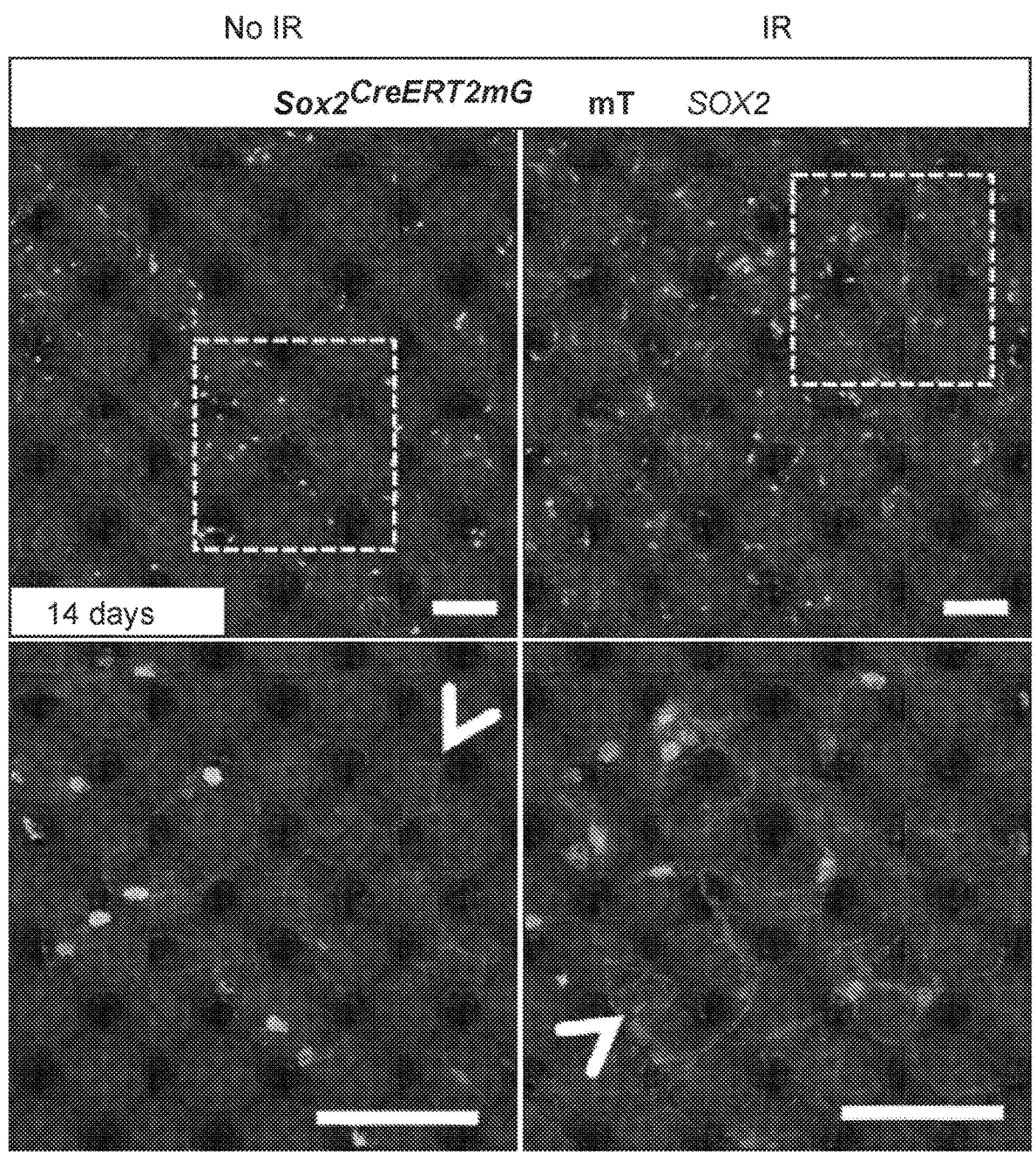

The murine salivary gland (predominantly the SMG) has been used extensively to investigate the effects of ionizing radiation (IR) on glandular function and structure, where typical analysis is limited to degenerative responses. The C57BL/6 background has been reported to undergo loss of acinar cells and a decline in salivary flow rate after a single 10 Gy dose (Zeilstra et al., 2000; Coppes et al., 2001, 2002). However, the regenerative capacity of the tissue and whether it remains innervated after IR are unknown. To test the effect of radiation on SOX2-mediated salivary gland regeneration, we analyzed innervation, SOX2+ cells and SOX2-mediated acinar cell replenishment in murine SLG after a single dose of gamma-radiation to the head and neck. Similar to previous studies in salivary glands (Avila et al., 2009), we found a 10 Gy dose induces DNA damage and cell cycle arrest, as well as reduces cell proliferation in the SLG in the first day following IR, as shown by a substantial increase in the pro-apoptotic gene Bax and the cell cycle inhibitor Cdkn1a (p21) (FIG. 13A) and a reduction in transcript levels of the cell proliferation marker Mki67 (FIG. 13A). We then measured changes in innervation and nerve function in IR SLG by immunolabeling for TUBB3+ nerves and performing semi-quantitative PCR (qPCR) for Tubb3 and the parasympathetic nerve-derived neurotransmitter Vip. As shown in FIGS. 5A and 5B TUBB3+ nerves were unchanged in the IR SLG compared to non-IR controls 1 and 3 days after radiation. However, transcript levels of Tubb3 and Vip were significantly reduced at 1 and 3 days following IR, suggesting nerve function is reduced at early stages (FIG. 13B). Similarly, transcripts for Sox2, Mist1, and Aqp5 were reduced immediately following IR but returned to control levels by day 7 post-IR (FIG. 13B). The number of SOX2+ cells was significantly reduced at day 1 post-IR (FIG. 5C), while the number of COND1+SOX2+ cells was significantly increased at days 3 and 7 post-IR (FIG. 5C). In order to determine whether SOX2-mediated cell replacement was affected following IR-induced damage, we analyzed the extent of SOX2-mediated replenishment in Sox2$^{CreERT2}$; Rosa26$^{mTmG}$ mice 14 days post-IR. Strikingly, we found acinar cells were replaced by SOX2+ cells in the IR SLG (GFP+ cells) similar to the non-IR control with the production of both SOX2+GFP+ and SOX2-negative progeny (FIG. 5D, white arrowheads indicate SOX2-negative progeny), suggestive of the presence of a transit-amplifying cell which is no longer SOX2+ but derived from a SOX2+ cell (i.e., lineage-traced). Furthermore, the number of SOX2+ cells in the IR SLG was similar to controls by day 14 (FIG. 5D). Thus, despite an initial loss of nerve signaling, SOX2, and acinar cell markers, the acinar compartment is capable of being replenished by SOX2+ cells after radiation-induced damage.

Figure 5E:
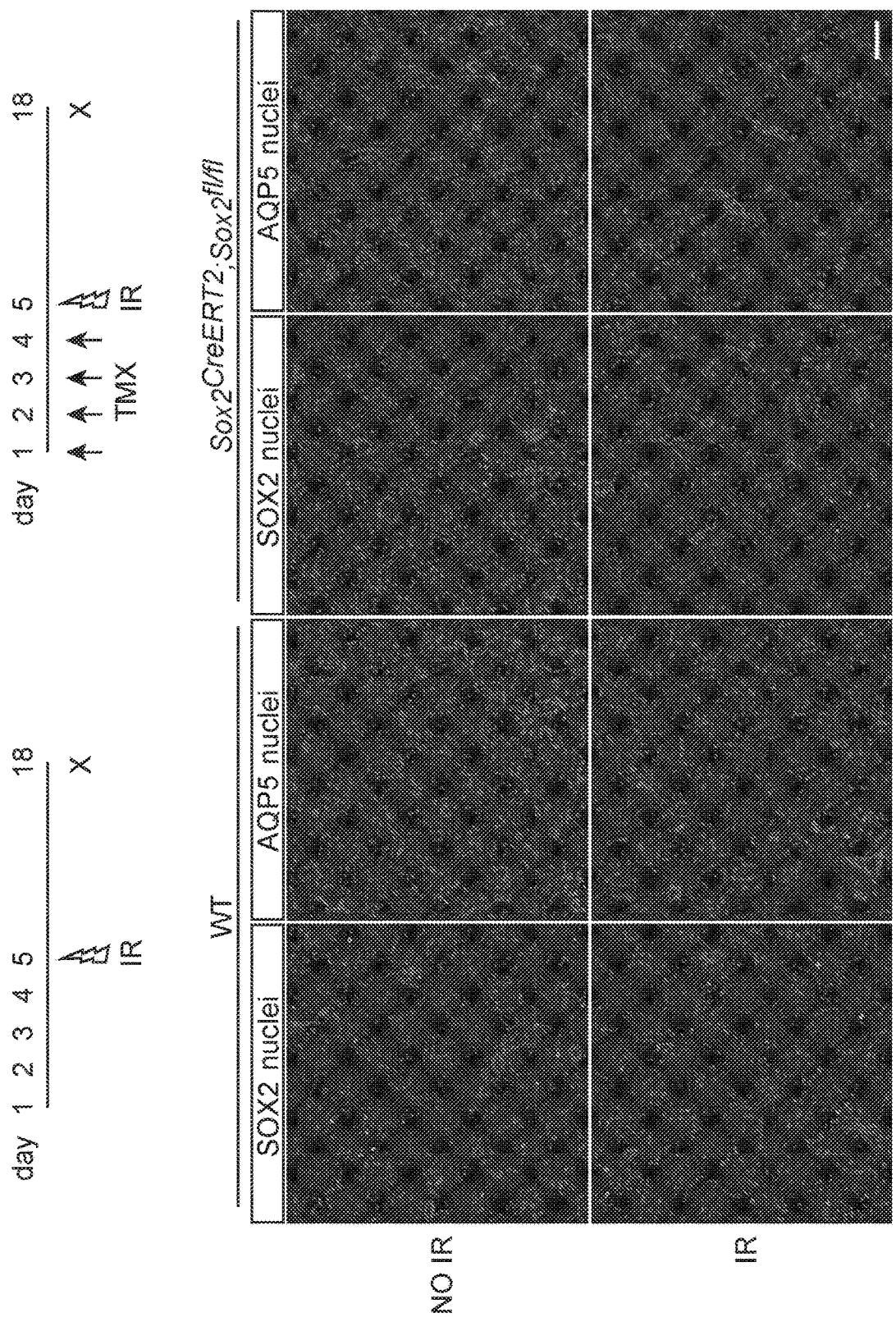

Next, we tested whether the SLG could regenerate following IR injury in the absence of Sox2. As shown in FIG. 5E, Sox2$^{CreERT2}$; Sox2$^{fl/fl}$ mice that had been irradiated with a single 10 Gy dose were unable to repopulate the tissue with functional AQP5+ acini. Indeed, in the absence of Sox2, we observed a loss of AQP5+ acinar cells and disrupted tissue architecture compared to wild-type mice at 14 days post-IR (FIG. 5E). This outcome further confirms that Sox2 is essential for SLG regeneration following radiation-induced injury.

Figure 6A:
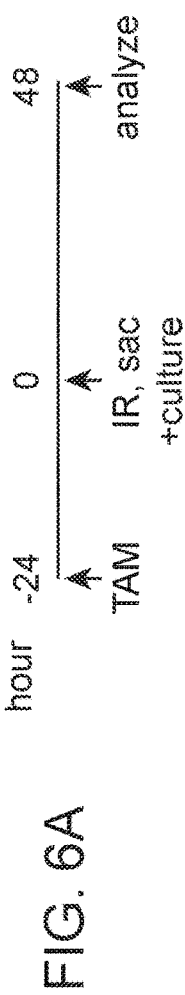
Figure 6B:
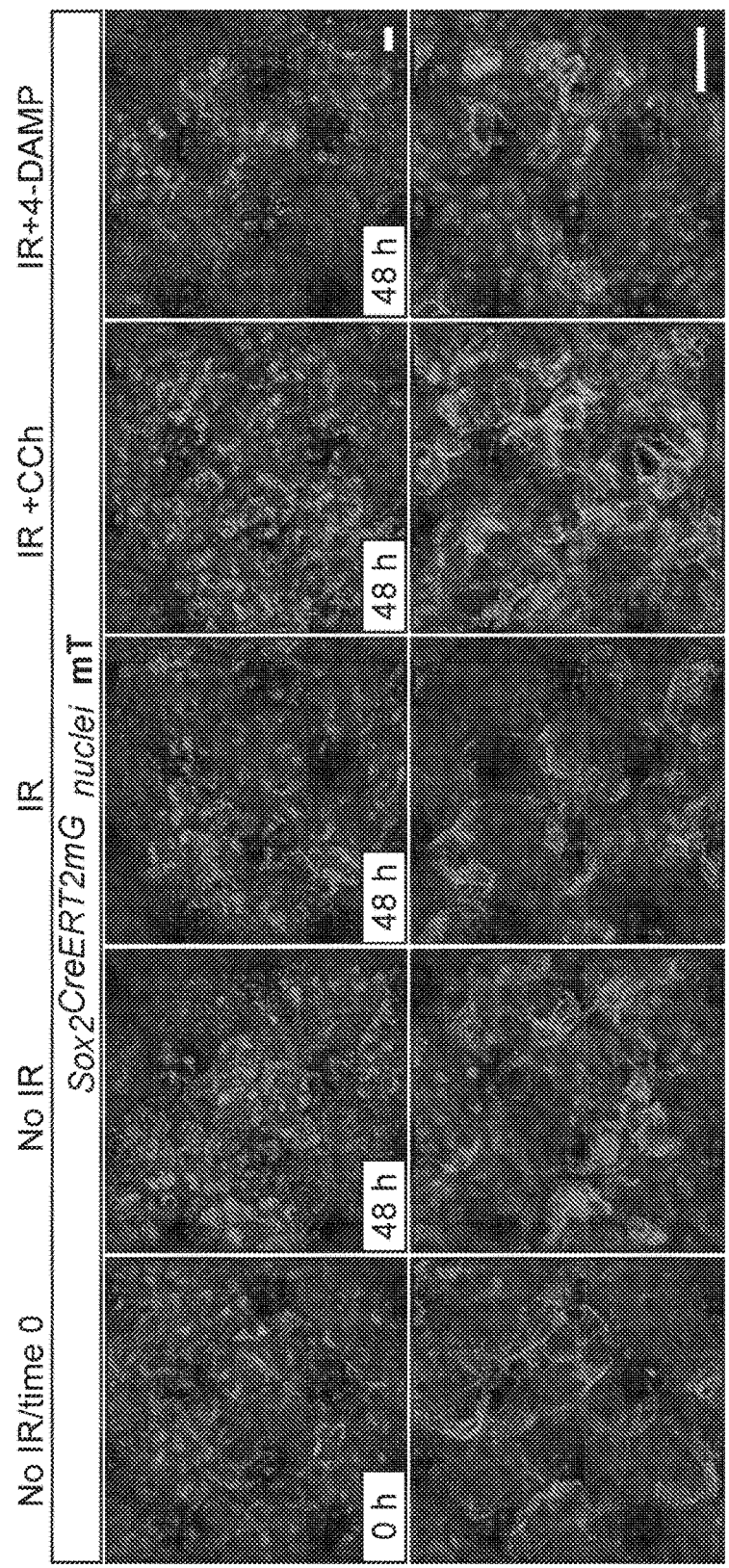

SOX2+ Cells can Replenish the Irradiated Salivary Gland in Response to Cholinergic Mimetics As our data suggest cholinergic cues replenish the acinar lineage in the SLG, we determined whether SOX2+ cells can replenish acini in response to muscarinic activation in healthy and irradiated SLG using our ex vivo lineage tracing model. As shown in FIGS. 6A and 6B, there was an increase in GFP+ clones in healthy SLG tissue cultured with the acetylcholine mimetic carbachol (CCh) for 48 h. This increase in GFP+ clones was associated with an increase in cell proliferation (Ki67+ cells) with CCh treatment (FIG. 13E). In our IR model, recombination was induced in Sox2$^{CreERT2}$; Rosa26$^{mTmG}$ mice 24 h before animals were subjected to a single dose of IR (FIG. 6A). This time-point was chosen as a lag time of 12-24 h has been previously reported for tamoxifen-induced recombination of Cre lines in mice (Nakamura et al., 2006). Thus, single SOX2+ cells are labeled by 24 h after injection (FIG. 6B, see 0 h panels). SLGs were collected within 1 h of radiation exposure and cultured ex vivo with or without CCh for 48 h. As shown in FIG. 6B and quantified in FIG. 6C, GFP+ clones were more abundant in IR SLG compared to the no IR controls, suggesting IR activated SOX2+ cells to repopulate the tissue. This was likely due to cholinergic signaling from remaining nerves as IR explants cultured with the muscarinic receptor antagonist 4-DAMP exhibited similar acinar cell replenishment to non-IR cultured salivary gland (FIGS. 6B and 6C). Importantly, treatment of IR explants with CCh increased GFP+ cells compared to IR alone (FIGS. 6B and 6C, and 13C and 13D). Based on these data, we conclude that SOX2+ cells are capable of repopulating the IR SLG in response to muscarinic activation.

Figure 7B:
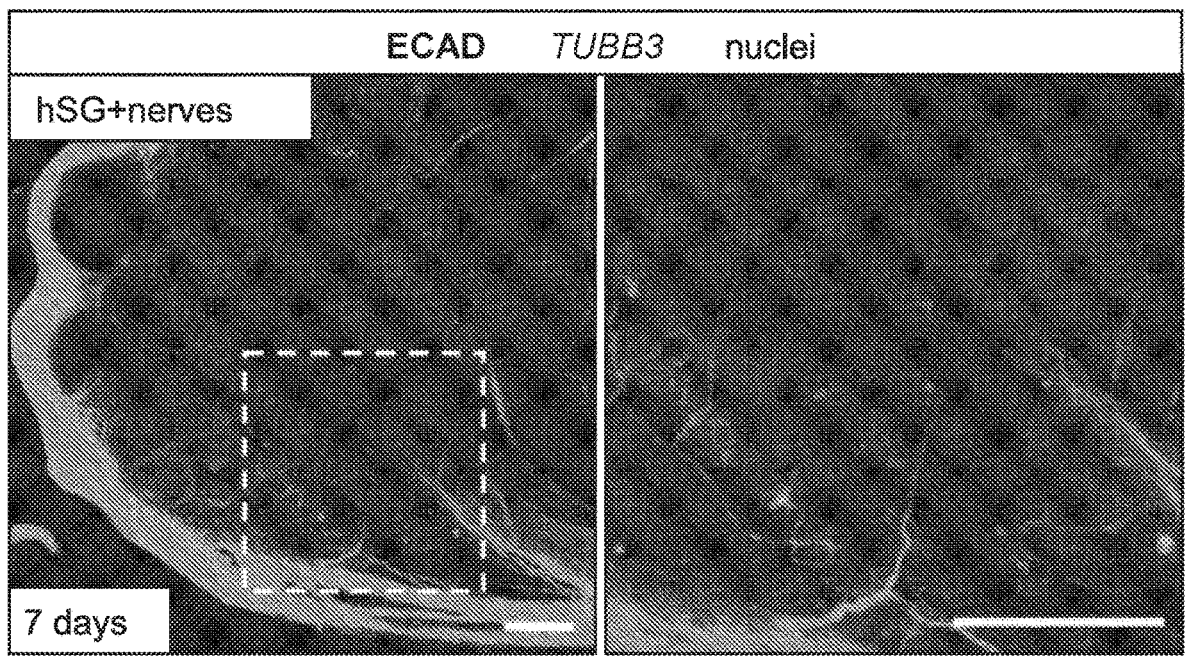
Figure 7C:
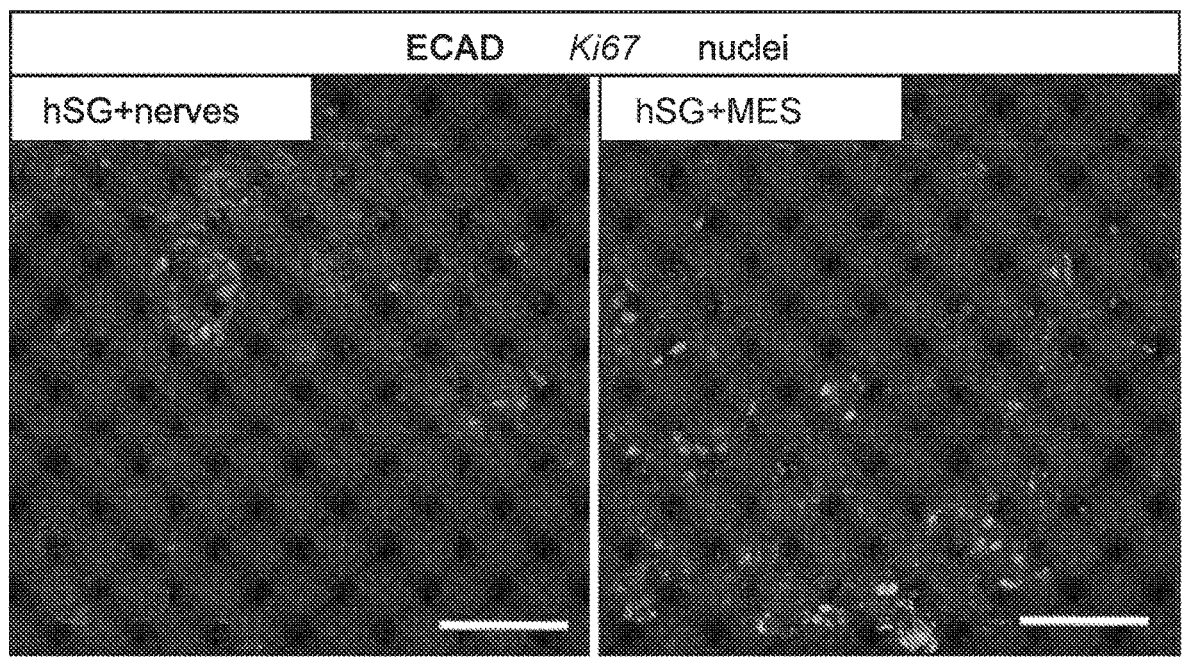
Figure 7D:
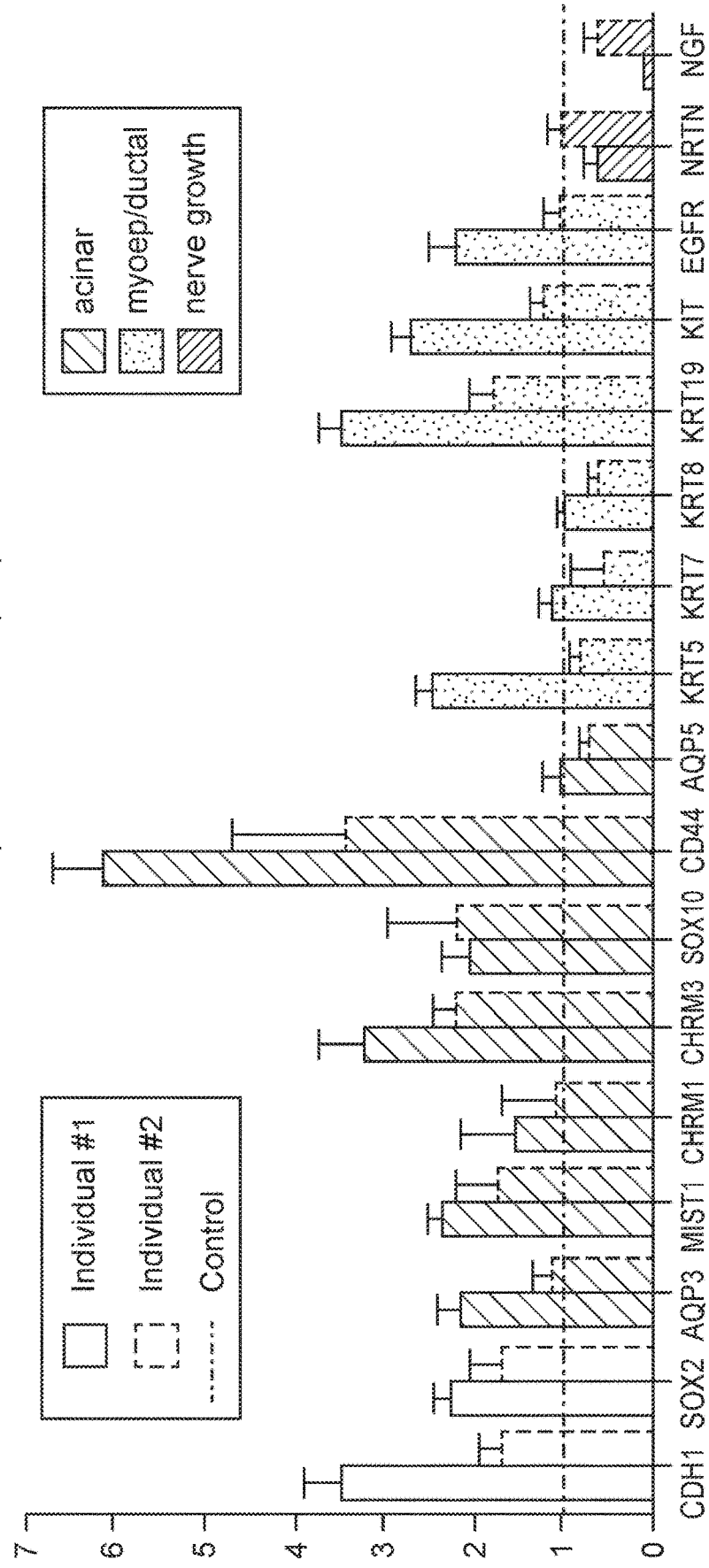

Acetylcholine/Muscarinic Signaling Maintains SOX2 and the Acinar Lineage in Human SG For humans, IR irreversibly reduces parasympathetic (and increases sympathetic) innervation in SG (Knox et al., 2013; FIG. 14A; GFRA2), as well as markers of the acinar lineage (AQP3, MIST1, AMY1) but not ductal lineage (EGFR, KRT19) compared to no IR controls (FIG. 7A; IR was delivered ~2 years prior to surgery, n=7 IR and 11 no IR). Lineage markers were confirmed in human tissue (SMG was used due to availability) by immunofluorescence (FIG. 14B). Furthermore, we found transcript levels for SOX2, GFRA2, CHRM1, and CHRM3, but not tyrosine hydroxylase (TH, sympathetic marker), were also significantly downregulated or trended toward downregulation following IR (FIGS. 7A and 14A), indicating parasympathetic function as well as the ability of cells to respond to acetylcholine was depleted. Thus, we hypothesized that the loss of regenerative capacity of human salivary glands following IR is due to reduced parasympathetic innervation of the SOX2$^+$ progenitor cells, and that acetylcholine/muscarinic signaling is sufficient to maintain SOX2 expression and promote the acinar lineage. To test this hypothesis, we established a novel human explant-murine nerve co-culture system. In this model, non-irradiated human SMG is dissected into <1-mm pieces and placed alongside an embryonic day 13 murine submandibular gland parasympathetic ganglia (contains mesenchyme) or mesenchyme only (control, no nerves). Tissues are then co-cultured on a filter floating above serum-free media for 7 days. Nerves migrated in and around the tissue (FIG. 7B) and actively maintained tissue structure as shown by higher levels of CDH1 (E-cadherin, gene, and protein expression) in the explants co-cultured with nerves compared to mesenchyme alone (FIGS. 7C and 7D). We analyzed the explants for the neuroattractants neurturin (NRTN) and nerve growth factor (NGF) (Knox et al., 2013) in an attempt to ascertain what factors induced this nerve migration. However, we found no increase in expression in the presence of the ganglia compared to the mesenchyme alone (FIG. 7D), suggesting that either other neuroattractants were being synthesized, that the epithelia produces these neuroattractants whether the nerves are present or not (i.e., the mesenchyme is supportive enough to maintain epithelial homeostasis) or that this phenomenon occurs earlier in culture (i.e., at an earlier stage when the nerves are just starting to envelop the epithelia) and any differences have been resolved by this later time point (day 7). Strikingly, glandular explants cultured with nerves also exhibited increased transcript levels of SOX2 (~1.8-fold to twofold) and the acinar markers MIST1 and CD44, muscarinic receptor CHRM3 (also expressed by acinar cells; Giraldo et al., 1988) but less consistently the ductal genes KRT19, KIT, and EGFR compared to the mesenchyme only controls (FIG. 7D, data normalized to mesenchyme only, n=2 separate individuals). In addition, epithelial cell proliferation, marked by the presence of Ki67$^+$ cells, was increased in the presence of the nerves (FIGS. 7C and 14C). Together, these data suggest that parasympathetic nerves are able to maintain SOX2 expression and acinar and ductal markers in the human salivary gland.

Figure 7E:
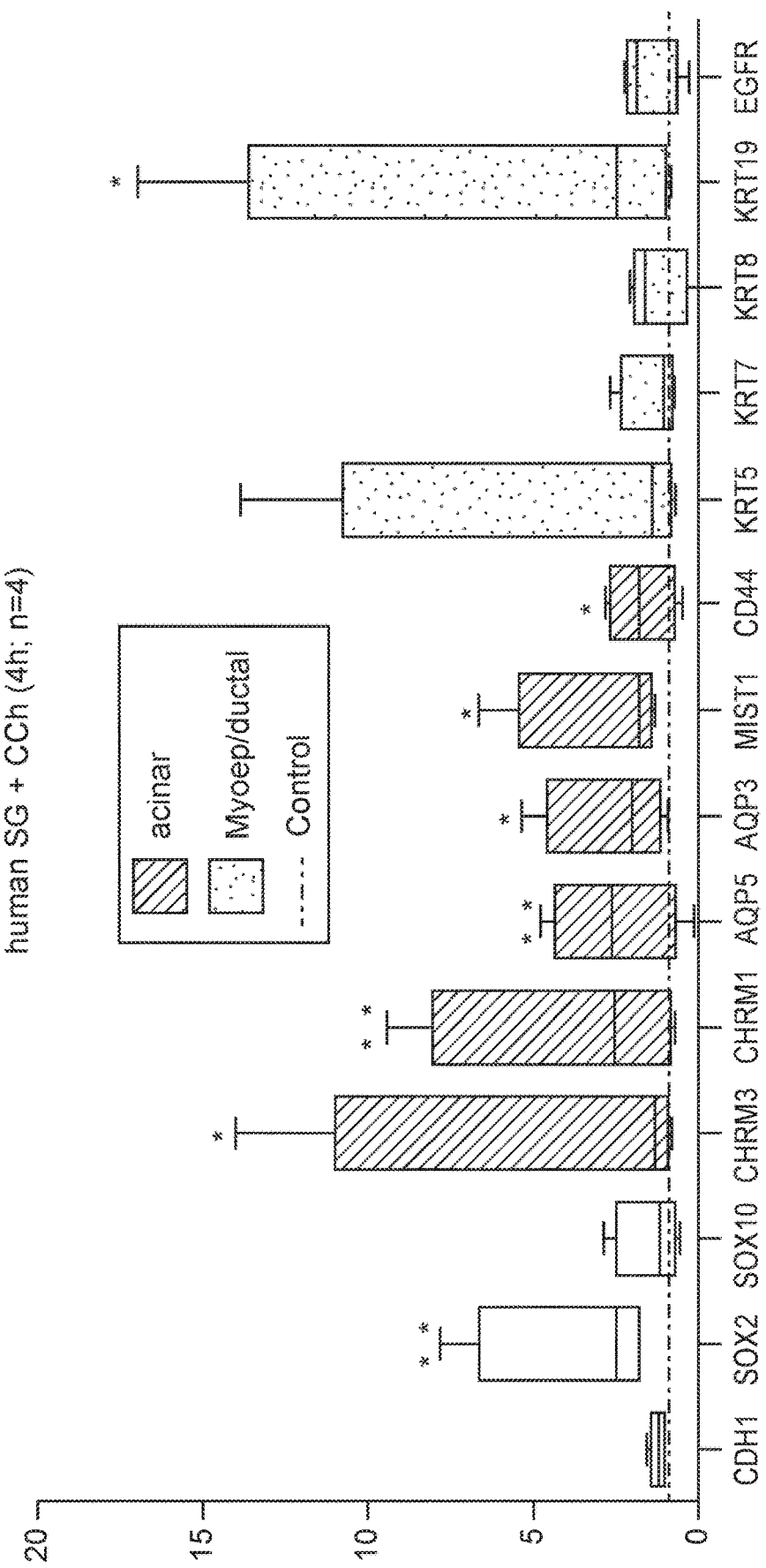

To address whether acetylcholine/muscarinic signaling is sufficient to maintain acini and SOX2$^+$ cells in human salivary gland, we subjected non-irradiated human SMG or PG (both express SOX2) tissue explants to muscarinic stimulation in an ex vivo system. Culture of patient-derived human tissue from four separate individuals (n=4) with CCh significantly increased expression of SOX2, muscarinic receptors CHRM1 and CHRM3 [both expressed by adult acinar cells (Giraldo et al., 1988; Mei et al., 1990)], as well as AQP3, AQP5 (Gresz et al., 2001), and MIST1 within 4 h of muscarinic stimulation (FIG. 7E, n=4, individual datasets shown in FIG. 14D). While surgical denervation does not adversely affect expression of Mist1 (FIGS. 3B and 3E), muscarinic stimulation is sufficient to increase MIST1 in human cultures and suggests that although not required for acinar cell identity, acetylcholine/muscarinic signaling may act as a positive regulator of the secretory program. The variability in response between the four patient-derived samples is likely due to biological diversity between human patients, differences in the type of gland sourced (SMG and PG used), and the age of the patient (age of donor ranges from 30 to 78 years). However, in all cases, we observed an increase in SOX2 and a number of acinar markers in the presence of CCh. Although we also measured an increase in KRT19 gene expression with CCh, the other exclusive ductal markers EGFR, KRT7, and KRT8 remained unchanged, suggesting ductal cells do not generally respond to muscarinic agonists (FIG. 7E). Given nerves increased ductal genes in the human salivary gland in co-culture, other factors may be produced by nerves to elicit changes in the ducts (compare FIGS. 7D and 7E). Thus, neuronal acetylcholine/muscarinic signaling is sufficient to promote the acinar lineage and maintain SOX2 expression in adult human salivary gland.

Discussion

Our study reveals SOX2$^+$ cells as progenitors in the adult salivary gland essential to the replenishment of acini with the unexpected capacity to repopulate the tissue after radiation-induced damage. We further show that cholinergic nerves play a vital role in controlling SOX2-mediated acinar cell replacement during homeostasis and that this neuronal influence can be replicated through addition of cholinergic mimetics to irradiated tissue. Thus, contrary to current dogma that murine salivary glands do not regenerate after radiation-induced damage (Zeilstra et al., 2000; Coppes et al., 2001, 2002), these data indicate that, at least in mice, salivary glands have extensive regenerative capacity after radiation-induced damage. Furthermore, as we find that the acinar lineage (and SOX2) in human tissue is also responsive to cholinergic mimetics, targeting SOX2$^+$ cells and maintaining cholinergic nerves may aid in the recovery of functional salivary acini after damage by radiation therapy.

SOX2 has an essential role in organism development and regulates the homeostasis of epithelial tissues such as the stomach, trachea, and intestine (Arnold et al., 2011). Similar to the reduced homeostatic capacity of adult tracheal cells after Sox2 ablation (Que et al., 2009), we found depletion of AQP5$^+$ acinar cells after ablation of Sox2 in SOX2$^+$ acinar progenitors under both homeostatic and damage conditions. Intriguingly, although atrophied, we did not find increased cell death in the absence of Sox2 but substantially fewer cycling acinar cells, suggesting that upon ablation, these cells exit the cell cycle and undergo differentiation to produce dormant AQP5-deficient acinar cells. The striking loss of acini upon ablation of SOX2$^+$ cells further confirmed that these are the sole progenitors for the acinar lineage in the SLG and is consistent with a recent report demonstrating pancreas acinar cells are not equipotent but contain a subset of progenitors (Wollny et al., 2016). Our results contrast to a recent report by Aure and co-workers showing that salivary acinar cells replenish through self-duplication of mature cells rather than via progenitor differentiation (Aure et al., 2015), similar to pancreatic beta cells (Dor et al., 2004). The conclusion that tissue repopulation is due to self-duplication of salivary acinar cells was based on the use of an inducible Mist1 promoter that is expressed by all acinar cells, including SOX2$^+$MUC19$^-$ cells. As such, subsets of cells traced upon recombination likely include progenitors; however, no analysis was conducted to determine whether these subsets possess a stem cell signature.

As with all epithelial organs, peripheral nerves are required to maintain the structural homeostasis of rodent and human salivary gland (Schneyer & Hall, 1967; Mandour et al., 1977; Wang et al., 1991; Fu & Gordon, 1995; Lujan et al., 1998; Kang et al., 2010; Batt & Bain, 2013). During organogenesis, parasympathetic nerves maintain a progenitor population that can contribute to the tissue after radiation damage via acetylcholine/muscarinic signaling (Knox et al., 2013). Although previous denervation studies in the salivary gland indicated that the organ and acinar cells decrease in size (Schneyer & Hall, 1967; Mandour et al., 1977; Kang et al., 2010), whether innervation was required for acinar cell replacement was not known. Here we reveal that nerves directly regulate SOX2 to drive acinar cell replacement from lineage-restricted progenitors. This outcome is consistent with the known role of SOX2 in the regulation of self-renewal and cell fate in many other organs (Arnold et al., 2011). However, to date, only cell-intrinsic signaling pathways including those mediated by the WNT, FGF, and EGFR families have been shown to regulate SOX2 (Hashimoto et al., 2012; Dogan et al., 2014; Rothenberg et al., 2015; Lee et al., 2016). This extrinsic nerve-based model has the distinct advantage over cell-intrinsic signals in that, unlike their target organs, neurons themselves are highly resistant to radiation damage (Tofilon & Fike, 2000; Wong & Van der Kogel, 2004). Whether this mechanism also regulates the maintenance of other SOX2-expressing epithelial organs, for example, taste buds (Suzuki, 2008), prostate and seminal vesicles (Wanigasekara et al., 2004), stomach (Tatsuta et al., 1985; Zhao et al., 2014), and cornea (Ueno et al., 2012), remains to be tested. However, these results suggest cholinergic nerves may function in the regeneration of these tissues.

Previous studies have utilized the murine salivary gland as a model of radiation-induced degeneration (Zeilstra et al., 2000; Coppes et al., 2001, 2002). These investigations have been based on the assumption that regeneration is impaired after moderate to high doses of radiation, a hypothesis supported by the reduced saliva flow measured in animals receiving radiation (Redman, 2008). However, to date, there has been no in vivo analysis of cell replacement after radiation. Our data indicate that murine acinar cells are highly regenerative, at least in the first 30 days after radiation exposure, and are capable of repopulating the acini similar to uninjured controls. It is clear, however, that this regenerative capacity cannot be sustained for the long term as degeneration/senescence in murine salivary glands occurs 3-6 months after radiation (Urek et al., 2005; Marmary et al., 2016). As such, it is likely that the regenerative capacity of SOX2$^+$ cells does fail eventually and further analysis is required to discern the cause. It also remains to be determined whether the human salivary gland can regenerate in the days/months after therapeutic radiation and if this regenerative capacity fails in the long term due to the absence of SOX2$^+$ cells in combination with parasympathetic nerves. Indeed, a time course analyzing changes in salivary glands from patients is required to understand how these organs are affected in the short term and long term. However, our results suggest that targeting these stem cells and their innervating nerves to control and sustain tissue regeneration in response to radiation damage may provide a means of maintaining/repairing tissue for the long term.

A number of recent studies have aimed to address gland regeneration after radiation damage in the mouse model by either isolating putative stem cell populations for reimplantation (Nanduri et al., 2013, 2014) or sparing the regions within the gland that are thought to harbor the stem cells (van Luijk et al., 2015). However, the identity of these endogenous stem cells and whether they contribute to the acinar cell compartment was unclear. Furthermore, the effect of such manipulations on salivary gland innervation has not been reported. Based on our study, it is possible that unintentional increases in innervation due to tissue perturbation lead to maintenance and expansion of SOX2$^+$ progenitor cells that regenerate acini to restore salivary function. Xiao et al. (2014) reported recovery of murine salivary function and architecture after radiation-induced damage with the addition of glial-derived nerve factor (GDNF), a neuroattractive factor (Knox et al., 2013). However, a recent study demonstrated that GDNF itself does not protect SG stem cells from radiation-induced damage directly (Peng et al., 2017), suggesting that such outcomes could be the result of improvements to the supporting niche.

Together, our study highlights the extensive regenerative capacity of salivary glands that occurs through the expansion and differentiation of a progenitor cell population, even in the face of genotoxic shock. Based on these data, we propose that by directly targeting SOX2$^+$ cells within the tissue, or by isolating and expanding these cells for transplantation and activation, we might regenerate the secretory units of salivary glands and return quality of life to the patient. This would also require maintenance of parasympathetic nerves, as proposed previously (Knox et al., 2013), to sustain the SOX2$^+$ population. Given organs, such as the intestine, glandular stomach, trachea, and taste buds express SOX2, are heavily innervated by the autonomic nervous system and are damaged by therapeutic radiation for the elimination of cancers, such a strategy may be applicable to the repair of multiple organ systems.

Materials and Methods

Mouse Lines

All procedures were approved by the UCSF Institutional Animal Care and Use Committee (IACUC) and were adherent to the NIH Guide for the Care and Use of Laboratory Animals. Mouse alleles used in this study were provided by The Jackson Laboratory and include Sox2$^{eGFP}$ (Arnold et al., 2011), Sox2$^{CreERT2}$ (Smith et al., 2009), Sox2$^{eGFP}$ (Taranova et al., 2006), Rosa26$^{mTmG}$ (Muzumdar et al., 2007), Rosa26$^{DTA}$ (Wu et al., 2006), and Kit$^{CreERT2}$ (Klein et al., 2013).

Animal Experiments

Adult female mice (aged between 6 and 8 weeks) were used in all experiments, unless otherwise stated. Mice were housed in the University of California San Francisco Parnassus campus Laboratory Animal Resource Center (LARC), which is AAALAC accredited. Mice were housed in groups of up to five per cage where possible, in individually ventilated cages (IVCs), with fresh water, regular cleaning, and environmental enrichment. Appropriate sample size was calculated using power calculations. For transgenic studies, sample size was restricted by length of time required to breed enough animals of the required genotype and gender. Wild-type animals were randomized into experimental groups using Microsoft Excel software. Transgenic animals were assigned to groups based on genotype. All animals were given a unique ID number and as such were blinded to the researcher during analysis.

Genetic ablation of Sox2 or SOX2$^+$ cells

Conditional ablation of Sox2 was achieved by injecting Sox2$^{CreERT2}$; Sox2$^{fl/fl}$:R26$^{mTmG}$ mice with 2.5 mg/20 g tamoxifen each day for four consecutive days, and every other third day, before euthanizing on day 18. Ablation of SOX2+ cells was performed by injecting Sox2$^{CreERT2}$; Rosa26$^{DTA}$:R26$^{mTmG}$ mice with 2.5 mg/20 g tamoxifen each day for four consecutive days, before euthanizing on day 7. The Rosa26$^{mTmG}$ mouse provides a valuable tool to lineage trace in conjunction with cell ablation/recombination (Muzumdar et al., 2007). In brief, this model consists of a double-fluorescent Cre reporter that expresses membrane-targeted tandem dimer Tomato (mT) prior to Cre-mediated excision and membrane-targeted green fluorescent protein (mG) after excision (FIG. 10D). Thus, in these mice, cells where recombination has occurred and are thus lacking Sox2 or expressing DTA will express GFP. Endogenous GFP was imaged in experiments where cryosections were used, while a GFP antibody was used for paraffin-embedded tissue (chicken anti-GFP; 1:500, Ayes Labs, GFP-1020).

Lineage Tracing of SOX2+ Cells

Sox2$^{CreERT2}$; Rosa26$^{mTmG}$ mice were injected with 2.5 mg tamoxifen and euthanized after 24 h, 14 days, or 30 days.

Lineage Tracing of KIT+ Cells

Kit$^{CreERT2}$; Rosa26$^{mTmG}$ mice were injected with 2.5 mg tamoxifen daily for four consecutive days and euthanized after 14 days or 6 months.

In Vivo Denervation Experiments

C57BL/6 or Sox2e$^{GFP}$ mice were administered with analgesics 30 min prior to surgery (carprofen and buprenorphine; Patterson Veterinary and Buprenex; 0.1 and 100 mg/kg (IP), respectively) and anesthetized via inhalation with 2% isoflurane/O$_2$ mix. The surgical area was shaved and prepared for incision with alternating iodine and alcohol washes, followed by local anesthetic (lidocaine; Hospira Inc., 8 mg/kg). An incision was made anterior to the ear and the chorda tympani located as previously described (Klimaschewski et al., 1996) and completely transected using spring scissors. The skin was sutured using non-absorbable silk sutures (Ethicon) and the wound further covered by surgical adhesive (Vetbond). The contralateral nerve was left intact as a control. Mice were euthanized after 7 or 30 days.

Pilocarpine Experiments

Adult male C57BL/6 mice (aged between 6 and 8 weeks) were treated with pilocarpine (Sigma-Aldrich, P0472; 0.68 mg/ml in 0.9% sterile saline). Mice were anesthetized using isoflurane and injected I.P. with pilocarpine at a dose of 4.5 mg/kg bodyweight (200 µl), or 0.9% saline as a vehicle control. Mice were euthanized after 18 h and glands processed for immunofluorescent analysis.

Gamma-Radiation Experiments

C57BL/6 mice were anesthetized with 1.25% 2,2,2-tribromoethanol (Alfa Aesar) in 0.9% saline (Vedco Inc.). The mice were irradiated using a $^{137}$Cs source by being placed into a Shepherd Mark-I-68A $^{137}$Cs Irradiator (JL Shepherd & Associates). Two lead blocks, positioned 1.5 cm apart, were used to shield the body and the very anterior part of the mouth (the snout) of the mice and expose only the neck and part of the head. The 1.5 cm opening was centered at position 3 (20 cm from the $^{137}$Cs source, 15.5 cm from the width of the irradiator cavity). Mice were exposed to two doses of 5 Gy at a dose rate of 167 Rads/min for 2.59 min (one of each side of the head, bilateral, and sequential but on the same day) for a total dose of 10 Gy, to irradiate the salivary glands. This dose was calculated by isodose plot mapping (dose distribution), provided by the manufacturer, and EBT films (Brady et al., 2009) were used to localize the 100% region of exposure for mouse placement. Control mice were anesthetized as per experimental mice, but did not undergo radiation treatment. All mice were allowed to completely recover before returning to normal housing and were given soft diet ad libitum (ClearH$_2$O). Mice were euthanized after 1 h or 1, 3, 7, 14, or 30 days.

Organ Culture Experiments

Ex Vivo Linage Tracing in Adult Salivary Gland

Salivary glands from Sox2$^{CreERT2}$; Rosa26$^{mTmG}$ mice (recombination induced 24 h prior) were mechanically dissected into <1-mm pieces, placed in complete media in the presence or absence of 200 nM CCh (Sigma-Aldrich) or 10 µM 4-DAMP (Tocris), and cultured for 48 h before being fixed for immunofluorescence. In some cases, mice were irradiated with three doses of 5 Gy before glands were taken for culture as above.

Human Salivary Gland Tissue Isolation and Culture

Adult human salivary gland was obtained from discarded, non-identifiable tissue with consent from patients undergoing neck resection (age 28-78, male and female). Informed consent was given by all subjects and experiments conformed to the principles set out in the WMA Declaration of Helsinki and the Department of Health and Human Services Belmont Report. Patients had either had no irradiation therapy (non-IR) or fractionated radiation therapy (IR)<2 years prior to surgery. Tissue was immediately placed in 4% PFA, RNAlater (Qiagen) or DMEM (Thermo Fisher) for live cell explant culture. For ex vivo culture, non-IR tissue was dissected into <1-mm pieces and cultured in serum-free DMEM/F12 containing holotransferrin and ascorbic acid. For explant assays, the tissue (SMG and PG) was incubated with 50-200 nM CCh (200 nM CCh shown in results) for 4 h before being lysed for RNA. For salivary gland explant-parasympathetic submandibular ganglia (SMG) co-culture, tissue was dissected into <1-mm pieces and cultured on a floating filter above serum-free media. E13 mouse parasympathetic submandibular ganglia were isolated as previously described (Knox et al., 2010). One parasympathetic submandibular ganglion per explant was placed next to the human salivary gland and cultured for 7 days and either fixed for immunofluorescent analysis or lysed for RNA.

Tissue Processing

After fixation, salivary glands (human and mouse) were either processed for OCT or paraffin embedding. For generation of frozen sections, tissue was incubated in increasing concentrations of sucrose (25-75%) and embedded in OCT. 12-µm sections were cut using a cryostat (Leica) and stored at −20° C. Tissue for paraffin was dehydrated by incubating in increasing concentrations of ethanol and subsequently Histo-Clear (National Diagnostics) before embedding in paraffin wax (Sigma-Aldrich). 12-µm sections were cut using a microtome (Leica) and stored at room temperature.

Immunofluorescent Analysis

Whole-mount salivary gland and tissue section immunofluorescence analysis has been previously described (Knox et al., 2010). In brief, tissue was fixed with either ice-cold acetone/methanol (1:1) for 1 min or 4% PFA for 20-30 min followed by permeabilizing with 0.1-0.3% Triton X. Tissue was blocked overnight at 4° C. with 10% Donkey Serum (Jackson Laboratories, ME), 1% BSA (Sigma-Aldrich), and MOM IgG-blocking reagent (Vector Laboratories, CA) in 0.01% PBS-Tween 20. Salivary glands were incubated with primary antibodies overnight at 4° C.: goat anti-SOX2 (1:200, Neuromics, GT15098); goat anti-SOX10 (1:500, Santa Cruz Biotechnology, sc-17342); mouse anti-TUBB3 (clone TUJ1 at 1:400, R&D Systems, MAB1195); goat anti-GFRa2 (1:100, R&D Systems, AF429); rabbit anti-tyrosine hydroxylase (1:100, Millipore, AB152); rat anti-E-cadherin (1:300, Life Technologies, 13-1900); rabbit anti-EGFR (1:200, Abcam, ab52894); rabbit anti-KRT5 (1:1,000, Covance, PRB-160P); rat anti-KRT8 (1:200, DSHB, troma I); mouse anti-KRT7 (1:50, Covance, MMS-1485); rat anti-CD44 (1:200, BioLegend, 103001); mouse anti-Ki67 (1:50, BD Biosciences, 550609); rabbit anti-CCND1 (1:200, Abcam, ab16663); rabbit anti-caspase-3 (1:100, Invitrogen, 34-1700); rabbit anti-AQP3 (1:400, Lifespan Biosciences Inc., LS-B8185); rabbit anti-AQP5 (1:100, Millipore, AB3559); goat anti-MUC19 (1:200, Abcore, AC21-2396); mouse anti-aSMA (1:400, Sigma-Aldrich, C6198); chicken anti-GFP (1:500, Ayes Labs, GFP-1020); rabbit anti-CHRM3 (1:1,000, Research and Diagnostics, AS-3741S); and rabbit anti-MIST1 (1:500, gift from Stephen Konieczny, Purdue University). Antibodies were detected using Cy2-, Cy3-, or Cy5-conjugated secondary Fab fragment antibodies (Jackson Laboratories) and nuclei stained using Hoechst 33342 (1:1,000, Sigma-Aldrich). Fluorescence was analyzed using a Leica Sp5 confocal microscope and NIH ImageJ software.

Morphometric Analysis and Cell Counts

For immunofluorescent analyses (e.g., FIG. 2D), cells positively stained for markers were counted using ImageJ. Acinar cell size was measured using ImageJ. All data were obtained using 3-5 fields of view/group, and each experiment was repeated three times. For nerve density analysis, immunofluorescence of nerve marker TUBB3 was analyzed and raw integrated density (displayed as arbitrary units, AU) was calculated using ImageJ.

Quantitative PCR Analysis

RNA was isolated from whole tissue using RNAqueous Micro Kit (Ambion). Total RNA samples were DNase-treated (Ambion) prior to cDNA synthesis using SuperScript reagents (Invitrogen, CA). SYBR green qPCR was performed using 5 ng (mouse) or 4-10 ng (human) of cDNA and primers designed using Primer3 and Beacon Designer software or described on PrimerBank (pga.mgh.harvard.edu/primerbank/). Primer sequences are listed in Tables 1 and 2. Melt curves and primer efficiency were determined as previously described (Hoffman et al., 2002). Gene expression was normalized to the housekeeping genes S18 and S29 (Rps18 and Rsp29) or GAPDH for mouse and GAPDH for human and to the corresponding experimental control. Reactions were run in triplicate and experiments performed 2-3 times.

Flow Cytometry

Adult mouse sublingual salivary glands (CD1) were dissected and washed in PBS containing gentamicin (Sigma-Aldrich). Cell isolation and flow cytometry were performed as previously described (Muench et al., 2002; Pringle et al., 2011). Briefly, a single cell suspension was created by mincing tissue in HBSS+1% BSA (Sigma-Aldrich) with a scalpel blade and incubating in a HBSS solution containing 50 mM $CaCl_2$) (Sigma-Aldrich), 40 mg/ml hyaluronidase (Sigma-Aldrich) and 23 mg/ml collagenase type II (Sigma-Aldrich) at 37° C. for 15-45 min. The enzyme reaction was quenched by the addition of BSA and the solution filtered through a 70 µm strainer (BD Falcon) and centrifuged at 400 g for 8 min. The resulting cell pellet was washed with sterile HBSS+1% BSA, centrifuged and resuspended in blocking buffer (5% serum and 0.01% NaN3, BioLegend). Cell surface staining was achieved by incubating cell suspensions with antibodies against CD326 (EpCAM; Miltenyi, 130-098-113), rabbit anti-CHRM1 (Research and Diagnostics, AS-3701S), rabbit anti-CHRM3 (Research and Diagnostics, AS-3741S) and rabbit anti-AQP5 (Millipore, AB3559). Subsequently, intracellular staining was achieved following fixation and permeabilization using an intracellular staining kit (eBioscience, 00-5523-00) and antibodies against SOX2 (BD Pharmingen, 562195) and Ki67 (BioLegend, 652405). Flow cytometry was performed on a LSRII (BD) using the appropriate single stained controls and data collected using FACSDiva (BD) and analyzed using FlowJo. 100,000 events were collected for each sample unless otherwise stated.

Statistical Tests

Normal distribution was assessed using the D'Agostino-Pearson omnibus test. Data were analyzed for statistical significance using Student's t-test (unpaired, two groups) or one-way ANOVA (multiple groups) with post hoc testing performed using Dunnett or Tukey tests (GraphPad Prism or SPSS). For multiple testing, we used a false discovery rate of 0.05. All graphs show the mean+standard deviation (SD) or mean±standard error of the mean (SEM), as indicated in the legends.

REFERENCES

Andreadis D, Epivatianos A, Poulopoulos A, Nomikos A, Papazoglou G, Antoniades D, Barbatis C (2006) Detection of C-KIT (CD117) molecule in benign and malignant salivary gland tumours. Oral Oncol 42: 57-65

Arnold K, Sarkar A, Yram M A, Polo J M, Bronson R, Sengupta S, Seandel M, Geijsen N, Hochedlinger K (2011) Sox2(+) adult stem and progenitor cells are important for tissue regeneration and survival of mice. Cell Stem Cell 9: 317-329

Aure M H, Konieczny S F, Ovitt C E (2015) Salivary gland homeostasis is maintained through acinar cell self-duplication. Dev Cell 33: 231-237

Avila J L, Grundmann O, Burd R, Limesand K H (2009) Radiation-induced salivary gland dysfunction results from p53-dependent apoptosis. Int J Radiat Oncol Biol Phys 73: 523-529

Barker N (2014) Adult intestinal stem cells: critical drivers of epithelial homeostasis and regeneration. Nat Rev Mol Cell Biol 15: 19-33

Batt J A, Bain J R (2013) Tibial nerve transection—a standardized model for denervation-induced skeletal muscle atrophy in mice. J Vis Exp 81: e50657

Brady S L, Toncheva G, Dewhirst M W, Yoshizumi T T (2009) Characterization of a 137Cs irradiator from a new perspective with modern dosimetric tools. Health Phys 97: 195-205

Brown L R, Dreizen S, Handler S, Johnston D A (1975) Effect of radiation-induced xerostomia on human oral microflora. J Dent Res 54: 740-750

Coppes R P, Zeilstra L J, Kampinga H H, Konings A W (2001) Early to late sparing of radiation damage to the parotid gland by adrenergic and muscarinic receptor agonists. Br J Cancer 85: 1055-1063

Coppes R P, Vissink A, Konings A W (2002) Comparison of radiosensitivity of rat parotid and submandibular glands after different radiation schedules. Radiother Oncol 63: 321-328

Dogan I, Kawabata S, Bergbower E, Gills J J, Ekmekci A, Wilson W III, Rudin C M, Dennis P A (2014) SOX2 expression is an early event in a murine model of EGFR mutant lung cancer and promotes proliferation of a subset of EGFR mutant lung adenocarcinoma cell lines. Lung Cancer 85: 1-6

Dor Y, Brown J, Martinez O I, Melton D A (2004) Adult pancreatic beta-cells are formed by self-duplication rather than stem-cell differentiation. Nature 429: 41-46

Dreizen S, Brown L R, Daly T E, Drane J B (1977) Prevention of xerostomia-related dental caries in irradiated cancer patients. J Dent Res 56: 99-104

Dusek M, Simmons J, Buschang P H, al-Hashimi I (1996) Masticatory function in patients with xerostomia. Gerodontology 13: 3-8

Emami B, Lyman J, Brown A, Coia L, Goitein M, Munzenrider J E, Shank B, Solin L J, Wesson M (1991) Tolerance of normal tissue to therapeutic irradiation. Int J Radiat Oncol Biot Phys 21: 109-122

Emmelin N, Holmberg J, Ohlin P (1965) Receptors for catechol amines in the submaxillary glands of rats. Br J Pharmacol Chemother 25: 134-138

Emmerson E, May A J, Nathan S, Cruz-Pacheco N, Lizama C O, Maliskova L, Zovein A C, Shen Y, Muench M O, Knox S M (2017) SOX2 regulates acinar cell development in the salivary gland. eLife 17: e26620

Erb W (1868) Zur Pathologie and pathologischen Autonomie peripherischer Paralysen. Dtsch Arch klin Med 4: 535

Fu S Y, Gordon T (1995) Contributing factors to poor functional recovery after delayed nerve repair: prolonged denervation. J Neurosci 15:3886-3895

Garrett J R, Ekstrom J, Anderson L C (1999) Neural mechanisms of salivary gland secretion. Basel: Karger Giraldo E, Martos F, Gomez A, Garcia A, Vigano M A, Ladinsky H, Sanchez de La Cuesta F (1988) Characterization of muscarinic receptor subtypes in human tissues. Life Sci 43: 1507-1515

Gresz V, Kwon T H, Hurley P T, Varga G, Zelles T, Nielsen S, Case R M, Steward M C (2001) Identification and localization of aquaporin water channels in human salivary glands. Am J Physiol Gastrointest Liver Physiol 281: G247-G254

Grundmann O, Mitchell G C, Limesand K H (2009) Sensitivity of salivary glands to radiation: from animal models to therapies. J Dent Res 88: 894-903

Hashimoto S, Chen H, Que J, Brockway B L, Drake J A, Snyder J C, Randell S H, Stripp B R (2012) beta-Catenin-SOX2 signaling regulates the fate of developing airway epithelium. J Cell Sci 125: 932-942

Hoffman M P, Kidder B L, Steinberg Z L, Lakhani S, Ho S, Kleinman H K, Larsen M (2002) Gene expression profiles of mouse submandibular gland development: FGFR1 regulates branching morphogenesis in vitro through BMP- and FGF-dependent mechanisms. Development 129: 5767-5778

Kang J H, Kim B K, Park B I, Kim H J, Ko H M, Yang S Y, Kim M S, Jung J Y, Kim W J, Oh W M et al (2010) Parasympathectomy induces morphological changes and alters gene-expression profiles in the rat submandibular gland. Arch Oral Biol 55: 7-14

Klein S, Seidler B, Kettenberger A, Sibaev A, Rohn M, Feil R, Allescher H D, Vanderwinden J M, Hofmann F, Schemann M et al (2013) Interstitial cells of Cajal integrate excitatory and inhibitory neurotransmission with intestinal slow-wave activity. Nat Commun 4: 1630

Klimaschewski L, Grohmann I, Heym C (1996) Targetdependent plasticity of galanin and vasoactive intestinal peptide in the rat superior cervical ganglion after nerve lesion and reinnervation. Neuroscience 72: 265-272

Knox S M, Lombaert I M, Reed X, Vitale-Cross L, Gutkind J S, Hoffman M P (2010) Parasympathetic innervation maintains epithelial progenitor cells during salivary organogenesis. Science 329: 1645-1647

Knox S M, Lombaert I M, Haddox C L, Abrams S R, Cotrim A, Wilson A J, Hoffman M P (2013) Parasympathetic stimulation improves epithelial organ regeneration. Nat Commun 4: 1494

Lee N Y, Le Q T (2008) New developments in radiation therapy for head and neck cancer: intensity-modulated radiation therapy and hypoxia targeting. Semin Oncol 35: 236-250

Lee M J, Kim E J, Otsu K, Harada H, Jung H S (2016) Sox2 contributes to tooth development via Wnt signaling. Cell Tissue Res 365: 77-84

Lombaert I M, Brunsting J F, Wierenga P K, Faber H, Stokman M A, Kok T, Visser W H, Kampinga H H, de Haan G, Coppes R P (2008) Rescue of salivary gland function after stem cell transplantation in irradiated glands. PLoS One 3: e2063

Lombaert I M, Abrams S R, Li L, Eswarakumar V P, Sethi A J, Witt R L, Hoffman M P (2013) Combined KIT and FGFR2b signaling regulates epithelial progenitor expansion during organogenesis. Stem Cell Reports 1: 604-619 van Luijk P, Pringle S, Deasy J O, Moiseenko V V, Faber H, Hovan A, Baanstra M, van der Laan H P, Kierkels R G, van der Schaaf A et al (2015) Sparing the region of the salivary gland containing stem cells preserves saliva production after radiotherapy for head and neck cancer. Sci Transl Med 7: 305ra147

Lujan M, Paez A, Llanes L, Angulo J, Berenguer A (1998) Role of autonomic innervation in rat prostatic structure maintenance: a morphometric analysis. J Urol 160: 1919-1923

Mandour M A, Helmi A M, El-Sheikh M M, El-Garem F, EI-Ghazzawi E (1977) Effect of tympanic neurectomy on human parotid salivary gland. Histopathologic, Histochemical, and Clinical Study. Arch Otolaryngol 103: 338-341

Marmary Y, Adar R, Gaska S, Wygoda A, Maly A, Cohen J, Eliashar R, Mizrachi L, Orfaig-Geva C, Baum B J et al (2016) Radiation-induced loss of salivary gland function is driven by cellular senescence and prevented by IL6 modulation. Can Res 76: 1170-1180

Mei L, Roeske W R, Izutsu K T, Yamamura H I (1990) Characterization of muscarinic acetylcholine receptors in human labial salivary glands. Eur J Pharmacol 176: 367-370

Muench M O, Suskind D L, Barcena A (2002) Isolation, growth and identification of colony-forming cells with erythroid, myeloid, dendritic cell and NK-cell potential from human fetal liver. Biol Proced Online 4: 10-23

Muzumdar M D, Tasic B, Miyamichi K, Li L, Luo L (2007) A global double-fluorescent Cre reporter mouse. Genesis 45: 593-605

Nakamura E, Nguyen M T, Mackem S (2006) Kinetics of tamoxifen-regulated Cre activity in mice using a cartilage-specific CreER(T) to assay temporal activity windows along the proximodistal limb skeleton. Dev Dyn 235: 2603-2612

Nanduri L S, Lombaert I M, van der Zwaag M, Faber H, Brunsting J F, van Os R P, Coppes R P (2013) Salisphere derived c-Kit cell transplantation restores tissue homeostasis in irradiated salivary gland. Radiother Oncol 108: 458-463

Nanduri L S, Baanstra M, Faber H, Rocchi C, Zwart E, de Haan G, van Os R, Coppes R P (2014) Purification and ex vivo expansion of fully functional salivary gland stem cells. Stem Cell Reports 3: 957-964

Nelson D A, Manhardt C, Kamath V, Sui Y, Santamaria-Pang A, Can A, Bello M, Corwin A, Dinn S R, Lazare M et al (2013) Quantitative single cell analysis of cell population dynamics during submandibular salivary gland development and differentiation. Biol Open 2: 439-447

Ogawa M, Oshima M, Imamura A, Sekine Y, Ishida K, Yamashita K, Nakajima K, Hirayama M, Tachikawa T, Tsuji T (2013) Functional salivary gland regeneration by transplantation of a bioengineered organ germ. Nat Commun 4: 2498

Owens D M, Watt F M (2003) Contribution of stem cells and differentiated cells to epidermal tumours. Nat Rev Cancer 3: 444-451

Patterson J, Lloyd L C, Titchen D A (1975) Secretory and structural changes in the parotid salivary gland of sheep and lambs after parasympathetic denervation. Q J Exp Physiol Cogn Med Sci 60: 223-232

Peng X, Varendi K, Maimets M, Andressoo J O, Coppes R P (2017) Role of glial-cell-derived neurotrophic factor in salivary gland stem cell response to irradiation. Radiother Oncol 124: 448-454

Peterson S C, Eberl M, Vagnozzi A N, Belkadi A, Veniaminova N A, Verhaegen M E, Bichakjian C K, Ward N L, Dlugosz A A, Wong S Y (2015) Basal cell carcinoma preferentially arises from stem cells within hair follicle and mechanosensory niches. Cell Stem Cell 16: 400-412

Pringle S, Nanduri L S, van der Zwaag M, van Os R, Coppes R P (2011) Isolation of mouse salivary gland stem cells. J Vis Exp 8: 2484

Pringle S, Maimets M, van der Zwaag M, Stokman M A, van Gosliga D, Zwart E, Witjes M J, de Haan G, van Os R, Coppes R P (2016) Human salivary gland stem cells functionally restore radiation damaged salivary glands. Stem cells 34: 640-652

Que J, Luo X, Schwartz R J, Hogan B L (2009) Multiple roles for Sox2 in the developing and adult mouse trachea. Development 136: 1899-1907

Raz E, Saba L, Hagiwara M, Hygino de Cruz L C Jr, Som P M, Fatterpekar G M (2013) Parotid gland atrophy in patients with chronic trigeminal nerve denervation. AJNR Am J Neuroradiol 34: 860-863

Redman R S (2008) On approaches to the functional restoration of salivary glands damaged by radiation therapy for head and neck cancer, with a review of related aspects of salivary gland morphology and development. Biotech Histochem 83: 103-130

Rothenberg S M, Concannon K, Cullen S, Boulay G, Turke A B, Faber A C, Lockerman E L, Rivera M N, Engelman J A, Maheswaran S et al (2015) Inhibition of mutant EGFR in lung cancer cells triggers SOX2-FOXO6-dependent survival pathways. eLife 4: e06132

Schneyer C A, Hall H D (1967) Effects of denervation on development of function and structure of immature rat parotid. Am J Physiol 212:871-876

Seidel K, Marangoni P, Tang C, Houshmand B, Du W, Maas R L, Murray S, Oldham M C, Klein O D (2017) Resolving stem and progenitor cells in the adult mouse incisor through gene co-expression analysis. eLife 5: e24712

Siegel R L, Miller K D, Jemal A (2015) Cancer statistics, 2015. CA Cancer J Clin 65: 5-29

Smith A N, Miller L A, Radice G, Ashery-Padan R, Lang R A (2009) Stage-dependent modes of Pax6-Sox2 epistasis regulate lens development and eye morphogenesis. Development 136: 2977-2985

Sullivan C A, Haddad R I, Tishler R B, Mahadevan A, Krane J F (2005) Chemoradiation-induced cell loss in human submandibular glands. Laryngoscope 115: 958-964

Suzuki Y (2008) Expression of Sox2 in mouse taste buds and its relation to innervation. Cell Tissue Res 332: 393-401

Taranova O V, Magness S T, Fagan B M, Wu Y, Surzenko N, Hutton S R, Pevny L H (2006) SOX2 is a dose-dependent regulator of retinal neural progenitor competence. Genes Dev 20: 1187-1202

Tatsuta M, Yamamura H, Iishi H, Ichii M, Noguchi S, Baba M, Taniguchi H (1985) Promotion by vagotomy of gastric carcinogenesis induced by N-methyl-N'-nitro-N-nitrosoguanidine in Wistar rats. Can Res 45:194-197

Tofilon P J, Fike J R (2000) The radioresponse of the central nervous system: a dynamic process. Radiat Res 153: 357-370

Ueno H, Ferrari G, Hattori T, Saban D R, Katikireddy K R, Chauhan S K, Dana R (2012) Dependence of corneal stem/progenitor cells on ocular surface innervation. Invest Ophthalmol Vis Sci 53: 867-872

Urek M M, Bralic M, Tomac J, Borcic J, Uhac I, Glazar I, Antonic R, Ferreri S (2005) Early and late effects of X-irradiation on submandibular gland: a morphological study in mice. Arch Med Res 36: 339-343

Von Vintschgau M, Honigschmied J (1877) Nervus Glossopharyngeus and Schmeckbecher. Arch Gesammte Physiol 14: 443-448

Wallace H (1972) The components of regrowing nerves which support the regeneration of irradiated salamander limbs. J Embryol Exp Morphol 28: 419-435

Wang J M, McKenna K E, McVary K T, Lee C (1991) Requirement of innervation for maintenance of structural and functional integrity in the rat prostate. Biol Reprod 44: 1171-1176

Wanigasekara Y, Airaksinen M S, Heuckeroth R O, Milbrandt J, Keast J R (2004) Neurturin signalling via GFRalpha2 is essential for innervation of glandular but not muscle targets of sacral parasympathetic ganglion neurons. Mol Cell Neurosci 25: 288-300

Wollny D, Zhao S, Everlien I, Lun X, Brunken J, Brune D, Ziebell F, Tabansky I, Weichert W, Marciniak-Czochra A et al (2016) Single-cell analysis uncovers clonal acinar cell heterogeneity in the adult pancreas. Dev Cell 39: 289-301

Wong C S, Van der Kogel A J (2004) Mechanisms of radiation injury to the central nervous system: implications for neuroprotection. Mol Interventions 4: 273-284

Wu S, Wu Y, Capecchi M R (2006) Motoneurons and oligodendrocytes are sequentially generated from neural stem cells but do not appear to share common lineage-restricted progenitors in vivo. Development 133:581-590

Xiao N, Lin Y, Cao H, Sirjani D, Giaccia A J, Koong A C, Kong C S, Diehn M, Le Q T (2014) Neurotrophic factor GDNF promotes survival of salivary stem cells. J Clin Invest 124: 3364-3377

Xiao Y, Thoresen D T, Williams J S, Wang C, Perna J, Petrova R, Brownell I (2015) Neural Hedgehog signaling maintains stem cell renewal in the sensory touch dome epithelium. Proc Natl Acad Sci USA 112: 7195-7200

Yawo H (1987) Changes in the dendritic geometry of mouse superior cervical ganglion cells following postganglionic axotomy. J Neurosci 7:3703-3711

Zeilstra L J, Vissink A, Konings A W, Coppes R P (2000) Radiation induced cell loss in rat submandibular gland and its relation to gland function. Int J Radiat Biol 76: 419-429

Zhao C M, Hayakawa Y, Kodama Y, Muthupalani S, Westphalen C B, Andersen G T, Flatberg A, Johannessen H, Friedman R A, Renz B W et al (2014) Denervation suppresses gastric tumorigenesis. Sci Transl Med 6: 250ra115

Example 2

Therapeutic Activation of Endogenous Salivary Gland Stem Cell Population Through Local Delivery of Muscarinic Agonist in an Injectable Alginate Hydrogel

An alternative regenerative approach for restoring salivary function is stem cell therapy where autologous stem/progenitor cells are transplanted into the injured organ or surviving stem cells within the tissue are reactivated. However, progenitor cells that give rise to saliva-secreting acinar cells, the major cell type damaged by radiation and autoimmune disease, were previously unknown. We recently identified SOX2 as a marker of epithelial progenitor cells in the murine salivary gland (Emmerson et al., 2018). SOX2+ acinar cells are found in all major human salivary gland (submandibular (SMG)) and compose 20% of the acinar compartment in the murine sublingual gland (SLG). We found that maintenance of SOX2+ cell and tissue homeostasis was dependent on parasympathetic nerve production of acetylcholine, which activates muscarinic receptors to promote cell proliferation. We further showed that the muscarinic mimetics carbachol and pilocarpine could promote SOX2+ cell proliferation after delivery in vivo and/or ex vivo and that muscarinic agonism promoted salivary gland regeneration after radiation induced damage. Together, these studies strongly suggest that reactivation of existing stem cells is a feasible strategy to regenerate the organ.

Here we test the capacity of local and sustained cevimeline delivery to promote stem cell mediated repopulation of salivary glands. Specifically, we have devised a combination product that involves the encapsulation of a muscarinic agonist into biodegradable calcium crosslinked alginate hydrogel for local, targeted and sustained delivery into the salivary gland. Using a combination of in vitro and in vivo tests, we have defined the chemistry of the alginate-based hydrogel that enables linear distribution within the tissue and sustained delivery of the muscarinic receptor agonist cevimeline. In vivo testing in mice has demonstrated the encapsulated drug is efficacious in promoting stem cell proliferation within the salivary glands of both control and irradiated animals in a fashion consistent with sustained delivery. Thus, we provide a novel therapeutic for the regeneration of salivary glands and the recovery of saliva flow.

Results

Cevimeline Promotes Cell Proliferation when Delivered Via Local Injection

Given our previous findings that systemic administration of a muscarinic mimetic promotes salivary gland proliferation, we next determined if local intraglandular injection was also able to promote a mitotic response. To determine if cevimeline could act locally on the salivary gland to induce acinar cell proliferation we injected cevimeline at 10 mg/kg of body weight (20 µL) directly into the sublingual gland and measured proliferation after 18 hrs. As shown in FIG. 15, acinar cell proliferation was significantly increased (FIG. 15), indicating that cevimeline can act directly on the salivary glands to boost cell mitosis.

Engineered Biodegradable Calcium Crosslinked Alginate Hydrogel

Based on the efficacy of local cevimeline delivery in promoting cell proliferation, we next set out to develop an injectable drug delivery platform for local and sustained release of cevimeline to drive acini regeneration. For this purpose, we chose to utilize a calcium crosslinked alginate-based biomaterial for delivery of cevimeline. Alginate is a naturally occurring anionic polymer extracted from brown algae. Alginate is an FDA-approved hydrogel used for many biomedical applications, due to its biocompatibility, minimal toxicity, relatively low cost, and ability to be cross-linked under cytocompatible conditions using divalent cations such as $Ca^{2+}$. (Lee et al. (2012) Prog. Polym. Sci. 37(1):106-126) Calcium cross-linked alginate has a structural similarity to extracellular matrices of living tissues and is highly hydrophilic to maintain a physiologically moist microenvironment. Importantly for our application, alginate can be resuspended at concentrations that enable injection through clinically relevant syringe-needles systems during which the sheer force will break the electrostatic cross-links to linearly deform the material, but gelation will spontaneously reform in vivo.

Alginate is inherently non-degradable in mammals due to the lack of the polymer chain cleaving enzyme alginase. However, ionically cross-linked alginate gels are dissolved through the release of the divalent ions cross-linking the gel into the surrounding media via exchange reactions with monovalent cations such as sodium ions. Alginate degradation rates can be further controlled through partial oxidation of the polymer chains. Critical for FDA approval as a therapeutic rather than an implantable, the alginate hydrogel must be degraded by 30 days post-injection. However, to achieve sustained delivery of cevimeline, the alginate should be present over a 7 day+ period. To meet this degradation profile, we partially oxidized the alginate chains at either 2% or 5%. In vitro degradation testing shows that the two hydrogels have significantly different degradation profiles with slower degradation achieved with the 2% oxidized alginate (OA) hydrogel. (FIG. 16A) The 2% OA hydrogels maintains more than 50% of their gel mass for almost 5 days in vitro, whereas the 5% OA hydrogels loses this mass by 1 day. After 7 days of culture in vitro degradation testing approximately 30% of the 2% OA hydrogel versus 14% of the 5% OA hydrogel remain.

Figure 16A:
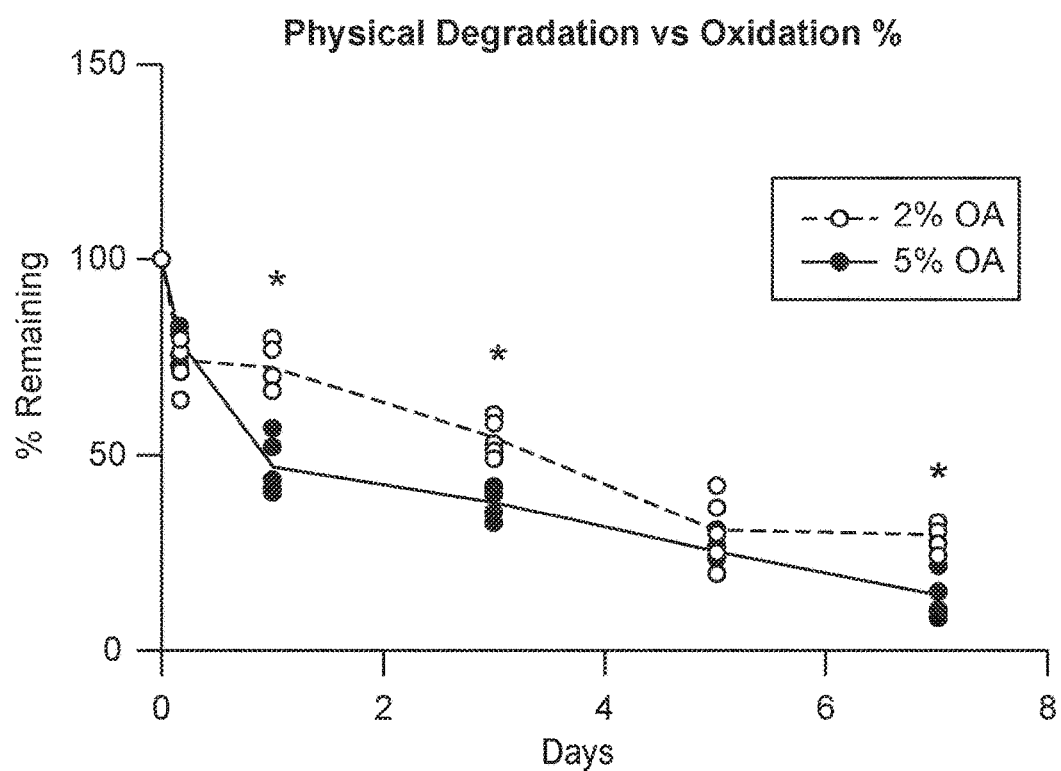
Figure 16B:
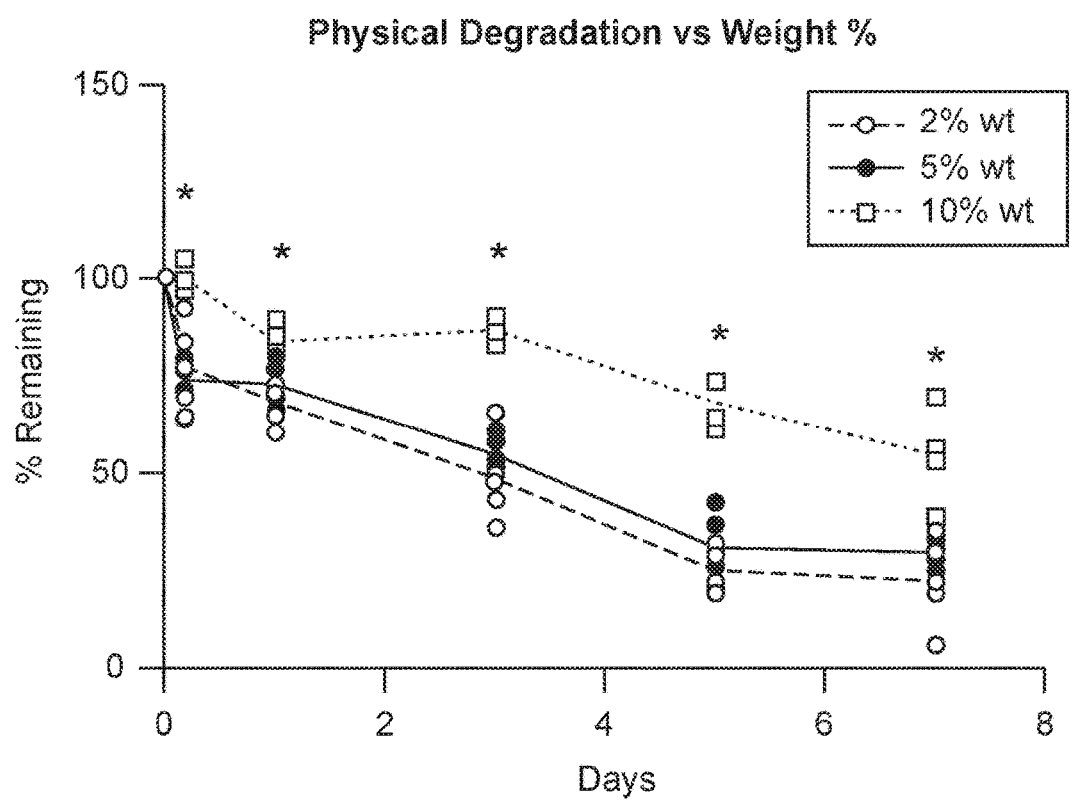
Figure 16D:
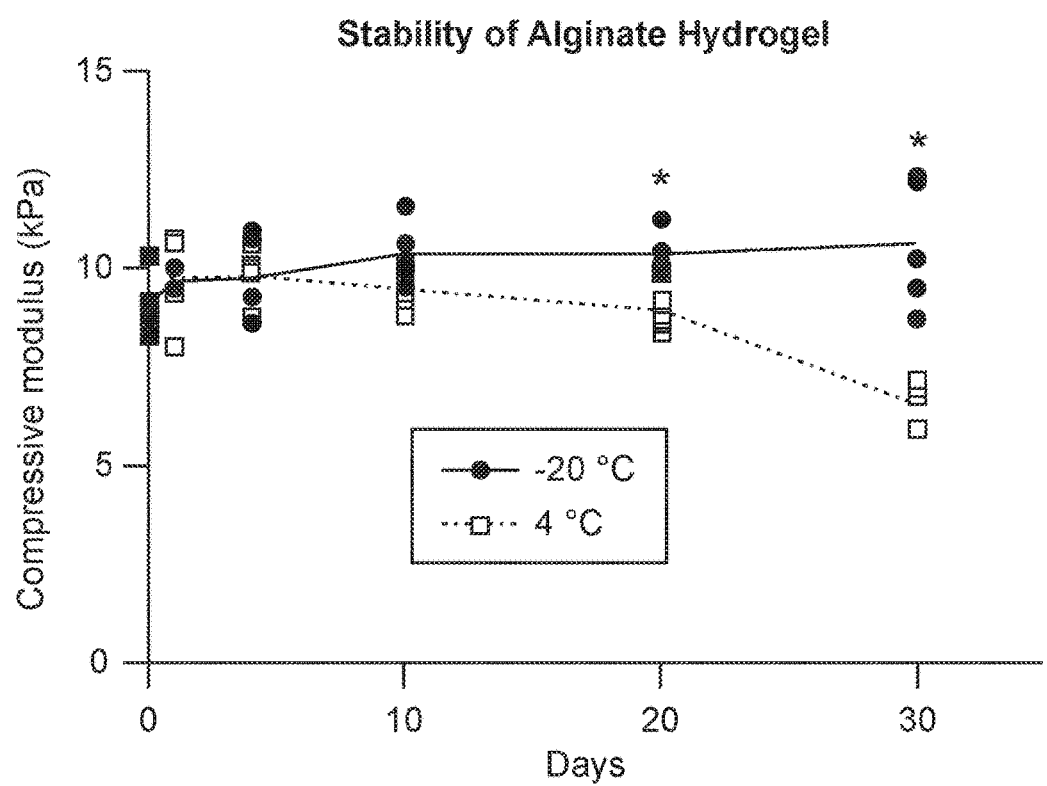

Based on this longer physical retention we chose to proceed with the 2% OA hydrogel. We next tested how weight percentage (wt %) of the 2% OA hydrogel influenced physical degradation. While 10 wt % of the 2% OA hydrogel degraded significantly more slowly than 2 or 5 wt %, this concentration could not be easily injected from the small caliber needles required for in vivo delivery to the salivary gland (>23 gauge). (FIG. 16B).

Physical degradation of the 2% OA hydrogel at a 5 wt % was subsequently tested under more physiologically relevant conditions by injecting 100 µl of the hydrogel into subcutaneous pockets on the dorsal aspect of wild type mice. This amount of hydrogel forms a small disk within minutes that can then be removed and weighed for analysis. In contrast to the in vitro system, in vivo we find nearly no mass loss at 7 days post injection (FIG. 16C), indicating that this hydrogel is suitable for in vivo delivery of cevimeline.

Another factor critical for commercial potential is the storage stability of the solubilized alginate. To slow degradation, the solubilized oxidized alginate we presumed the material must either be stored at 4° C. or <–20° C., but the specific impact of these storage conditions on material stability is unknown. We therefore tested changes in compressive modulus of calcium cross-linked alginate following storage of the solubilized oxidized alginate at 4 or –20° C. for 30 days. When the 2% OA hydrogel at a 5 wt % was stored under refrigeration conditions (4° C.), the cross-linking efficacy was significantly impacted with a reduction in the compressive modulus by 20 days suggesting degradation of the oxidized alginate (FIG. 16C). However, maintaining the alginate under frozen conditions (−20° C.) stabilized initial material properties at 30 days post-synthesis.

Local and Sustained Release of Cevimeline from Alginate Hydrogel

Figure 17A:
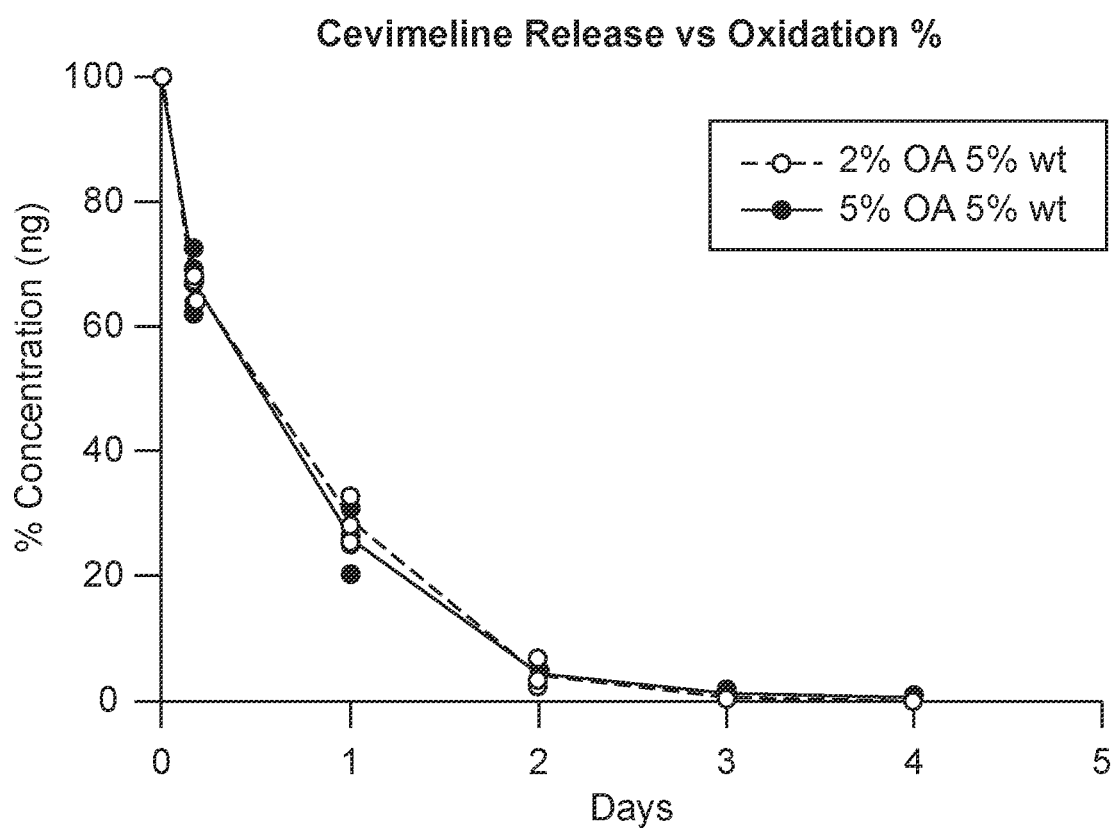
Figure 17B:
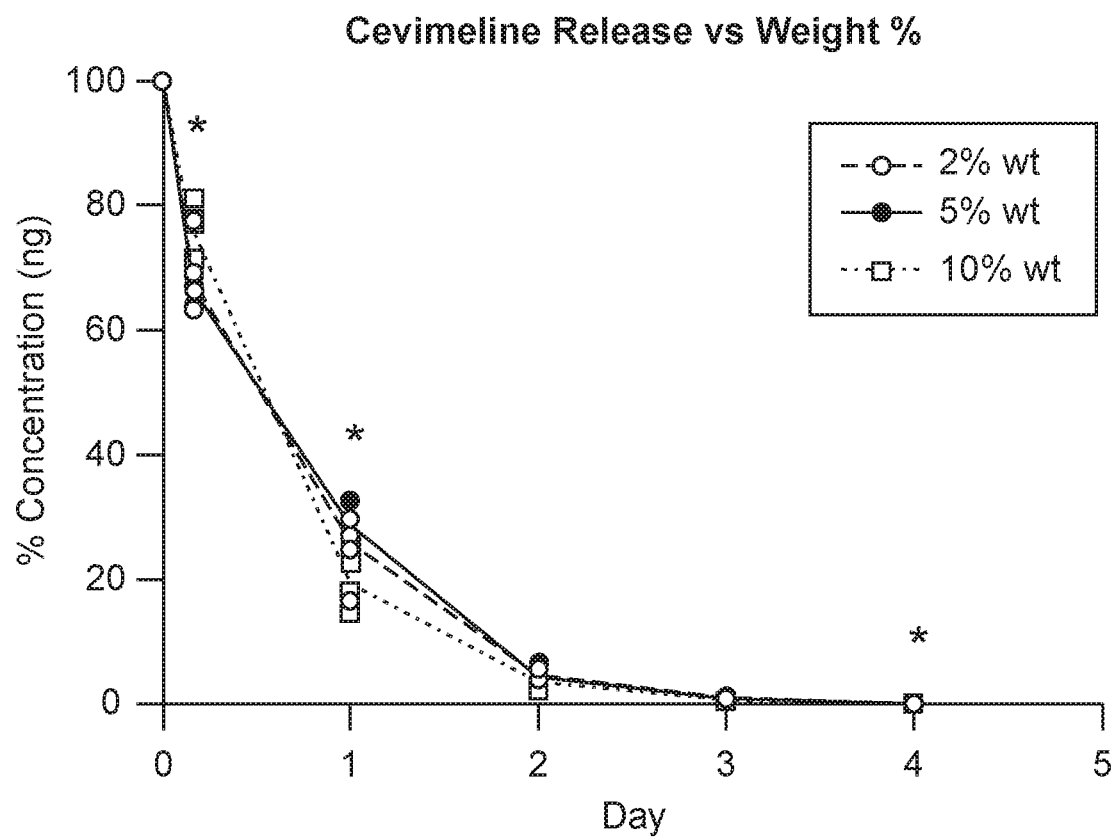
Figure 17C:
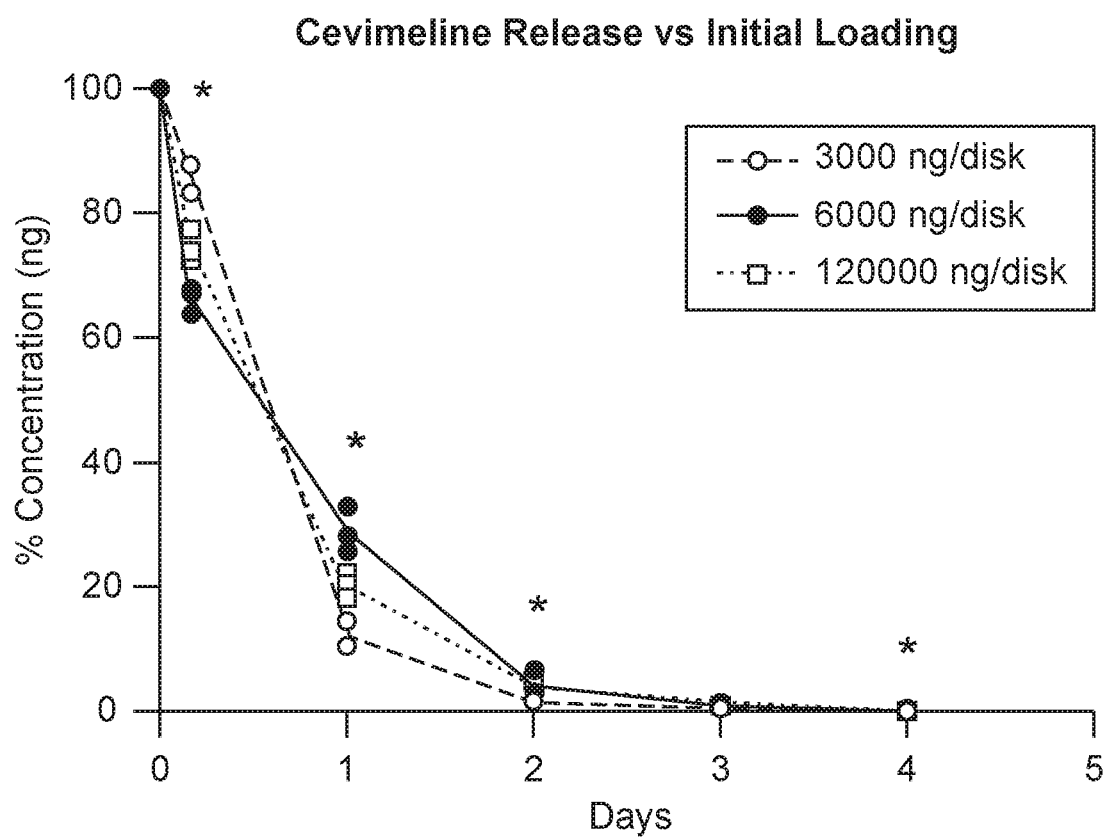
Figure 17D:
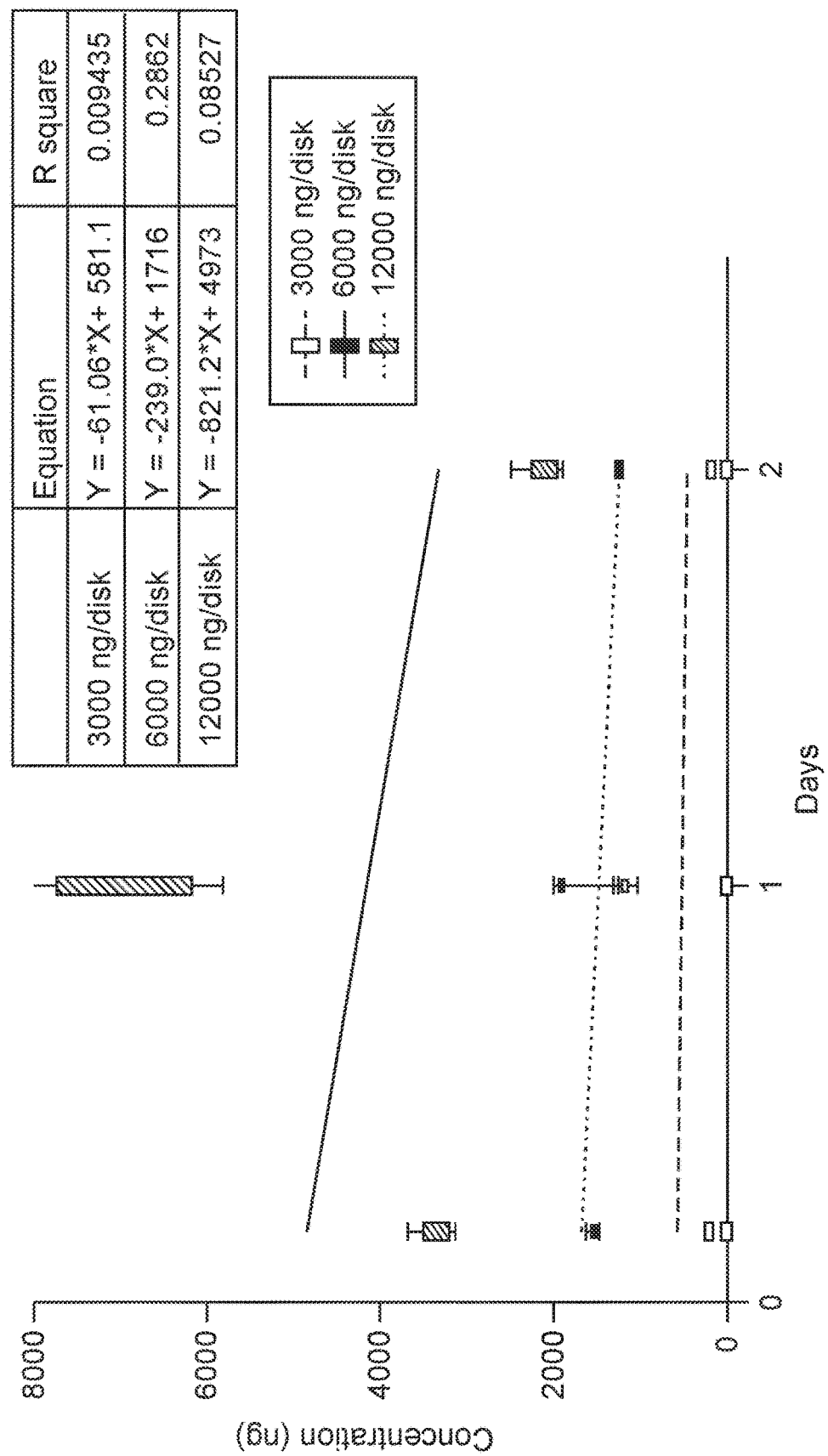

Pharmaceutical application of alginate has traditionally involved utilizing the hydrogel for controlled release of a variety of low molecular weight drugs. Crosslinked alginate forms a nanoporous materials with a theoretical pore size for our material predicted at ~5 nm given the starting molecular weight of 197 kDa. Controlled release of the drug is predominantly regulated through electrostatic interactions between the positively charged cevimeline (pKA=9.5) and the negatively charged alginate hydrogel. In vitro cevimeline release studies demonstrate that we can sustain release of the drug over the course of 2 days. (FIG. 17) Despite changing the physical degradation properties (FIGS. 16A-16B), neither amount of oxidation (OA %) nor the weight percentage (wt %) of the alginate hydrogel had a significant impact on drug release kinetics and over 85±5% of cevimeline has been released in vitro by 2 days. (FIGS. 17A-17B) To test whether changing the starting concentration of the drug influenced release we loaded either 3000, 60000, or 12000 ng cevimeline into each disk and tested release in vitro. Release rates remain relatively consistent (FIG. 17C) and therefore generate a predictable increase in the amount of drug delivered over the course of two days (FIG. 17D).

Cevimeline Promotes Glandular Cell Proliferation when Encapsulated in Alginate

Given this successful drug delivery platform we next tested the efficacy, toxicity and degradation of alginate+cevimeline in vivo. Due to the small size of the mouse salivary gland, we chose not to inject the hydrogel directly into the glands so as to avoid complications caused by tissue damage, but rather into the region directly adjacent to the gland as can be visualized on x-ray (FIG. 18A; Omnipaque encapsulated as a radio-opaque contrast reagent). Alginate, with or without 10 mg/kg cevimeline, or saline were injected adjacent to the salivary glands and the salivary glands analyzed at 18 hr (FIG. 18C, n=3-4 per group) or 3 days post-injection (FIG. 18, n=3-6 per group). As shown in FIG. 18, we measured a significant increase in the number of proliferating Ki67+ and EdU+ acinar cells at 3 days in response to 10 mg/kg alginate+cevimeline compared to alginate alone (FIGS. 18C, 18D), consistent with the drug having prolonged activity when combined with alginate. We saw a similar increase in proliferating Ki67+ acinar cells at 3 days in response to a higher 25 mg/kg alginate+cevimeline, suggesting that increasing dose does not significantly improve efficacy (FIG. 18). We also tested if alginate itself is pro-mitotic by comparing cell proliferation in glands from mice treated with alginate alone to those receiving an intraperitoneal (IP) injection of saline only. We found that alginate alone was sufficient to promote epithelial cell proliferation and did so over a 3-7 day period (FIG. 23), indicating that the combination has a beneficial impact.

Figure 19A:
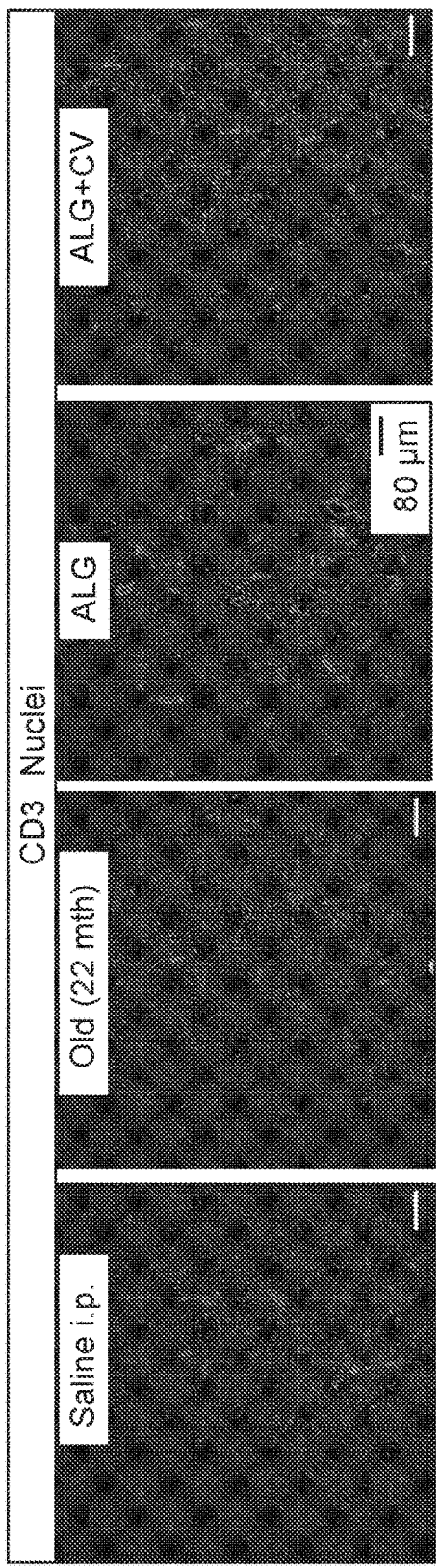
Figure 19B:
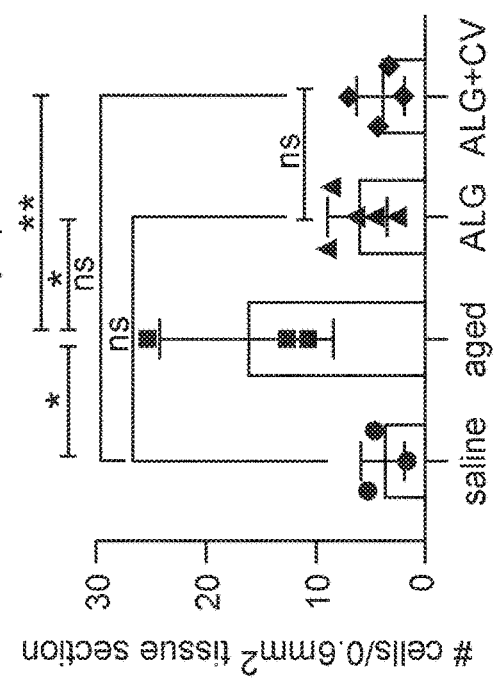
Figure 19C:
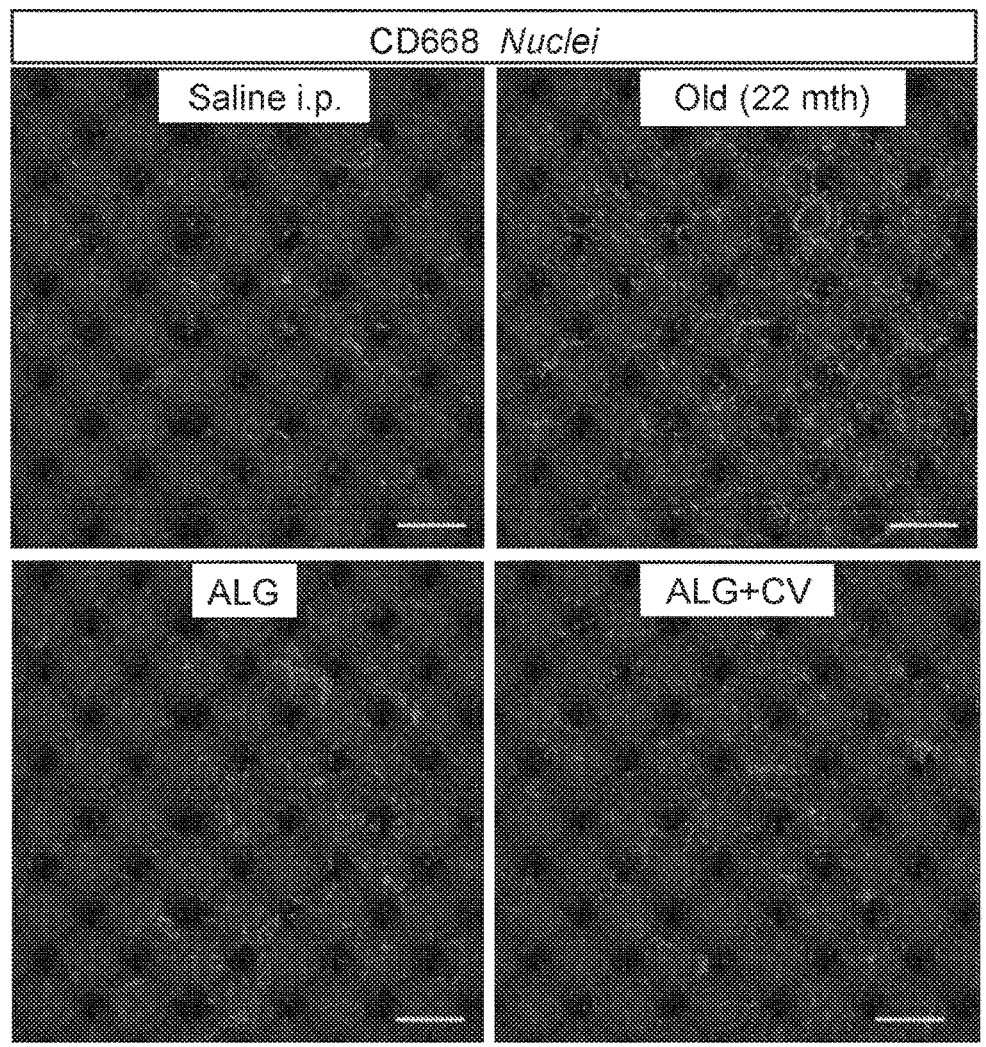
Figure 19D:
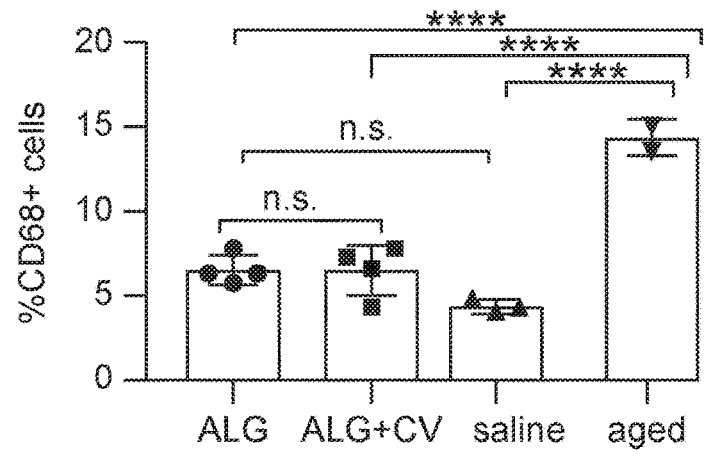

To determine if alginate or alginate+cevimeline treatment exhibited toxic effects in mice we measured mouse weight and characterized inflammatory cells in the salivary glands. We found that increasing doses of alginate+cevimeline did not cause a reduction in weight by 3 days post-injection (FIG. 24). Furthermore, no toxic effects such as diarrhea were observed compared to saline injected controls. Our immunohistological analysis of CD3+ T cells also showed no increase when compared to tissue derived from untreated or aged (positive control) mice (FIGS. 19A, 19B). Our analysis of CD68+ macrophages, a key innate immune cell and first responder to damage, suggested a small increase in these cells in response to alginate or alginate+cevimeline treatment when compared directly to untreated controls (FIGS. 19C, 19D). Further analysis of macrophage populations indicated that the pro-repair CD206+ macrophage was significantly increased in alginate treated tissue when compared to saline treated controls (FIG. 19E), suggesting that alginate may have a beneficial impact on salivary glands by activating anti-inflammatory macrophages.

Impact of Cevimeline-Alginate on Salivary Glands after Radiation-Induced Damage

Figure 20C:
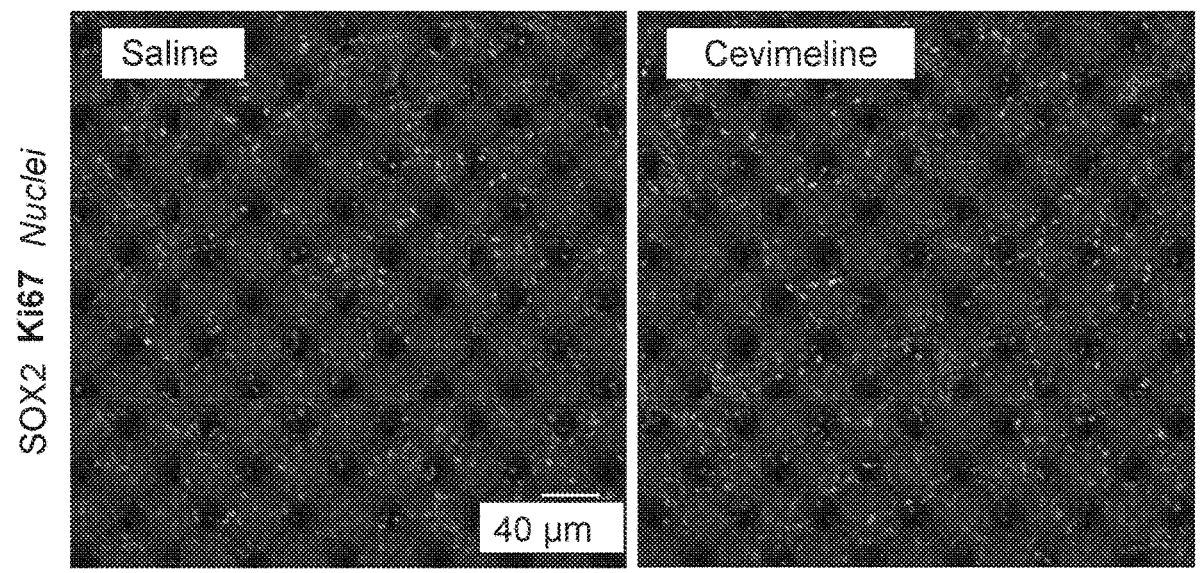
Figure 20D:
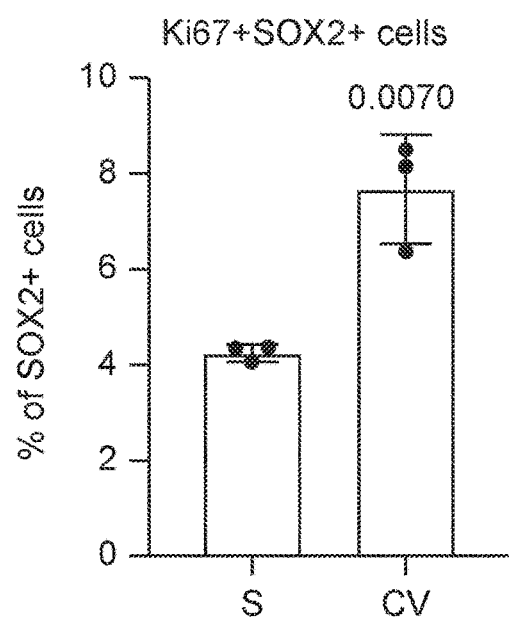
Figure 20E:
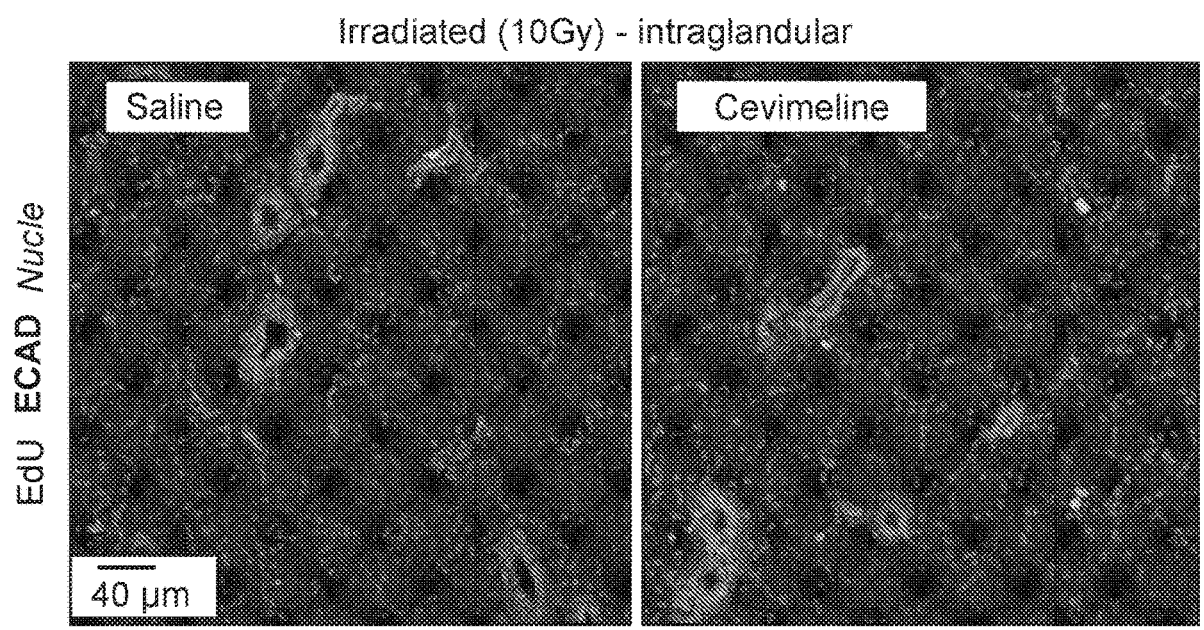
Figure 20F:
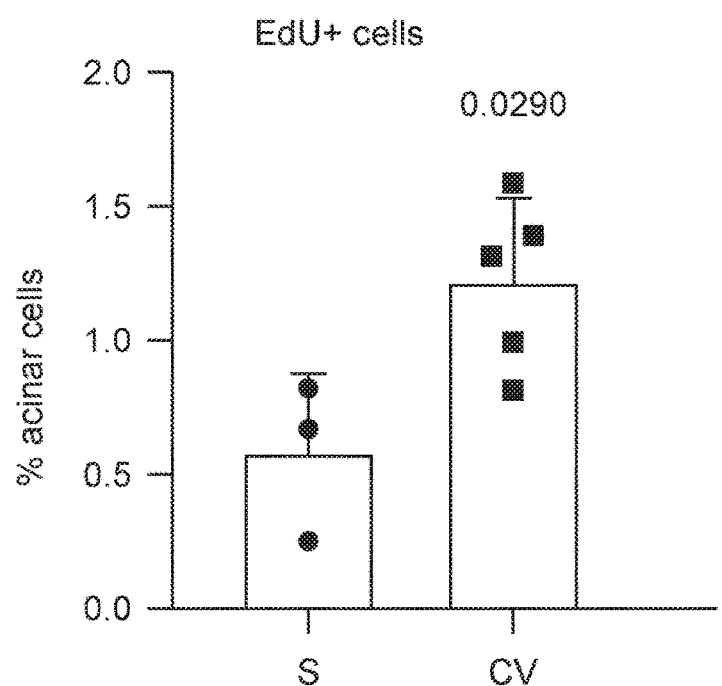

Next, we tested whether cevimeline or alginate+cevimeline were capable of promoting cell proliferation in salivary glands after gamma-radiation induced damage. The necks of 7-8 week old C57BL6 were given a single 10Gy dose of radiation and 14 days later were systemically or intraglandularly injected with either saline or 10 mg/kg of cevimeline with the numbers of proliferating acinar cells were analyzed after 18 hrs (see schematic in FIG. 20A). This level of radiation reduces citrate induced salivary flow by 30% (FIG. 20B). We found that both systemic and local administration of cevimeline increased proliferation of acinar cells in irradiated mice (FIGS. 20C-20E), indicating cevimeline is efficacious in damaged salivary glands.

Finally, we tested whether cevimeline encapsulated in alginate promoted cell proliferation and salivary flow. Mice were injected with alginate or alginate+cevimeline 14 days post-radiation and sacrificed at 3 days for analysis of proliferation (FIG. 21A schematic). Alginate+cevimeline increased proliferation rates above alginate only levels (FIGS. 21B, 21C). We further determined if treatment with alginate or alginate+cevimeline aided salivary flow. Surprisingly, both alginate and alginate+cevimeline were able to increase citrate induced salivary flow by 7 days (FIG. 21D), suggesting that alginate itself benefits the irradiated organ.

Discussion

Oral administration of muscarinic agonists is prescribed to stimulate the temporary production of saliva in patients suffering from xerostomia but is associated with common side effects such as excessive sweating, flushing, urinary urgency, gastrointestinal discomfort and headaches. Here we show that local release of the muscarinic agonist cevimeline from an injectable calcium cross-linked alginate hydrogel can promote acinar cell replenishment and improve salivary gland function after radiation induced damage without eliciting an immune response. This represents the first in vivo evidence that acinar progenitors in irradiated tissue can be stimulated to proliferate and that muscarinic receptor activation is sufficient to achieve this outcome. We also demonstrate that, in addition to sustaining the release of the small molecule cevimeline over three days, calcium cross-linked alginate alone stimulates a pro-regenerative response. Taken together, these findings offer a potential new combination therapy for reversing salivary gland dysfunction after radiation induced damage that may be suitable for a range of dry mouth conditions.

Our therapy is based on evidence from over the last 100 years that peripheral nerves are essential for salivary gland function, homeostasis, and regeneration. Ablation of parasympathetic nerves results in atrophy of the secretory acini that can be reversed through reinnervating the tissue (Emmerson et al., 2018). As parasympathetic innervation is severely diminished in salivary glands from patients who have received therapeutic radiation for head and neck cancer (Emmerson et al., 2018), we questioned whether re-supplying the atrophied tissue with nerve-derived factors may restore tissue structure and function. The in vivo experiments shown here follow on from our previous ex vivo studies demonstrating that increasing neuronal survival and function after radiation exposure in fetal salivary glands or treating irradiated adult tissue with a muscarinic agonist is sufficient to promote acinar cell replenishment via a progenitor cell-mediated mechanism (Knox 2013; Emmerson 2018). Furthermore, our current data also suggests that the improvement in saliva flow after long term oral administration of muscarinic agonists in mice and humans with irradiated salivary glands (Barbe 2017; Taniguchi 2019) is likely due to acinar cell replenishment rather than a reduction in cell death. However, whether human acinar cells are capable of proliferating in response to muscarinic stimulation remains to be determined.

A number of strategies have been explored for the regeneration of irradiated salivary glands. Our therapeutic application aims to mimic the endogenous regulation of tissue by the parasympathetic nervous system through the provision of an acetylcholine homolog. This approach parallels recent gene therapy studies aimed at resupplying the organ with functional nerves through the expression of neurturin, a neurotrophic growth factor. Other strategies utilize growth factors known to promote branching morphogenesis during embryonic development: intraglandular administration of fibroblast growth factor 7 (FGF7; Lombaert et al., 2009; Xiao et al., 2014), or systemic delivery of insulin-like growth factor 1 Grundmann (2010) BMC Cancer 10:417) or gene delivery of Sonic hedgehog (Shh) via ductal cannulation (Hai et al. (2016) Hum. Gene Ther. 27(5):390-399) to irradiated salivary glands improved salivary function and tissue preservation. However, uptake of these factors by the clinic has been stymied by their potential to accelerate cancer growth. Although long term administration of oral pilocarpine was not shown to be tumorigenic, further studies are needed to determine whether local administration of cevimeline impacts cancer initiation, progression or metastasis.

Previous studies have shown calcium cross-linked alginate hydrogels to promote wound healing in a variety of organ systems including bone, cartilage and skin (Wang et al. (2015) Int. J. Clin. Exp. Pathol. 8(6):6636-6645). Yet, whether this function is mediated directly via cell proliferation, survival and/or migration remains poorly understood. Our data indicates that calcium alginate has the ability to promote tissue regeneration in the irradiated salivary glands via inducing cell proliferation. A possible mechanism by which this is achieved is by an elevation in extracellular calcium. Calcium that has not been crosslinked to the polysaccharide backbone is released from alginate directly into the extracellular space (Doyle et al. (1996) J. Biomed. Mater. Res. 32(4):561-568) or can be released during degradation of the material. This $Ca^{2+}$ depot can then activate calcium sensing receptors to mediate intracellular $Ca^{2+}$ release and/or other signaling pathways to promote cell proliferation. As calcium sensing receptors are present on many cell types, including acinar cells, we propose that $Ca^{2+}$ ions derived from alginate may act as a pro-mitotic agent via stimulating these receptors.

It was recently reported that release of $Ca^{2+}$ from calcium alginate gels can also be pro-inflammatory (Chan et al. (2013) Acta Biomater. 9(12):9281-9291). Calcium alginate subcutaneously into mice significantly upregulated IL-1β in surrounding tissue and enhanced the inflammatory effects of LPS. However, our results indicate that calcium alginate, with or without cevimeline, is highly biocompatible and elicits little to no inflammation when injected in the area immediately surrounding the salivary glands.

One of the key properties required from the hydrogel is the ability to provide sustained drug release. Drug molecules, from small chemical drugs to macromolecular proteins, can be released from alginate gels in a controlled manner, depending on the cross-linker types and cross-linking methods. Indeed, multiple chemistries have been applied to control the kinetics of drug release such as crosslinking.

Materials & Methods

Synthesis of OA

The oxidized alginate (OA) was prepared by reacting sodium alginate (Protanal LF 20/40, alginate MW=197,000 Da, FMC Biopolymer #S18407) with sodium periodate (Sigma, cat #311448) using a modification of a previously described method. [1] Briefly, sodium alginate (10 g) was dissolved in ultrapure deionized water (diH$_2$O, 900 ml) overnight. Sodium periodate (0.22 g) was dissolved in 100 ml diH$_2$O and added to alginate solution under stirring in the dark at room temperature (RT). After reacting for 24 hrs, the reaction was stopped by addition of ethylene glycol (52 µl, Sigma). The OA was purified by dialysis (MWCO=3500 Da, Spectrum Laboratories Inc.) against diH$_2$O for 3 days, treated with activated charcoal (5 g/l, 50-200 mesh, Fisher, 05-690B) for 30 min, filtered (0.22 µm filter) and lyophilized.

To analyze the oxidation efficiency of the OA, the OA was dissolved in deuterium oxide (5 weight/volume %) and placed in an NMR tube. $^{13}$C-NMR spectrum was recorded on a Bruker ADVANCE III 400 MHz NMR spectrometer (Bruker) using 3-(trimethylsilyl)propionic acid-d$_4$ sodium salt (0.05 w/v %) as an internal standard. The actual oxidation was determined from $^{13}$H-NMR spectrum based on the ratio of the integrals for the carbons to the newly formed carbonyl carbons of aldehydes by oxidation of alginate. (FIG. 25).

Synthesis of Calcium Crosslinked OA Hydrogels

OA is maintained at −20° C. in a lyophilized form until ready to form the hydrogel. Hydrogels are formed by dissolving the OA in Dulbecco's Modified Eagle's Medium (DMEM, Gibco #11885084) under constant stirring to the desired weight/volume (wt %) at RT for a minimum of 30 minutes. OA is crosslinked by mixing with a super saturated calcium sulfate (CaSO$_4$, 84 mg/mL) solution at a concentration of 20 µL CaSO$_4$ per 1 wt % per mL of alginate (e.g. 40-, 100-, and 200-µL of CaSO$_4$ mixed with 1 mL of a 2%-, 5%-, and 10-wt % alginate, respectively). OA solution and CaSO$_4$ slurry were loaded separately into two 1 mL syringes. After the two syringes were connected together with a female-female luer lock coupler (Value Plastics), the two syringes were mixed (~30 times).

Physical Degradation of Oxidized Alginate Hydrogel

In vitro physical degradation of the OA hydrogels was tested by creating 1 mm×4 mm disks with either a 2 or 5% oxidation at a weight/volume of 2, 5, or 10 wt %. Disk were formed by using a 25-gauge needle to inject the OA hydrogel between two glass plates separated by a 1.0 mm spacer. The gel polymerized at RT after 30-45 minutes and 4 mm diameter disks were created using a biopsy punch. Gels were transferred to a 0.4 µm transwell (Millicell, #MCHT12H48) in a 12-well plate containing 3.2 ml of DMEM and the plate was continuously shaken (100 RPM) at 37° C. Hydrogels were collected at T$_0$ (initial control), 4 hrs, 1-, 3-, 5-, and 7-days (D). Three hydrogels were pooled together with an average of 3-5 separate replicates (samples) at each time point. Samples were frozen in −80° C. and subsequently lyophilized (VirTis Wizard 2.0). Dry weight was measured with an analytical balance (Mettler Toledo AT201).

In vivo degradation assays were performed using a murine subcutaneous assay. All experiments were approved by the UCSF Institutional Animal Care and Use Committee (IACUC). Animals were anesthetized using isoflurane (2.5% induction, 1.5% maintenance), skin was cleaned with 70% ethanol, then 100 µl of OA hydrogel gels were injected into individual subcutaneous pockets on the dorsal aspect of mice using a 25-gauge needle (up to 6 hydrogels/animal). Mice were socially housed and monitored for signs of pain and distress for 48 hours. Animals were survived 18 hours, 3-, 5-, or 7-days. At terminal time points, gels were microdissected from the subcutaneous pockets, frozen at −80° C., lyophilized, and dry weight recorded as done for the in vitro degradation.

Stability of OA

The 2% OA polymers were dissolved at 5 wt % as described above, aspirated into a 3-ml syringe and stored at 4° C. or −20° C. Syringes (n=5/time) were removed from storage at 1-, 4-, 10-, 20- or 30-days post dissolution, allowed to return to RT, then crosslinked by mixing OA solutions with the super saturated calcium sulfate slurries as described above. After mixing the crosslinked OA was immediately placed between two glass plates separated by 0.75 mm spacers and allowed to form a hydrogel for 30 min at RT. Calcium crosslinked OA hydrogel disks were created using a 6 mm diameter biopsy punch. To evaluate the stability of OA solution, the modulus of calcium crosslinked OA hydrogels over time was measured. The elastic moduli of hydrogels were determined by performing uniaxial, unconfined constant strain rate compression testing at RT using a constant crosshead speed of 1% per sec on a mechanical testing machine (225 lbs Actuator, TestResources) equipped with a 5 N load cell. Elastic moduli were calculated from the first non-zero linear slope of the stress versus strain plots and was limited to the first 5% of strain.

Mass Spectroscopy to Measure Cevimeline

A Shimadzu Prominence LC-20ADXR system interfaced to a 4500 QTrap mass spectrometer with an electrospray ionization (ESI) source was operated for LC-MS/MS analysis. The chromatographic separation was achieved using a Phenomenex KineteX® C18 (50×3 mm, 2.6 µm) column coupled with a Phenomenex SecurityGuard C18 guard column (3 mm×2.0 mm). The column temperature was controlled at 30° C. Mobile phase A was 0.1% Trifluoroacetic acid in water and mobile phase B was acetonitrile (ACN). The injection volume was 10 µL and the flow rate was 0.5 mL/min. The gradient condition was: (time/minute, % mobile phase B): (0, 15), (1, 15), (2.5, 22.8), (2.6, 98), (5, 98), (5.1, 15), and (8, 15). The source parameters included curtain gas of 45 psi, ion spray voltage of 4000 V, ion source temperature of 550, and medium collision gas. A summary of MS/MS parameter settings in positive ion ESI mode is presented in Table 1.

Standard working solutions of cevimeline were prepared over the range from of 10.0-10000.0 ng/mL in methanol. Working solutions were spiked into 100 µL of DMEM to generate the standards or QC samples. The final concentrations of the calibration standards were 0.5, 1.0, 2.5, 5.0, 10.0, 25.0, 50.0 and 100.0, 250.0 and 500 ng/mL in DMEM. The QC samples were 0.9, 4, 30.0 and 400.0 ng/mL.

For the sample preparation step, to each 100 µL DMEM, 10 µL IS working solution (1000 ng/mL) was added. 96-Well Protein Precipitation Filter Plate Sigma-Aldrich (St. Louis, MO) and 300 µl of MeOH:ACN (15:85) were used for protein precipitation. 200 µl of $NH_4OH$ 5% was added to 200 µl of the sample after filtration and 10 µl was injected to the LCMS system. The bioanalytical method was validated in accordance with current U.S. FDA guidelines including selectivity, linearity, intra- and interday precision and accuracy, recovery and stability ("Guidance for Industry, Bioanalytical Method Validation,"2018 fda.gov/media/70858/download).

TABLE 1

Optimized ESI (+) mass spectrometric conditions for multiple reaction monitoring (MRM) of compounds.

| Analyte | Q1 (m/z) | Q3 (m/z) | CE (volt) | DP, volts | CXP, volts |
| --- | --- | --- | --- | --- | --- |
| Cevimeline | 200.114 | 156.2 | 31 | 90 | 10 |
|  |  | 126.1 | 45 |  |  |
| Cevimeline-D4 | 204.074 | 156.0 | 31 | 76 | 12 |
|  |  | 126.0 | 47 |  |  |

Cevimeline Release from Alginate Hydrogels

In vitro cevimeline (CV) release from OA hydrogels was tested by creating 1 mm×4 mm disks with either a 2 or 5% oxidation at a weight/volume of 2, 5, or 10%. Alginate+cevimeline (Abcam, ab141317) hydrogels were created by resuspending the drug at the desired concentration in the DMEM prior to mixing with the lyophilized OA, subsequent crosslinking proceeds as described above to encapsulate the drug with the OA hydrogel. Three 4 mm alginate+cevimeline hydrogels were placed in 0.4 µm transwell in a 12-well plate containing 3.2 ml of DMEM incubating in 37° C. with slow continuous agitation (100 RPM). Sample media (3 ml DMEM) was collected and replenished at 4 hours, 1-, 2-, 3-, 4-, 5-, and 7 days (D). Three hydrogels were pooled together with an average of 3-5 separate replicates (samples) at each time point. Sample media was stored at −20° C. until mass spectroscopy analysis was performed. Graphs only show through day 4 since all cevimeline had been released by that point. To (initial control) gels were dissolved in DMEM to establish baseline of cevimeline encapsulated in hydrogel.

Animal Experiments

Adult female mice (aged between 6-8 weeks) from the C57/BL6 inbred strain (Harlan Laboratories) were used in all experiments, unless otherwise stated. All procedures were approved by the UCSF Institutional Animal Care and Use Committee (IACUC) and were adherent to the NIH Guide for the Care and Use of Laboratory Animals.

In Vivo Cevimeline Delivery

Cevimeline was prepared as previously described and delivered by intraperitoneal (IP) injection using a 0.5 ml Monoject™ Tuberculin Syringes with a 28G ½ needle (Covidien) for free cevimeline or by subcutaneous injection using a 1 ml TB Syringe with a 25G×⅝ needle (Becton Dickinson) for cevimeline mixed with alginate.

For Intraglandular injection of cevimeline, mice were administered with analgesics 30 min prior to surgery (carprofen and buprenorphine; Patterson Veterinary and Buprenex; 0.1 mg/kg and 100 mg/kg (IP), respectively) and anaesthetized via inhalation with 2% isoflurane/$O_2$mix. The surgical area was shaved and prepared for incision with alternating iodine and alcohol washes, followed by local anesthetic (lidocaine; Hospira Inc., 8 mg/kg). An incision was made in the throat following the craniocaudal axis using spring scissors. Cevimeline was then injected in the lobes of submandibular and sublingual salivary glands using a 2 27G×½ Needle (Becton Dickinson) mounted on a slip tip Tuberculin syringe (Becton Dickinson). The skin was sutured using non-absorbable silk sutures (Ethicon). Mice were euthanized 18 hrs, 3 days or 7 days later with some animals being injected with 0.9% saline containing 0.25 mg/25 g of 5-ethynyl-2'-deoxyuridine (EdU, Thermofisher Scientific) 2 hours before sacrifice.

γ-Radiation Treatment

Animals were anaesthetized with 100 μl/10 g bw of 2.5% Avertin (2,2,2-Tribromoethanol (Alfa Aesar), tert-Amyl Alcohol (2-Methyl-2-butanol) (Spectrum)) in 0.9% saline (Vedco Inc.). The mice were placed into a Shepherd Mark I Irradiator (JL Shepherd & Associates). The body was shielded from radiation using lead blocks and the head and neck regions were exposed to 2 doses of 5 Gy (10 Gy total) to irradiate the salivary glands (SGs). Control mice were anaesthetized but did not undergo radiation treatment. All mice were allowed to completely recover before returning to normal housing and were given soft diet ad libitum (ClearH$_2$O).

Saliva Collection

Mice were anesthetized using 2% inhaled isoflurane or Avertin (for radiation studies). 5 mg of sodium citrate (Spectrum Chemical) in 12.5 μl sterile water was dropped in the mouth of the mice. After 2 min, a piece of filter paper was inserted in the mouth of the animals and left for 5 min, under anesthesia. The amount of saliva secreted was determined by measuring the weight of filter paper before and after collection, using a precision scale (Denver Instrument SI-64, di=0.1 mg).

Tissue Processing

After euthanasia, SGs were collected, snap frozen and embedded in OCT. 10 μm frozen sections were cut using a cryostat (Leica) and used for immunofluorescence studies.

Immunofluorescence Studies

Tissue section immunofluorescence analysis was processed as follows. In brief, fresh-frozen tissue was fixed with 4% PFA for 10 min at RT followed by permeabilizing with 0.5% Triton-X100 for 10 min at RT. Tissue was blocked for 2 hrs at RT with 10% Donkey Serum (Jackson Laboratories, ME), 5% BSA (Sigma Aldrich), and MOM IgG-blocking reagent (Vector Laboratories, CA) in 0.01% PBS-Tween-20. SG sections were incubated with primary antibodies overnight at 4° C.: rabbit anti-AQP5 (1:200, Millipore, AB3559), goat anti-SOX2 (1:200, Neuromics, GT15098), rabbit anti-Ki67 (1:200, AbCam, ab16667), rat anti-Ki67 (1:200, DAKO, M7249), rabbit-CHRM3 (1:1000, Research Diagnostics, AS-3741S), rat anti-E-Cadherin (1:400, Invitrogen, 13-1900). Antibodies were detected using Cy2-, Cy3- or Cy5-conjugated secondary Fab fragment antibodies (1:300, Jackson Laboratories) and nuclei stained using Hoescht 33342 (1:1000, AnaSpec Inc.). EdU staining was performed using the Click-iT EdU Alexa-Fluor 488 or 647 kit (Invitrogen). Slides were mounted using Fluoromount-G (SouthernBiotech) and fluorescence was analyzed using a Leica Sp5 confocal microscope. Image processing and quantification was performed using NIH ImageJ software.

Statistics

Statistical tests were performed using GraphPad Prism software v8. Data are presented as mean±SD and were subjected to 2-tailed unpaired Student's t test for two datasets or ordinary one-way ANOVA using the Tukey's multiple comparisons test for more than 2 datasets. Significance was assessed using P-value cutoffs indicated as follows: *P<0.05, P<0.01, *P<0.001, and ****P<0.0001. Specific data set analyses are described in the figure legends.

What is claimed is:

1. A method of promoting salivary gland regeneration in a subject in need thereof, the method comprising: administering locally to acinar progenitor cells and acinar cells of the salivary gland a muscarinic agonist to promote proliferation of the acinar progenitor cells and the acinar cells and thereby increase saliva production, wherein the muscarinic agonist is encapsulated in a hydrogel formulated for local administration into the salivary gland.

2. The method of claim 1, wherein the acinar progenitor cells are SOX2$^+$ acinar progenitor cells.

3. The method of claim 1, wherein the hydrogel comprises ionically cross-linked alginate.

4. The method of claim 3, wherein the alginate is ionically cross-linked by divalent calcium cations.

5. The method of claim 3, wherein the alginate concentration in the hydrogel ranges from 2 to 10 percentage by weight (wt %).

6. The method of claim 3, wherein about 2% to about 10% of the alginate is oxidized.

7. The method of claim 1, wherein the muscarinic agonist is selective for an M1 and/or an M3 muscarinic receptor subtype.

8. The method of claim 7, wherein the muscarinic agonist is cevimeline or pilocarpine.

9. The method of claim 1, wherein the hydrogel sustains delivery of the muscarinic agonist for at least 1 week, at least 2 weeks, at least 3 weeks, or at least 4 weeks after administration to the subject.

10. The method of claim 1, wherein the salivary gland is a sublingual gland.

* * * * *